US008304547B2

(12) United States Patent
Sugasawa et al.

(10) Patent No.: US 8,304,547 B2
(45) Date of Patent: Nov. 6, 2012

(54) AZOLECARBOXAMIDE COMPOUND OR SALT THEREOF

(75) Inventors: Keizo Sugasawa, Tokyo (JP); Kenichi Kawaguchi, Tokyo (JP); Takaho Nomura, Tokyo (JP); Shunichiro Matsumoto, Tokyo (JP); Takashi Shin, Tokyo (JP); Hidenori Azami, Tokyo (JP); Tomoaki Abe, Tokyo (JP); Akira Suga, Tokyo (JP); Ryushi Seo, Tokyo (JP); Masayuki Tanahashi, Tokyo (JP); Toru Watanabe, Tokyo (JP)

(73) Assignee: Astellas Pharma Inc., Tokyo (JP)

( * ) Notice: Subject to any disclaimer, the term of this patent is extended or adjusted under 35 U.S.C. 154(b) by 133 days.

(21) Appl. No.: 12/739,433

(22) PCT Filed: Oct. 23, 2008

(86) PCT No.: PCT/JP2008/069263
§ 371 (c)(1),
(2), (4) Date: Apr. 23, 2010

(87) PCT Pub. No.: WO2009/054468
PCT Pub. Date: Apr. 30, 2009

(65) Prior Publication Data
US 2010/0249088 A1 Sep. 30, 2010

(30) Foreign Application Priority Data

Oct. 24, 2007 (JP) ................................ 2007 276894

(51) Int. Cl.
| C07D 211/68 | (2006.01) |
| C07D 221/20 | (2006.01) |
| C07D 491/20 | (2006.01) |
| C07D 413/14 | (2006.01) |
| C07D 239/09 | (2006.01) |
| A61K 31/535 | (2006.01) |
| A61K 31/505 | (2006.01) |
| A61K 31/44 | (2006.01) |
| A61K 31/445 | (2006.01) |

(52) U.S. Cl. ............ 546/194; 546/16; 546/19; 544/124; 544/298; 514/235.5; 514/269; 514/278; 514/318; 514/342

(58) Field of Classification Search .................. None
See application file for complete search history.

(56) References Cited

U.S. PATENT DOCUMENTS

| 2004/0110802 A1 | 6/2004 | Thorarensen et al. |
| 2004/0157845 A1 | 8/2004 | Doherty et al. |
| 2004/0220191 A1 | 11/2004 | Schwink et al. |
| 2006/0069102 A1 | 3/2006 | Leban et al. |
| 2006/0084640 A1 | 4/2006 | Gore et al. |
| 2006/0084650 A1 | 4/2006 | Dong et al. |
| 2006/0100201 A1 | 5/2006 | Illig et al. |
| 2006/0247253 A1 | 11/2006 | Leban et al. |
| 2007/0054939 A1 | 3/2007 | Guedat et al. |
| 2007/0299077 A1 | 12/2007 | Schwink et al. |
| 2009/0023758 A1 | 1/2009 | Wahling et al. |
| 2009/0286766 A1 | 11/2009 | Sugasawa et al. |
| 2010/0152219 A1 | 6/2010 | Block et al. |

FOREIGN PATENT DOCUMENTS

| EP | 1 340 757 | 9/2003 |
| EP | 1 881 001 A1 | 1/2008 |
| FR | 2 856 685 | 12/2004 |
| JP | 2001 278872 | 10/2001 |
| JP | 2003 231687 | 8/2003 |
| JP | 2007 91733 | 4/2007 |
| WO | 94 25456 | 11/1994 |
| WO | 96 16954 | 6/1996 |
| WO | 99 00121 | 1/1999 |
| WO | 00 27823 | 5/2000 |
| WO | 00 62778 | 10/2000 |
| WO | 01 14380 | 3/2001 |
| WO | 01 32653 | 5/2001 |
| WO | 01 78698 | 10/2001 |
| WO | 02 20479 | 3/2002 |
| WO | 02 20513 | 3/2002 |
| WO | 02 064558 | 8/2002 |
| WO | 03 013484 | 2/2003 |
| WO | 03 027111 | 4/2003 |
| WO | 2004 002948 | 1/2004 |

(Continued)

OTHER PUBLICATIONS

Extended Supplementary European Search Report issued on Jul. 18, 2011 in corresponding European Application No. 08 84 2145.

(Continued)

Primary Examiner — Kamal Saeed
Assistant Examiner — Nyeemah A Grazier
(74) Attorney, Agent, or Firm — Oblon, Spivak, McClelland, Maier & Neustadt, L.L.P.

(57) ABSTRACT

[Object] To provide a therapeutic and/or prophylactic agent for urinary frequency, urinary urgency, and urinary incontinence associated with various lower urinary tract diseases including overactive bladder, various lower urinary tract diseases accompanied by lower urinary tract pain, such as interstitial cystitis, chronic prostatitis, and the like, and various diseases accompanied by pain, based on an excellent trkA receptor inhibitory action.

[Means for Solution] A novel azolecarboxamide compound in which a thiazole ring or an oxazole ring is bonded to a benzene ring, a pyridine ring, a pyridazine ring, a thiophene ring, a pyrazole ring or a pyrrole ring through carboxamide, or a salt thereof is confirmed to have a potent trkA receptor inhibitory activity, and found to be capable of being used as a therapeutic and/or prophylactic agent which is excellent in efficacy and safety for urinary frequency, urinary urgency, and urinary incontinence associated with various lower urinary tract diseases including overactive bladder, various lower urinary tract diseases accompanied by lower urinary tract pain, such as interstitial cystitis, chronic prostatitis, and the like, and various diseases accompanied by pain, thereby completing the present invention.

28 Claims, No Drawings

FOREIGN PATENT DOCUMENTS

| | | |
|---|---|---|
| WO | 2004 018428 | 3/2004 |
| WO | 2004 071440 | 8/2004 |
| WO | 2004 072025 | 8/2004 |
| WO | 2004 096795 | 11/2004 |
| WO | 2005 003128 | 1/2005 |
| WO | 2005 030704 | 4/2005 |
| WO | 2005 030705 | 4/2005 |
| WO | 2005 042488 | 5/2005 |
| WO | 2005 049018 | 6/2005 |
| WO | 2005 049033 | 6/2005 |
| WO | 2005 076695 | 8/2005 |
| WO | 2005 103010 | 11/2005 |
| WO | 2006 018280 | 2/2006 |
| WO | 2006 020767 | 2/2006 |
| WO | 2006 047479 | 5/2006 |
| WO | 2006 047503 | 5/2006 |
| WO | 2006 047504 | 5/2006 |
| WO | 2006 116355 | 11/2006 |
| WO | 2006 122011 | 11/2006 |
| WO | 2007 000582 | 1/2007 |
| WO | 2007 014926 | 2/2007 |
| WO | 2007 017144 | 2/2007 |
| WO | 2007 026959 | 3/2007 |
| WO | 2007 030934 | 3/2007 |
| WO | 2007 030939 | 3/2007 |
| WO | 2007 031440 | 3/2007 |
| WO | 2007 035478 | 3/2007 |
| WO | 2007 049532 | 5/2007 |
| WO | 2007 060140 | 5/2007 |
| WO | 2007 061882 | 5/2007 |
| WO | 2007 103550 | 9/2007 |
| WO | 2007 104557 | 9/2007 |
| WO | 2007 123269 | 11/2007 |
| WO | 2007 146066 | 12/2007 |
| WO | 2008 006793 | 1/2008 |
| WO | 2008 054701 | 5/2008 |
| WO | 2008 054702 | 5/2008 |
| WO | 2008 054749 | 5/2008 |
| WO | 2008 059214 | 5/2008 |

OTHER PUBLICATIONS

Rogelio P. Frutos et al., "Practical Synthesis of 2-(2-Isopropylaminothiazol-4-yl)-7-methoxy-1*H*-quinolin-4-one: Key Intermediate for the Synthesis of Potent HCV NS3 Protease Inhibitor BILN 2061", Synthesis, vol. 2006, No. 15, Aug. 1, 2006, XP 002507667, pp. 2563-2567.

Tao Wang et al., "Trk Kinase Inhibitors as New Treatments for Cancer and Pain", Expert Opinion on Therapeutic Patents, Informa Healthcare, vol. 19, No. 3, Mar. 1, 2009, XP 002557234, pp. 305-319.

Office Action mailed Sep. 20, 2010, in co-pending U.S. Appl. No. 12/297,275.

Office Action issued Apr. 29, 2011 in European Patent Application No. 07 742 444.8-1211.

Chinese Office Action issued on Apr. 25, 2011 in corresponding Chinese Application No. 200780014053.7 filed on Apr. 19, 2007 (with an English Translation).

Li, Jianke et al., "Preparation of novel antibacterial agents. Replacement of the central aromatic ring with heterocycles", Bioorganic & Medicinal Chemistry Letters, vol. 17, No. 8, pp. 2347-2350, (2007).

Conover, C. Joanne., "Neurotrophin Regulation of the Developing Nervous System: Analyses of Knockout Mice", Reviews in the Neurosciences, vol. 8, No. 1, pp. 13-27, (1997).

Lowe, E.M. et al., "Increased nerve growth factor levels in the urinary bladder of women with idiopathic sensory urgency and interstitial cystitis", British Journal of Urology, vol. 79, pp. 572-577, (1997).

Dmitrieva, N. et al., "The Role of Nerve Growth Factor in a Model of Visceral Inflammation", Neuroscience, vol. 78, No. 2, pp. 449-459, (1997).

Dimitrakov, D. Jordan et al., "Efficacy and Safety of Recombinant Human Anti-NGF Antibody in the Treatment of IC", General Outline Preliminarily Described for the 99$^{th}$ American Urology Association, p. 363 (2004).

Hu, Y. Vivian et al., "Decrease in Bladder Overactivity With Ren1820 in Rats With Cyclophosphamide Induced Cystitis", The Journal of Urology, vol. 173, pp. 1016-1021, Mar. 2005.

Theodosiou, M. et al., "Hyperalgesia due to nerve damage: role of nerve growth factor", PAIN, vol. 81, pp. 245-255, (1999).

Shelton, L. David et al., "Nerve growth factor mediates hyperalgesia and cachexia in auto-immune arthritis", PAIN, vol. 116, pp. 8-16, (2005).

George, J. Daniel et al., Sustained in Vivo Regression of Dunning H Rat Prostate Cancers Treated with Combinations of Androgen Ablation and Trk Tyrosine Kinase Inhibitors, CEP-751 (KT-6587) or CEP-701 (KT-5555)[1], Cancer Research, vol. 59, pp. 2395-2401, May 15, 1999.

Das, Jagabandhu et al., "2-Aminothiazole as a Novel Kinase Inhibitor Template. Structure-Activity Relationship Studies toward the Discovery of N-(2-Chloro-6-methylphenyl)-2-[[6-[4-(2-hydroxyethyl)-1-piperazinyl)]-2-methyl-4-pyrimidinyl]amino)]-1,3-thiazole-5-carboxamide (Dasatinib, BMS-354825) as a Potent *pan*-Src Kinase Inhibitor", Journal of Medicinal Chemistry, vol. 49, No. 23, pp. 6819-6832, (2006).

Stillman, M. , "Clinical Approach to Patients With Neuropathic Pain", Cleveland Clinic Journal of Medicine, vol. 73 , No. 8, pp. 726-730, 733-739 (Aug. 2006).

"Pain Merck Manual Home Edtion" The Merck Manual Online Medical Library, (http://www.merck.com/mmhe/sec06/ch078/ch078a.html>) Total pp. 15 (Accessed Mar. 24, 2009).

Office Action issued Oct. 8, 2010, in Chinese Patent Application No. 200780014053.7 with English translation.

Office Action issued Oct. 4, 2011, in co-pending U.S. Appl. No. 12/297,275.

AZOLECARBOXAMIDE COMPOUND OR SALT THEREOF

CROSS REFERENCES TO RELATED APPLICATIONS

This application is a 371 of International Patent Application No. PCT/JP2008/069263, filed on Oct. 23, 2008, and claims priority to Japanese Patent Application No. 2007-276894, filed on Oct. 24, 2007.

TECHNICAL FIELD

The present invention relates to an azolecarboxamide compound which is useful as a pharmaceutical, in particular, a therapeutic agent for urinary frequency, urinary urgency, urinary incontinence, and lower urinary tract pain associated with various lower urinary tract diseases including overactive bladder, and various diseases accompanied by pain.

BACKGROUND ART

An overactive bladder is a clinical condition showing urinary urgency regardless of incontinence, which is usually accompanied by urinary frequency and nocturia (Non-Patent Document 1). At present, for a treatment thereof, an anticholinergic agent is mainly used for a treatment thereof, and constant treatment results are given. However, it has been reported that the use thereof is difficult with patients with prostatic hypertrophy or elderly patients because it is known to cause side-effects such as dry mouth, constipation and blurred vision, as well as a risk of urinary retention. In addition, there are patients who show no improvement with the anticholinergic-treatment. From the above, there is great expectation of a drug with a new mechanism of action for overactive bladder.

A nerve growth factor (NGF) is one of the humoral factors named generically as a neurotrophic factor, which plays an important role in the development, differentiation and functional maintenance of neurons in the living body. As a receptor of NGF, a high-affinity trkA receptor (tyrosine kinase receptor) and a low-affinity p75 receptor have been known. It has been reported that p75 binds to all neurotrophic factors, and is involved in apoptosis in the process of neuron development, but the role has not yet been fully understood. It has been known that NGF and trkA receptor-knockout mice show the similar phenotype (Non-Patent Document 1), and it is believed that the physiological action of NGF is exhibited mainly through the trkA receptor.

It has been known that the NGF level in bladder is increased in a patient with overactive bladder or interstitial cystitis (Non-Patent Document 2), and there have been reports that an intravesical instillation of NGF reduces the bladder capacity of a rat and that the inhibition of NGF improves urination function in the urinary frequency-model rat (Non-Patent Document 3). In addition, it has been reported that the inhibition of NGF improved urinary frequency or urinary incontinence in a patient with interstitial cystitis (Non-Patent Document 4), and it is thus believed that a trkA receptor inhibitor is useful as a therapeutic agent for lower urinary tract diseases such as overactive bladder, interstitial cystitis, prostatitis, and the like.

Moreover, a trkA receptor inhibitor has different mechanisms of action, and thus the side effects specific to the anticholinergic agent are expected to be avoided as well as an effect on patients who showed no improvement with the anticholinergic treatment is expected. In addition, this agent is expected to have potent effects of improving the subjective symptoms by acting on sensory nerves. Furthermore, this agent has been reported to exhibit an effect of improving the clinical condition without lowering urinary pressure in the urinary frequency-model rat (Non-Patent Document 5), and thus is expected to be administered safely to a patient with prostatic hypertrophy or an elderly patient.

It has been known that when NGF is administered to a human or a rat, pain is induced, and that pain sensation in the trkA receptor-knockout mice is lost. Consequently, NGF is believed to be strongly related to expression of pain. An NGF inhibition shows efficacy in model animals with neuropathic pain or inflammatory pain, such as a model with pain induced by damage to the ischiadic nerves (Non-Patent Document 6) and a model with pain induced by damage to the knee joint (Non-Patent Document 7), and a trkA receptor inhibitor is believed to be useful as a therapeutic agent for various pains such as lower urinary tract disease accompanied by lower urinary tract pain, osteoarthritis, or the like.

As the compound mentioned above, there have been known an indolocarbazole derivative (Non-Patent Document 8), a pyrrolocarbazole derivative (Patent Document 1), a pyrazolone derivative (Patent Document 2), an oxyindole derivative (Patent Documents 3 and 4), an azaoxyindole derivative (Patent Document 5), a pyrazoryl condensed ring compound (Patent Document 6), a pyrazole derivative (Patent Documents 7 and 8), a tricyclic derivative (Patent Document 9), ALE-0540 (Patent Document 10), a benzo[de]isoquinoline derivative (Patent Document 11), a benzo[lmn]phenanthroline derivative (Patent Document 12), and a pyrrolotriazine derivative (Patent Document 13).

Patent Document 1: Pamphlet of International Publication WO01/14380
Patent Document 2: Pamphlet of International Publication WO01/32653
Patent Document 3: Pamphlet of International Publication WO02/20479
Patent Document 4: Pamphlet of International Publication WO02/20513
Patent Document 5: Pamphlet of International Publication WO03/027111
Patent Document 6: JP-A-2003-231687
Patent Document 7: Pamphlet of International Publication WO2005/049033
Patent Document 8: Pamphlet of International Publication WO2005/103010
Patent Document 9: Pamphlet of International Publication WO2005/076695
Patent Document 10: Pamphlet of International Publication WO01/78698
Patent Document 11: Pamphlet of International Publication WO2007/030939
Patent Document 12: Pamphlet of International Publication WO2007/030934
Patent Document 13: Pamphlet of International Publication WO2007/061882
Non-Patent Document 1: 'Reviews in the Neurosciences', (UK), 1997, vol 8, pp. 13 to 27
Non-Patent Document 2: 'British Journal of Urology', (UK), 1997, vol 79, pp. 572 to 7
Non-Patent Document 3: 'Neuroscience', (USA), 1997, vol 78, 2th Issue, pp. 449 to 59
Non-Patent Document 4: 'General Outline preliminarily described for the 99$^{th}$ American Urology Association', San Francisco, 2004, #363
Non-Patent Document 5: 'The Journal of Urology', (USA), 2005, vol 173, pp. 1016 to 21

Non-Patent Document 6: 'Pain', (USA), 1999, vol 81, pp. 245 to 55

Non-Patent Document 7: 'Pain', (USA), 2005, vol 116, pp. 8 to 16

Non-Patent Document 8: 'Cancer Research', 1999, vol 59, pp. 2395 to 2401

DISCLOSURE OF THE INVENTION

Problem that the Invention is to Solve

As described above, existing therapeutic agents for urinary frequency, urinary urgency, and urinary incontinence associated with overactive bladder, and various lower urinary tract diseases accompanied by lower urinary tract pain, such as interstitial cystitis, chronic prostatitis, and the like are not satisfactory from the viewpoint of efficacy, safety, or the like. Thus, there has been a strong demand for a therapeutic agent for lower urinary tract disease which is excellent in efficacy and safety.

Means for Solving the Problem

As described above, a trkA receptor inhibitor can be expected to be a safe therapeutic agent for lower urinary tract disease, with few side effects such as dry mouth, urinary retention, and the like. The present inventors thoroughly investigated a compound having trkA receptor inhibitory activity for the purpose of providing a novel compound useful for treating lower urinary tract disease and so forth. As a result, the inventors found that an azolecarboxamide compound represented by the following formula (I) exhibits potent trkA receptor inhibitory action, thereby completing the present invention.

That is, the present invention relates to an azolecarboxamide compound represented by the following formula (I) or a salt thereof.

[1] An azolecarboxamide compound represented by the following formula (I) or a salt thereof:

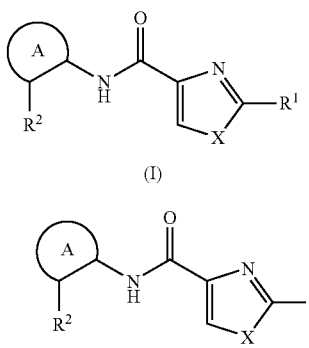

(the symbols in the formula have the following meanings:

X: S or O, $R^1$: halogen, aryl, heteroaryl, cycloalkyl, 4-piperidyl, 4-tetrahydropyranyl, -Alk-aryl, -Alk-O-aryl, -Alk-O-lower alkyl, -Alk-NH—CO-lower alkyl, -Alk-NH—CO—O-lower alkyl, —NH-aryl, —NH-(4-piperidyl), a group represented by the formula (II), or a group represented by the formula (III):

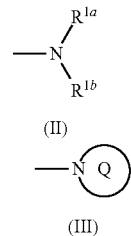

wherein in $R^1$, each aryl may be substituted with group(s) selected from the group consisting of halogen and halogeno-lower alkyl, the heteroaryl may be substituted with amino or —NH—CO—O-lower alkyl, the cycloalkyl may be substituted with —O-Alk-aryl or —O-heteroaryl, and the N atom of each 4-piperidyl may be substituted with lower alkyl, heteroaryl, —CO-lower alkyl, or —CO—O-lower alkyl, Alk: the same as or different from each other, each representing lower alkylene, $R^{1a}$: lower alkyl substituted with one or two —OH, -Alk-O-lower alkyl, -Alk-$SO_2$-lower alkyl, -Alk-O—$SO_2$-lower alkyl, -Alk-aryl, -Alk-O-aryl, -Alk-heteroaryl, -Alk-O-heteroaryl, -Alk-CO-saturated hetero ring group, -Alk-$NR^A R^B$, -Alk-CO—$NR^A R^B$, saturated hetero ring group, wherein the saturated hetero ring group may be substituted with lower alkyl, lower alkenyl, -Alk-O-lower alkyl or -Alk-aryl, or -Alk-saturated hetero ring group, wherein the saturated hetero ring group in the -Alk-saturated hetero ring group may be substituted with lower alkyl or —OH, $R^A$ and $R^B$: the same as or different from each other, each representing —H or lower alkyl, $R^{1b}$: lower alkyl or -Alk-aryl, Q: cyclic amino which may be substituted with group(s) selected from Group $G_1$ below:

Group $G_1$: halogen, —OH, —CN, lower alkyl, halogeno-lower alkyl, -Alk-OH, —O-lower alkyl, —O-halogeno-lower alkyl, -Alk-O-lower alkyl, —O-Alk-O-lower alkyl, —O-cycloalkyl, —O-Alk-cycloalkyl, —$CO_2H$, —CO—O-lower alkyl, —CO-lower alkyl, —CO—$NR^A R^B$, —CO—NH-Alk-OH, -Alk-CO—$NR^A R^B$, —$SO_2$-lower alkyl, —$SO_2$—$NR^A R^B$, aryl, —O-aryl, heteroaryl which may be substituted with (—O-lower alkyl), -Alk-heteroaryl, —O-(heteroaryl which may be substituted with group(s) selected from the group consisting of halogen, lower alkyl, —O-lower alkyl, —CN and —OH), -Alk-O-heteroaryl, —$SO_2$-heteroaryl, —S-(heteroaryl which may be substituted with lower alkyl), oxo, —$NR^C R^D$, and -Alk-aryl, wherein, in -Alk-aryl of Group $G_1$, the Alk may be substituted with —OH, and the aryl may be substituted with —$CO_2H$ or —CO—O-lower alkyl, and two substituents on the ring group Q may be combined to form -Alk-, saturated hetero ring which may be substituted with group(s) selected from the group consisting of lower alkyl and oxo, or cycloalkane, may be spiro bonded on the ring group Q, heteroarene which may be substituted with lower alkyl, arene, or cycloalkane, may be condensed with the ring group Q, $R^C$: —H or lower alkyl, $R^D$: lower alkyl, —CO-lower alkyl, —CO—O-lower alkyl, -Alk-CO—$NR^A R^B$, or heteroaryl, R²: a group selected from (i) or (ii) below,
(i) a group represented by the formula (IV) or (V),

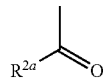

(IV)

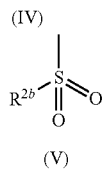

(V)

R²ᵃ: —O—Rᴱ, —CH₂—Rᶠ, —NRᴳRᴴ, or heteroaryl,
Rᴱ: —H or lower alkyl,
Rᶠ: —H, heteroaryl, or saturated hetero ring group,
Rᴳ: —H or lower alkyl,
Rᴴ: (1) —H, (2) —O-lower alkyl, (3) cycloalkyl which may be substituted with group(s) selected from the group consisting of —OH, —NRᴬRᴮ, —NH—CO—O-lower alkyl, —CN, —CO₂H, —CO—O-lower alkyl and —CONH₂, (4) cycloalkenyl which may be substituted with -Alk-OH or —CONH₂, (5) saturated hetero ring group which may be substituted with group(s) selected from the group consisting of —OH, lower alkyl, -Alk-cycloalkyl, —CO-lower alkyl and oxo, (6) aryl which may be substituted with group(s) selected from the group consisting of —OH, —CN and halogen, (7) heteroaryl, or (8) lower alkyl which may be substituted with group(s) selected from Group G₂ below:

Group G₂: halogen, halogeno-lower alkyl, —OH, cycloalkyl, —O-lower alkyl, —O-cycloalkyl, —O-Alk-OH, —CN, —S-lower alkyl, —SO₂-lower alkyl, —CONH₂, —CONH-lower alkyl, —NHCO-lower alkyl, —CO₂H, —CO—O-lower alkyl, —NRᴬRᴮ, saturated hetero ring group, —CO-saturated hetero ring group, aryl, and heteroaryl, wherein, in Group G₂, the cycloalkyl may be substituted with —OH, —CO—O-lower alkyl, -Alk-OH or -Alk-NRᴬRᴮ, the saturated hetero ring group may be substituted with —OH, lower alkyl, -Alk-OH, -Alk-O-lower alkyl, -Alk-aryl, —NRᴬRᴮ, —CO—O-lower alkyl or oxo, and the heteroaryl may be substituted with —OH, lower alkyl, —CO₂H or —CO—O-lower alkyl, and Rᴳ and Rᴴ may be combined with the N atom to which they are bonded to form nitrogen-containing saturated hetero ring which may be substituted with group(s) selected from the group consisting of —OH, lower alkyl, —CO—O-lower alkyl, -Alk-aryl and —CO-saturated hetero ring group, R²ᵇ: lower alkyl, halogeno-lower alkyl, -Alk-Rᴷ, —NRᴸRᴹ, aryl or saturated hetero ring group, wherein the saturated hetero ring group may be substituted with —CO—O-Alk-aryl, Rᴷ: —CN, —OH, —N₃, —CONH₂, —O—CO-lower alkyl, —NRᴬRᴮ, —NH—CO-lower alkyl, —O—SO₂-lower alkyl, heteroaryl or saturated hetero ring group, Rᴸ: —H or lower alkyl, Rᴹ: heteroaryl or saturated hetero ring group, (ii) —H, halogen, —OH, lower alkyl, halogeno-lower alkyl, —CN, —O-lower alkyl, —O-halogeno-lower alkyl, heteroaryl which may be substituted with lower alkyl, -Alk-OH, -Alk-CONH₂, -Alk-saturated hetero ring group or —S—Rᴺ, Rᴺ: (1) -Alk-OH, (2) -Alk-CONH₂, (3) -Alk-heteroaryl, (4) -Alk-saturated hetero ring group, or (5) saturated hetero ring group which may be substituted with (—CO—O-Alk-aryl),

A:

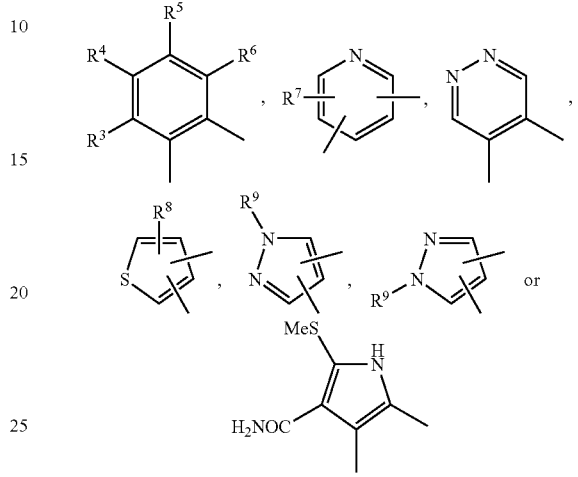

R³: —H, halogen, lower alkyl, —O-lower alkyl or —CN,
R⁴: —H, halogen, —OH, —O-Alk-R⁴ᵃ, cycloalkyl which may be substituted with —CN, —CN, —CO₂H, —CO—O-lower alkyl, —CO—NH-heteroaryl, —CO—NH—SO₂-lower alkyl, —CO—NH—SO₂—NRᴬRᴮ, saturated hetero ring group, —O-saturated hetero ring group, —CO-saturated hetero ring group, —SO₂-saturated hetero ring group, —CO—NR⁴ᵇR⁴ᶜ, or lower alkyl which may be substituted with group(s) selected from Group G₃ below, R⁴ᵃ: —H, —OH, —O-lower alkyl, —O-Alk-aryl, —S-lower alkyl, —SO₂-lower alkyl or —NH—Rᴼ, Rᴼ: —H, —CO—O-lower alkyl, —CO-lower alkyl or —SO₂-lower alkyl, R⁴ᵇ: the same as or different from each other, each representing —H or lower alkyl, R⁴ᶜ: the same as or different from each other, each representing —H, lower alkyl, -Alk-O-lower alkyl, -Alk-NRᴬRᴮ, -Alk-aryl, -Alk-saturated hetero ring group, cycloalkyl, aryl or saturated hetero ring group, Group G₃: halogen, —OH, —O-lower alkyl, —O—CO-lower alkyl, —O-Alk-O-lower alkyl, —CN, —CO₂H, —CO—O-lower alkyl, —NR⁴ᵇR⁴ᶜ, cyclic amino and —CO-saturated hetero ring group, wherein each saturated hetero ring group in R⁴, the saturated hetero ring group in the —CO-saturated hetero ring group of Group G₃, and the cyclic amino in Group G₃ may be substituted with group(s) selected from Group G₄ below, and two substituents on the cyclic amino in Group G₃ may be combined to form -Alk-, saturated hetero ring which may be substituted with group(s) selected from the group consisting of lower alkyl and oxo, or cycloalkane, may be spiro bonded on the cyclic amino, and arene which may be substituted with group(s) selected from the group consisting of halogen, lower alkyl, and —O-lower alkyl, heteroarene, cycloalkane or saturated hetero ring, may be condensed with the cyclic amino, Group G₄: halogen, lower alkyl, halogeno-lower alkyl, —OH, —O-lower alkyl, —O-aryl, —O—CO-lower alkyl, —CO—O-lower alkyl, —NR$^A$R$^B$, —NH—CO-lower alkyl, -Alk-OH, -Alk-O-lower alkyl, —CO-lower alkyl, —CO—NR$^A$R$^B$, -Alk-aryl, -Alk-heteroaryl, -Alk-NR$^A$R$^B$, -Alk-CO—NR$^A$R$^B$, -Alk-cyclic amino, -Alk-NH-aryl, -Alk-S-lower alkyl, -Alk-halogeno-lower alkyl, cycloalkyl, aryl, heteroaryl, cyclic amino, —SO$_2$-lower alkyl, —SO$_2$—NR$^A$R$^B$, oxo and —CN, wherein each aryl and each heteroaryl in Group G$_4$ may be substituted with group(s) selected from Group G$_5$ below, Group G$_5$: halogen, lower alkyl, halogeno-lower alkyl, —O-lower alkyl, —NR$^A$R$^B$ and -Alk-O-lower alkyl, R$^5$: —H, halogen, lower alkyl, —OH, —O-lower alkyl, —CN, halogeno-lower alkyl, -Alk-OH, -Alk-O-lower alkyl, -Alk-CN, —O-Alk-NH$_2$, —O-Alk-NH—CO—O-lower alkyl, —O-Alk-aryl or —CONH$_2$, wherein R$^4$ and R$^5$ may be combined with the carbon atom on the benzene ring to which they are bonded to form (1) pyrazole ring, (2) 2,3-dihydro-1,4-dioxine ring, or (3) cyclopentene ring which may be substituted with —OH or oxo, R$^6$: —H, halogen, lower alkyl, or —O-lower alkyl, R$^7$: —H, lower alkyl, —CO$_2$H, —CO—O-lower alkyl, —CO-saturated hetero ring group or -Alk-saturated hetero ring group, R$^8$: —H or lower alkyl, and R$^9$: —H, lower alkyl or -Alk-saturated hetero ring group, provided that 1) in the case where R$^2$ is a group selected from (ii), R$^1$ is a group represented by the formula (II) or (III), 2) in the case where R$^2$ is —H, any one group of R$^3$ to R$^6$ and R$^7$ are a group other than —H, and 3) in the case where R$^1$ is heteroaryl, A is phenylene which may be substituted.
The same applies hereinafter.)

[2] The compound or a salt thereof of [1], wherein R$^1$ is a group represented by the formula (II) or the formula (III), and R$^2$ is a group represented by the formula (IV) or the formula (V).

[3] The compound or a salt thereof of [2], wherein R$^2$ is a group represented by the formula (IV).

[4] The compound or a salt thereof of [3], wherein A is a ring group represented by the following formula:

A:

[Chem. 5]

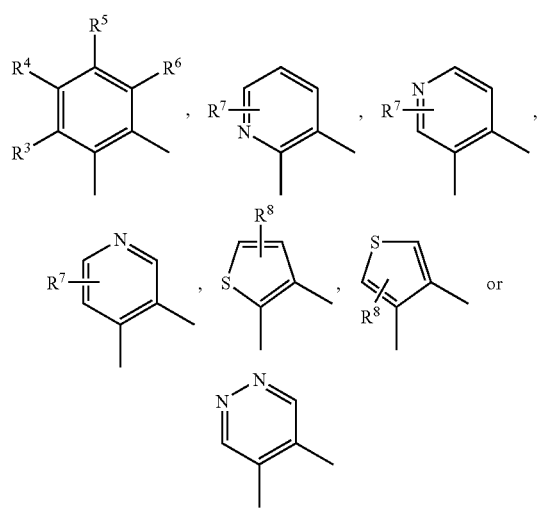

[5] The compound or a salt thereof of [4], wherein R$^3$ and R$^5$ are the same as or different from each other, and each represents —H, halogen, lower alkyl or —O-lower alkyl, R$^4$ is (1) —H, (2) halogen, (3) —O-lower alkyl, (4) cycloalkyl which may be substituted with —CN, (5) saturated hetero ring group which may be substituted with group(s) selected from the group consisting of lower alkyl and -Alk-O-lower alkyl, (6) —O-saturated hetero ring group, or (7) lower alkyl which may be substituted with group(s) selected from Group G$_{3A}$, R$^6$ is —H or —O-lower alkyl, and R$^7$ and R$^8$ are the same as or different from each other, and each represents —H or -lower alkyl;

wherein

Group G$_{3A}$: —O-lower alkyl, —O-Alk-O-lower alkyl, —NR$^{4d}$R$^{4e}$ and cyclic amino, R$^{4d}$: lower alkyl, R$^{4e}$: lower alkyl, -Alk-O-lower alkyl, or -Alk-saturated hetero ring group, and the cyclic amino in Group G$_{3A}$ may be substituted with group(s) selected from the group consisting of F, lower alkyl, —O-lower alkyl and -Alk-O-lower alkyl, two substituents on the cyclic amino in Group G$_{3A}$ may be combined to form -Alk-, saturated hetero ring which may be substituted with group(s) selected from the group consisting of lower alkyl and oxo, or cycloalkane, may be Spiro bonded on the cyclic amino, and arene which may be substituted with group(s) selected from the group consisting of halogen, lower alkyl and —O-lower alkyl, heteroarene, cycloalkane or saturated hetero ring, may be condensed with the cyclic amino.

[6] The compound or a salt thereof of [5], wherein in R$^1$, R$^{1a}$ of the group represented by the formula (II) is (1) -Alk-O-lower alkyl, (2) saturated hetero ring group which may be substituted with group(s) selected from the group consisting of lower alkyl, lower alkenyl, -Alk-O-lower alkyl and -Alk-aryl, or (3) -Alk-(saturated hetero ring group which may be substituted with lower alkyl or —OH), R$^{1b}$ is lower alkyl, and the cyclic amino represented by the formula (III) is cyclic amino which may be substituted with group(s) selected from Group G$_{1A}$ below;

Group G$_{1A}$: F, —OH, lower alkyl, —O-lower alkyl, -Alk-O-lower alkyl and —O-(heteroaryl which may be substituted with group(s) selected from the group consisting of halogen, lower alkyl, —O-lower alkyl, —CN and —OH).

[7] The compound or a salt thereof of [6], wherein in R$^2$, R$^{2a}$ of the group represented by the formula (IV) is —O—R$^E$, —CH$_2$—R$^F$ or —NR$^G$R$^H$, wherein R$^E$ is lower alkyl, R$^F$ is —H, heteroaryl or saturated hetero ring group, R$^G$ is —H, and R$^H$ is (1) —H, (2) cycloalkyl, (3) saturated hetero ring group which may be substituted with lower alkyl, (4) heteroaryl which may be substituted with lower alkyl, or (5) lower alkyl which may be substituted with group(s) selected from the group consisting of F, —OH, cycloalkyl, —O-lower alkyl, saturated hetero ring group, and heteroaryl.

[8] The compound or a salt thereof of [7], wherein R$^3$, R$^6$, R$^7$, and R$^8$ are —H.

[9] An azolecarboxamide compound represented by the following formula (I-A) or a salt thereof:

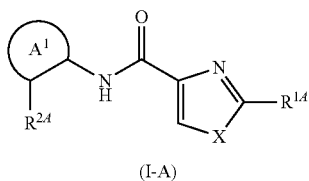

(I-A)

(the symbols in the formula have the following meanings:

X: S or O, $R^{1A}$: a group represented by the formula (II-A) or a group represented by the formula (III-A),

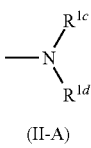

(II-A)

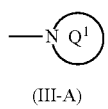

(III-A)

Alk: the same as or different from each other, each representing lower alkylene, $R^{1c}$: -Alk-O-lower alkyl, saturated hetero ring group which may be substituted with lower alkyl, or -Alk-saturated hetero ring group, $R^{1d}$: lower alkyl, $Q^1$: cyclic amino which may be substituted with group(s) selected from Group $G_{1B}$ below, Group $G_{1B}$: F, —OH, —O-lower alkyl, or —O-(heteroaryl which may be substituted with group(s) selected from the group consisting of halogen, lower alkyl, —O-lower alkyl, —CN, and —OH), $R^2A$:

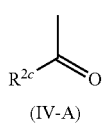

(IV-A)

$R^{2c}$: —O-lower alkyl, —CH$_2$—$R^W$ or —NH—$R^X$, $R^W$: —H, heteroaryl or saturated hetero ring group, $R^X$: (1) —H, (2) cycloalkyl, (3) saturated hetero ring group, (4) heteroaryl, or (5) lower alkyl which may be substituted with group(s) selected from the group consisting of F, cycloalkyl, —O-lower alkyl and saturated hetero ring group, $A^1$:

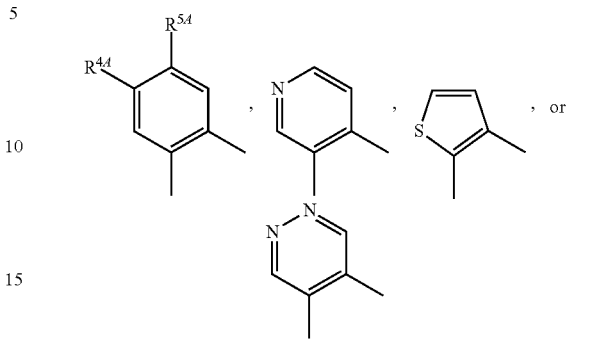

$R^{4A}$: (1) —H, (2) cycloalkyl substituted with one —CN, (3) saturated hetero ring group which may be substituted with group(s) selected from the group consisting of lower alkyl and -Alk-O-lower alkyl, (4) —O-lower alkyl, (5) —O-saturated hetero ring group, or (6) lower alkyl which may be substituted with one group selected from Group $G_{3B}$ below, Group $G_{3B}$: —O-lower alkyl, —NR$^{4f}$R$^{4g}$ and cyclic amino, $R^{4f}$: lower alkyl, $R^{4g}$: lower alkyl which is the same as or different from $R^{4f}$, which may be substituted with one group selected from the group consisting of —O-lower alkyl and saturated hetero ring group, wherein the cyclic amino in Group $G_{3B}$ may be substituted with group(s) selected from the group consisting of F, lower alkyl, —O-lower alkyl and -Alk-O-lower alkyl, and cycloalkane may be Spiro bonded on the cyclic amino in Group $G_{3B}$, and arene or cycloalkane may be condensed with the cyclic amino in Group $G_{3B}$, and $R^{5A}$: —H, lower alkyl or —O-lower alkyl.

The same applies hereinafter.)

[10] The compound or a salt thereof of [9], wherein $R^{2C}$ is —NH—$R^X$.

[11] The compound of [1], which is selected from the group consisting of:
2-morpholin-4-yl-N-[2-(pyridin-3-ylcarbamoyl)phenyl]-1,3-oxazole-4-carboxamide,
2-(4-ethoxypiperidin-1-yl)-N-[2-(tetrahydro-2H-pyran-4-ylcarbamoyl)phenyl]-1,3-thiazole-4-carboxamide,
2-[(2-methoxyethyl)(methyl)amino]-N-[2-(pyridin-3-ylcarbamoyl)phenyl]-1,3-thiazole-4-carboxamide,
2-[(3S)-3-methoxypyrrolidin-1-yl]-N-[2-(pyridin-3-ylcarbamoyl)phenyl]-1,3-oxazole-4-carboxamide,
2-[(2-methoxyethyl)(methyl)amino]-N-[2-(tetrahydro-2H-pyran-4-ylcarbamoyl)phenyl]-1,3-oxazole-4-carboxamide,
N-{2-[(2-methoxyethyl)carbamoyl]-4-(morpholin-4-ylmethyl)phenyl}-2-[4-(pyrimidin-2-yloxy)piperidin-1-yl]-1,3-thiazole-4-carboxamide,
4-[({2-[4-(pyrimidin-2-yloxy)piperidin-1-yl]-1,3-thiazol-4-yl}carbonyl)amino]-N-(tetrahydro-2H-pyran-4-yl) nicotinamide,
2-[(2-methoxyethyl)(methyl)amino]-N-[4-methoxy-2-(pyridin-3-ylcarbamoyl)phenyl]-1,3-thiazole-4-carboxamide,
2-[methyl(tetrahydro-2H-pyran-4-ylmethyl)amino]-N-[4-(morpholin-4-ylmethyl)-2-(tetrahydro-2H-pyran-4-ylcarbamoyl)phenyl]-1,3-thiazole-4-carboxamide,
N-(2-[(2-methoxyethyl)carbamoyl]-4-{[(2S)-2-methylmorpholin-4-yl]methyl}phenyl)-2-[(3S)-3-methoxypyrrolidin-1-yl]-1,3-thiazole-4-carboxamide, N-{4-[(3,3-dimethylmorpholin-4-yl)methyl]-2-[(2-methoxyethyl)carbamoyl]phenyl}-2-[(3S)-3-methoxypyrrolidin-1-yl]-1,3-thiazole-4-carboxamide, 2-(3-methoxyazetidin-1-yl)-N-{2-[(2-methoxyethyl)carbamoyl]-4-(morpholin-4-ylmethyl)phenyl}-1,3-thiazole-4-carboxamide, 2-(3-methoxyazetidin-1-yl)-N-[2-{[(1R)-2-methoxy-1-methylethyl]carbamoyl}-4-(morpholin-4-ylmethyl)phenyl]-1,3-thiazole-4-carboxamide, N-{4-(ethoxymethyl)-2-[(2-methoxyethyl)carbamoyl]phenyl}-2-[(3S)-3-methoxypyrrolidin-1-yl]-1,3-thiazole-4-carboxamide, N-{2-[(2-methoxyethyl)carbamoyl]-4-(morpholin-4-ylmethyl)phenyl}-2-[(2-methoxyethyl)(methyl)amino]-1,3-thiazole-4-carboxamide, and 2-[(3S)-3-fluoropyrrolidin-1-yl]-N-{2-[(2-methoxyethyl)carbamoyl]-4-(morpholin-4-ylmethyl)phenyl}-1,3-thiazole-4-carboxamide, or a salt thereof.

[12] A pharmaceutical composition comprising the compound or a salt thereof of [1], and a pharmaceutically acceptable excipient.

[13] The pharmaceutical composition of [12], which is a trkA receptor inhibitor.

[14] The pharmaceutical composition of [12], which is a prophylactic and/or therapeutic agent for urinary frequency, urinary urgency, urinary incontinence and lower urinary tract pain associated with various lower urinary tract diseases, and various diseases accompanied by pain.

[15] The pharmaceutical composition of [14], wherein the lower urinary tract disease is overactive bladder, interstitial cystitis, or chronic prostatitis.

[16] Use of the compound or a salt thereof of [1] for the manufacture of a prophylactic and/or therapeutic agent for urinary frequency, urinary urgency, urinary incontinence and lower urinary tract pain associated with various lower urinary tract diseases, and various diseases accompanied by pain.

[17] The use of [16], wherein the lower urinary tract disease is overactive bladder, interstitial cystitis, or chronic prostatitis.

[18] A method for preventing and/or treating urinary frequency, urinary urgency, urinary incontinence and lower urinary tract pain associated with various lower urinary tract diseases, and various diseases accompanied by pain, which comprises administering to a patient an effective amount of the compound or a salt thereof of [1].

[19] The method for preventing and/or treating of [18], wherein the lower urinary tract disease is overactive bladder, interstitial cystitis, or chronic prostatitis.

Effect of the Invention

The compound of the present invention has potent trkA receptor inhibitory activity and excellent action for improving the condition of urinary frequency, and is expected to have effects of improving pain, and thus, it is useful as a therapeutic and/or prophylactic agent for urinary frequency, urinary urgency and urinary incontinence associated with various lower urinary tract diseases including overactive bladder, and various lower urinary tract diseases accompanied by lower urinary tract pain, such as interstitial cystitis, chronic prostatitis, and the like as well as various diseases accompanied by pain.

BEST MODE FOR CARRYING OUT THE INVENTION

Hereinafter, the present invention will be described in more detail. Furthermore, in the present specification, the "azolecarboxamide compound represented by the formula (I) or a salt thereof" may be simply referred to as "the compound (I) of the present invention", "the compound of the formula (I)", or the like.

In the present specification, the term "lower" means a linear or branched carbon chain having 1 to 6 carbon atoms (hereinafter simply referred to as $C_{1-6}$), unless otherwise specifically mentioned.

The "lower alkyl" is $C_{1-6}$ alkyl, and preferably linear alkyl such as methyl, ethyl, n-propyl, n-butyl, and the like, and branched alkyl such as isopropyl, isobutyl, tert-butyl, neopentyl, and the like. More preferred is $C_{1-4}$ alkyl, and particularly preferred is methyl, ethyl, n-propyl, isopropyl, or tert-butyl. The "lower alkylene" preferably refers to a divalent group formed by the removal of any hydrogen atoms of the $C_{1-6}$ alkylene, and preferably $C_{1-5}$ alkylene such as methylene, ethylene, methylmethylene, ethylmethylene, methylethylene, trimethylene, tetramethylene, dimethylethylene, pentamethylene, or 2,2-dimethyltrimethylene.

The "lower alkenyl" means $C_{2-6}$ alkenyl, preferably vinyl, allyl, or 2-butenyl, and more preferably 2-butenyl.

The "halogen" means F, Cl, Br, and I.

The "halogeno-lower alkyl" means $C_{1-6}$ alkyl substituted with one or more halogens, preferred is $C_{1-6}$ alkyl substituted with one or more F or Cl, and more preferred is fluoroethyl, fluoropropyl, difluoromethyl, difluoroethyl, or trifluoromethyl.

The "cycloalkyl" is a $C_{3-10}$ saturated hydrocarbon ring group, which may have a bridge. Preferred is $C_{3-8}$ cycloalkyl, and more preferred is cyclopropyl, cyclobutyl, cyclopentyl, or cyclohexyl. The cycloalkyl having a bridge is preferably a bicyclo[2.2.1]heptyl or adamantyl. In addition, the "cycloalkane" means a ring constituting the "cycloalkyl", for example, a cyclohexane ring corresponding to cyclohexyl.

The "cycloalkenyl" is a $C_{3-10}$ unsaturated hydrocarbon ring group, which may have a bridge. Preferred is $C_{3-8}$ cycloalkenyl, and more preferred is cyclopentenyl or cyclohexenyl.

The "aryl" is a $C_{6-14}$ mono- to tricyclic aromatic hydrocarbon ring group, preferred is a phenyl or naphthyl group, and more preferred is phenyl. The aryl may be condensed with a monocyclic saturated hetero ring or monocyclic cycloalkane. Further, the "arene" means a ring constituting the "aryl", for example, a benzene ring corresponding to phenyl.

The "heteroaryl" is a generic term referring to i) a 5- to 6-membered monocyclic aromatic ring group (monocyclic heteroaryl) containing 1 to 4 hetero atoms selected from O, S, and N, and ii) a bicyclic or tricyclic heteroaryl, formed by condensation between monocyclic heteroaryls, between a benzene ring and monocyclic heteroaryl, or between saturated hetero ring as described later and monocyclic heteroaryl. The monocyclic heteroaryl is preferably pyridyl, pyridazinyl, pyrimidinyl, pyrazinyl, triazinyl, furyl, thienyl, pyrrolyl, imidazolyl, pyrazolyl, triazolyl, tetrazolyl, thiazolyl, isothiazolyl, oxazolyl, isoxazolyl, oxadiazolyl, or thiadiazolyl, and more preferably pyridyl, pyridazinyl, pyrimidinyl, pyrazinyl, pyrrolyl, imidazolyl, pyrazolyl, furyl, thienyl, thiazolyl, oxadiazolyl, or tetrazolyl. The bicyclic or tricyclic heteroaryl formed by condensation between a benzene ring and monocyclic heteroaryl is preferably benzofuranyl, benzothienyl, indolyl, benzimidazolyl, indazolyl, benzothiazolyl, benzoisothiazolyl, benzoxazolyl, benzoisoxazolyl, quinolyl, isoquinolyl, quinazolyl, or quinoxalinyl, and more preferably indolyl, benzimidazolyl, or quinolyl.

Further, specific examples of the bicyclic or tricyclic heteroaryl formed by condensation between saturated hetero ring and monocyclic heteroaryl include 6,7,8,9-tetrahydro-5H-[1,2,4]triazolo[4,3-a]azepin-3-yl and the like.

In the "heteroaryl", the ring atom S may be oxidized to form an oxide or dioxide, and N may be oxidized to form an oxide.

The "heteroarene" means a ring constituting the "heteroaryl", and examples thereof include a thiophene ring corresponding to thienyl.

The "saturated hetero ring group" is a 3- to 10-membered saturated hetero ring group containing 1 to 4 hetero atoms of N, O and/or S, and preferably the following groups.

(1) the groups containing 1 to 2 N atoms, specifically azetidinyl, pyrrolidinyl, imidazolidinyl, pyrazolidinyl, piperidyl, piperadinyl, azepanyl, diazepanyl, and the like, and more preferably azetidinyl, pyrrolidinyl, piperidyl, piperadinyl, azepanyl, or diazepanyl;

(2) the groups containing one N atom, and one S atom and/or one O atom, specifically thiazolidinyl, isothiazolidinyl, oxazolidinyl, thiomorpholinyl, morpholinyl, oxazepanyl, and the like, and more preferably oxazolidinyl, morpholinyl, thiomorpholinyl, or oxazepanyl;

(3) the groups containing 1 to 2 S atoms, and specifically tetrahydrothienyl and the like;

(4) the groups containing one S atom and one O atom, and specifically oxathiolanyl and the like; and (5) the groups containing 1 to 2 O atoms, specifically oxetanyl, tetrahydrofuryl, dioxolanyl, tetrahydropyranyl, 1,4-dioxanyl, and the like, and more preferably oxetanyl, tetrahydrofuryl, tetrahydropyranyl, or 1,4-dioxanyl.

The "saturated hetero ring" means a ring constituting the "saturated hetero ring group", for example, a tetrahydrofuran ring corresponding to tetrahydrofuryl.

In the "saturated hetero ring", the saturated hetero ring may have a bridge, and may be condensed with arene, heteroarene, or cycloalkane. Further, the ring atom S may be oxidized to form an oxide or dioxide, and N may be oxidized to form an oxide.

The saturated hetero ring group having a bridge is specifically quinuclidinyl, 8-azabicyclo[3.2.1]octyl, 2-oxa-5-azabicyclo[2.2.1]heptyl, 7-azabicyclo[2.2.1]heptyl, or the like.

The saturated hetero ring group formed by condensation with arene, heteroarene, or cycloalkane is specifically indolinyl, isoindolinyl, tetrahydroquinolyl, tetrahydroisoquinolyl, decahydroisoquinolyl, tetrahydrothienopyridyl, tetrahydrothiazolopyridyl, chromanyl, isochromanyl, 2,3-dihydrobenzofuranyl, 2,3-dihydrofuro[2,3-b]pyridyl, or the like, and more preferably 2,3-dihydrobenzofuranyl or 2,3-dihydropyridofuranyl.

The "nitrogen-containing saturated hetero ring group" means, among the "saturated hetero ring group", a 3- to 8-membered saturated hetero ring group containing at least one N atom as in (1) and (2). It is preferably a 4- to 7-membered nitrogen-containing saturated hetero ring group, and specifically azetidinyl, pyrrolidinyl, piperidyl, piperadinyl, morpholinyl, thiomorpholinyl, azepanyl, diazepanyl, oxazepanyl, and the like.

The "nitrogen-containing saturated hetero ring" means a ring constituting the "nitrogen-containing saturated hetero ring group", for example, a pyrrolidine ring corresponding to pyrrolidinyl.

The nitrogen-containing saturated hetero ring may have a bridge, and may be formed by condensation with arene, heteroarene, or cycloalkane.

The nitrogen-containing saturated hetero ring formed by condensation of arene, heteroarene, or cycloalkane is specifically indolinyl, isoindolinyl, tetrahydroquinolyl, tetrahydroisoquinolyl, decahydroisoquinolyl, tetrahydrothieno[3,2-c]pyridyl, tetrahydro[1,3]thiazolo[5,4-c]pyridyl, and the like.

The "cyclic amino" particularly means a ring group having a binding arm on an N atom among the "nitrogen-containing saturated hetero ring group", the nitrogen-containing heteroaryl, and a partially saturated nitrogen-containing heteroaryl, and specifically 1-azetidinyl, 1-pyrrolidinyl, 1-piperidyl, 1-piperadinyl, 4-morpholinyl, 4-thiomorpholinyl, 1-azepanyl, 1,4-diazepan-1-yl, 1,4-oxazepan-4-yl, 1-imidazolidinyl, 1,3-oxazolidin-3-yl, 1-dihydropyrrolyl, 1-tetrahydropyridyl, 1-azepinyl, 1-pyrrolyl, 1-imidazolyl, and the like. It is preferably a nitrogen-containing saturated hetero ring group having a binding arm on an N atom, and more preferably 1-azetidinyl, 1-pyrrolidinyl, 1-piperidyl, 1-piperadinyl, 4-morpholinyl, 4-thiomorpholinyl, 1-azepanyl, or 1,4-diazepan-1-yl.

In the "cyclic amino", the cyclic amino may have a bridge (the cyclic amino in which two substituents on the cyclic amino are combined to form -Alk-), may be condensed with arene, heteroarene, cycloalkane, or saturated hetero ring, or formed by the Spiro bonding with the cycloalkane or saturated hetero ring.

Specific examples of the cyclic amino having a bridge include 2-oxa-5-azabicyclo[2.2.1]hept-5-yl, 8-azabicyclo[3.2.1]oct-8-yl, 7-azabicyclo[2.2.1]hept-7-yl, and the like.

Specific examples of the cyclic amino formed by condensation with arene, heteroarene, cycloalkane, or saturated hetero ring include 4-benzoxadinyl, 1-indolinyl, 1-tetrahydroquinolyl, 2-tetrahydroisoquinolyl, 1-tetrahydroquinoxalinyl, tetrahydrothieno[3,2-c]pyridin-5-yl, tetrahydro[1,3]thiazolo[5,4-c]pyridin-5-yl, tetrahydropyrrolo[1,2-a]pyradin-2-yl, 1-decahydroquinolyl, 2-decahydroquinolyl, octahydrocyclopenta[b][1,4]oxadin-4-yl, octahydropyrrolo[1,2-a]pyrazin-2-yl, octahydro-2H-pyrido[1,2-a]pyrazin-2-yl, and the like.

Specific examples of the cyclic amino formed by the spiro bonding with a cycloalkane or saturated hetero ring include 2-azaspiro[4.4]nonan-2-yl, 2-azaspiro[4.5]decan-2-yl, 8-azaspiro[4.5]decan-8-yl, 8-oxa-5-azaspiro[3.5]nonan-5-yl, 2-azaspiro[5.5]undecan-2-yl, 1-oxa-8-azaspiro[4.5]decan-8-yl, 2-oxa-8-azaspiro[4.5]decan-8-yl, 1-oxa-3,8-diazaspiro[4.5]decan-8-yl, 1,4-dioxa-8-azaspiro[4.5]decan-8-yl, 2,8-diazaspiro[4.5]decan-8-yl, and the like.

The expression "which may be substituted" represents "which is unsubstituted" or "which is substituted with 1 to 5 substituents and preferably 1 to 3 substituents, which are the same as or different from each other". Further, if it has a plurality of substituents, the substituents may be the same as or different from each other, or the substitutions may be present at the same atom.

Preferred embodiments of the compound (I) of the present invention are presented below.

(1) X is preferably S. In other preferred embodiments, X is O.

(2) $R^1$ is preferably a group represented by the formula (II) or the formula (III).

In this connection, $R^{1a}$ in the formula (II) is preferably (a) -Alk-O-lower alkyl, (b) saturated hetero ring group which may be substituted with group(s) selected from the group consisting of lower alkyl, lower alkenyl, -Alk-O-lower alkyl, and -Alk-aryl, or (c) -Alk-(saturated hetero ring group which may be substituted with lower alkyl or —OH), more preferably -Alk-O-lower alkyl, saturated hetero ring group which may be substituted with lower alkyl, or an -Alk-saturated hetero ring group.

The saturated hetero ring group in the saturated hetero ring group and the -Alk-saturated hetero ring group of $R^{1a}$ is preferably azetidinyl, pyrrolidinyl, piperidyl, oxetanyl, tetrahydrofuryl or tetrahydropyranyl, each of which has a binding arm on a carbon atom of the ring.

$R^{1b}$ in the formula (II) is preferably lower alkyl, and more preferably methyl.

The ring group Q represented by the formula (III) is preferably cyclic amino which may be substituted with group(s) selected from the Group $G_{1A}$, more preferably cyclic amino which may be substituted with group(s) selected from the Group $G_{1B}$, still more preferably 1-azetidinyl, 1-pyrrolidinyl, 1-piperidyl or 4-morpholinyl, each of which may each be substituted with group(s) selected from the Group $G_{1B}$, and yet still more preferably 1-pyrrolidinyl, 1-piperidyl or 4-morpholinyl, each of which may each be substituted with group(s) selected from the Group $G_{1B}$.

(3) $R^2$ is preferably a group represented by the formula (IV) or the formula (V), and more preferably a group represented by the formula (IV).

In this connection, the compound wherein $R^{2a}$ in the formula (IV) is —O—$R^E$, —$CH_2$—$R^F$ or —$NR^G R^H$, in which $R^E$ is lower alkyl, $R^F$ is —H, heteroaryl or saturated hetero ring group, $R^G$ is —H, and $R^H$ is (1) —H, (2) cycloalkyl, (3) saturated hetero ring group which may be substituted with lower alkyl, (4) heteroaryl which may be substituted with lower alkyl, or (5) lower alkyl which may be substituted with group(s) selected from the group consisting of F, —OH, cycloalkyl, —O-lower alkyl, saturated hetero ring group and heteroaryl is preferable, the compound wherein $R^{2a}$ is —O-lower alkyl, methyl, —$CH_2$-heteroaryl, —$CH_2$-saturated hetero ring group, or —NH—Rx, in which Rx is (1) —H, (2) cycloalkyl, (3) saturated hetero ring group, (4) heteroaryl, or (5) lower alkyl which may be substituted with group(s) selected from the group consisting of F, cycloalkyl, —O-lower alkyl, and saturated hetero ring group is more preferable, and the compound wherein $R^{2a}$ is —NH—$R^X$ is still more preferable.

(4) A is preferably

[Chem. 10]

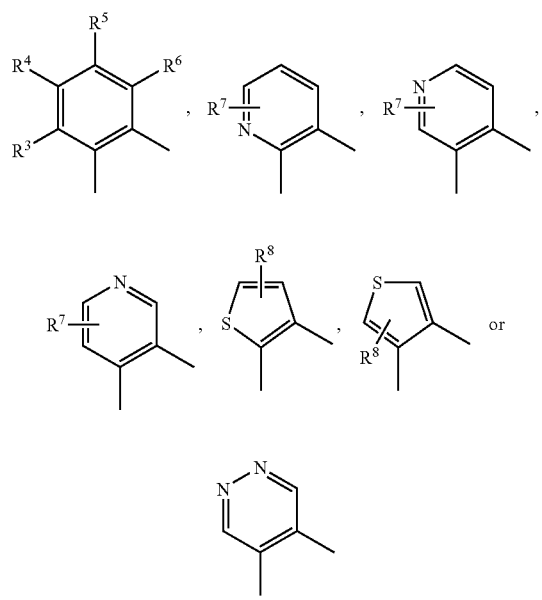

and more preferably

[Chem. 11]

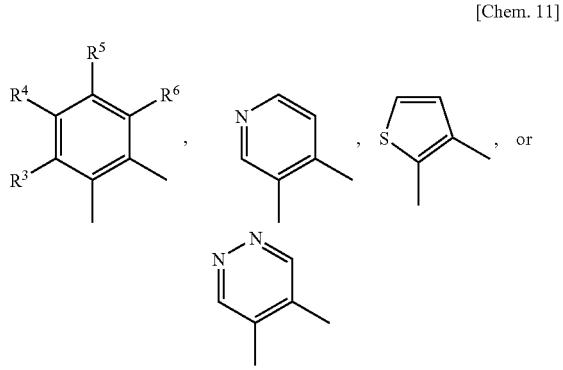

In this connection, $R^3$ is preferably —H, halogen, lower alkyl, or —O-lower alkyl, and more preferably —H.

$R^4$ is preferably (a) —H, (b) halogen, (c) —O-lower alkyl, (d) cycloalkyl which may be substituted with —CN, (e) saturated hetero ring group which may be substituted with group(s) selected from the group consisting of lower alkyl and -Alk-O-lower alkyl, (f) —O-saturated hetero ring group, or (g) lower alkyl which may be substituted with group(s) selected from the Group $G_{3A}$, more preferably (a) —H, (b) cycloalkyl substituted with one —CN, (c) saturated hetero ring group which may be substituted with group(s) selected from the group consisting of lower alkyl and -Alk-O-lower alkyl, (d) —O-lower alkyl, (e) —O-saturated hetero ring group, or (f) lower alkyl substituted with one group selected from the Group $G_{3B}$, and still more preferably —H, cycloalkyl substituted with one —CN, —O-lower alkyl, or lower alkyl substituted with one group selected from the Group $G_{3B}$.

$R^5$ is preferably —H, halogen, lower alkyl, or —O-lower alkyl, more preferably —H, lower alkyl, or —O-lower alkyl, and still more preferably —H.

$R^6$ is preferably —H or —O-lower alkyl, and more preferably —H.

$R^7$ is preferably —H or lower alkyl, and more preferably —H.

$R^8$ is preferably —H or lower alkyl, and more preferably —H.

In particularly preferred embodiments, the compound (I) of the present invention is a compound formed by the combination of preferred groups as described in (1) to (4) above, and specific examples thereof include the compounds as described in [1] to [11] above.

Another preferred embodiment of the compound (I) of the present invention is a compound represented by the formula (I-A).

Further, a particularly preferred embodiment of the compound represented by the formula (I-A) is the compound in which $R^{2C}$ is —NH—$R^X$.

The compound of the formula (I) may have tautomers or geometrical isomers in some cases, depending on the kind of substituents. In the present specification, the compound of the formula (I) shall be described in only one form of isomer, yet the present invention includes other isomers, isolated forms of the isomers, or a mixture thereof. Examples of the tautomers include tautomers between 3-hydroxypyridazine and 2,3-dihydropyridazin-3-one.

In addition, the compound of the formula (I) may have asymmetric carbon atom(s) or axial asymmetry in some cases, and correspondingly, it may exist in the form of optical isomers. The present invention includes both an isolated form of these optical isomers of the compound of the formula (I) or a mixture thereof.

In addition, the pharmaceutically acceptable prodrugs of the compound represented by the formula (I) are also included in the present invention. The pharmaceutically acceptable prodrug refers to a compound having a group which can be converted into amino group, hydroxyl group, carboxyl group, or the like, by solvolysis or under a physiological condition. Examples of the group for forming a prodrug include those as described in Prog. Med., 5, 2157-2161 (1985) or "Iyakuhin no Kaihatsu (Pharmaceutical Research and Development)" (Hirokawa Publishing Company, 1990), vol. 7, Bunshi Sekkei (Drug Design), 163-198.

Furthermore, the compound of the formula (I) may form an acid addition salt or a salt with a base, depending on the kind of substituents, and these salts are included in the present invention as long as they are pharmaceutically acceptable salts. Specifically, examples thereof include acid addition salts with inorganic acids such as hydrochloric acid, hydrobromic acid, hydroiodic acid, sulfuric acid, nitric acid, phosphoric acid, and the like, and salts with organic acids such as formic acid, acetic acid, propionic acid, oxalic acid, malonic acid, succinic acid, fumaric acid, maleic acid, lactic acid, malic acid, mandelic acid, tartaric acid, dibenzoyl tartaric acid, ditolyl tartaric acid, citric acid, methanesulfonic acid, ethanesulfonic acid, benzenesulfonic acid, p-toluenesulfonic acid, aspartic acid, glutamic acid, and the like, and salts with inorganic bases such as sodium, potassium, magnesium, calcium, aluminum, and the like or salts with organic bases such as methylamine, ethylamine, ethanolamine, lysine, ornithine, and the like, salts with various amino acids or amino acid derivatives such as acetylleucine and the like, ammonium salts, and others.

In addition, the present invention also includes various hydrates or solvates, and any of crystalline polymorphs of the compound of the formula (I) and a pharmaceutically acceptable salt thereof. Also, the present invention includes compounds labeled with various radioactive or non-radioactive isotopes.

(Production Processes)

The compound of the formula (I) and a pharmaceutically acceptable salt thereof can be prepared by applying various known synthetic methods, using the characteristics based on their basic skeletons or the kind of substituents. At this time, depending on the type of the functional groups, it is in some cases effective, from the viewpoint of the preparation techniques, to substitute the functional group with an appropriate protective group (a group which is capable of being easily converted into the functional group), during the stage of starting material or intermediate. Examples of the protective group include the protective groups described in "Protective Groups in Organic Synthesis ($3^{rd}$ edition, 1999)", written by Greene and Wuts, and the like, which may be appropriately selected and used depending on reaction conditions. In these methods, a desired compound can be obtained by introducing the protective group to carry out the reaction, and then, if desired, removing the protective group.

In addition, the prodrug of the compound of formula (I) can be prepared by introducing a specific group during the stage of starting material or intermediate, in the same manner as for the aforementioned protective groups, or by carrying out the reaction using the obtained compound of formula (I). The reaction can be carried out by applying a method known to a person skilled in the art, such as common esterification, amidation, dehydration, and the like.

Hereinbelow, the representative production processes for the compound of formula (I) will be described. Each of the production processes may also be carried out with reference to the References appended in the explanation. Further, the production processes of the present invention are not limited to the examples as shown below.

(First Production Process)

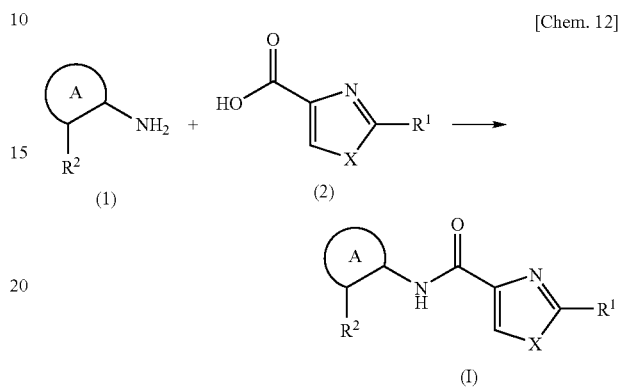

[Chem. 12]

This step is a step for preparing the compound (I) of the present invention by subjecting a compound (2) or a reactive derivative thereof, and a compound (I) or a salt thereof to amidation by a conventional method, and then if desired, removing the protective group.

Examples of the reactive derivative of the compound (2) include a common ester such as methyl ester, ethyl ester, tert-butyl ester, and the like; an acid halide such as acid chloride, acid bromide, and the like; an acid azide; an active ester with 1-hydroxybenzotriazole, p-nitrophenol, N-hydroxysuccinimide, or the like; a symmetric acid anhydride; a mixed acid anhydride with a halocarboxylic acid alkyl ester such as an alkyl halocarbonate, a pivaloyl halide, a p-toluenesulfonic acid chloride, and the like; a mixed acid anhydride such as a phosphoric mixed acid anhydride obtained by the reaction of diphenylphosphoryl chloride, N-methylmorpholine, and the like; etc.

If the compound (2) is reacted as a free acid, or is reacted without isolation of an active ester, or the like, amidation usually used by a person skilled in the art can be used, but a method in which a condensing agent such as 1-ethyl-3-(3-dimethylaminopropyl)carbodiimide hydrochloride (WSC-HCl), or dicyclohexylcarbodiimide (DCC), carbonyldiimidazole (CDI), diphenylphosphoryl azide (DPPA), diethylphosphorylcyanide (DEPC), O-(7-azabenzotriazol-1-yl)-N,N,N',N'-tetramethyluronium hexafluorophosphate (HATU), N,N,N',N'-tetramethylfluoroformamidinium hexafluorophosphate (TFFH), and the like are allowed to undergo the reaction in the presence of 1-hydroxybenzotriazole (HOBt), a method in which phosphorus oxychloride is allowed to undergo the reaction in a pyridine solvent, or a condensing agent-supported polystyrene resin, for example, PS-carbodiimide (Argonaut Technologies, Inc., USA) or PL-DCC resin (Polymer Laboratories, UK) is preferably used.

Also, in some cases, it is preferable to use an isocyanate-supported polystyrene resin, for example, PS-Isocyanate (Argonaut Technologies, Inc., USA) and the like in order to remove an excess amount of amine after completion of the reaction. Further, it is preferable in some cases to use a quaternary ammonium salt-supported polystyrene resin such as MP-Carbonate (Argonaut Technologies, Inc., USA) and the like in order to remove an excess amount of carboxylic acid, and the aforementioned additive such as HOBt and the like after completion of the reaction. In addition, it is preferable in some cases to use a primary ammine-supported polystyrene resin such as PS-Trisamine (Argonaut Technologies, Inc., USA) and the like in order to remove an excess amount of electrophilic reagents (acid chlorides and the like) after completion of the reaction.

Particularly, in the present invention, an acid chloride method, and a method for performing a reaction in the coexistence of an active esterifying agent and a condensing agent are convenient.

The reaction varies according to the reactive derivatives, condensing agents, or the like used, but usually, is carried out under cooling, from under cooling to at room temperature, or from at room temperature to under heating, in a organic solvent inert to the reaction, for example, halogenated hydrocarbons such as methylenechloride, dichloroethane, chloroform, and the like; aromatic hydrocarbons such as benzene, toluene, xylene, and the like; ethers such as ether, tetrahydrofuran (THF), and the like; esters such as ethyl acetate (EtOAc) and the like; acetonitrile, N,N-dimethylformamide (DMF), N,N-dimethylacetamide (DMA), dimethyl sulfoxide (DMSO), and the like.

Furthermore, in the reaction, it is in some cases advantageous in advancing the reaction smoothly to carry out the reaction with an excess amount of the compound (I) or in the presence of a base such as N-methylmorpholine, trimethylamine, triethylamine, diisopropylethylamine, N,N-dimethylaniline, pyridine, 4-(N,N-dimethylamino)pyridine, picoline, lutidine, and the like. Also, a salt formed from a weak base and a strong acid, such as pyridine hydrochloride, pyridine p-toluenesulfonate, N,N-dimethylaniline hydrochloride, and the like, may be used. Pyridine may be used as a solvent.

Particularly, it is preferable to carry out the reaction in the presence of a base such as triethylamine and the like in a solvent such as THF, DMF, and the like.

(Second Production Process)

[Chem. 13]

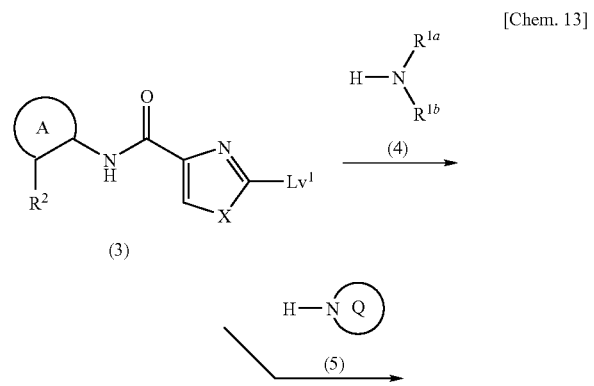

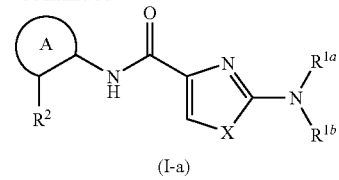

(I-a)

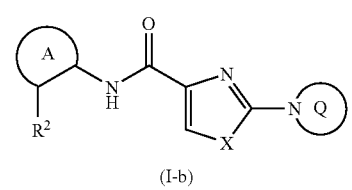

(I-b)

(wherein $Lv^1$ represents a leaving group, and preferably halogen, —SMe, —SOMe, —SO$_2$Me, —SO$_3$H, or —O—SO$_2$CF$_3$. The same applies hereinafter.)

This step is a step for preparing a compound (I-a) in which $R^1$ is a group represented by the formula (II) or a compound (I-b) in which $R^1$ is a group represented by the formula (III) in the compound (I) of the present invention, by reacting a compound (3) having a leaving group at the 2-position on the azole and a compound (4) or (5). Furthermore, the compound (3) can be prepared in accordance with the first production process, and in the case where $Lv^1$ is halogen, it is included in the compound (I) of the present invention.

The nucleophilic substitution reaction of this step can be carried out in a organic solvent inert to the reaction, such as halogenated hydrocarbons, aromatic hydrocarbons, ethers, esters, alcohols such as methanol, ethanol, isopropanol, and the like, acetonitrile, DMF, DMA, DMSO, and others in the presence of an organic base such as triethylamine, diisopropylethylamine, and the like and/or an inorganic base such as potassium carbonate, sodium carbonate, cesium carbonate, sodium hydrogen carbonate, sodium hydride, and the like. Further, in order to accelerate the reaction, a catalyst such as 4-(N,N-dimethylamino)pyridine and the like may be added. Also, instead of the organic base and/or the inorganic base, the compound (4) or (5) may be used in an excess amount. The reaction is carried out in a manner varying according to the base to be used, but it can be carried out from under cooling to at room temperature, from at room temperature to under heating, or from at room temperature to under reflux.

Also, depending on the case, it is preferable in some cases to use an isocyanate-supported polystyrene resin, for example, PS-Isocyanate (Argonaut Technologies, Inc., USA) or the like in order to remove an excess amount of amine after completion of the reaction.

(Third Production Process)

[Chem. 14]

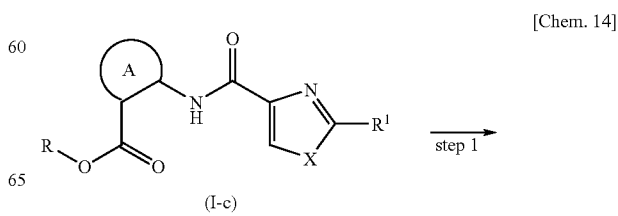

(I-c)

-continued

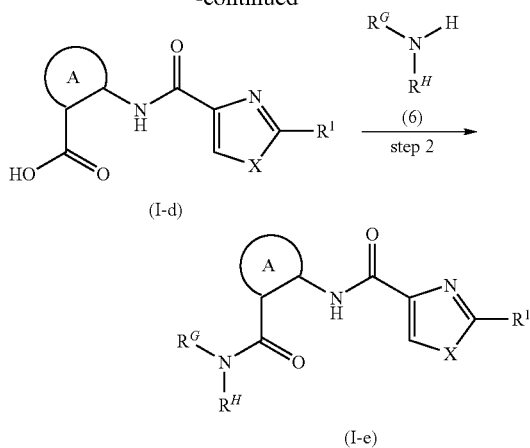

(wherein R represents lower alkyl. The same applies hereinafter.)

Step 1

This step is a step for preparing a compound (I-d) in which $R^2$ is a carboxylic group by hydrolyzing a compound (I-c) in which $R^2$ is an ester with respect to the compound (I) of the present invention. The hydrolysis reaction of this step can be carried out in accordance with, for example, the deprotection reaction as described in the "Protective Groups in Organic Synthesis (third edition)" above. Further, the compound (I-c) can be prepared in accordance with the first production process.

Step 2

This step is a step for preparing a compound (I-e) by subjecting a compound (I-d) and a compound (6) to an amidation reaction. The amidation reaction of this step can be carried out in accordance with the first production process.

(Fourth Production Process)

[Chem. 15]

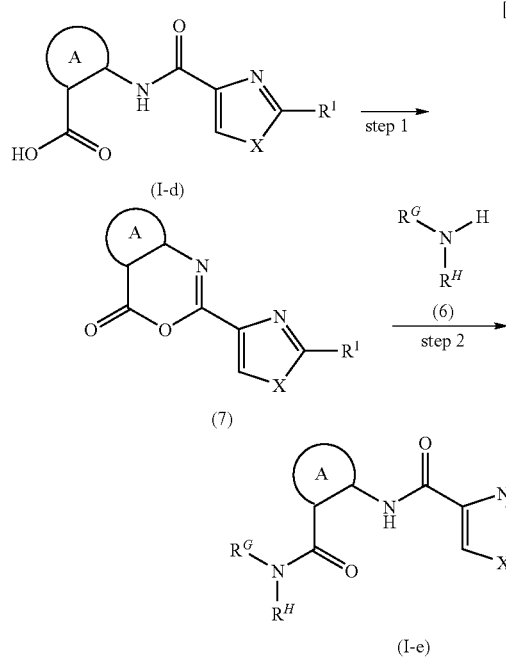

Step 1

This step is a step for preparing a compound (7) by subjecting the compound (I-d) synthesized according to the third production process or a reactive derivative thereof to an intramolecular cyclization reaction. The cyclization reaction of this step can be carried out by subjecting a condensing agent to react with a carboxylic acid, or by using the reactive derivative of carboxylic acid in accordance with the first production process. In order to accelerate the reaction, a catalyst such as 4-(N,N-dimethylamino)pyridine and the like may be added. The reaction can be carried out in an organic solvent inert to the reaction such as halogenated hydrocarbons, aromatic hydrocarbons, ethers, esters, acetonitrile, DMF, DMA, DMSO, and the like, from under cooling to room temperature, from at room temperature to under heating, or from at room temperature to under reflux.

Step 2

This step is a step for preparing a compound (I-e) by allowing a compound (7) to undergo a reaction with a compound (6). The ring-opening reaction can be carried out in an organic solvent inert to the reaction, such as halogenated hydrocarbons, aromatic hydrocarbons, ethers, esters, alcohols, acetonitrile, acetic acid, DMF, DMA, DMSO, and the like. Furthermore, in order to accelerate the reaction, a catalyst such as p-toluenesulfonic acid and the like may be added. The reaction can be carried out from under cooling to room temperature, from at room temperature to under heating, or from at room temperature to under reflux.

(Fifth Production Process)

[Chem. 16]

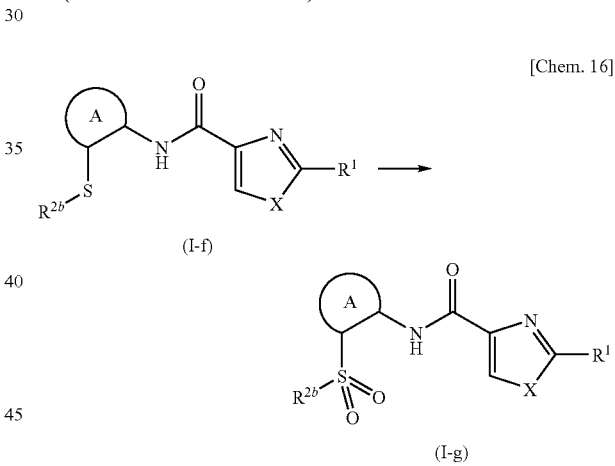

This step is a step for preparing a compound (I-g) by oxidizing a compound (I-f). The oxidation reaction of this step can employ a sulfide oxidation reaction, which is usually employed by a person skilled in the art. For example, an oxidation reaction using peracids such as hydrogen peroxide, m-chloroperbenzoic acid, and the like may be mentioned. The reaction can be carried out, for example, with reference to a method as described in "Jikken Kagaku Koza (Courses in Experimental Chemistry) ($4^{th}$ edition)", edited by The Chemical Society of Japan, vol. 23 (1992) (Maruzen).

(Sixth Production Process)

Moreover, the compounds of the present invention represented by formula (I) having various functional groups can be prepared from the compound of the present invention obtained by the first production process, the second production process, the third production process, the fourth production process, or the fifth production process, by any combination of the steps that can usually be employed by a person skilled in the art, such as alkylation, acylation, a substitution reaction, oxidation, reduction, hydrolysis, and the like. This step is not limited to a one-step reaction, but it may consist of a multi-step reaction. Further, the processes that can usually be employed by a person skilled in the art are not limited to the application for the compound of the present invention, but they may be used in the application for the preparation of synthetic intermediates.

Representative reactions are exemplified as below.

(1) Amidation

A compound having an amide group among the compounds (I) of the present invention can be prepared by reacting a compound having an amino group as a starting material with carboxylic acid and a reactive derivative thereof, or by reacting a compound having carboxylic acid as a starting material with an amine. The reaction can be carried out in accordance with Step 1 of First Production Process, for example, with reference to a method as described in "Jikken Kagaku Koza (Courses in Experimental Chemistry) ($4^{th}$ edition)", vol. 22 (1992) (Maruzen), or "Compendium of Organic Synthetic Methods", vols. 1 to 3, or the like.

(2) Sulfonylation

A compound having a sulfonamide group, sulfonic ester among the compounds (I) of the present invention can be prepared by reacting a corresponding compound having an amino group, hydroxyl group as a starting material with sulfonic acid and a reactive derivative thereof. The reaction can be carried out, for example, with reference to a method as described in "Jikken Kagaku Koza (Courses in Experimental Chemistry) ($4^{th}$ edition)", edited by The Chemical Society of Japan, vol. 24 (1992) (Maruzen).

(3) Carbamation

A compound having a carbamate group among the compounds (I) of the present invention can be prepared by reacting a compound having an amino group as a starting material with a carbonate derivative. The reaction can be carried out, for example, with reference to a method as described in "Jikken Kagaku Koza (Courses in Experimental Chemistry) ($4^{th}$ edition)", edited by The Chemical Society of Japan, vol. (1992) (Maruzen).

(4) O-Acylation

A compound having an ester group among the compounds (I) of the present invention can be prepared by reacting a compound having an hydroxyl group as a starting material with a carboxylic derivative. The reaction can be carried out, for example, with reference to a method as described in "Jikken Kagaku Koza (Courses in Experimental Chemistry) ($4^{th}$ edition)", edited by The Chemical Society of Japan, vol. 22 (1992) (Maruzen).

(5) O-Alkylation

A compound having an ether skelton among the compounds (I) of the present invention can be prepared by reacting a compound having a hydroxyl group as a starting material with another alkylating agent. As the alkylating agents, an alkyl halide, an organic sulfonic ester of an alcohol, and the like are preferred. The reaction can be carried out, for example, with reference to a method as described in "Jikken Kagaku Koza (Courses in Experimental Chemistry) ($4^{th}$ edition)", edited by The Chemical Society of Japan, vol. 20 (1992) (Maruzen).

(6) Amination

A compound having a secondary amine or a tertiary amine among the compounds (I) of the present invention can be prepared by reacting a compound having an alkyl halide, an organic sulfonic ester of an alcohol, and the like as a starting material with another compound having a primary amine or a secondary amine. The reaction can be carried out, for example, with reference to a method as described in "Jikken Kagaku Koza (Courses in Experimental Chemistry) ($4^{th}$ edition)", edited by The Chemical Society of Japan, vol. 20 (1992) (Maruzen).

(7) N-alkylation

A compound having a secondary amine or a tertiary amine among the compounds (I) of the present invention can be prepared by reacting a compound having a primary amino group or a secondary amino group as a starting material with another alkylating agent. As the alkylating agent, alkyl halide, an organic sulfonic ester of alcohol, and the like are preferred. The reaction can be carried out, for example, with reference to a method as described in "Jikken Kagaku Koza (Courses in Experimental Chemistry) ($4^{th}$ edition)", edited by The Chemical Society of Japan, vol. (1992) (Maruzen).

(8) Reductive Alkylation

A compound having a secondary amine or a tertiary amine among the compounds (I) of the present invention can have an alkyl group introduced thereinto by reacting a compound having a primary amine or a secondary amine as a starting material with an aldehyde and a ketone for performing reductive alkylation, in the presence of a reducing agent such as sodium borohydride, sodium triacetoxyborohydride, and the like, or under a catalytic reduction condition by palladium-carbon, under a hydrogen atmosphere. For example, a method as described in "Jikken Kagaku Koza (Courses in Experimental Chemistry) ($4^{th}$ edition)", edited by The Chemical Society of Japan, vol. 20 (1992) (Maruzen), or the like, can be exemplified.

(9) Oxidation

A compound having a sulfonyl group among the compounds (I) of the present invention can be prepared by subjecting a compound having a sulfide group to an oxidation reaction. The reaction can be carried out, for example, with reference to a method as described in "Jikken Kagaku Koza (Courses in Experimental Chemistry) ($4^{th}$ edition)", edited by The Chemical Society of Japan, vol. 23 (1992) (Maruzen).

(10) Reduction

A compound having a primary alcohol among the compounds (I) of the present invention can be prepared by subjecting a corresponding compound having a carboxyl group or ester group to a reduction reaction. The reaction can be carried out, for example, with reference to a method as described in "Jikken Kagaku Koza (Courses in Experimental Chemistry) ($4^{th}$ edition)", edited by The Chemical Society of Japan, vol. 26 (1992) (Maruzen).

(11) Ipso Substitution

A compound having an alkoxypyridine or alkoxypyrimidine skelton among the compounds (I) of the present invention can be prepared by subjecting a corresponding compound having an alcohol as a starting material to an ipso substitution for chloropyridine, chloropyrimidine, or the like. This reaction can be carried out in an organic solvent inert to the reaction, such as halogenated hydrocarbons, aromatic hydrocarbons, ethers, esters, acetonitrile, DMF, DMA, DMSO, and the like, in the presence of an inorganic base such as cesium carbonate, sodium hydride, and the like, from under cooling to room temperature, from at room temperature to under heating, or from at room temperature to under reflux.

(12) Hydrolysis

A compound having a carboxylic group or an amide group among the compounds (I) of the present invention can be prepared by hydrolyzing a corresponding compound having an ester group, an amide group, or a cyano group. The reaction can be carried out, for example, with reference to a method as described in "Protective Groups in Organic Synthesis (third edition)" or "Jikken Kagaku Koza (Courses in Experimental Chemistry) (4th edition)", edited by The Chemical Society of Japan, vol. 22 (1992) (Maruzen).

(13) Dehydration

A compound having a cyano group among the compounds (I) of the present invention can be prepared by subjecting a corresponding compound having a carboxamide group to a dehydration reaction. The reaction can be carried out, for example, with reference to a method as described in "Jikken Kagaku Koza (Courses in Experimental Chemistry) (4th edition)", edited by The Chemical Society of Japan, vol. 20 (1992) (Maruzen).

The starting compounds used in the preparation of the compounds (I) of the present invention can be prepared, for example, by using the following methods, methods described in Preparative Examples as described below, well-known methods, or methods apparent to a person skilled in the art, or variations thereof (Starting Material Synthesis 1)

[Chem. 17]

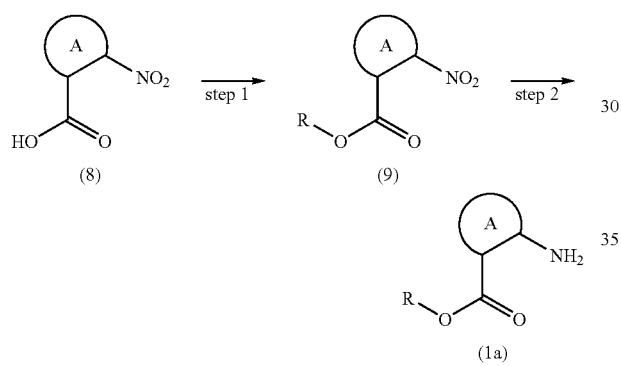

Step 1

This step is a step for preparing a compound (9) by esterification of a carboxylic acid group of a compound (8). The reaction can use a conventional esterification condition, and can use a method described, for example, in the protection reaction of a carboxylic group in "Protective Groups in Organic Synthesis (third edition)" above, or the like.

Step 2

This step is a step for preparing a compound (1a) by subjecting the nitro compound (9) to reduction. The reduction reaction of a nitro group of this step can be carried out by using a reduction reaction of a nitro group, which can be usually employed by a person skilled in the art. For example, it can be exemplified by a reduction reaction using a reducing agent such as reduced iron, tin chloride, and the like and a hydrogenation reaction using palladium-carbon, rhodium-carbon, or the like as a catalyst. The reaction can be carried out, for example, with reference to a method as described in "Jikken Kagaku Koza (Courses in Experimental Chemistry) (4th edition)", edited by The Chemical Society of Japan, vol. 26 (1992) (Maruzen).

(Starting Material Synthesis 2)

[Chem. 18]

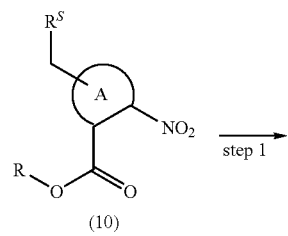

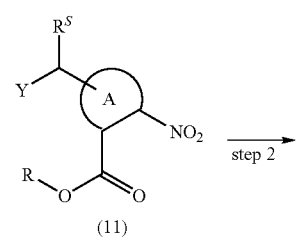

(wherein $R^S$ represents —H or lower alkyl, and Y represents halogen. Further, $R^T$ represents —$NR^{4b}R^{4c}$ or cyclic amino above.)

Step 1

This step is a step for preparing a compound (11) by halogenating a compound (10). The halogenation reaction of this step can be carried out by using a reaction which can usually be employed by a person skilled in the art, for example, a halogenation reaction using N-bromosuccinimide, N-chlorosuccinimide, or the like. The reaction can be carried out, for example, with reference to a method as described in "Jikken Kagaku Koza (Courses in Experimental Chemistry) (4th edition)", edited by The Chemical Society of Japan, vol. 19 (1992) (Maruzen).

Step 2

This step is a step for preparing a compound (12) by allowing a compound (11) to undergo a reaction with an amine. The amination reaction of this step can be carried out, for example, with reference to a method as described in "Jikken Kagaku Koza (Courses in Experimental Chemistry) (4th edition)", edited by The Chemical Society of Japan, vol. 20 (1992) (Maruzen).

Step 3

This step is a step for preparing a compound (1b) by reducing a nitro compound (12). The reduction reaction of a nitro group of this step can be carried out by the same method as in the step 2 in the starting material synthesis 1.

(Starting Material Synthesis 3)

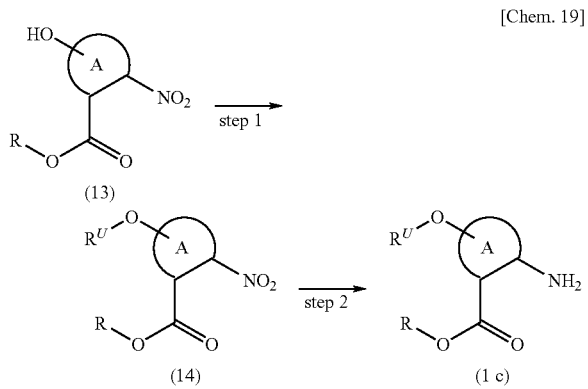

(wherein $R^U$ represents -Alk-$R^{4a}$ or saturated hetero ring group above)

Step 1

This step is a step for preparing a compound (14) by alkylating a compound (13). The alkylation reaction of this step can use a reaction which can usually be employed by a person skilled in the art. For example, an alkylation reaction using an alkyl halide under basic condition and Mitsunobu reaction are exemplified. The reaction can be carried out, for example, with reference to a method as described in "Jikken Kagaku Koza (Courses in Experimental Chemistry) (4th edition)", edited by The Chemical Society of Japan, vol. 20 (1992) (Maruzen).

Step 2

This step is a step for preparing a compound (1c) by reducing a nitro compound (14). The reduction reaction of a nitro group of this step can be carried out by the same method as in the step 2 in the starting material synthesis 1.

(Starting Material Synthesis 4)

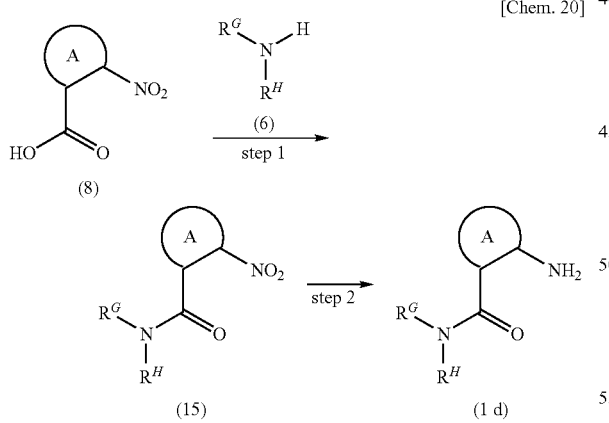

Step 1

This step is a step for carrying out an amidation reaction from the compound (8) and the compound (6). The reaction can be carried out in accordance with step 1 in the first production process.

Step 2

This step is a step for preparing a compound (1d) by reducing a nitro compound (15). The reduction reaction of a nitro group of this step can be carried out by the same method as in step 2 in the starting material synthesis 1.

(Starting Material Synthesis 5)

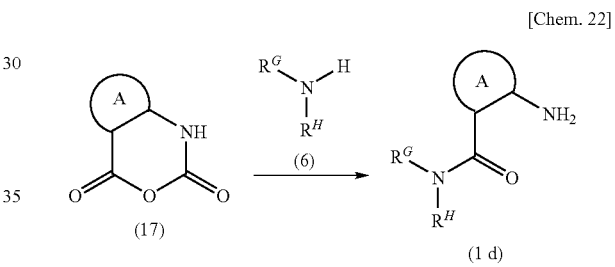

(wherein $Lv^2$ represents a leaving group, and preferably halogen or —O—$SO_2CF_3$. $R^v$ represents —O—$R^E$ or —$CH_2$—$R^F$ above.)

This synthesis method is a reaction in which a reaction with carbon monoxide or a coupling reaction is carried out in the presence of transition metal catalyst such as palladium and the like and suitable additives, and an ester or a ketone is introduced, to the compound (16). Examples of the representative methods include a method as described in "Jikken Kagaku Koza (Courses in Experimental Chemistry) (4th edition)", edited by The Chemical Society of Japan, vol. 25 (1992) (Maruzen).

(Starting Material Synthesis 6)

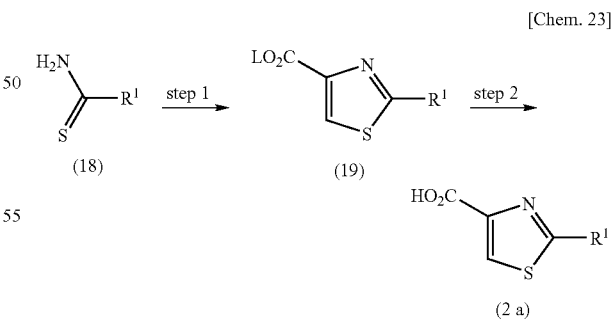

This synthesis method is a reaction for preparing a compound (1d) by allowing a compound (17) to undergo a reaction with the compound (6). This ring-opening reaction can be carried out in accordance with step 2 of the fourth production process.

(Starting Material Synthesis 7)

[Chem. 23]

$H_2N$—C(=S)—$R^1$ (18) → $LO_2C$-thiazole-$R^1$ (19) → $HO_2C$-thiazole-$R^1$ (2a)

(wherein L represents a protective group for a carboxylic acid. The same applies hereinafter.)

Step 1

This step is a method for constructing a thiazole ring by allowing a thioamide or thiourea (18) to undergo the reaction with an α-haloketone, representatively such as bromopyruvic ester and the like. A method described in "Comprehensive Organic Chemistry", vol. 4, or an equivalent method thereof can be employed. In addition, it is preferable in some cases to add an acid such as anhydrous trifluoroacetic acid and the like in order to promote a cyclization reaction.

Step 2

This step is a step for preparing carboxylic acid (2a) by hydrolyzing carboxylic ester (19). For the reaction, hydrolysis condition of a conventional method can be used, and for example, a method as described in the deprotection reaction of a carboxyl group in "Protective Groups in Organic Synthesis (third edition)" as described above, or the like can be applied.

(Starting Material Synthesis 8)

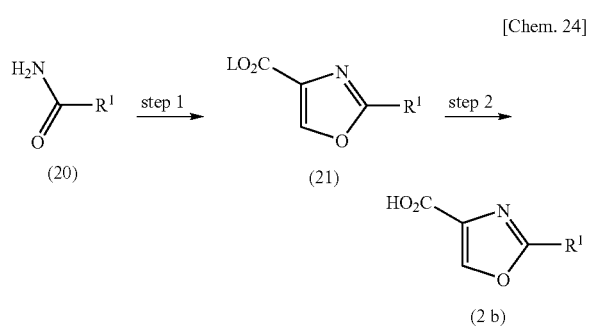

Step 1

This step is a method for constructing an oxazole ring by allowing an amide or urea (20) to undergo the reaction with an α-haloketone, representatively such as bromopyruvic ester and the like. A method as described in "Heterocyclic Compounds" edited by Turchi, vol. 45, or "Heterocyclic Compounds" edited by Palmer, vol. 60, Part A, or an equivalent method thereof can be employed.

Step 2

This step is a step for preparing a compound (2b) by hydrolyzing a carboxylic ester (21). The hydrolysis reaction of this reaction can be carried out by the same method as in step 2 in the starting material synthesis 7.

(Starting Material Synthesis 9)

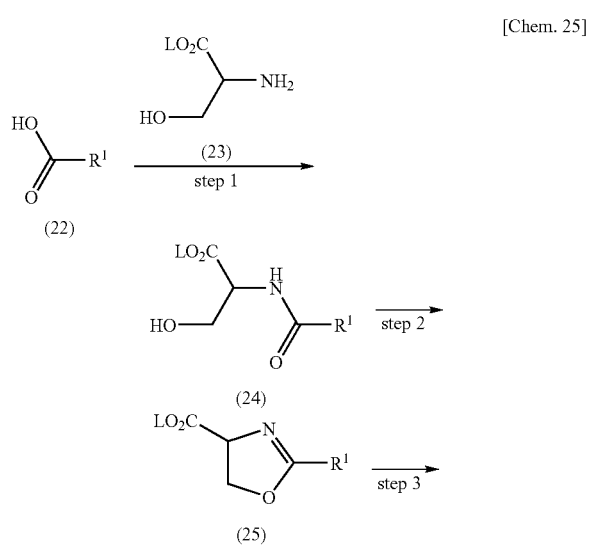

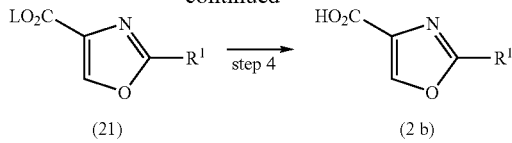

Step 1

This step is a step for carrying out an amidation reaction from a compound (22) and a compound (23). The reaction can be carried out in accordance with step 1 in the first production process.

Step 2

This step is a method for constructing an oxazoline ring by carrying out a dehydration-cyclization reaction from a compound (24). The cyclization reaction of this step can be carried out, for example, with reference to a method as described in Phillips, A. J.; Wipf, P.; Williams, D. R.; et al., Org Lett, 2000, 2(8), 1165-1168, or "Heterocyclic Compounds" as described above, vol. 60, Part A, Part B, or the like.

Step 3

This step is a method for constructing an oxazole ring by carrying out an oxidation reaction from a compound (25). The oxidation reaction of this step can be carried out, for example, with reference to a method as described in Phillips, A. J.; Wipf, P.; Williams, D. R.; et al., Org Lett, 2000, 2(8), 1165-1168, or "Heterocyclic Compounds", vol. 60, Part A, etc. as described above, or the like.

Step 4

This step is a step for preparing a compound (2b) by hydrolyzing the carboxylic ester (21). The hydrolysis reaction of this step can be carried out by the same method as in step 2 in the starting material synthesis 7.

(Starting Material Synthesis 10)

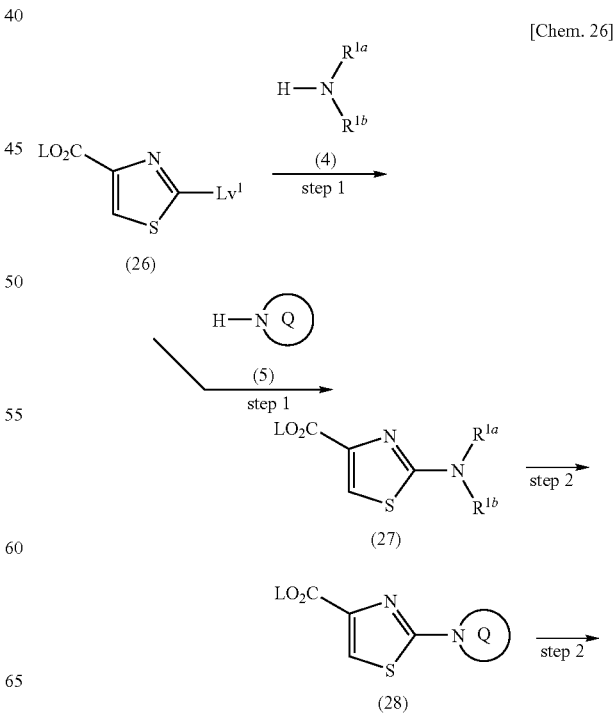

-continued

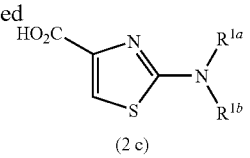

(2 c)

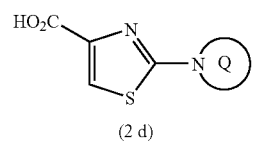

(2 d)

Step 1

This step is a step for preparing compounds (27) and (28) by carrying out a substitution reaction at the 2-position on the thiazole ring of a compound (26). The substitution reaction of this step can be carried out by the same method as the second production process.

Step 2

This step is a step for preparing compounds (2c) and (2d) by hydrolyzing the carboxylic esters (27) and (28). The hydrolysis reaction of this step can be carried out by the same method as in step 2 in the starting material synthesis 7.

Further, in Starting Material Syntheses 1 to 10, the substituents which bonds to the compound (I) of the present invention can be converted in a suitable period of time in the above-described steps for proceeding in the next step. Examples of the method for conversion include a method in which in Starting Material Synthesis 2, an ester group is hydrolyzed at a suitable period of time, before Step 1, before Step 2, or before Step 3, and an amidation reaction is then carried out, for conversion into a partial structure $R^2$ of the compound according to the present invention, and the like.

The compounds of formula (I) can be isolated and purified as their free compounds, pharmaceutically acceptable salts, hydrates, solvates, or crystalline polymorphous substances thereof. The pharmaceutically acceptable salts of the compound of formula (I) can be prepared by subjecting the compound to a conventional salt formation reaction.

Isolation and purification can be carried out by employing general chemical operations such as extraction, fractional crystallization, various types of fractional chromatography, and the like.

Various isomers can be prepared by selecting an appropriate starting compound or separated by making use of the difference in the physicochemical properties among the isomers. For example, the optical isomers can be obtained by means of general optical resolution methods of racemic products (for example, by fractional crystallization converting the compound into diastereomer salts with optically active bases or acids, by chromatography using a chiral column or the like, and others), or can also be prepared from an appropriate optically active starting compound.

The pharmacological activity of the compound (I) of the present invention was confirmed by the following tests.

Test Example 1

Experiment to Measure trkA Receptor Inhibitory Activity Using a Cell Expressing a Nerve Growth Factor Receptor (trkA Receptor)

The trkA receptor inhibitory activity was measured by using the increase in a ligand-dependent calcium concentration in cells as an index. HEK293 cells (American Type Culture Collection) that stably expressed a human trkA receptor were dispensed onto a 96-well poly-D-lysine-coated plate (Product Name: Biocoat, PDL96W black/clear, by Nippon Becton Dickinson) to a $2 \times 10^4$ cells/well on the day before the experiment, and incubated overnight at 37° C. under 5% carbon dioxide ($CO_2$) in a culture medium containing 10% fetal bovine serum (FBS) (Product Name: DMEM, Invitrogen Corporation). The culture medium was replaced by a loading buffer (a washing solution containing a 1.5 μM fluorescent-labelled indicator (Product Name: Fluo4-AM, Tong Ren Tang Technologies Co. Ltd.): a Hank's balanced salt solution (HBSS), 20 mM 2-[4-(2-hydroxyethyl)-1-piperazinyl]ethanesulfonic acid (HEPES)-sodium hydroxide (NaOH), 2.5 mM Probenecid, and 0.1% bovine serum albumin (BSA)), and left to stand at room temperature for 3 hours, and the cells were washed using a plate washer (Product Name: ELx405, BIO-TEK instrument Corporation) in which a washing solution had been set up. The compound that had been preliminarily dissolved and diluted in a washing solution was added thereto, and set up in a system for measuring a calcium (Ca) concentration in a cell (Product Name: FLIPR, Molecular Devices Corporation). After 5 minutes, a nerve growth factor (NGF, mouse derived 2.5S, Alomone) corresponding to 80% stimulation of a maximum response was added (to a final concentration of about 100 to 150 ng/ml) to measure the change in Ca concentrations in cells. The difference between a maximum value and a minimum value in the change of Ca concentrations in cells was determined, and kept as measurement data. With a response upon addition of NGF being set at 0%, and a response upon addition of a buffer being set at 100%, the concentration causing 50% inhibition was determined as an $IC_{50}$ value. The results of several Example compounds are shown in Table 1 as below. In the table, Ex represents Example Compound No. as below (the same applies hereinafter). From the results of this test, it was confirmed that the representative compounds of the present invention as below have a trkA receptor inhibitory action.

TABLE 1

| Ex | $IC_{50}$ (nM) |
| --- | --- |
| 3 | 5.4 |
| 11 | 6.9 |
| 28 | 27 |
| 30 | 0.57 |
| 103 | 2.9 |
| 206 | 6.8 |
| 220 | 4.2 |
| 361 | 35 |
| 564 | 3.1 |
| 602 | 1.1 |
| 611 | 2.1 |
| 628 | 1.7 |
| 842 | 3.1 |
| 853 | 4.9 |
| 930 | 6.8 |
| 1181 | 12 |
| 1343 | 9.9 |
| 1435 | 36 |
| 1439 | 25 |
| 1449 | 8.8 |
| 1469 | 9.8 |
| 1470 | 18 |

Test Example 2

Evaluation of the Inhibitory Activity of the Compound on Enhanced Vascular Permeability Caused by Rat NGF The in vivo NGF inhibitory activity of the compound was examined. A Wistar female rat (Japan SLC) was forced to be orally administered with the compound (0.5% methylcellulose solution) 10 mg/3 ml/kg or a solvent (0.5% methylcellulose solution) 3 ml/kg. Under ether anesthesia performed at 60 minutes after administration, physiological saline or 1 µg/ml NGF (NGF, mouse derived 2.5 S, Alomone) was intracutaneously administered to the back at 50 µl/site, and then immediately a 1% Evans blue solution (dissolved in physiological saline) was administered through the caudal vein at 3 ml/kg. At a time point of 10 minutes after administration, the skin on the back was taken, and shaken in formamide for 16 hours. After shaking, an absorbance of Evans blue extracted in formamide was measured by an absorbance meter (wavelength: 620 nm), and the concentration was determined by a calibration curve method. A value obtained by subtracting the concentration of Evans blue at a site administered with physiological saline from the concentration of Evans blue at a site administered with NGF was determined as an NGF-dependent action, and an inhibitory rate of the compound group was determined with a group administered with a solvent being set at 100%. The results are shown in Table 2 below. In this test, it was confirmed that the representative compounds as below of the present invention have an excellent inhibitory action on enhanced vascular permeability caused by Rat NGF.

TABLE 2

| Ex | Inhibitory rate (%) |
| --- | --- |
| 11 | 69 |
| 28 | 92 |
| 30 | 90 |
| 103 | 98 |
| 361 | 78 |
| 564 | 90 |
| 930 | 86 |
| 1181 | 81 |
| 1343 | 87 |
| 1435 | 71 |
| 1439 | 76 |
| 1449 | 76 |
| 1469 | 90 |
| 1470 | 76 |

Test Example 3

Action of the Compound on a Rat Having Urinary Frequency Caused by Cyclophosphamide (CPA)

CPA (150 mg/5 ml/kg) was intraperitoneally administered to a Wistar female rat (Charles River Laboratories), and after 2 days, the experiment was carried out. It was forced to be orally administered with distilled water (30 ml/kg), and then confined in a metabolic cage, and urine weight and urination frequency were continuously measured for 1 hour. 3 or 10 mg/5 ml/kg of the compound (0.5% methylcellulose solution), or 5 ml/kg of a solvent (0.5% methylcellulose solution) was orally administered, and after 5 to 30 minutes, urination functions were measured after water-loading in the same manner as described above. A total urine weight was divided by the total urination frequency to determine an effective bladder capacity. With the value before administration of the compound being set at 100%, a rate of change in the effective bladder capacity caused by administration of the compound was determined. The results are shown in Table 3 below.

In this test, at 2 days after CPA treatment, the effective bladder capacity had decreased (about 0.5 ml), indicating urinary frequency. On the other hand, the representative compounds as below of the present invention improved the urinary frequency condition.

TABLE 3

| Ex | Dose (mg/kg) | Evaluation period after administration (minutes) | Rate in cange of effective bladder capacity (%) |
| --- | --- | --- | --- |
| 11 | 3 | 5-65 | 136 |
| 28 | 10 | 5-65 | 152 |
| 103 | 3 | 5-65 | 145 |
| 206 | 10 | 5-65 | 159 |
| 361 | 10 | 5-65 | 144 |
| 564 | 10 | 15-75 | 146 |
| 602 | 10 | 15-75 | 152 |
| 842 | 3 | 5-65 | 149 |
| 930 | 10 | 15-75 | 170 |

Test Example 4

Action of the Compound on a Model Having Pain Caused by Acetic Acid in a Rat

1% Acetic acid (99% distilled water) is intraperitoneally administered to a Wistar male rat (Charles River Laboratories), and the frequency of pain behavior (writhing) between 10 minutes and 20 minutes after administration is measured. The compound (10 mg/5 ml/kg) or a solvent (0.5% methylcellulose solution) is orally administered 5 minutes before the administration of 1% acetic acid. With the writhing frequency of the group administered with the solvent being set at 100%, the inhibition rate of the writhing frequency by the compound administration is determined. In this test, the pain-improving action of the compound of the present invention can be confirmed.

From the results the above-described tests, the compound of formula (I) has a potent in vitro trkA receptor inhibitory activity and a potent in vivo NGF inhibitory activity, and thus it is expected that the compound of the formula (I) has urinary frequency condition-ameliorating actions and pain-improving actions. Accordingly, it is clear that it is useful as a therapeutic and/or prophylactic agent for urinary frequency, urinary urgency, and urinary incontinence associated with lower urinary tract diseases including overactive bladder, various lower urinary tract diseases accompanied by lower urinary tract pain, such as interstitial cystitis, chronic prostatitis, and the like, and various diseases accompanied by pain, such as arthrosis osteoarthritis and the like.

A pharmaceutical composition containing one or two or more kinds of the compound of formula (I) or a pharmaceutically acceptable salt thereof as an active ingredient can be prepared in accordance with a generally used method, using an a pharmaceutical excipient, a pharmaceutical carrier, or the like, that is usually used in the art.

The administration can be carried out through any mode of oral administration via tablets, pills, capsules, granules, powders, liquid preparations, or the like, or parenteral administration via injections such as intraarticular, intravenous, intramuscular, or others, suppositories, eye drops, eye ointments, percutaneous liquid preparations, ointments, percutaneous patches, transmucosal liquid preparations, transmucosal patches, inhalations, and the like.

Regarding solid composition for oral administration, tablets, powders, granules, or the like are used. In such a solid composition, one or two or more active ingredients are mixed with at least one inactive excipient such as lactose, mannitol, glucose, hydroxypropylcellulose, microcrystalline cellulose, starch, polyvinyl pyrrolidone, magnesium aluminometasilicate, and/or the like. According to a conventional method, the composition may contain inactive additives such as lubricants such as magnesium stearate and the like, disintegrators such as sodium carboxymethyl starch and the like, stabilizers, and solubilizing agents. Tablets or pills may be coated with sugar coating, or with a film of gastric or enteric substance if necessary.

The liquid composition for oral administration includes pharmaceutically acceptable emulsions, solutions, suspensions, syrups, elixirs, or the like, and contains a generally used inert diluent, such as purified water or ethanol. In addition to the inert diluent, the liquid composition may contain adjuvants such as solubilizing agents, moistening agents, and suspending agents, sweeteners, flavors, aromatics, and antiseptics.

Injections for parenteral administration include sterile, aqueous or non-aqueous solutions, suspensions, or emulsions. As the aqueous solvent, for example, distilled water for injection or physiological saline is included. Examples of the non-aqueous solvent include propylene glycol, polyethylene glycol, vegetable oils such as olive oil and the like, alcohols such as ethanol and the like, Polysorbate 80 (Pharmacopeia), etc. Such a composition may further contain tonicity agents, antiseptics, moistening agents, emulsifying agents, dispersing agents, stabilizers, or solubilizing agents. These are sterilized, for example, by filtration through a bacteria-retaining filter, blending with bactericides, or irradiation. In addition, these can also be used by producing sterile solid compositions, and dissolving or suspending it in sterile water or a sterile solvent for injection prior to their use.

Regarding transmucosal agents such as inhalations, transnasal agents, and the like, in solid, liquid or semi-solid state are used, and can be prepared in accordance with conventionally known methods. For example, known excipients, as well as pH adjusting agents, antiseptics, surfactants, lubricants, stabilizers, thickeners, or the like may be appropriately added thereto. For their administration, appropriate devices for inhalation or insufflation may be used. For example, a compound may be administered alone or as powders of formulated mixture, or as solution or suspension by combining it with pharmaceutically acceptable carriers, using conventionally known devices or sprayers, such as a measured administration inhalation device and the like. The dry powder inhalers or the like may be for single or multiple administration use, and dry powders or powder-containing capsules may be used. Alternatively, this may be in a form of a pressurized aerosol spray which uses an appropriate propellant such as chlorofluoroalkane or hydrofluoroalkane, or a suitable gas such as carbon dioxide, or the like.

In the case of oral administration, it is appropriate that the daily dose may be usually from about 0.001 to 100 mg/kg, preferably from 0.1 to 30 mg/kg, and more preferably 0.1 to 10 mg/kg per body weight, and this is administered in a single portion or divided into 2 to 4 portions. Also, in the case of intravenous administration, the daily dose is from about 0.0001 to 10 mg/kg per body weight, and administration is made once a day or two or more times a day. In addition, a transmucosal agent is administered at a dose from about 0.001 to 100 mg/kg per body weight, once a day or two or more times a day. The dose is appropriately determined in response to an individual case by taking the symptoms, age, and sex, and the like into consideration.

The compound of formula (I) can be used in combination with various therapeutic or prophylactic agents for the diseases, in which the compound of the formula (I) is considered effective, as described above. The combined preparation may be administered simultaneously or separately and continuously, or at a desired time interval. The preparations to be co-administered may be a blend, or prepared individually.

EXAMPLES

Hereinbelow, the production processes for the compound (I) of the present invention will be described in more detail with reference to the following Examples. Further, the present invention is not limited to the compounds described in the Examples as described below. Furthermore, the production processes for the starting compounds will be described in Preparative Examples. Further, the production processes for the compound of formula (I) are not limited to the production processes of the specific Examples as below, but the compound of formula (I) can be prepared by any combination of the production processes or the methods that are apparent to a person skilled in the art.

The following abbreviations may be used in some cases in the Examples, Preparative Examples, and Tables below.

Me: methyl, Et: ethyl, Ac: acetyl, Ms: mesyl, Ph: phenyl, Bn: benzyl, Cbz: benzyloxycarbonyl, Boc: tert-butoxycarbonyl, TBS: tert-butyldimethylsilyl, Tf: trifluoromethanesulfonyl, $CF_3$: trifluoromethyl.

Preparative Example 1

5-[(4-Hydroxypiperidin-1-yl)methyl]-2-nitro-N-(tetrahydro-2H-pyran-4-yl)benzamide was allowed to undergo a reaction with acetyl chloride in pyridine to prepare 1-[4-nitro-3-(tetrahydro-2H-pyran-4-ylcarbamoyl)benzyl]piperidin-4-yl acetate.

Preparative Example 2

Methyl 5-(bromomethyl)-2-nitrobenzoate was allowed to undergo a reaction with morpholine in DMF to prepare methyl 5-(morpholin-4-ylmethyl)-2-nitrobenzoate.

Preparative Example 3

Methyl 2-[4-(pyrimidin-2-yloxy)piperidin-1-yl]-1,3-thiazole-4-carboxylate was allowed to undergo a reaction with a 1 M aqueous sodium hydroxide solution in a methanol-THF mixed solution to prepare 2-[4-(pyrimidin-2-yloxy)piperidin-1-yl]-1,3-thiazole-4-carboxylic acid.

Preparative Example 4

Methyl 2-amino-5-ethylbenzoate was allowed to undergo a reaction with di-tert-butyldicarbonate in tert-butanol to prepare methyl 2-[(tert-butoxycarbonyl)amino]-5-ethylbenzoate.

Preparative Example 5

3-Fluoropiperidine hydrochloride was allowed to undergo a reaction with benzoylthioisocyanate in methylenechloride in the presence of triethylamine to prepare N-[(3-fluoropiperidin-1-yl)carbonothioyl]benzamide.

Preparative Example 6

N-(cis-4-Carbamoylcyclohexyl)-2-nitrobenzamide was allowed to undergo a reaction with anhydrous trifluoroacetic acid in THF in the presence of triethylamine to prepare N-(cis-4-cyanocyclohexyl)-2-nitrobenzamide.

Preparative Example 7

1-(4-Amino-3-iodophenyl)cyclopropanecarbonitrile was allowed to undergo a reaction with a 1,1'-bis(diphenylphosphino)ferrocene palladium dichloride dichloromethane complex in an acetonitrile-methanol mixed solution in the presence of potassium carbonate and triethylamine under a carbon monoxide atmosphere to prepare methyl 2-amino-5-(1-cyanocyclopropyl)benzoate.

Preparative Example 8

Under an argon atmosphere, tert-butyl 4-(vinyloxy)piperidine-1-carboxylate was allowed to undergo a reaction with diethyl zinc and diiodomethane to prepare tert-butyl 4-(cyclopropyloxy)piperidine-1-carboxylate.

Preparative Example 9

Under an argon atmosphere, ethyl 2-bromo-1,3-thiazole-4-carboxylate was allowed to undergo a reaction with copper iodide (I), N,N-dimethylethane-1,2-diamine, and pyrrolidin-2-one in 1,4-dioxane in the presence of potassium carbonate to prepare ethyl 2-(2-oxopyrrolidin-1-yl)-1,3-thiazole-4-carboxylate.

Preparative Example 10

Ethyl 2-[(3S)-3-hydroxypyrrolidin-1-yl]-1,3-oxazole-4-carboxylate was allowed to undergo a reaction with 2-methoxy-N-(2-methoxyethyl)-N-(trifluorosulfanyl)ethanamine in methylenechloride to prepare ethyl 2-[(3R)-3-fluoropyrrolidin-1-yl]-1,3-oxazole-4-carboxylate.

Preparative Example 11

2-Amino-4,6-difluorobenzoic acid was subjected to an esterification reaction in ethanol in the presence of sulfuric acid to prepare ethyl 2-amino-4,6-difluorobenzate.

Preparative Example 12

Methyl 4-(chloromethyl)-2-nitrobenzoate was allowed to undergo a reaction with sodium methoxide in methanol to prepare methyl 4-(methoxymethyl)-2-nitrobenzoate.

Preparative Example 13

Methyl 5-(morpholin-4-ylmethyl)-2-nitrobenzoate was allowed to undergo a reaction with iron and ammonium chloride in an ethanol-water mixed solvent to obtain methyl 2-amino-5-(morpholin-4-ylmethyl)benzoate.

Preparative Example 14

1-(4-Aminophenyl)cyclopropanecarbonitrile was allowed to undergo a reaction with bis(pyridine)iodonium tetrafluoroboric acid in methylenechloride to prepare 1-(4-amino-3-iodophenyl)cyclopropanecarbonitrile.

Preparative Example 15

Isatoic anhydride was allowed to undergo a reaction with 4-aminotetrahydropyrane hydrochloride in DMF in the presence of triethylamine and 4-(N,N-dimethylamino)pyridine to prepare 2-amino-N-(tetrahydro-2H-pyran-4-yl)benzamide.

Preparative Example 16 tert-Butyl [(1R)-2-methoxy-1-methylethyl]carbamate was allowed to undergo a reaction with lithium aluminum hydride in THF to prepare (2R)-1-methoxy-N-methylpropane-2-amine hydrochloride.

Preparative Example 17

3-(Benzyloxy)cyclopentanecarboxamide was allowed to undergo a reaction with 2,4-bis(4-methoxyphenyl)-1,3,2,4-dithiadiphosphetane2,4-sulfide in THF to prepare 3-(benzyloxy)cyclopentane carbothioamide.

Preparative Example 18

1-tert-Butyl 2-methyl (2R,4S)-4-methoxypyrrolidine-1,2-dicarboxylate was allowed to undergo a reaction with lithium borohydride in THF to prepare tert-butyl (2R,4S)-2-(hydroxymethyl)-4-methoxypyrrolidine-1-carboxylate.

Preparative Example 19 tert-Butyl 4-(ethylsulfanyl)piperidine-1-carboxylate was allowed to undergo a reaction with m-chloroperbenzoic acid in chloroform to prepare tert-butyl 4-(ethylsulfonyl)piperidine-1-carboxylate.

Preparative Example 20 tert-Butyl [(1R)-2-hydroxy-1-methylethyl]carbamate was allowed to undergo a reaction with methyl iodide in acetonitrile in the presence of silver oxide (I) to prepare tert-butyl [(1R)-2-methoxy-1-methylethyl]carbamate.

Preparative Example 21

Methyl 2-nitro-5-pyridin-2-yl benzoate was allowed to undergo a reaction with methyl iodide in acetonitrile. Subsequently, this was allowed to undergo a reaction with platinum oxide in acetic acid under a hydrogen atmosphere to prepare methyl 2-amino-5-(1-methylpiperidin-2-yl)benzoate.

Preparative Example 22

Ethyl 2-piperidin-4-yl-1,3-thiazole-4-carboxylate was allowed to undergo a reaction with propanoyl chloride in methylenechloride in the presence of pyridine to prepare ethyl 2-(1-propionylpiperidin-4-yl)-1,3-thiazole-4-carboxylate.

Preparative Example 23

3-Methyl-4-nitrobenzonitrile was allowed to undergo a reaction with a mixed aqueous solution of nickel (II) chloride hexahydrate and 2,2'-bipyridyl, and a sodium hydrochlorite solution in acetonitrile to prepare 5-cyano-2-nitrobenzoic acid.

Preparative Example 24

5-Methyl-2-nitro-N-(tetrahydro-2H-pyran-4-yl)benzamide was allowed to undergo a reaction with benzoyl peroxide and N-bromosuccinimide in chloroform to prepare 5-(bromomethyl)-2-nitro-N-(tetrahydro-2H-pyran-4-yl)benzamide.

Preparative Example 25

(S)-1-Methoxy-2-propyl amine was allowed to undergo a reaction with ethyl chloroformate in THF in the presence of triethylamine to prepare ethyl [(1S)-2-methoxy-1-methylethyl]carbamate.

Preparative Example 26

1-(4-Aminophenyl)cyclopropanecarbonitrile was allowed to undergo a reaction with N-chlorosuccinimide in 2-propanol to prepare 1-(4-amino-3-chlorophenyl)cyclopropanecarbonitrile.

Preparative Example 27

Methyl 3-hydroxycyclopentanecarboxylate was allowed to undergo a reaction with benzyl bromide in THF in the presence of sodium hydride to prepare benzyl 3-(benzyloxy) cyclopentanecarboxylate.

Preparative Example 28

Benzyl 4-hydroxypiperidine-1-carboxylate was allowed to undergo a reaction with difluoro(fluorosulfonyl)acetic acid and sodium sulfate in acetonitrile to prepare benzyl 4-(difluoromethoxy)piperidine-1-carboxylate.

Preparative Example 29

2-Fluoropyridine was allowed to undergo a reaction with a mixture of 2,2,6,6-tetramethylpiperidine and n-butyl lithium, and tert-butyl 1-oxa-6-azaspiro[2.5]octane-6-carboxylate in THF to prepare tert-butyl 4-[(2-fluoropyridin-3-yl)methyl]-4-hydroxypiperidine-1-carboxylate.

Preparative Example 30 tert-Butyl {[1-(hydroxymethyl)cyclobutyl]methyl}carbamate was allowed to undergo a reaction with phthalimide, triphenyl phosphine, and diethyl azodicarboxylate in THF to prepare tert-butyl({1-[(1,3-dioxo-1,3-dihydro-2H-isoindol-2-yl)methyl]cyclobutyl}methyl)carbamate.

Preparative Example 31 tert-Butyl 4-hydroxypiperidine-1-carboxylate was allowed to undergo a reaction with tert-butyl vinyl ether in the presence of palladium acetate and 4,7-diphenyl-1,10-phenanthroline to prepare tert-butyl 4-(vinyloxy)piperidine-1-carboxylate.

Preparative Example 32

2-Fluoro-6-nitro-N-pyridin-3-yl benzamide was allowed to undergo a reaction with palladium-carbon in a methanol-DMF mixed solution under a hydrogen atmosphere to prepare 2-amino-6-fluoro-N-pyridin-3-yl benzamide.

Preparative Example 33

Benzyl 4-(difluoromethoxy)piperidine-1-carboxylate was allowed to undergo a reaction with palladium-carbon in methanol under a hydrogen atmosphere to prepare 4-(difluoromethoxy)piperidine.

Preparative Example 34

4-[(5-Bromopyridin-2-yl)methyl]morpholine was allowed to undergo a reaction with benzophenoneimine in toluene in the presence of sodium tert-butoxide, 2,2'-bis(diphenylphosphino)-1,1'-binaphthyl, and tris(dibenzylideneacetone)dipalladium to prepare N-(diphenylmethylene)-6-(morpholin-4-ylmethyl)pyridin-3-amine. Then, this was allowed to undergo a reaction with an aqueous hydrochloric acid solution in THF to prepare 6-(morpholin-4-ylmethyl)pyridin-3-amine dihydrochloride.

Preparative Example 35 and Preparative Example 36

Methyl 4-nitro-1H-pyrazole-3-carboxylate was allowed to undergo a reaction with 4-(2-chloroethyl)morpholine hydrochloride in DMF in the presence of potassium carbonate and potassium iodide to prepare methyl 1-(2 morpholin-4yl-ethyl)-4-nitro-1H-pyrazole-5-carboxylate and methyl 1-(2 morpholin-4ylethyl)-4-nitro-1H-pyrazole-3-carboxylate.

Preparative Example 37

Ethyl 2-piperidin-4-yl-1,3-thiazole-4-carboxylate was allowed to undergo a reaction with formaldehyde, and sodium triacetoxyborohydride in methylenechloride in the presence of acetic acid to prepare ethyl 2-(1-methylpiperidin-4-yl)-1,3-thiazole-4-carboxylate.

Preparative Example 38

1-(Morpholin-4-ylmethyl)-1H-benzotriazole was allowed to undergo a reaction with zinc and methyl 5-(bromomethyl)-2-nitrobenzoate in DMF to prepare methyl 5-(2-morpholin-4-ylethyl)-2-nitrobenzoate.

Preparative Example 39

Benzyl cis-3-fluoro-4-hydroxypiperidine-1-carboxylate was allowed to undergo a reaction with 2-chloropyrimidine in THF-DMSO in the presence of sodium hydride to prepare benzyl cis-3-fluoro-4-(pyrimidin-2-yloxy)piperidine-1-carboxylate.

Preparative Example 40

1-Fluoro-2-nitrobenzene was allowed to undergo a reaction with 2-mercaptoacetamide in methanol in the presence of ammonia to prepare 2-[(2-nitrophenyl)sulfanyl]acetamide.

Preparative Example 41 tert-Butyl (3R)-3-(hydroxymethyl)pyrrolidine-1-carboxylate was allowed to undergo a reaction with methyl iodide in THF in the presence of sodium hydride to prepare tert-butyl (3R)-3-(methoxymethyl)pyrrolidine-1-carboxylate.

Preparative Example 42

Ethyl 2-(chloromethyl)-1,3-thiazole-4-carboxylate was allowed to undergo a reaction with 2-bromophenol in DMF in the presence of potassium carbonate to prepare ethyl 2-[(2-bromophenoxy)methyl]-1,3-thiazole-4-carboxylate.

Preparative Example 43 tert-Butyl 4-[(methylsulfonyl)oxy]piperidine-1-carboxylate was allowed to undergo a reaction with sodium ethanethiolate in a THF-DMF mixed solution to prepare tert-butyl 4-(ethylsulfanyl)piperidine-1-carboxylate.

Preparative Example 44

2-Aminobenzenethiol was allowed to undergo a reaction with 5-{[tert-butyl(dimethyl)silyl]oxy}-n-pentylmethanesulfonate in DMF in the presence of sodium hydride. This was allowed to undergo a reaction with tetrabutyl ammonium fluoride in THF to prepare 5-[(2-aminophenyl)sulfanyl]pentan-1-ol.

Preparative Example 45

Methyl (2S)-2-({2-[(tert-butoxycarbonyl)amino]isonicotinoyl}amino)-3-hydroxypropionate was allowed to undergo a reaction with 2-methoxy-N-(2-methoxyethyl)-N-(trifluorosulfanyl)ethanamine in methylenechloride. Subsequently, this was allowed to undergo a reaction with bromotrichloromethan in the presence of 1,8-diazabicyclo[5.4.0]-7-undecene to prepare methyl 2-{2-[(tert-butoxycarbonyl)amino]pyridin-4-yl}-1,3-oxazole-4-carboxylate.

Preparative Example 46

2-[(tert-Butoxycarbonyl)amino]isonicotinic acid was allowed to undergo a reaction with L-serine methyl ester hydrochloride, WSC-HCl, and HOBt in DMF in the presence of triethylamine to prepare methyl (2S)-2-({2-[(tert-butoxycarbonyl)amino]isonicotinoyl}amino)-3-hydroxypropionate.

Preparative Example 47

Tetrahydro-2H-pyran-4-amine hydrochloride was allowed to undergo a reaction with 2-nitrobenzenesulfonyl chloride in methylenechloride in the presence of triethylamine to prepare 2-nitro-N-(tetrahydro-2H-pyran-4-yl)benzenesulfonamide.

Preparative Example 48

1-(4-Amino-3-iodophenyl)cyclopropanecarbonitrile was allowed to undergo a reaction with tributyl(1-ethoxy vinyl) tin, tetrakistriphenyl phosphine palladium in toluene, and the reaction liquid was concentrated. This was allowed to undergo a reaction with an aqueous hydrochloric acid solution in ethanol to prepare 1-(3-acetyl-4-aminophenyl)cyclopropanecarbonitrile.

Preparative Example 49

Methyl 2-nitro-5-{[(trifluoromethyl)sulfonyl]oxy}benzoate was allowed to undergo a reaction with 4,4,4',4',5,5,5',5'-octamethyl-2,2'-bi-1,3,2-dioxaboronate, and 1,1'-bis(diphenylphosphino)ferrocene palladium in 1,4-dioxane in the presence of potassium carbonate to prepare methyl 2-nitro-5-(4,4,5,5-tetramethyl-1,3,2-dioxaborolan-2-yl)benzoate.

Preparative Example 50

Methyl 2-nitro-5-(4,4,5,5-tetramethyl-1,3,2-dioxaborolan-2-yl)benzoate was allowed to undergo a reaction with 2-chloropyridine in dimethoxyethane in the presence of tetrakis(triphenylphosphine)palladium and cesium fluoride to prepare methyl 2-nitro-5-pyridin-2-yl benzoate.

Preparative Example 51

Methyl 1-(2-morpholin-4-ylethyl)-4-nitro-1H-pyrazole-5-carboxylate was allowed to undergo a reaction with an aqueous sodium hydroxide solution in methanol to prepare 1-(2-morpholin-4-ylethyl)-4-nitro-1H-pyrazole-5-carboxylic acid.

Preparative Example 52

Methyl 5-hydroxy-2-nitrobenzoate was allowed to undergo a reaction with trifluoromethanesulfonic anhydride in pyridine to prepare methyl 2-nitro-5-{[(trifluoromethyl)sulfonyl]oxy}benzoate.

Preparative Example 53

3-Fluoropiperidine-1-carbothioamide was allowed to undergo a reaction with ethyl 3-bromo-2-oxopropanoate in ethanol to prepare ethyl 2-(3-fluoropiperidin-1-yl)-1,3-thiazole-4-carboxylate.

Preparative Example 54

Methyl 2-bromo-1,3-thiazole-4-carboxylate was allowed to undergo a reaction with 2-(piperidin-4-yloxy)pyrimidine in DMA in the presence of triethylamine to prepare methyl 2-[4-(pyrimidin-2-yloxy)piperidin-1-yl]-1,3-thiazole-4-carboxylate.

Preparative Example 55

N-[(3-Fluoropiperidin-1-yl)carbothioyl]benzamide was allowed to undergo a reaction with methylamine in methanol to prepare 3-fluoropiperidine-1-carbothioamide.

Preparative Example 56

3-Methoxyazetidine hydrochloride was allowed to undergo a reaction with trimethylsilyl isocyanate in DMF in the presence of triethylamine to prepare 3-methoxyazetidine-1-carboxamide.

Preparative Example 57

4-[(6-Methoxypyridazin-3-yl)oxy]piperidine-1-carboxamide was allowed to undergo a reaction with ethyl 3-bromo-2-oxopropanoate in ethanol to prepare ethyl 2-{4-[(6-oxo-1,6-dihydropyridazin-3-yl)oxy]piperidin-1-yl}-1,3-oxazole-4-carboxylate.

Preparative Example 58

N-(2-Methoxyethyl)-N-methylurea was allowed to undergo a reaction with ethyl 3-bromo-2-oxopropanoate in ethanol to prepare ethyl 2-[(2-methoxyethyl)(methyl)amino]-1,3-oxazole-4-carboxylate.

Preparative Example 59

Methyl 5-formyl-2-nitrobenzoate was allowed to undergo a reaction with (methoxymethyl)(triphenyl)phosphonium chloride in THF in the presence of lithium bis(trimethylsilyl)amide to prepare methyl 5-[(E)-2-methoxy vinyl]-2-nitrobenzoate.

Preparative Example 60

1-(4-Aminophenyl)cyclopropanecarbonitrile was allowed to undergo a reaction with 2-bromo-1,3-thiazole-4-carboxylic acid, WSC-HCl, and HOBt in DMF to prepare 2-bromo-N-[4-(1-cyanocyclopropyl)phenyl]-1,3-thiazole-4-carboxamide.

Preparative Example 61

2-Fluoro-6-nitrobenzoic acid was allowed to undergo a reaction with oxalyl chloride and a catalytic amount of DMF in dichloroethane to prepare an acid chloride. This was allowed to undergo a reaction with 3-aminopyridine in pyridine to prepare 2-fluoro-6-nitro-N-pyridin-3-yl benzamide.

Preparative Example 62

2-Nitrobenzoic acid was allowed to undergo a reaction with 1-(3-methyloxetan-3-yl)methanamine, WSC-HCl, and HOBt in DMF to prepare N-[(3-methyloxetan-3-yl)methyl]-2-nitrobenzamide.

Preparative Example 63

Methyl 2-amino-5-hydroxybenzoate was allowed to undergo a reaction with tert-butyl(3-hydroxy propyl)carbamate, triphenyl phosphine, and diethyl azodicarboxylate in THF to prepare methyl 2-amino-5-{3-[(tert-butoxycarbonyl) amino]propoxy}benzoate.

Preparative Example 64

Methyl 5-[(E)-2-methoxyvinyl]-2-nitrobenzoate was allowed to undergo a reaction with p-toluene sulfonic acid monohydrate and silica gel in methylenechloride. Subsequently, it was allowed to undergo a reaction with pyrrolidine and sodium triacetoxyborohydride in methylenechloride in the presence of acetic acid to prepare methyl 2-nitro-5-(2-pyrrolidin-1-ylethyl)benzoate.

Preparative Example 65 tert-Butyl 4-(ethylsulfonyl)piperidine-1-carboxylate was allowed to undergo a reaction with hydrogen chloride in 1,4-dioxane to prepare 4-(ethylsulfonyl)piperidine hydrochloride.

Preparative Example 66 tert-Butyl({1-[(1,3-dioxo-1,3-dihydro-2H-isoindol-2-yl) methyl]cyclobutyl}methyl)carbamate was allowed to undergo a reaction with hydrazine monohydrate in ethanol to prepare tert-butyl {[1-(aminomethyl)cyclobutyl] methyl}carbamate.

Preparative Example 67

2-[({2-[Methyl(tetrahydro-2H-pyran-4-ylmethyl)amino]-1,3-thiazol-4-yl}carbonyl)amino]-5-(morpholin-4-ylmethyl)benzoic acid hydrochloride was allowed to undergo a reaction with WSC-HCl and HOBt in DMF in the presence of triethylamine to prepare 2-{2-[methyl(tetrahydro-2H-pyran-4-ylmethyl)amino]-1,3-thiazol-4-yl}-6-(morpholin-4-ylmethyl)-4H-3,1-benzoxazin-4-one.

Preparative Example 68 tert-Butyl {4-(aminomethyl)-2-[(2-methoxyethyl)carbamoyl]-5-methylphenyl}carbamate was allowed to undergo a reaction with bis(2-chloroethyl)ether in a THF-DMF mixed solution in the presence of diisopropylethylamine to prepare tert-butyl {2-[(2-methoxyethyl)carbamoyl]-5-methyl-4-(morpholin-4-ylmethyl)phenyl}carbamate.

Preparative Example 69

Methyl 2-[(tert-butoxycarbonyl)amino]-5-[(1,3-dioxo-1,3-dihydro-2H-isoindol-2-yl)methyl]-4-methylbenzoate was allowed to undergo a reaction with 2-methoxyethylamine in ethanol to prepare tert-butyl {4-(aminomethyl)-2-[(2-methoxyethyl)carbamoyl]-5-methylphenyl}carbamate.

Preparative Example 70

Methyl 2-amino-4-methylbenzoate was allowed to undergo a reaction with N-(hydroxymethyl)phthalimide in sulfuric acid solution to prepare methyl 2-amino-5-[(1,3-dioxo-1,3-dihydro-2H-isoindol-2-yl)methyl]-4-methylbenzoate.

Preparative Example 435

Methyl 5-(bromomethyl)-2-nitrobenzoate was allowed to undergo a reaction with sodium hydride and pyrrolidin-2-one in THF to prepare methyl 2-nitro-5-[(2-oxopyrrolidin-1-yl) methyl]benzoate.

Preparative Example 436

Methyl 5-{[(2-hydroxyethyl)amino]methyl}-2-nitrobenzoate was allowed to undergo a reaction with CDI and triethylamine in THF to prepare methyl 2-nitro-5-[(2-oxo-1,3-oxazolidin-3-yl)methyl]benzoate.

Preparative Example 437

Benzyl cis-3-fluoro-4-hydroxypiperidine-1-carboxylate was allowed to undergo a reaction with (2R)-3,3,3-trifluoro-2-methoxy-2-phenyl propanoic acid, dicyclohexylcarbodiimide, and 4-(N,N-dimethylamino)pyridine in methylenechloride to prepare benzyl (3S,4R)-3-fluoro-4-{[(2R)-3,3,3-trifluoro-2-methoxy-2-phenylpropanoyl] oxy}piperidine-1-carboxylate.

Preparative Example 438

Methyl 5-chloro-2-nitrobenzoate was allowed to undergo a reaction with (2R)-2-(methoxymethyl)pyrrolidine in DMA in the presence of potassium carbonate to prepare methyl 5-[(2R)-2-(methoxymethyl)pyrrolidin-1-yl]-2-nitrobenzoate.

Preparative Example 439

Methyl 2-nitro-5-vinylbenzoate was allowed to undergo a reaction with N-benzyl-1-methoxy-N-[(trimethylsilyl)methyl]methanamine and trifluoroacetic acid in toluene to prepare methyl 5-(1-benzylpyrrolidin-3-yl)-2-nitrobenzoate.

Preparative Example 440

(2-Chloroethoxy)cyclopropane was allowed to undergo a reaction with a phthalimide potassium salt in DMF, and then with hydrazine monohydrate in EtOH. This was allowed to undergo a reaction with a 4 M hydrogen chloride/EtOAc solution to prepare 2-(cyclopropyloxy)ethanamine hydrochloride.

Preparative Example 441

Methyl 5-[(tert-butoxycarbonyl)amino]-2-chloroisonicotinate was allowed to undergo a reaction with trimethylboroxin, triphenyl phosphine palladium, and cesium fluoride in dimethoxyethane to prepare methyl 5-[(tert-butoxycarbonyl)amino]-2-methyl isonicotinate.

Preparative Example 442

5-Benzyl-8-oxa-5-azaspiro[3,5]nonane was allowed to undergo a reaction with 10% palladium-carbon in methanol under 4 atm a hydrogen atmosphere. This was allowed to undergo a reaction with a 4 M hydrogen chloride/EtOAc solution to prepare 8-oxa-5-azaspiro[3,5]nonane hydrochloride.

Preparative Example 443

(3-Endo)-8-methyl-3-(pyrimidin-2-yloxy)-8-azabicyclo[3.2.1]octane was allowed to undergo a reaction with M-chloroperbenzoic acid and a 1 M aqueous iron dichloride solution in methylenechloride to prepare (3-endo)-3-(pyrimidin-2-yloxy)-8-azabicyclo[3.2.1]octane.

Preparative Example 444

(2R,3S)-1-(Diphenylmethyl)-3-methoxy-2-methylazetidine was allowed to undergo a reaction with palladium hydroxide in ethanol under a hydrogen atmosphere and then with a 4 M hydrogen chloride/1,4-dioxane solution to prepare (2R,3S)-3-methoxy-2-methylazetidine hydrochloride.

Preparative Example 445

Methyl 5-(bromomethyl)-2-nitrobenzoate was allowed to undergo a reaction with ethanol and silver oxide (I) in 1,2-dichloroethane to prepare methyl 5-(ethoxymethyl)-2-nitrobenzoate.

Preparative Example 446

Methyl 2-nitro-5-oxylan-2-yl benzoate was allowed to undergo a reaction with 2-(methylamino)ethanol in methanol to prepare methyl 5-{1-hydroxy-2-[(2-hydroxyethyl)(methyl)amino]ethyl}-2-nitrobenzoate.

Preparative Example 447

Methyl 5-{1-hydroxy-2-[(2-hydroxyethyl)(methyl)amino]ethyl}-2-nitrobenzoate was allowed to undergo a reaction with triphenyl phosphine and diethyl azodicarboxylate in THF to prepare methyl 5-(4-methylmorpholin-2-yl)-2-nitrobenzoate.

Preparative Example 448

A mixture of methyl dichloroacetate, morpholine, and methyl 2-nitrobenzoate was allowed to undergo a reaction with potassium tert-butoxide in DMF, and then treated with a 1 M aqueous HCl solution to prepare methyl 5-(1-chloro-2-morpholin-4-yl-2-oxoethyl)-2-nitrobenzoate.

In the same manner as the methods of Preparative Examples 1 to 70 and 435 to 448, the compounds of Preparative Examples 71 to 434 and 449 to 534 shown in Tables 4 to 61 below were prepared, respectively, using a corresponding starting materials. For Tables 4 to 61, Pre denotes Preparative Example numbers and Str denotes the structural formulae. The structural formulae marked with * in the tables indicate that the compounds are optically active. The head in each cell of the right columns of Tables 4 to 61 shows the Preparative Example numbers which were referred to for the production processes as Syn, with numbers marked by P in front. For example, in the production process including "P30-P66" as described therein means that the same Production Process as Preparative Example 30 is performed, and then the same Production Process as in Preparative Example 66 is performed. The materials horizontally described in the right hand of Syn (Sal) represent salts, and the materials without such a description represent free compounds. (HCl) represents hydrochloride, (2HCl) represents dihydrochloride, and (Na) represents sodium salt. The bottom in the right hand columns show values by mass spectrum (MS) as Dat (physicochemical data).

Furthermore, as for the description of MS data, for example, in the columns of the compound of Preparative Example 1, MS (ESI) m/z: 406 ([M+H]+) is described, which means MS (ESI) m/z: 406 ([M+H]$^+$). Similarly, in the case of Preparative Example 71, MS (ESI) m/z: 214 ([M−H]−) is described, which means MS (ESI) m/z: 214 ([M−H]$^-$) (the description of the MS data applies in similarly in Tables 62 to 211 below having the description of Examples 1 to 1767).

Example 1

To 128 mg of 2-{methyl[(3R)-pyrrolidin-3-yl]amino}-N-[2-(pyridin-3-ylcarbamoyl)phenyl]-1,3-thiazole-4-carboxamide were added 1 ml of DMA, 88 mg of 2-chloroethylmethyl ether, 50 mg of potassium iodide, and 158 µl of diisopropylethylamine, followed by stirring at 100° C. for 8 hours. To the reaction mixture was added water, followed by extraction with chloroform. The organic layer was washed with water and saturated brine, and then dried over anhydrous magnesium sulfate, and the solvent was evaporated under reduced pressure. The residue was purified by preparative thin layer chromatography (chloroform:methanol=9:1). This was dissolved in chloroform, and a 4 M hydrogen chloride/EtOAc solution and hexane was added thereto, followed by stirring at room temperature. The precipitate was collected by filtration to prepare 92 mg of 2-{[(3R)-1-(2-methoxyethyl)pyrrolidin-3-yl](methyl)amino}-N-[2-(pyridin-3-ylcarbamoyl)phenyl]-1,3-thiazole-4-carboxamide dihydrochloride.

Example 2

To 110 mg of methyl 5-(morpholin-4-ylmethyl)-2-[({2-[4-(pyrimidin-2-yloxy)piperidin-1-yl]-1,3-thiazol-4-yl}carbonyl)amino]benzoate was added 2.1 ml of a 9.8 M methylamine/methanol solution, followed by leaving to stand at room temperature for 14 days. The reaction mixture was concentrated under reduced pressure, and the obtained residue was then purified by preparative thin layer chromatography (chloroform:methanol=9:1). A 4 M hydrogen chloride/EtOAc solution was added thereto, followed by stirring, and the solid in the system was collected by filtration to prepare 76.5 mg of N-[2-(methylcarbamoyl)-4-(morpholin-4-ylmethyl)phenyl]-2-[4-(pyrimidin-2-yloxy)piperidin-1-yl]-1,3-thiazole-4-carboxamide hydrochloride.

Example 3

To 500 mg of 3-chloro-4-[({2-[4-(pyrimidin-2-yloxy)piperidin-1-yl]-1,3-thiazol-4-yl}carbonyl)amino]benzoic acid were added 5 ml of THF and 1.0 g of CDI, followed by heating under reflux for 2 hours. The reaction liquid was ice-cooled, and a solution of 200 mg of sodium borohydride in 1 ml of water was added thereto, followed by stirring at room temperature for 12 hours. The reaction mixture was concentrated under reduced pressure, and then water was added to the residue, followed by extraction with chloroform. The organic layer was dried over anhydrous magnesium sulfate, and the solvent was evaporated under reduced pressure. The residue was purified by silica gel column chromatography (chloroform:methanol=20:1) to prepare 226 mg of N-[2-chloro-4-(hydroxymethyl)phenyl]-2-[4-(pyrimidin-2-yloxy) piperidin-1-yl]-1,3-thiazole-4-carboxamide.

Example 4

To a reaction mixture of 200 mg of N-[5-(hydroxymethyl)-2-(tetrahydro-2H-pyran-4-ylcarbamoyl)phenyl]-2-[(2-methoxyethyl)(methyl)amino]-1,3-thiazole-4-carboxamide, 0.1 ml of triethylamine, and 4 ml of methylenechloride was added 0.05 ml of methanesulfonylchloride under ice-cooling, followed by stirring at room temperature for 3 hours. To the reaction liquid was added water, followed by extraction with chloroform. The organic layer was dried over anhydrous magnesium sulfate, and the solvent was evaporated under reduced pressure. The residue was dissolved in 5 ml of acetonitrile, and 180 mg of tetrabutylammonium cyanide was added thereto, followed by stirring at room temperature for 6 hours. The insoluble materials generated in the reaction liquid were collected by filtration and washed with water and ethanol to prepare 142 mg of N-[5-(cyanomethyl)-2-(tetrahydro-2H-pyran-4-ylcarbamoyl)phenyl]-2-[(2-methoxyethyl)(methyl)amino]-1,3-thiazole-4-carboxamide.

Example 5

To a solution of 200 mg of rel-N-(2-{[(1R,3S)-3-carbamoylcyclohexyl]carbamoyl}phenyl)-2-morpholin-4-yl-1,3-thiazole-4-carboxamide in 2 ml of DMF was added 105 mg of 2,4,6-trichloro-1,3,5-triazine under ice-cooling, followed by stirring at 0° C. for 1 hour and at room temperature for 1 hour. To the reaction liquid was added a saturated aqueous sodium hydrogen carbonate solution, followed by extraction with chloroform. The organic layer was washed with saturated brine and then dried over anhydrous magnesium sulfate, and the solvent was evaporated under reduced pressure. The residue was purified by silica gel column chromatography (chloroform:methanol=100:1). This was heated and dissolved in 2-propanol, and then cooled to room temperature. The precipitate was collected by filtration to prepare 122 mg of rel-N-(2-{[(1R,3S)-3-cyanocyclohexyl]carbamoyl}phenyl)-2-morpholin-4-yl-1,3-thiazole-4-carboxamide.

Example 6

To a suspension of 598 mg of 2-[4-(pyrimidin-2-yloxy) piperidin-1-yl]-1,3-thiazole-4-carboxylic acid in 6 ml of methylenechloride were added 0.51 ml of oxalyl chloride and 7.5 µl of DMF, followed by stirring at room temperature for 2 hours. The reaction mixture was concentrated under reduced pressure, and then to the residue were added 6 ml of THF, 631 mg of methyl 2-amino-5-(morpholin-4-ylmethyl)benzoate dihydrochloride, and 1 ml of diisopropylethylamine, followed by stirring at room temperature overnight. To the reaction liquid was added a saturated aqueous sodium hydrogen carbonate solution, followed by extraction with EtOAc. The organic layer was washed with saturated brine and then dried over anhydrous magnesium sulfate, and the solvent was evaporated under reduced pressure. To the residue were added ethanol and diisopropyl ether, followed by stirring at 100° C., and then cooled to room temperature. The solid in the system was collected by filtration to prepare 700 mg of methyl 5-(morpholin-4-ylmethyl)-2-[({2-[4-(pyrimidin-2-yloxy)piperidin-1-yl]-1,3-thiazol-4-yl}carbonyl)amino]benzoate.

Example 7

To a solution of 202 mg of methyl 5-(morpholin-4-ylmethyl)-2-[({2-[4-(pyrimidin-2-yloxy)piperidin-1-yl]-1,3-thiazol-4-yl}carbonyl)amino]benzoate in 8.1 ml of THF was added 6.7 mg of lithium hydride, followed by stirring for 1 hour while heating under reflux. To the reaction mixture was added 0.56 ml of a 1 M methyl magnesium bromide/THF solution at 0° C., followed by stirring at 45° C. for 3 hours. Further, 1.69 ml of a 1 M methyl magnesium bromide/THF solution was added thereto at 0° C., followed by stirring at 45° C. for 2 hours. To the reaction liquid was added a saturated aqueous ammonium chloride solution, followed by extraction with EtOAc. The organic layer was washed with saturated brine and then dried over anhydrous magnesium sulfate, and the solvent was evaporated under reduced pressure. The residue was purified by preparative thin layer chromatography (chloroform:methanol=9:1 and chloroform:acetone=7:3). To this was added a 4 M hydrogen chloride/EtOAc solution, and ethanol and diisopropyl ether were then added thereto, followed by stirring. The solid in the system was collected by filtration to prepare 15.5 mg of N-[2-(1-hydroxy-1-methylethyl)-4-(morpholin-4-ylmethyl)phenyl]-2-[4-(pyrimidin-2-yloxy)piperidin-1-yl]-1,3-thiazole-4-carboxamide hydrochloride.

Example 8

Under an argon atmosphere, to 1.3 g of trimethylsulfoxonium chloride were added 20 ml of THF and 1.2 g of potassium tert-butoxide, followed by stirring at 50° C. for 4 hours. The reaction mixture was cooled to room temperature, and 700 mg of methyl 2-[({2-[(2-methoxyethyl)(methyl)amino]-1,3-thiazol-4-yl}carbonyl)amino]benzoate was then added thereto, followed by stirring at room temperature for 3 days. To the reaction mixture was added water, followed by extraction with EtOAc. The organic layer was washed with saturated brine and then dried over anhydrous sodium sulfate, and the solvent was evaporated under reduced pressure to obtain 451 mg of N-(2-{[dimethyl(oxide)-$\lambda^4$-sulfanylidene]acetyl}phenyl)-2-[(2-methoxyethyl)(methyl)amino]-1,3-thiazole-4-carboxamide.

To this were added 5 ml of THF, 700 µl of a 4 M hydrogen chloride/1,4-dioxane solution, and 1.5 ml of DMSO, followed by stirring at 70° C. for 2 hours, and 800 µl of morpholine was added thereto, followed by stirring at room temperature for 3 days. To the reaction mixture was added EtOAc, the organic layer was washed with a saturated aqueous sodium hydrogen carbonate solution and saturated brine, and then dried over anhydrous sodium sulfate, and the solvent was evaporated under reduced pressure. The residue was purified by silica gel column chromatography (chloroform:methanol=1000:1, 500:1). This was dissolved in EtOAc, a 0.4 M hydrogen chloride/EtOAc solution was added thereto, and the solvent was evaporated. The residue was heated and dissolved in EtOH, and then cooled to room temperature. The precipitate was collected by filtration to prepare 43 mg of 2-[(2-

Example 9

To a solution of 115 mg of 2-(3-fluoropiperidin-1-yl)-1,3-thiazole-4-carboxylic acid in 3 ml of DMF was added 110 mg of 2-amino-N-pyridin-3-yl benzamide, and 228 mg of HATU, followed by stirring at room temperature for 7 days. To the reaction liquid was added water, and the precipitate was collected by filtration. This was purified by silica gel column chromatography (chloroform:methanol=99:1-30:1). This was heated and dissolved in 2-propanol, and then cooled to room temperature. The precipitate was collected by filtration to prepare 102 mg of 2-(3-fluoropiperidin-1-yl)-N-[2-(pyridin-3-ylcarbamoyl)phenyl]-1,3-thiazole-4-carboxamide.

Example 10

To a solution of 193 µl of diisopropylamine in 8 ml of THF was added 790 µl of a 1.6 M n-butyl lithium/hexane solution under ice-cooling, followed by stirring for 15 minutes, and 123 µl of 3-methylpyridine was added thereto, followed by stirring at 0° C. for 15 minutes. Subsequently, a solution of 400 mg of methyl 2-[({2-[(2-methoxyethyl)(methyl)amino]-1,3-thiazol-4-yl}carbonyl)amino]benzoate in 4 ml of THF was added thereto, followed by stirring at 0° C. for 20 minutes. To the reaction mixture was added a saturated aqueous sodium hydrogen carbonate solution, followed by extraction with EtOAc. The organic layer was washed with saturated brine and then dried over anhydrous sodium sulfate, and the solvent was evaporated under reduced pressure. The residue was purified by silica gel column chromatography (hexane:EtOAc=2:1 and chloroform:methanol=100:1-50:1). This was washed with 1 ml of EtOAc to prepare 46 mg of 2-[(2-methoxyethyl)(methyl)amino]-N-[2-(pyridin-3-ylacetyl)phenyl]-1,3-thiazole-4-carboxamide.

Example 11

To a solution of 397 mg of 2-morpholin-4-yl-1,3-oxazole-4-carboxylic acid and 450 µl of 4-methylmorpholine in 10 ml of THF was added 260 µl of isobutyl chloroformate under ice-cooling, followed by stirring at room temperature for 30 minutes. Under ice-cooling, a solution of 426 mg of 2-amino-N-pyridin-3-yl benzamide in 8 ml of THF was added thereto, followed by stirring at room temperature for 1 hour and at 60° C. overnight. The reaction mixture was concentrated under reduced pressure, water was then added thereto, and the precipitated solid was collected by filtration. This was suspended in ethanol, and 1.5 ml of a 4 M hydrogen chloride/EtOAc solution was added thereto, followed by stirring for 2 hours. The solid in the system was collected by filtration to prepare 250 mg of 2-morpholin-4-yl-N-[2-(pyridin-3-ylcarbamoyl)phenyl]-1,3-oxazole-4-carboxamide hydrochloride.

Example 12

To a solution of 578 mg of N-{2-[(5-hydroxypentyl)sulfanyl]phenyl}-2-morpholin-4-yl-1,3-thiazole-4-carboxamide in 5.78 ml of chloroform was added 734 mg of m-chloroperbenzoic acid, followed by stirring at room temperature for 6 hours. To the reaction mixture was added a saturated aqueous sodium hydrogen carbonate solution, and an aqueous sodium thiosulfate solution, followed by extraction with chloroform. The organic layer was washed with a saturated aqueous sodium hydrogen carbonate solution and saturated brine, and then dried over anhydrous magnesium sulfate, and the solvent was evaporated under reduced pressure. The residue was purified by silica gel column chromatography (chloroform:methanol=92:8), and then by preparative thin layer chromatography (chloroform:methanol=95:5) to prepare 560 mg of N-{2-[(5-hydroxypentyl)sulfonyl]phenyl}-2-morpholin-4-yl-1,3-thiazole-4-carboxamide.

Example 13

To 168 mg of 2-[methyl(4-{[2-(pyridin-3-ylcarbamoyl)phenyl]carbamoyl}-1,3-thiazol-2-yl)amino]ethylmethanesulfonate were added 0.84 ml of DMA, 0.58 ml of pyrrolidine and 58 mg of potassium iodide, followed by stirring at 70° C. for 6 hours. The reaction mixture was concentrated under reduced pressure, and the residue was then purified by preparative thin layer chromatography (chloroform:methanol=80:20). To this were added chloroform and diisopropyl ether, followed by stirring. The solid in the system was collected by filtration to prepare 122 mg of 2-[methyl(2-pyrrolidin-1-ylethyl)amino]-N-[2-(pyridin-3-ylcarbamoyl)phenyl]-1,3-thiazole-4-carboxamide.

Example 14 and Example 15

To a solution of 114 mg of 2-(cis-3-fluoro-4-hydroxypiperidin-1-yl)-N-[2-(tetrahydro-2H-pyran-4-ylcarbamoyl)phenyl]-1,3-thiazole-4-carboxamide in 5 ml of methylenechloride were added 180 mg of (2R)-3,3,3-trifluoro-2-methoxy-2-phenylpropionic acid, 160 mg of WSC-HCl, and 60 mg of 4-(N,N-dimethylamino)pyridine, followed by stirring at room temperature for 15 hours. The reaction liquid was purified by silica gel column chromatography (hexane:ether=1:3) as it is to prepare 10 mg of (2R)-3,3,3-trifluoro-2-methoxy-2-phenylpropionic acid (3S,4R)-3-fluoro-1-(4-{[2-(tetrahydro-2H-pyran-4-ylcarbamoyl)phenyl]carbamoyl}-1,3-thiazol-2-yl)piperidin-4-yl ester and 10 mg of (2R)-3,3,3-trifluoro-2-methoxy-2-phenylpropionic acid (3R,4S)-3-fluoro-1-(4-{[2-(tetrahydro-2H-pyran-4-ylcarbamoyl)phenyl]carbamoyl}-1,3-thiazol-2-yl)piperidin-4-yl ester.

Among these, to a solution of 10 mg of (2R)-3,3,3-trifluoro-2-methoxy-2-phenylpropionic acid (3S,4R)-3-fluoro-1-(4-{[2-(tetrahydro-2H-pyran-4-ylcarbamoyl)phenyl]carbamoyl}-1,3-thiazol-2-yl)piperidin-4-yl ester in 1 ml of methanol was added 0.06 ml of a 1 M aqueous sodium hydroxide solution, followed by leaving to stand for 1 day. The reaction liquid was concentrated under reduced pressure, and then to the residue was added 0.06 ml of a 1 M aqueous hydrochloric acid solution. The insoluble materials were collected by filtration to prepare 3.8 mg of 2-[(3S,4R)-3-fluoro-4-hydroxypiperidin-1-yl]-N-[2-(tetrahydro-2H-pyran-4-ylcarbamoyl)phenyl]-1,3-thiazole-4-carboxamide.

Similarly, 5.5 mg of 2-[(3R,4S)-3-fluoro-4-hydroxypiperidin-1-yl]-N-[2-(tetrahydro-2H-pyran-4-ylcarbamoyl)phenyl]-1,3-thiazole-4-carboxamide was prepared from 10 mg of (2R)-3,3,3-trifluoro-2-methoxy-2-phenylpropionic acid (3R,4S)-3-fluoro-1-(4-{[2-(tetrahydro-2H-pyran-4-ylcarbamoyl)phenyl]carbamoyl}-1,3-thiazol-2-yl)piperidin-4-yl ester.

Example 16

To a solution of 315 mg of 5-[(2-{[(2-morpholin-4-yl-1,3-thiazol-4-yl)carbonyl]amino}phenyl)sulfonyl]pentyl-methanesulfonate in 1.9 ml of DMF was added 119 mg of sodium azide, followed by stirring at 60° C. for 6 hours. To the reaction mixture was added a saturated aqueous sodium hydrogen carbonate solution, followed by extraction with EtOAc. The organic layer was washed with a saturated aqueous sodium hydrogen carbonate solution and saturated brine, and then dried over anhydrous magnesium sulfate, and the solvent was evaporated under reduced pressure. The residue was purified by preparative thin layer chromatography (EtOAc) to prepare 261 mg of N-{2-[(5-azidepentyl)sulfonyl]phenyl}-2-morpholin-4-yl-1,3-thiazole-4-carboxamide.

Example 17

To a solution of 261 mg of N-{2-[(5-azidepentyl)sulfonyl]phenyl}-2-morpholin-4-yl-1,3-thiazole-4-carboxamide in 2.61 ml of ethanol and 1.305 ml of THF was added palladium-carbon, followed by stirring at room temperature for 6 hours under a hydrogen atmosphere. After filtering the catalyst, the filtrate was concentrated. This was purified by preparative thin layer chromatography (chloroform:methanol:aqueous ammonia=4:1:0.1) to prepare 133 mg of N-{2-[(5-aminopentyl)sulfonyl]phenyl}-2-morpholin-4-yl-1,3-thiazole-4-carboxamide.

Example 18

To a mixture of 115 mg of N-[4-(3-aminopropoxy)-2-(tetrahydro-2H-pyran-4-ylcarbamoyl)phenyl]-2-[(2-methoxyethyl)(methyl)amino]-1,3-thiazole-4-carboxamide hydrochloride in 2 ml of THF were added 17 µl of acetyl chloride and 64 µl of triethylamine, followed by stirring at room temperature for 2 hours. To the reaction mixture was added a saturated aqueous sodium hydrogen carbonate solution, followed by extraction with chloroform. The organic layer was washed with saturated brine, and the solvent was then evaporated under reduced pressure. The residue was purified by silica gel chromatography (chloroform:methanol=20:1) to prepare 81 mg of N-[4-(3-acetamidepropoxy)-2-(tetrahydro-2H-pyran-4-ylcarbamoyl)phenyl]-2-[(2-methoxyethyl)(methyl)amino]-1,3-thiazole-4-carboxamide.

Example 19

To a mixture of 220 mg of N-(3-carbonyl-1-methyl-1H-pyrazol-4-yl)-2-phenyl-1,3-thiazole-4-carboxamide in 10 ml of acetic acid were added 10 ml of concentrated sulfuric acid and 3 ml of an aqueous solution of 116 mg of sodium nitrite under ice-cooling, followed by stirring at room temperature for 5 hours. To the reaction mixture was added water, and the resulting insoluble materials were collected by filtration to prepare 220 mg of 1-methyl-4-{[(2-phenyl-1,3-thiazol-4-yl)carbonyl]amino}-1H-pyrazole-3-carboxylic acid.

Example 20

To a mixture of 115 mg of N-[4-(3-aminopropoxy)-2-(tetrahydro-2H-pyran-4-ylcarbamoyl)phenyl]-2-[(2-methoxyethyl)(methyl)amino]-1,3-thiazole-4-carboxamide hydrochloride in 2 ml of THF were added 19 µl of methanesulfonylchloride and 64 µl of triethylamine, followed by stirring at room temperature for 2 hours. To the reaction mixture was added a saturated aqueous sodium hydrogen carbonate solution, followed by extraction with chloroform. The organic layer was washed with saturated brine, and the solvent was then evaporated under reduced pressure. The residue was purified by silica gel chromatography (chloroform:methanol=20:1) to prepare 96 mg of 2-[(2-methoxyethyl)(methyl)amino]-N-[4-{3-[(methylsulfonyl)amino]propoxy}-2-(tetrahydro-2H-pyran-4-ylcarbamoyl)phenyl]-1,3-thiazole-4-carboxamide.

Example 21

To a solution of 90 mg of N-{2-[(5-hydroxypentyl)sulfonyl]phenyl}-2-morpholin-4-yl-1,3-thiazole-4-carboxamide in 1.8 ml of methylenechloride were added 58 µl of acetic anhydride, 0.33 ml of pyridine, and 25 mg of 4-(N,N-dimethylamino)pyridine, followed by stirring at room temperature for 3 days. The reaction liquid was concentrated under reduced pressure, and the residue was then purified by preparative thin layer chromatography (EtOAc). To this were added EtOAc and hexane, followed by stirring at room temperature. The solid in the system was collected by filtration to prepare 72 mg of 5-[(2-{[(2-morpholin-4-yl-1,3-thiazol-4-yl)carbonyl]amino}phenyl)sulfonyl]pentyl acetate.

Example 22

To a solution of 508 mg of 2-[(2-hydroxyethyl)(methyl)amino]-N-[2-(pyridin-3-ylcarbamoyl)phenyl]-1,3-thiazole-4-carboxamide in 5.08 ml of methylenechloride were added 0.36 ml of triethylamine and 0.2 ml of methanesulfonylchloride under ice-cooling, followed by stirring for 1 hour. To the reaction mixture was added water, followed by extraction with methylenechloride. The organic layer was washed with water and saturated brine, and then dried over anhydrous magnesium sulfate, and the solvent was evaporated under reduced pressure to prepare 608 mg of 2-[methyl(4-{[2-(pyridin-3-ylcarbamoyl)phenyl]carbamoyl}-1,3-thiazol-2-yl)amino]ethylmethanesulfonate.

Example 23

Under an argon atmosphere, a mixture of 380 mg of 2-[(2-methoxyethyl)(methyl)amino]-1,3-oxazole-4-carboxylic acid and 476 mg of methyl 2-amino-5-(morpholin-4-ylmethyl)benzoate in 11 ml of pyridine was cooled to −15° C., and 195 µl of phosphorous oxychloride was added slowly thereto, followed by stirring for 2 hours. To the reaction mixture was added a saturated aqueous sodium hydrogen carbonate solution, followed by extraction with chloroform. The organic layer was washed with saturated brine and the solvent was evaporated under reduced pressure. The residue was purified by silica gel chromatography (chloroform:methanol=20:1) to prepare 288 mg of methyl 2-[({2-[(2-methoxyethyl)(methyl)amino]-1,3-oxazol-4-yl}carbonyl)amino]-5-(morpholin-4-ylmethyl)benzoate.

Example 24

To a mixture of 95 mg of 2-(methyl[(3R)-pyrrolidin-3-yl]amino}-N-[2-(pyridin-3-ylcarbamoyl)phenyl]-1,3-thiazole-4-carboxamide in 3.8 ml of methylenechloride and 1.9 ml of acetonitrile were added 375 µl of a 36% aqueous formaldehyde solution and 143 mg of sodium triacetoxyborohydride, followed by stirring at room temperature overnight. To the reaction mixture was added a saturated aqueous sodium hydrogen carbonate solution, followed by filtration with granular Presep diatomaceous earth (Wako Pure Chemical Industries, Ltd.), and the filtrate was concentrated. The residue was purified by preparative thin layer chromatography (chloroform:methanol=80:20). To a solution thereof in chloroform was added a 4 M hydrogen chloride/EtOAc solution, and hexane was added thereto, followed by stirring. The precipitate was collected by filtration to prepare 78 mg of 2-(methyl[(3R)-1-methylpyrrolidin-3-yl]amino}-N-[2-(pyridin-3-ylcarbamoyl)phenyl]-1,3-thiazole-4-carboxamide dihydrochloride.

Example 25

Under an argon atmosphere, to a suspension of 172 mg of 2-cyano-6-{[(2-morpholin-4-yl-1,3-thiazol-4-yl)carbonyl]amino}benzoic acid in 3 ml of THF were added 53 µl of 4-methylmorpholine and 62 µl of isobutyl chloroformate, followed by stirring at room temperature for 10 minutes. Subsequently, 45 mg of pyridin-3-amine was added thereto, followed by stirring at 50° C. for 15 hours. To the reaction mixture was added a saturated aqueous sodium hydrogen carbonate solution, followed by extraction with chloroform. The organic layer was washed with saturated brine and the solvent was evaporated under reduced pressure. The residue was purified by silica gel column chromatography (chloroform:methanol=50:1). This was suspended in 1 ml of ethanol, and 37 µl of 4 M hydrogen chloride/EtOAc was added thereto, followed by stirring for 1 hour. The precipitated solid was collected by filtration and washed with EtOAc to prepare 13 mg of N-[3-cyano-2-(pyridin-3-ylcarbamoyl)phenyl]-2-morpholin-4-yl-1,3-thiazole-4-carboxamide hydrochloride.

Example 26

To a solution of 80 mg of 5-(morpholin-4-ylmethyl)-2-[({2-[4-(pyrimidin-2-yloxy)piperidin-1-yl]-1,3-thiazol-4-yl}carbonyl)amino]benzoic acid in 1.1 ml of DMF were added 40 mg of WSC-HCl, 30 mg of HOBt, 16 mg of ethylamine hydrochloride, and 0.04 ml of diisopropylethylamine, followed by stirring at room temperature for 2 days. To the reaction mixture was added a saturated aqueous sodium hydrogen carbonate solution, followed by extraction with EtOAc. The organic layer was dried over anhydrous magnesium sulfate and the solvent was evaporated under reduced pressure. The residue was purified by silica gel column chromatography (chloroform:methanol=20:1) to prepare 74 mg of N-[2-(ethylcarbamoyl)-4-(morpholin-4-ylmethyl)phenyl]-2-[4-(pyrimidin-2-yloxy)piperidin-1-yl]-1,3-thiazole-4-carboxamide.

Example 27

To a suspension of 200 mg of 2-(3-methoxyazetidin-1-yl)-1,3-thiazole-4-carboxylic acid in 9 ml of DMF were added 250 mg of fluoro-N,N,N',N'-tetramethylformamidinium hexafluorophosphate, 219 mg of 2-amino-N-(cis-4-hydroxy cyclohexyl)benzamide, and 260 µl of triethylamine under ice-cooling, followed by stirring at 0° C. for 30 minutes and at room temperature for 3 hours. Further, 250 mg of fluoro-N,N,N',N'-tetramethylformamidinium hexafluorophosphate was added thereto, followed by stirring under ice-cooling for 45 minutes and at room temperature overnight. The reaction mixture was concentrated under reduced pressure, and then water and an aqueous hydrochloric acid solution were added thereto, followed by extraction with chloroform. The organic layer was washed with saturated brine and then dried over anhydrous magnesium sulfate, and the solvent was evaporated under reduced pressure. The residue was purified by silica gel column chromatography (chloroform:methanol=100:0-90:10). This was heated and dissolved in 2-propanol, and then cooled to room temperature. The precipitate was collected by filtration to prepare 126 mg of N-{2-[(cis-4-hydroxy cyclohexyl)carbamoyl]phenyl}-2-(3-methoxyazetidin-1-yl)-1,3-thiazole-4-carboxamide.

Example 28

To a solution of 148 mg of 4-ethoxypiperidine hydrochloride in 2 ml of DMA were added 339 µl of triethylamine and 200 mg of 2-bromo-N-[2-(tetrahydro-2H-pyran-4-ylcarbamoyl)phenyl]-1,3-thiazole-4-carboxamide, followed by stirring at 100° C. for 8 hours. After air-cooling, water was added thereto and the precipitate was collected by filtration. This was purified by silica gel column chromatography (hexane:EtOAc=1:1). This was heated and dissolved in methanol, and then cooled to room temperature. The precipitate was collected by filtration to prepare 127 mg of 2-(4-ethoxypiperidin-1-yl)-N-[2-(tetrahydro-2H-pyran-4-ylcarbamoyl)phenyl]-1,3-thiazole-4-carboxamide.

Example 29

A solution of 800 mg of 2-bromo-N-[2-(pyridin-3-ylcarbamoyl)phenyl]-1,3-thiazole-4-carboxamide, 1.38 g of (3R)—N-methyl-1-(trifluoroacetyl)pyrrolidin-3-amine hydrochloride, and 1.73 ml of diisopropylamine in 6 ml of 1-methyl-2-pyrrolidinone was radiated with microwave (Biotage, Infinity Sixty) at 200° C. for 45 minutes. To the reaction mixture was added water, followed by extraction with EtOAc. The organic layer was washed with water and saturated brine, and then dried over anhydrous magnesium sulfate, and the solvent was evaporated under reduced pressure. The residue was purified by silica gel column chromatography (chloroform:methanol=90:10).

To a solution thereof in 10 ml of methanol was added 4 ml of a 1 M aqueous sodium hydroxide solution, followed by stirring at room temperature overnight. To a reaction mixture was added water and brine, followed by extraction with chloroform. The organic layer was dried over anhydrous sodium sulfate, and the solvent was evaporated under reduced pressure. The residue was purified by preparative thin layer chromatography (chloroform:methanol:aqueous ammonia=4:1:0.1) to prepare 445 mg of 2-(methyl[(3R)-pyrrolidin-3-yl]amino}-N-[2-(pyridin-3-ylcarbamoyl)phenyl]-1,3-thiazole-4-carboxamide.

Example 30

To a solution of 180 mg of 2-[methyl(tetrahydro-2H-pyran-4-ylmethyl)amino]-1,3-thiazole-4-carboxylic acid in 1.2 ml of DMF were added 117 mg of 2-amino-N-pyridin-3-yl benzamide, 110 mg of WSC-HCl, and 100 mg of HOBt, followed by stirring at 60° C. for 3 days. To the reaction liquid was added an aqueous sodium hydrogen carbonate solution, and the resulting insoluble materials were collected by filtration. This was washed with acetonitrile to prepare 195 mg of 2-[methyl(tetrahydro-2H-pyran-4-ylmethyl)amino]-N-[2-(pyridin-3-ylcarbamoyl)phenyl]-1,3-thiazole-4-carboxamide.

Example 31

To a solution of 35 mg of 2-{2-[methyl(tetrahydro-2H-pyran-4-ylmethyl)amino]-1,3-thiazol-4-yl}-6-(morpholin-4-ylmethyl)-4H-3,1-benzoxazin-4-one in 5 ml of acetonitrile was added 41 mg of 1-pyridin-3-yl methanamine, followed by heating under reflux for 6 hours. The reaction mixture was concentrated under reduced pressure, and then to the residue was added water, followed by extraction with EtOAc. The organic layer was dried over anhydrous magnesium sulfate and the solvent was evaporated under reduced pressure. The residue was heated and dissolved in EtOAc and then cooled to room temperature. The precipitate was collected by filtration to prepare 31 mg of 2-[methyl(tetrahydro-2H-pyran-4-ylmethyl)amino]-N-{4-(morpholin-4-ylmethyl)-2-[(pyridin-3-ylmethyl)carbamoyl]phenyl}-1,3-thiazole-4-carboxamide.

Example 32

To a solution of 174 mg of 2-{2-[methyl(tetrahydro-2H-pyran-4-ylmethyl)amino]-1,3-thiazol-4-yl}-4H-3,1-benzoxadin-4-one in 2.6 ml of THF was added 1.41 ml of a 0.96 M methyl magnesium bromide/THF solution at 0° C., followed by stirring at room temperature overnight. To the reaction mixture was added a saturated aqueous ammonium chloride solution, followed by extraction with EtOAc. The organic layer was washed with saturated brine and then dried over anhydrous magnesium sulfate, and the solvent was evaporated under reduced pressure. The residue was purified by preparative thin layer chromatography (chloroform:methanol=95:5 and chloroform) to prepare 5.3 mg of N-(2-acetylphenyl)-2-[methyl(tetrahydro-2H-pyran-4-ylmethyl)amino]-1,3-thiazole-4-carboxamide.

Example 33

To a suspension of 464 mg of methyl 5-(morpholin-4-ylmethyl)-2-[({2-[4-(pyrimidin-2-yloxy)piperidin-1-yl]-1,3-thiazol-4-yl}carbonyl)amino]benzoate in 5 ml of THF was added 1.03 ml of a 1 M aqueous sodium hydroxide solution, followed by stirring at room temperature for 13 hours and at 50° C. for 4 hours with heating. To the reaction mixture were added 1.03 ml of a 1 M aqueous hydrochloric acid solution and 5 ml of water, and the precipitated solid was collected by filtration to prepare 325 mg of 5-(morpholin-4-ylmethyl)-2-[({2-[4-(pyrimidin-2-yloxy)piperidin-1-yl]-1,3-thiazol-4-yl}carbonyl)amino]benzoic acid.

Example 34

To a solution of 141 mg of 1-{4-[({2-[4-(pyrimidin-2-yloxy)piperidin-1-yl]-1,3-thiazol-4-yl}carbonyl)amino]-3-tetrahydro-2H-pyran-4-ylcarbamoyl)benzyl}piperidin-4-yl acetate hydrochloride in 3 ml of methanol was added 56 mg of potassium carbonate, followed by stirring for 2 hours. To the reaction mixture was added water, followed by extraction with chloroform. The organic layer was washed with saturated brine, and the solvent was then evaporated under reduced pressure. The residue was purified by silica gel column chromatography (chloroform:methanol=30:1). This was dissolved in ethanol, and 4 M hydrogen chloride/EtOAc was added thereto, followed by stirring for 1 hour. The precipitate was collected by filtration to prepare 95 mg of N-{4-[(4-hydroxypiperidin-1-yl)methyl]-2-(tetrahydro-2H-pyran-4-ylcarbamoyl)phenyl}-2-[4-(pyrimidin-2-yloxy)piperidin-1-yl]-1,3-thiazole-4-carboxamide hydrochloride.

Example 35

To 302 mg of tert-butyl (3-{4-[({2-[(2-methoxyethyl)(methyl)amino]-1,3-thiazol-4-yl}carbonyl)amino]-3-(tetrahydro-2H-pyran-4-ylcarbamoyl)phenoxy}propyl)carbamate was added 3 ml of 4 M hydrogen chloride/EtOAc, followed by stirring at room temperature for 40 minutes.
To the reaction liquid was added 3 ml of ethanol, and the solvent was evaporated under reduced pressure. The residue was washed with EtOAc to prepare 259 mg of N-[4-(3-aminopropoxy)-2-(tetrahydro-2H-pyran-4-ylcarbamoyl)phenyl]-2-[(2-methoxyethyl)(methyl)amino]-1,3-thiazole-4-carboxamide hydrochloride.

Example 36

To 179 mg of N-[5-(benzyloxy)-2-(tetrahydro-2H-pyran-4-ylcarbamoyl)phenyl]-2-morpholin-4-yl-1,3-thiazole-4-carboxamide were added 253 mg of 1,2,3,4,5-pentamethylbenzene and 5 ml of trifluoroacetic acid, followed by stirring at room temperature for 24 hours. The reaction mixture was concentrated under reduced pressure, and then a 1 M aqueous hydrochloric acid solution was added thereto, followed by extraction with chloroform. The organic layer was washed with saturated brine, and the solvent was then evaporated under reduced pressure. The residue was purified by silica gel column chromatography (chloroform:methanol=80:20) to prepare 93 mg of N-[5-hydroxy-2-(tetrahydro-2H-pyran-4-ylcarbamoyl)phenyl]-2-morpholin-4-yl-1,3-thiazole-4-carboxamide.

Example 37

Under an argon atmosphere, to a solution of 91 mg of N-{4-[3-(benzyloxy) propoxy]-2-(tetrahydro-2H-pyran-4-ylcarbamoyl)phenyl}-2-[(2-methoxyethyl)(methyl)amino]-1,3-thiazole-4-carboxamide and 116 mg of 1,2,3,4,5-pentamethylbenzene in 4 ml of methylenechloride was added slowly 780 µl of a 1.0 M trichloroborane/heptane solution at −78°, followed by warming to room temperature and stirring for 2 hours. To the reaction mixture were added MeOH and water, followed by extraction with chloroform. The organic layer was washed with saturated brine, and the solvent was then evaporated under reduced pressure. The residue was purified by silica gel column chromatography (chloroform:methanol=30:1). This was washed with hexane to prepare 41 mg of N-[4-(3-hydroxypropoxy)-2-(tetrahydro-2H-pyran-4-ylcarbamoyl)phenyl]-2-[(2-methoxyethyl)(methyl)amino]-1,3-thiazole-4-carboxamide.

Example 38

To a solution of 400 mg of benzyl 4-[(2-{[(2-morpholin-4-yl-1,3-thiazol-4-yl)carbonyl]amino}phenyl)sulfonyl]piperidine-1-carboxylate in 10 ml of acetonitrile and 10 ml of methylenechloride was added 700 mg of trimethylsilyl iodide, followed by stirring at room temperature for 2 hours. To the reaction liquid was added a saturated aqueous sodium hydrogen carbonate solution, followed by extraction with chloroform. The organic layer was washed with an aqueous sodium thiosulfate solution and then dried over anhydrous magnesium sulfate, and the solvent was evaporated under reduced pressure. The residue was purified by washed with acetonitrile to prepare 35 mg of 2-morpholin-4-yl-N-[2-(piperidin-4-ylsulfonyl)phenyl]-1,3-thiazole-4-carboxamide.

Example 39

To a solution of 160 mg of 2,5-difluoro-4-[({2-[4-(pyrimidin-2-yloxy)piperidin-1-yl]-1,3-thiazol-4-yl}carbonyl)amino]benzoic acid in 5 ml of methanol was added 0.05 ml of thionyl chloride under ice-cooling, followed by stirring at room temperature for 2 days. The reaction mixture was concentrated under reduced pressure, and the residue was then purified by silica gel column chromatography (chloroform:methanol=20:1). This was heated and dissolved in a mixed solvent of EtOAc and acetonitrile, and then cooled to room temperature. The precipitate was collected by filtration to prepare 52 mg of methyl 2,5-difluoro-4-[({2-[4-(pyrimidin-2-yloxy)piperidin-1-yl]-1,3-thiazol-4-yl}carbonyl)amino] benzoate.

Example 40

A solution of 7.3 mg of N-methyl-1-phenyl methanamine, 12.1 mg of 2-bromo-N-[2-(pyridin-3-ylcarbamoyl)phenyl]-1,3-thiazole-4-carboxamide, and 20.9 µl of triethylamine in 0.2 ml of DMA was stirred at 100° C. for 5 days. The reaction mixture was cooled to room temperature and filtrated, and the filtrate was then purified by preparative high performance liquid chromatography (methanol-aqueous 0.1% formic acid solution) to prepare 4.7 mg of 2-[benzyl(methyl)amino]-N-[2-(pyridin-3-ylcarbamoyl)phenyl]-1,3-thiazole-4-carboxamide.

Example 41

To a solution of 2.6 mg of N,N-dimethylethane-1,2-diamine in 60 µl of 1-methyl-2-pyrrolidinone were added 8.1 mg of 2-{[(2-phenyl-1,3-thiazol-4-yl)carbonyl] amino}benzoic acid, 3.5 µl of triethylamine, a solution of 3.4 mg of HOBt in 1 ml of DMF, and 75 mg of PL-DCC Resin (Polymer Laboratories Ltd.), followed by stirring at room temperature overnight. To the reaction mixture was added 50 mg of MP-Carbonate (Argonaut Technologies, Inc.) and 50 mg of PS-Isocyanate (Argonaut Technologies, Inc.), followed by stirring at room temperature for 4 hours, and the insoluble materials were filtered. The filtrate was concentrated under reduced pressure, and the obtained residue was purified by preparative high performance liquid chromatography (methanol-aqueous 0.1% formic acid solution) to prepare 2.1 mg of N-(2-{[2-(dimethylamino)ethyl]carbamoyl}phenyl)-2-phenyl-1,3-thiazole-4-carboxamide.

Example 42

To a solution of 4.1 mg of 2-aminobenzamide, 5.3 mg of 2-(2-thienyl)-1,3-thiazole-4-carboxylic acid, and 3.4 mg of HOBt in 1 ml of DMF was added 100 mg of PS-carbodiimide (Argonaut Technologies, Inc.), followed by stirring at room temperature overnight. To the reaction liquid were added 50 mg of MP-carbonate (Argonaut Technologies, Inc.) and 50 mg of PS-Isocyanate (Argonaut Technologies, Inc.), followed by stirring at room temperature for 4 hours, and the insoluble materials were filtered. The filtrate was concentrated under reduced pressure to prepare 7.5 mg of N-(2-carbamoylphenyl)-2-(2-thienyl)-1,3-thiazole-4-carboxamide.

Example 43

To a solution of 821 mg of 2-phenyl-1,3-thiazole-4-carboxylic acid in 30 ml of methylenechloride were added dropwise 520 µl of oxalyl chloride and 15 µl of DMF at 0° C., followed by stirring at room temperature for 3 hours. From this reaction liquid, 300 µl portion was collected, a solution of 8.3 mg of 2-(methylsulfonyl)aniline hydrochloride and 11 µl of triethylamine in 200 µl of methylenechloride was added thereto at room temperature, followed by stirring overnight. To the reaction liquid were added 100 mg of PS-Isocyanate (Argonaut Technologies, Inc.), 75 mg of PS-Trisamine (Argonaut Technologies, Inc.), and 1 ml of DMF, followed by stirring at room temperature overnight, and the insoluble materials were filtered. The filtrate was concentrated under reduced pressure and the obtained residue was purified by preparative high performance liquid chromatography (methanol-aqueous 0.1% formic acid solution) to prepare 8.4 mg of N-[2-(methylsulfonyl)phenyl]-2-phenyl-1,3-thiazole-4-carboxamide.

Example 1181

To 100 mg of N-{4-(chloromethyl)-2-[(2-methoxyethyl)carbamoyl]phenyl}-2-[(3S)-3-methoxypyrrolidin-1-yl]-1,3-thiazole-4-carboxamide were added 2 mL of DMF, 61 mg of (2S)-2-methylmorpholine hydrochloride, and 92 µl of triethylamine, followed by stirring at room temperature for 4 days. To the reaction mixture was added a saturated aqueous sodium hydrogen carbonate solution, followed by extraction with chloroform. The organic layer was washed with saturated brine and then dried over anhydrous sodium sulfate, and the solvent was evaporated under reduced pressure. The residue was purified by silica gel column chromatography (chloroform:methanol=100:0-30:1). This was dissolved in ethanol, and 26 mg of fumaric acid was then added thereto, followed by concentration. Acetonitrile was added thereto, followed by stirring, and then the solid was collected by filtration to prepare 88 mg of N-(2-[(2-methoxyethyl)carbamoyl]-4-{[(2S)-2-methylmorpholin-4-yl] methyl}phenyl)-2-[(3S)-3-methoxypyrrolidin-1-yl]-1,3-thiazole-4-carboxamide fumarate.

Example 1182

Under an argon atmosphere, to 388 mg of N-{2-[(2-methoxyethyl)carbamoyl-4-(morpholin-4-ylmethyl)phenyl}-2-[(3S)-3-methoxypyrrolidin-1-yl]-1,3-thiazole-4-carboxamide were added 10 mL of 1,2-dichloroethane, 0.11 mL of ethyl chloroformate, and 0.18 mL of isopropanol, followed by heating under reflux at 100° C. for 3 hours. After air-cooling, to the reaction mixture was added water, followed by extraction with chloroform. The organic layer was washed with saturated brine and then dried over anhydrous sodium sulfate, and the solvent was evaporated under reduced pressure. The residue was purified by silica gel column chromatography (chloroform:methanol=99:1-10:1) to prepare 11 mg of N-{4-(isopropoxymethyl)-2-[(2-methoxyethyl)carbamoyl]phenyl}-2-[(3S)-3-methoxypyrrolidin-1-yl]-1,3-thiazole-4-carboxamide.

Example 1183

To a suspension of 120 mg of N-(1-oxo-2,3-dihydro-1H-inden-5-yl)-2-[4-(pyrimidin-2-yloxy)piperidin-1-yl]-1,3-thiazole-4-carboxamide in 2 ml of methanol-3 ml of THF was added 21 mg of sodium borohydride, followed by stirring at room temperature for 15 hours. The reaction mixture was concentrated, and a saturated aqueous sodium hydrogen carbonate solution was then added thereto, followed by extraction with chloroform. The organic layer was washed with saturated brine and then dried over anhydrous sodium sulfate, and the solvent was evaporated under reduced pressure. The residue was purified by silica gel column chromatography (chloroform/methanol=100/1-50/1) to prepare 89 mg of N-(1-hydroxy-2,3-dihydro-1H-inden-5-yl)-2-[4-(pyrimidin-2-yloxy)piperidin-1-yl]-1,3-thiazole-4-carboxamide.

Example 1184

To 131 mg of 5-(morpholin-4-ylmethyl)-2-[({2-[4-(pyrimidin-2-yloxy)piperidin-1-yl]-1,3-thiazol-4-yl}carbonyl)

amino]benzoic acid were added 25 ml of methylenechloride and 75 mg of (isocyanoimino)triphenylphosphorane, followed by stirring at room temperature for 18 hours. The reaction mixture was purified by preparative thin layer chromatography (chloroform:methanol=94:6) to prepare 16 mg of N-[4-(morpholin-4-ylmethyl)-2-(1,3,4-oxadiazol-2-yl) phenyl]-2-[4-(pyrimidin-2-yloxy)piperidin-1-yl]-1,3-thiazole-4-carboxamide.

Example 1185

To 100 mg of 5-[(3,3-dimethylmorpholin-4-yl)methyl]-2-[({2-[(3S)-3-methoxypyrrolidin-1-yl]-1,3-thiazol-4-yl}carbonyl)amino]benzoic acid were added 2 mL of methylenechloride and 51 mg of CDI, followed by stirring at room temperature for 3 hours. The reaction mixture was concentrated, and then to the residue were added toluene (2 mL) and 31 mg of N-hydroxyacetamidine, followed by stirring at room temperature for 3 hours and then heating under reflux for 3 days. After air-cooling, the reaction mixture was concentrated. The residue was purified by silica gel column chromatography (chloroform:methanol=99:1) to prepare 35 mg of N-{4-[(3,3-dimethylmorpholin-4-yl)methyl]-2-(3-methyl-1,2,4-oxadiazol-5-yl)phenyl}-2-[(3S)-3-methoxypyrrolidin-1-yl]-1,3-thiazole-4-carboxamide.

Example 1186

To 100 mg of 4-[({2-[4-(pyrimidin-2-yloxy)piperidin-1-yl]-1,3-thiazol-4-yl}carbonyl)amino]-3-(trifluoromethoxy) benzoic acid were added 1 ml of DMF, 61 mg of 1,8-diazabicyclo[5.4.0]-7-undecene, 100 mg of CDI, and 100 mg of methanesulfonamide, followed by stirring at 60° C. for 1 hour. The reaction mixture was concentrated, and then to the resulting residue were added water and a 1 M aqueous hydrochloric acid solution. The resulting insoluble materials were collected by filtration. This was washed with acetonitrile to prepare 110 mg of N-{4-[(methanesulfonyl)carbamoyl]-2-(trifluoromethoxy)phenyl}-2-[4-pyrimidin-2-yloxy)piperidin-1-yl]-1,3-thiazole-4-carboxamide.

Example 1187

To 110 mg of 5-[(3,3-dimethylmorpholin-4-yl)methyl]-2-[({2-[(3S)-3-methoxypyrrolidin-1-yl]-1,3-thiazol-4-yl}carbonyl)amino]benzoic acid were added 2 mL of DMF, 106 mg of HATU, 162 µL of triethylamine, and 79 mg of 3-fluoropropylamine hydrochloride, followed by stirring at room temperature for 24 hours. To the reaction mixture was added a saturated aqueous sodium hydrogen carbonate solution, followed by extraction with chloroform. The organic layer was washed with saturated brine and then dried over anhydrous sodium sulfate, and the solvent was evaporated under reduced pressure. The residue was purified by silica gel column chromatography (chloroform). This was dissolved in 2 mL of ethanol, and 22 mg of fumaric acid was added thereto, followed by stirring, heating, and dissolving, and then cooling by leaving to stand. After addition of diisopropyl ether, the precipitated solid was collected by filtration to prepare 41 mg of N-{4-[(3,3-dimethylmorpholin-4-yl)methyl]-2-[(3-fluoropropyl)carbamoyl]phenyl}-2-[(3S)-3-methoxypyrrolidin-1-yl]-1,3-thiazole-4-carboxamide fumarate.

Example 1188

To 2.0 g of N-{2-[(2-methoxyethyl)carbamoyl-4-(morpholin-4-ylmethyl)phenyl}-2-[(3S)-3-methoxypyrrolidin-1-yl]-1,3-thiazole-4-carboxamide was added 0.57 ml of ethyl chloroformate in 50 ml of 1,2-dichloroethane, followed by heating under reflux for 1.5 hours. To the reaction liquid was added a saturated aqueous sodium hydrogen carbonate solution, followed by extraction with chloroform. The organic layer was washed with saturated brine and then dried over anhydrous sodium sulfate, and the solvent was evaporated under reduced pressure. The residue was purified by silica gel column chromatography (chloroform/methanol=100/0-40/1) to prepare 740 mg of N-{4-(chloromethyl)-2-[(2-methoxyethyl)carbamoyl]phenyl}-2-[(3S)-3-methoxypyrrolidin-1-yl]-1,3-thiazole-4-carboxamide.

Example 1189

To 292 mg of N-{4-(1-benzylpyrrolidin-3-yl)-2-[(2-methoxyethyl)carbamoyl]phenyl-2-[(3S)-3-methoxypyrrolidin-1-yl]-1,3-thiazole-4-carboxamide was added 84 µl of 1-chloroethyl chlorocarbonate in 6 ml of 1,2-dichloroethane, followed by heating under reflux for 2 hours. The reaction mixture was concentrated under reduced pressure, and then 6 ml of methanol was added thereto, followed by heating under reflux for 1 hour. The reaction mixture was concentrated under reduced pressure, and then 130 mg of di-tert-butyl dicarbonate in 3 ml of methylenechloride and 166 µl of triethylamine, followed by stirring at room temperature for 16 hours. To the reaction liquid was added a saturated aqueous sodium hydrogen carbonate solution, followed by extraction with chloroform. The organic layer was washed with saturated brine and then dried over anhydrous sodium sulfate, and the solvent was evaporated under reduced pressure. The residue was purified by silica gel column chromatography (chloroform/methanol=100/0-20/1) to prepare 68 mg of tert-butyl 3-{3-[(2-methoxyethyl)carbamoyl]-4-[({2-[(3S)-3-methoxypyrrolidin-1-yl]-1,3-thiazol-4-yl}carbonyl)amino] phenyl}pyrrolidine-1-carboxylate.

Example 1190

To 172 mg of N-{4-(2-chloroethyl)-2-[(2-methoxyethyl) carbamoyl]phenyl}-2-[(3S)-3-methoxypyrrolidin-1-yl]-1,3-thiazole-4-carboxamide were added 87 mg of potassium acetate and 6 mg of potassium iodide in DMF, followed by stirring at 70° C. for 6 days. To the reaction mixture was added a saturated aqueous sodium hydrogen carbonate solution, followed by extraction with chloroform. The organic layer was washed with saturated brine and then dried over anhydrous sodium sulfate, and the solvent was evaporated under reduced pressure. The residue was purified by silica gel column chromatography (chloroform/methanol=100/0-40/1) to prepare 120 mg of 2-{3-[(2-methoxyethyl)carbamoyl]-4-[({2-[(3S)-3-methoxypyrrolidin-1-yl]-1,3-thiazol-4-yl}carbonyl)amino]phenyl}ethyl acetate.

Example 1191

To 64 mg of N-{4-(2-hydroxyethyl)-2-[(2-methoxyethyl) carbamoyl]phenyl}-2-[(3S)-3-methoxypyrrolidin-1-yl]-1,3-thiazole-4-carboxamide were added 10 µl of methyl iodide in acetonitrile and 36 mg of silver carbonate, followed by stirring at room temperature with light-shielding for 10 days. The reaction mixture was filtered through Celite, and then the solvent was evaporated from the filtrate under reduced pressure. The residue was purified by silica gel column chromatography (chloroform/methanol=100/0-30/1) to prepare 5 mg of N-{4-(2-methoxyethyl)-2-[(2-methoxyethyl)carbamoyl]phenyl}-2-[(3S)-3-methoxypyrrolidin-1-yl]-1,3-thiazole-4-carboxamide.

Example 1192

A solution of 11.3 mg of N-{4-(chloromethyl)-2-[(2-methoxyethyl)carbamoyl]phenyl}-2-[(3S)-3-methoxypyrrolidin-1-yl]-1,3-thiazole-4-carboxamide, 3.6 mg of pyrrolidine, and 10.5 μl of triethylamine in 0.25 ml of DMF was stirred at room temperature for 3 days. To the reaction mixture was added an aqueous sodium hydrogen carbonate solution, followed by extraction with chloroform, and the organic layer was concentrated under reduced pressure. The obtained residue was purified by preparative high performance liquid chromatography (methanol-aqueous 0.1% formic acid solution) to prepare 3.5 mg of N-{2-[(2-methoxyethyl)carbamoyl]-4-(pyrrolidin-1-ylmethyl)phenyl}-2-[(3S)-3-methoxypyrrolidin-1-yl]-1,3-thiazole-4-carboxamide.

Example 1193

To a solution of 11.3 mg of N-{4-(chloromethyl)-2-[(2-methoxyethyl)carbamoyl]phenyl}-2-[(3S)-3-methoxypyrrolidin-1-yl]-1,3-thiazole-4-carboxamide and 5.4 mg of N-methyl aniline in 0.25 ml of DMF was added 24.4 mg of cesium carbonate, followed by stirring at room temperature for 3 days and then stirring at 50° C. for 1 hour. To the reaction mixture was added water, followed by extraction with chloroform, and the organic layer was concentrated under reduced pressure. The obtained residue was purified by preparative high performance liquid chromatography (methanol-aqueous 0.1% formic acid solution) to prepare 3.5 mg of N-(2-[(2-methoxyethyl)carbamoyl]-4-{[methyl(phenyl)amino]methyl}phenyl)-2-[(3S)-3-methoxypyrrolidin-1-yl]-1,3-thiazole-4-carboxamide.

Example 1194

To a solution of 11.3 mg of N-{4-(chloromethyl)-2-[(2-methoxyethyl)carbamoyl]phenyl}-2-[(3S)-3-methoxypyrrolidin-1-yl]-1,3-thiazole-4-carboxamide and 4.1 mg of 2-methyl imidazole in 0.25 ml of DMF was added 2.0 mg of 60% sodium hydride, followed by stirring at room temperature for 3 days and then stirring at 50° C. for 1 hour. To the reaction mixture was added water, followed by extraction with chloroform, and the organic layer was concentrated under reduced pressure. The obtained residue was purified by preparative high performance liquid chromatography (methanol-aqueous 0.1% formic acid solution) to prepare 1.6 mg of N-{2-[(2-methoxyethyl)carbamoyl]-4-[(2-methyl-1H-imidazol-1-yl)methyl]phenyl}-2-[(3S)-3-methoxypyrrolidin-1-yl]-1,3-thiazole-4-carboxamide.

Example 1195

To a solution of 11.3 mg of N-{4-(chloromethyl)-2-[(2-methoxyethyl)carbamoyl]phenyl}-2-[(3S)-3-methoxypyrrolidin-1-yl]-1,3-thiazole-4-carboxamide and 13.1 mg of tert-butyl 3-phenyl-piperazine-1-carboxylate in 0.25 ml of DMF was added 24.4 mg of cesium carbonate, followed by stirring at room temperature for 3 days and then stirring at 50° C. for 1 hour. To the reaction mixture was added water, followed by extraction with chloroform, and the organic layer was concentrated under reduced pressure. This was dissolved in 0.5 ml of 1,4-dioxane, and then 0.5 ml of a 4 M hydrogen chloride/1,4-dioxane solution was added thereto, followed by stirring at room temperature for 2 hours. The reaction solvent was evaporated under reduced pressure, and to the resulting residue was added a saturated aqueous sodium hydrogen carbonate solution, followed by extraction with chloroform. The organic layer was concentrated under reduced pressure, and the residue was purified by preparative high performance liquid chromatography (methanol-aqueous 0.1% formic acid solution) to prepare 2.5 mg of N-{2-[(2-methoxyethyl)carbamoyl]-4-[(2-phenyl piperazin-1-yl)methyl]phenyl}-2-[(3S)-3-methoxypyrrolidin-1-yl]-1,3-thiazole-4-carboxamide.

In the same manner as the methods of Examples 1 to 43 and 1181 to 1195 above, the compounds of Examples 44 to 1180 and 1196 to 1767 shown in Tables 62 to 211 below were prepared, respectively, using a corresponding starting materials. For Tables 62 to 211, Str denotes the structural formulae. The structural formulae marked with * in the tables indicate that the compounds are optically active. Further, in Examples 1234 and 1269, the substituents on carbon adjacent on piperidine ring are in cis configuration, giving a mixture of two diastereomers. The head in each cell of in the right columns of Tables 62 to 211 shows the Example numbers which were referred to for the production processes as Syn, with numbers marked by E in front. For example, in the production process including "E33→E26" as described therein means that the same Production Process as in Example 33 is performed, and then the same Production Process as in Example 26 is performed. The materials horizontally described in the right hand of Syn (Sal) represent salts, and the materials without such a description represent free compounds. (HCl) represents hydrochloride, (2HCl) represents dihydrochloride, (3HCl) represents trihydrochloride, (Fum) represents fumarate, (1.5Fum) represents 1.5 fumarate, (2Fum) represents 2 fumarate, (3Fum) represents 3 fumarate, (0.5 L-Tart) represents 0.5 L-tartrate, (L-Tart) represents L-tartrate, and (Na) represents sodium salt. The bottom in the right hand columns show values by mass spectrum as Dat (physicochemical data).

TABLE 4

| Pre | Str | Syn (Sal) Dat |
|---|---|---|
| 71 | Boc-NH-[cyclobutane]-CH2-OH | P16 MS(ESI) m/z: 214([M − H]−) |
| 30 | Boc-NH-CH2-[cyclobutane]-CH2-N(phthalimide) | P30 MS(ESI) m/z: 345([M + H]+) |
| 72 | Boc-NH-CH2-[cyclopropane]-CH2-N(phthalimide) | P30 MS(ESI) m/z: 331([M + H]+) |

TABLE 4-continued
| Pre | Str | Syn (Sal) Dat |
|---|---|---|
| 73 | 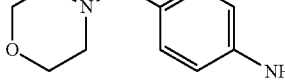 | P66 MS(ESI) m/z: 201([M + H]+) |
| 66 | 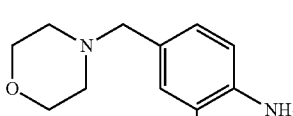 | P66 MS(ESI) m/z: 215([M + H]+) |
| 74 | 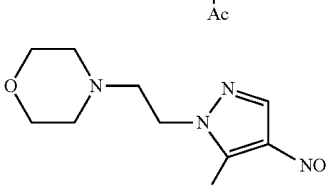 | P30→P66 (2HCl) MS(ESI) m/z: 167([M + H]+) |
| 75 |  | P14 MS(EI) m/z: 258([M]+) |
| 14 | 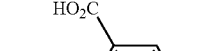 | P14 MS(ESI) m/z: 285([M + H]+) |
| 26 | 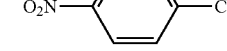 | P26 MS(ESI) m/z: 193([M + H]+) |
| 48 | 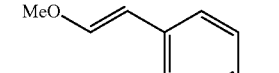 | P48 MS(ESI) m/z: 201([M + H]+) |
TABLE 5
| 34 |  | P34 (2HCl) MS(ESI) m/z: 194([M + H]+) |
|---|---|---|
| 76 |  | P48 MS(ESI) m/z: 235([M + H]+) |
| 51 | 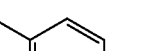 | P51 MS(ESI) m/z: 271([M + H]+) |
TABLE 5-continued
| 77 |  | P51 MS(EI) m/z: 270([M]+) |
|---|---|---|
| 23 | 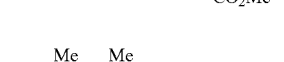 | P23 MS(ESI) m/z: 191([M − H]−) |
| 59 | 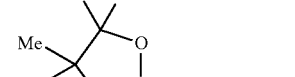 | P59 MS(ESI) m/z: 238([M + H]+) |
| 64 | 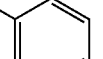 | P64 MS(FAB) m/z: 279([M + H]+) |
| 49 |  | P49 MS(CI) m/z: 308([M + H]+) |
| 50 |  | P50 MS(ESI) m/z: 259([M + H]+) |
TABLE 6
| 12 |  | P12 MS(FAB) m/z: 226([M + H]+) |
|---|---|---|
| 52 |  | P52 MS(ESI) m/z: 330([M + H]+) |

TABLE 6-continued

| | | |
|---|---|---|
| 35 | morpholine-ethyl pyrazole with MeO2C and NO2 | P35 MS(ESI) m/z: 285([M + H]+) |
| 36 | MeO2C pyrazole-N-ethyl-morpholine with O2N | P36 MS(ESI) m/z: 285([M + H]+) |
| 61 | N-(pyridin-3-yl) 2-fluoro-6-nitrobenzamide | P61 MS(API) m/z: 262([M + H]+) |
| 78 | N-(pyridin-3-yl) 5-fluoro-2-nitrobenzamide | P61 MS(ESI) m/z: 260([M − H]−) |
| 79 | N-(pyridin-3-yl) 4-fluoro-2-nitrobenzamide | P61 MS(ESI) m/z: 260([M − H]−) |
| 80 | N-(pyridin-3-yl) 4,5-difluoro-2-nitrobenzamide | P61 MS(ESI) m/z: 280([M + H]+) |

TABLE 7

| | | |
|---|---|---|
| 81 | N-(pyridin-3-yl) 5-methoxy-2-nitrobenzamide | P61 MS(API) m/z: 274([M + H]+) |
| 82 | N-(pyridin-3-yl) 4-methoxy-2-nitrobenzamide | P61 MS(API) m/z: 274([M + H]+) |

TABLE 7-continued

| | | |
|---|---|---|
| 83 | N-(pyridin-3-yl) 2-nitro-3-methoxybenzamide | P61 MS(ESI) m/z: 272([M − H]−) |
| 84 | N-(pyridin-3-yl) 5-cyano-2-nitrobenzamide | P61 MS(ESI) m/z: 267([M − H]−) |
| 85 | N-(pyridin-3-yl) 4-methyl-2-nitrobenzamide | P61 MS(FAB) m/z: 256([M − H]−) |
| 86 | N-methyl-N-(pyridin-3-yl) 2-nitrobenzamide | P61 MS(ESI) m/z: 258([M + H]+) |
| 87 | N-cyclobutyl 2-nitrobenzamide | P61 MS(ESI) m/z: 221([M + H]+) |
| 88 | N-(3-hydroxy-2,2-dimethylpropyl) 2-nitrobenzamide | P61 MS(ESI) m/z: 251([M − H]−) |

TABLE 8

| | | |
|---|---|---|
| 62 | N-((3-methyloxetan-3-yl)methyl) 2-nitrobenzamide | P62 MS(ESI) m/z: 249([M − H]−) |
| 89 | N-(3-(dimethylamino)-2,2-dimethylpropyl) 2-nitrobenzamide | P61 MS(ESI) m/z: 280([M + H]+) |

TABLE 8-continued

| # | Structure | Ref | MS |
|---|---|---|---|
| 90 | MeO2C-cyclohexyl-NHC(O)-(2-NO2)phenyl | P61 | MS(FAB) m/z: 307([M + H]+) |
| 91 | HO2C-cyclohexyl-NHC(O)-(2-NO2)phenyl | P51 | MS(ESI) m/z: 291([M − H]−) |
| 92 | H2NOC-cyclohexyl-NHC(O)-(2-NO2)phenyl | P62 | MS(API) m/z: 290([M − H]−) |
| 6 | NC-cyclohexyl-NHC(O)-(2-NO2)phenyl | P6 | MS(ESI) m/z: 274([M + H]+) |
| 93 | HO-cyclohexyl-NHC(O)-(2-NO2)phenyl | P62 | MS(ESI) m/z: 265([M + H]+) |
| 94 | tetrahydropyran-4-yl-NHC(O)-(5-F,2-NO2)phenyl | P62 | MS(FAB) m/z: 269([M + H]+) |
| 95 | tetrahydropyran-4-yl-NHC(O)-(4-F,2-NO2)phenyl | P62 | MS(ESI) m/z: 269([M + H]+) |

TABLE 9

| # | Structure | Ref | MS |
|---|---|---|---|
| 96 | tetrahydropyran-4-yl-NHC(O)-(4-Cl,2-NO2)phenyl | P61 | MS(ESI) m/z: 283([M − H]−) |
| 97 | tetrahydropyran-4-yl-NHC(O)-(5-OMe,2-NO2)phenyl | P62 | MS(FAB) m/z: 281([M + H]+) |

TABLE 9-continued

| # | Structure | Ref | MS |
|---|---|---|---|
| 98 | tetrahydropyran-4-yl-NHC(O)-(4-OMe,2-NO2)phenyl | P62 | MS(ESI) m/z: 281([M + H]+) |
| 99 | tetrahydropyran-4-yl-NHC(O)-(5-Me,2-NO2)phenyl | P61 | MS(ESI) m/z: 265([M + H]+) |
| 24 | tetrahydropyran-4-yl-NHC(O)-(5-CH2Br,2-NO2)phenyl | P24 | MS(FAB) m/z: 343([M + H]+) |
| 100 | tetrahydropyran-4-yl-NHC(O)-(4-Me,2-NO2)phenyl | P61 | MS(FAB) m/z: 265([M + H]+) |
| 101 | morpholino-ethyl-pyrazole-NO2-C(O)NH-tetrahydropyran-4-yl | P62 | MS(ESI) m/z: 354([M + H]+) |
| 102 | morpholino-ethyl-pyrazole-NO2-C(O)NH-tetrahydropyran-4-yl (isomer) | P62 | MS(ESI) m/z: 354([M + H]+) |

TABLE 10

| # | Structure | Ref | MS |
|---|---|---|---|
| 103 | pyrrolidin-1-yl-CH2-(3-CO2Me,4-NO2)phenyl | P2 | MS(FAB) m/z: 265([M + H]+) |
| 104 | (3-MeO-pyrrolidin-1-yl)-CH2-(3-CO2Me,4-NO2)phenyl * | P2 | MS(FAB) m/z: 295([M + H]+) |

TABLE 10-continued

| | Structure | Ref / MS |
|---|---|---|
| 105 | 5-((2S)-2-(methoxymethyl)pyrrolidin-1-ylmethyl)-2-nitrobenzoic acid methyl ester* | P2 MS(ESI) m/z: 309([M + H]+) |
| 106 | 5-((4-methoxypiperidin-1-yl)methyl)-2-nitrobenzoic acid methyl ester | P2 MS(ESI) m/z: 309([M + H]+) |
| 107 | 5-((4-hydroxypiperidin-1-yl)methyl)-2-nitrobenzoic acid methyl ester | P2 MS(ESI) m/z: 295([M + H]+) |
| 2 | 5-(morpholin-4-ylmethyl)-2-nitrobenzoic acid methyl ester | P2 MS(FAB) m/z: 281([M + H]+) |
| 108 | 5-((3,3-dimethylmorpholin-4-yl)methyl)-2-nitrobenzoic acid methyl ester | P2 MS(ESI) m/z: 309([M + H]+) |
| 109 | 5-((4-methylpiperazin-1-yl)methyl)-2-nitrobenzoic acid methyl ester | P2 MS(FAB) m/z: 294([M + H]+) |
| 110 | 5-((4-acetylpiperazin-1-yl)methyl)-2-nitrobenzoic acid methyl ester | P2 MS(ESI) m/z: 322([M + H]+) |
| 111 | 5-((3-oxopiperazin-1-yl)methyl)-2-nitrobenzoic acid methyl ester | P2 MS(FAB) m/z: 294([M + H]+) |

TABLE 11

| | Structure | Ref / MS |
|---|---|---|
| 112 | methyl(2-methoxyethyl)amino analog | P2 MS(ESI) m/z: 283([M + H]+) |
| 113 | morpholine-4-carbonyl analog | P62 MS(FAB) m/z: 295([M + H]+) |

TABLE 11-continued

| | Structure | Ref / MS |
|---|---|---|
| 114 | 4-methylpiperazine carbonyl analog | P62 MS(ESI) m/z: 308([M + H]+) |
| 115 | 1,4-oxazepan-4-ylmethyl analog | P2 MS(FAB) m/z: 295([M + H]+) |
| 116 | (1,4-oxazinan-4-yl)methyl analog* | P2 MS(ESI) m/z: 293([M + H]+) |
| 117 | thiomorpholin-4-ylmethyl analog | P2 MS(ESI) m/z: 297([M + H]+) |
| 38 | morpholin-4-yl ethyl analog | P38 MS(FAB) m/z: 295([M + H]+) |
| 118 | pyrrolidin-1-ylmethyl analog | P51 MS(ESI) m/z: 251([M + H]+) |
| 119 | N-(pyridin-3-yl) benzamide pyrrolidinyl analog | P62 MS(ESI) m/z: 327([M + H]+) |

TABLE 12

| | Structure | Ref / MS |
|---|---|---|
| 120 | N-(pyridin-3-yl)-5-(morpholin-4-ylmethyl)-2-nitrobenzamide | P51→P62 MS(ESI) m/z: 343([M + H]+) |
| 121 | N-methyl-N-(2-methoxyethyl)amino analog | P62 MS(ESI) m/z: 345([M + H]+) |

TABLE 12-continued

| | | | |
|---|---|---|---|
| 122 | 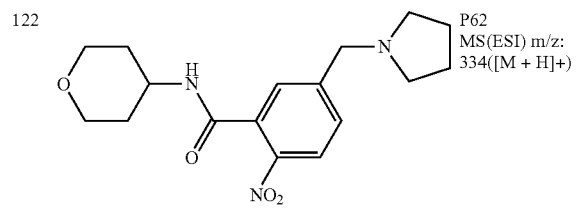 | | P62<br>MS(ESI) m/z:<br>334([M + H]+) |
| 123 | 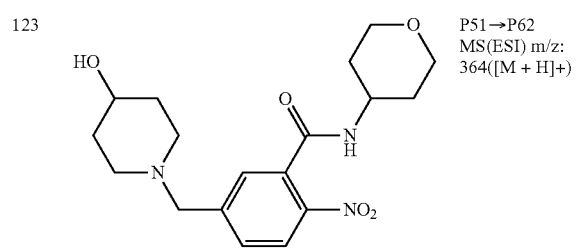 | | P51→P62<br>MS(ESI) m/z:<br>364([M + H]+) |
| 1 | 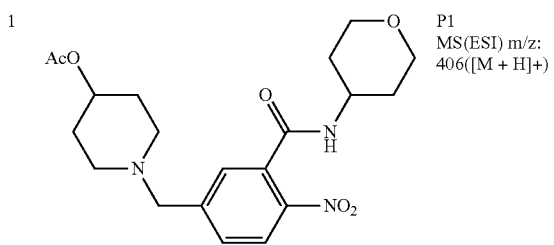 | | P1<br>MS(ESI) m/z:<br>406([M + H]+) |
| 124 | 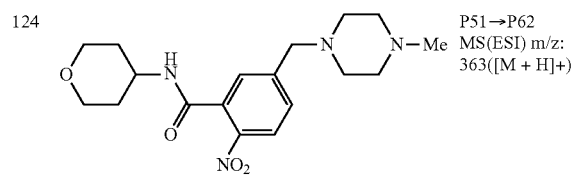 | | P51→P62<br>MS(ESI) m/z:<br>363([M + H]+) |
| 125 | 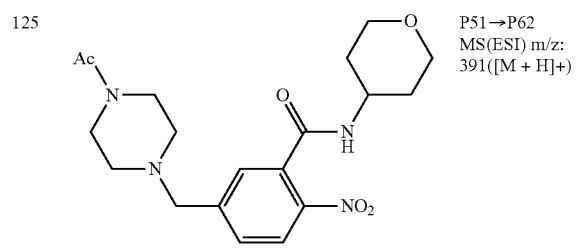 | | P51→P62<br>MS(ESI) m/z:<br>391([M + H]+) |

TABLE 13

| | | | |
|---|---|---|---|
| 126 | 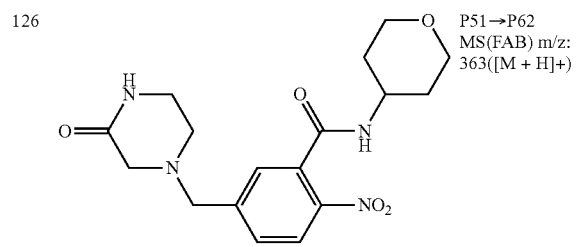 | | P51→P62<br>MS(FAB) m/z:<br>363([M + H]+) |

TABLE 13-continued

| | | | |
|---|---|---|---|
| 127 | 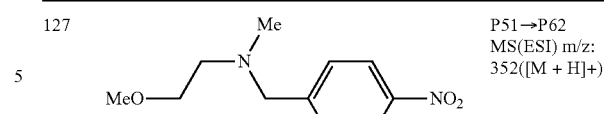 | | P51→P62<br>MS(ESI) m/z:<br>352([M + H]+) |
| 128 | 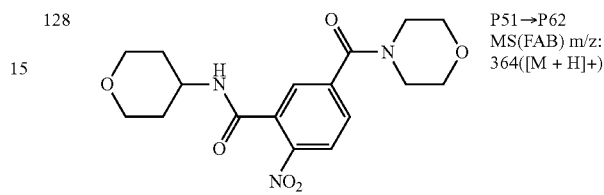 | | P51→P62<br>MS(FAB) m/z:<br>364([M + H]+) |
| 129 | 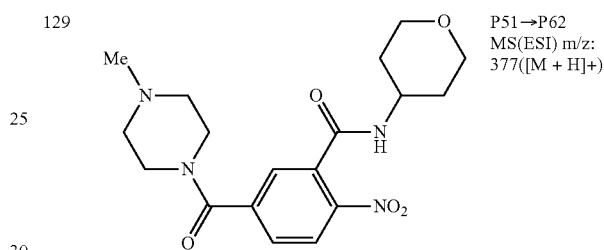 | | P51→P62<br>MS(ESI) m/z:<br>377([M + H]+) |
| 4 | 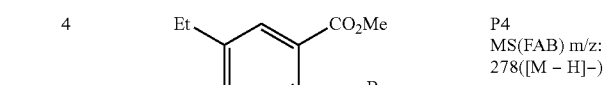 | | P4<br>MS(FAB) m/z:<br>278([M − H]−) |
| 130 | 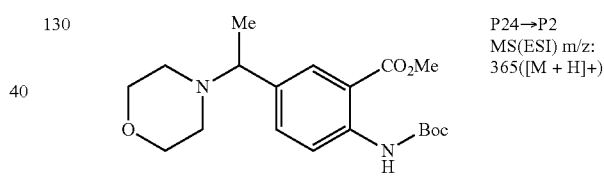 | | P24→P2<br>MS(ESI) m/z:<br>365([M + H]+) |
| 131 | 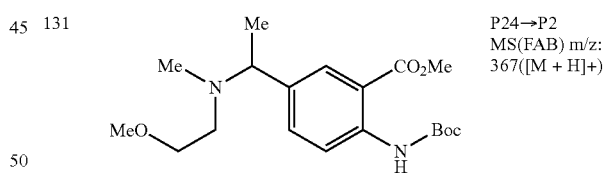 | | P24→P2<br>MS(FAB) m/z:<br>367([M + H]+) |
| 132 | 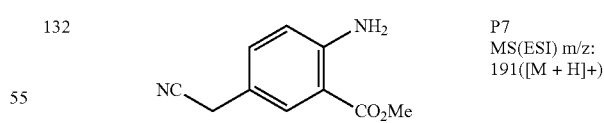 | | P7<br>MS(ESI) m/z:<br>191([M + H]+) |

TABLE 14

| | | | |
|---|---|---|---|
| 7 | 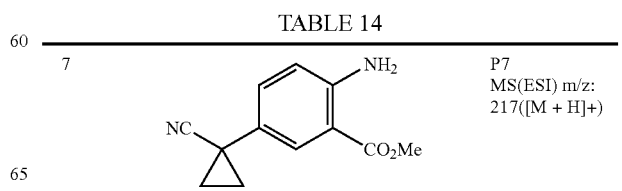 | | P7<br>MS(ESI) m/z:<br>217([M + H]+) |

TABLE 14-continued

| # | Structure | Notes |
|---|---|---|
| 133 | 2-amino-6-cyanobenzoate methyl ester (NH2, CO2Me, CN) | P13 MS(EI) m/z: 176([M]+) |
| 11 | ethyl 2-amino-3,5-difluorobenzoate (NH2, CO2Et, 2F) | P11 MS(EI) m/z: 201([M]+) |
| 63 | Boc-NH-(CH2)3-O-C6H3(CO2Me)(NH2) | P63 MS(ESI) m/z: 325([M + H]+) |
| 134 | MeS-(CH2)3-O-C6H3(CO2Me)(NH2) | P63 MS(FAB) m/z: 256([M + H]+) |
| 135 | tetrahydropyran-4-yloxy-C6H3(CO2Me)(NH2) | P63 MS(FAB) m/z: 252([M + H]+) |
| 136 | morpholino-(CH2)2-C6H3(NH2)(CO2Me) | P13 MS(FAB) m/z: 265([M + H]+) |
| 137 | Boc-NH-(CH2)2-O-C6H3(NH2)(CO2Me) | P63→P13 MS(ESI) m/z: 311([M + H]+) |
| 138 | MeO-CH2-C6H3(CO2Me)(NH2) | P13 MS(EI) m/z: 195([M]+) |
| 139 | tetrahydropyran-4-yl-NHC(O)-C6H3(Me)(NH2) | P13 MS(ESI) m/z: 235([M + H]+) |

TABLE 15

| # | Structure | Notes |
|---|---|---|
| 140 | Me2CH-CH2-CH2-O-C6H3(CO2Me)(NH2) | P63 MS(FAB) m/z: 238([M + H]+) |
| 141 | BnO-(CH2)3-O-C6H3(CO2Me)(NH2) | P63 MS(FAB) m/z: 316([M + H]+) |
| 142 | MeO-(CH2)3-O-C6H3(CO2Me)(NH2) | P63 MS(FAB) m/z: 240([M + H]+) |
| 143 | 5-amino-pyridazine-4-carboxylate methyl ester | P11 MS(ESI) m/z: 154([M + H]+) |
| 144 | (3R)-3-methoxy-pyrrolidin-1-ylmethyl-C6H3(NH2)(CO2Me) | * P13 MS(EI) m/z: 264([M]+) |
| 145 | (2S)-2-methoxymethyl-pyrrolidin-1-ylmethyl-C6H3(NH2)(CO2Me) | * P13 MS(ESI) m/z: 279([M + H]+) |
| 146 | 4-methoxypiperidin-1-ylmethyl-C6H3(NH2)(CO2Me) | P13 MS(ESI) m/z: 279([M + H]+) |
| 13 | morpholin-4-ylmethyl-C6H3(CO2Me)(NH2) | P13 MS(FAB) m/z: 251([M + H]+) |
| 147 | 3,3-dimethylmorpholin-4-ylmethyl-C6H3(NH2)(CO2Me) | P13 MS(ESI) m/z: 279([M + H]+) |
| 148 | N-methyl-N-(2-methoxyethyl)amino-ethyl-C6H3(CO2Me)(NH2) | P65 MS(FAB) m/z: 267([M + H]+) |

TABLE 16

| # | Structure | Notes |
|---|---|---|
| 21 | 1-methyl-piperidin-2-yl-C6H3(NH2)(CO2Me) | P21 MS(ESI) m/z: 249([M + H]+) |

TABLE 16-continued

| No. | Structure | Ref | MS |
|---|---|---|---|
| 149 | morpholine-CH(Me)-C6H3(NH2)-CO2Me | P65 | MS(FAB) m/z: 265([M + H]+) |
| 150 | 1,4-oxazepane-CH2-C6H3(NH2)-CO2Me | P13 | MS(EI) m/z: 264([M]+) |
| 151 | 2-oxa-5-azabicyclo-CH2-C6H3(NH2)-CO2Me * | P13 | MS(FAB) m/z: 263([M + H]+) |
| 152 | thiomorpholine-CH2-C6H3(NH2)-CO2Me | P13 | MS(FAB) m/z: 267([M + H]+) |
| 153 | 2-CN-C6H4-NHC(O)-C6H4-NH2 | P32 | MS(ESI) m/z: 236([M − H]−) |
| 32 | pyridin-3-yl-NHC(O)-C6H3(F)(NH2) | P32 | MS(API) m/z: 230([M − H]−) |
| 154 | pyridin-3-yl-NHC(O)-C6H3(F)(NH2) | P32 | MS(ESI) m/z: 230([M − H]−) |
| 155 | pyridin-3-yl-NHC(O)-C6H3(F)(NH2) | P32 | MS(ESI) m/z: 230([M − H]−) |

TABLE 17

| No. | Structure | Ref | MS |
|---|---|---|---|
| 156 | pyridin-3-yl-NHC(O)-C6H2(F)2(NH2) | P32 | MS(ESI) m/z: 250([M + H]+) |
| 157 | pyridin-3-yl-NHC(O)-C6H3(Me)(NH2) | P13 | MS(FAB) m/z: 228([M + H]+) |
| 158 | pyridin-3-yl-NHC(O)-C6H3(OMe)(NH2) | P32 | MS(API) m/z: 244([M + H]+) |
| 159 | pyridin-3-yl-NHC(O)-C6H3(OMe)(NH2) | P32 | MS(ESI) m/z: 242([M − H]−) |
| 160 | pyridin-3-yl-NHC(O)-C6H3(OMe)(NH2) | P32 | MS(ESI) m/z: 242([M − H]−) |
| 161 | pyridin-3-yl-NHC(O)-C6H3(CN)(NH2) | P32 | MS(ESI) m/z: 239([M + H]+) |
| 162 | pyridin-3-yl-N(Me)C(O)-C6H4-NH2 | P32 | MS(ESI) m/z: 228([M + H]+) |
| 15 | tetrahydropyran-4-yl-NHC(O)-C6H4-NH2 | P15 | MS(EI) m/z: 220([M]+) |

TABLE 18

| No. | Structure | Ref | MS |
|---|---|---|---|
| 163 | tetrahydropyran-4-yl-NHC(O)-C6H3(F)(NH2) | P13 | MS(ESI) m/z: 240([M + 2H]+) |

TABLE 18-continued

| | | |
|---|---|---|
| 164 | [structure: N-(tetrahydropyran-4-yl)-2-amino-4-fluorobenzamide] | P13 MS(ESI) m/z: 240([M + 2H]+) |
| 165 | [structure: N-(tetrahydropyran-4-yl)-2-amino-4-chlorobenzamide] | P13 MS(FAB) m/z: 255([M + H]+) |
| 166 | [structure: N-(tetrahydropyran-4-yl)-2-amino-5-methoxybenzamide] | P13 MS(ESI) m/z: 252([M + 2H]+) |
| 167 | [structure: N-(tetrahydropyran-4-yl)-2-amino-4-methoxybenzamide] | P13 MS(ESI) m/z: 252([M + 2H]+) |
| 168 | [structure: N-(tetrahydropyran-4-yl)-2-amino-5-(2-pyrrolidin-1-ylethyl)benzamide] | P51→P62→P13 MS(FAB) m/z: 318([M + H]+) |
| 169 | [structure: N-cyclobutyl-2-aminobenzamide] | P13 MS(ESI) m/z: 191([M + H]+) |
| 170 | [structure: N-((3-methyloxetan-3-yl)methyl)-2-aminobenzamide] | P32 MS(ESI) m/z: 219([M − H]−) |
| 171 | [structure: N-(3-hydroxy-2,2-dimethylpropyl)-2-aminobenzamide] | P32 MS(ESI) m/z: 223([M + H]+) |

TABLE 19

| | | |
|---|---|---|
| 172 | [structure: N-(3-dimethylamino-2,2-dimethylpropyl)-2-aminobenzamide] | P32 MS(ESI) m/z: 250([M + H]+) |

TABLE 19-continued

| | | |
|---|---|---|
| 173 | [structure: methyl 4-(2-aminobenzamido)cyclohexanecarboxylate] | P13 MS(ESI) m/z: 277([M + H]+) |
| 174 | [structure: 4-(2-aminobenzamido)cyclohexanecarboxamide] | P32 (HCl) MS(ESI) m/z: 262([M + H]+) |
| 175 | [structure: 4-(2-aminobenzamido)cyclohexanecarbonitrile] | P32 MS(ESI) m/z: 244([M + H]+) |
| 176 | [structure: N-(4-hydroxycyclohexyl)-2-aminobenzamide] | P32 MS(ESI) m/z: 233([M − H]−) |
| 177 | [structure: 4-amino-1-(2-morpholinoethyl)-N-(tetrahydropyran-4-yl)-1H-pyrazole-3-carboxamide] | P32 MS(ESI) m/z: 324([M + H]+) |
| 178 | [structure: 4-amino-1-(2-morpholinoethyl)-N-(tetrahydropyran-4-yl)-1H-pyrazole-5-carboxamide] | P32 MS(ESI) m/z: 324([M + H]+) |
| 179 | [structure: 2-amino-5-((pyrrolidin-1-yl)methyl)-N-(pyridin-3-yl)benzamide] | P13 MS(ESI) m/z: 297([M + H]+) |

TABLE 20

| | | |
|---|---|---|
| 180 | [structure: 2-amino-5-(morpholinomethyl)-N-(pyridin-3-yl)benzamide] | P13 MS(ESI) m/z: 313([M + H]+) |

TABLE 20-continued
| | | | |
|---|---|---|---|
| 181 | 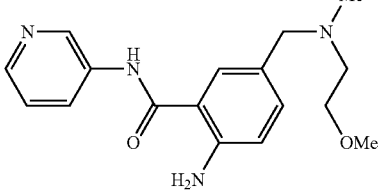 | P13 MS(ESI) m/z: 315([M + H]+) | |
| 182 | 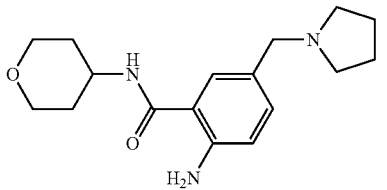 | P13 MS(ESI) m/z: 304([M + H]+) | |
| 183 | 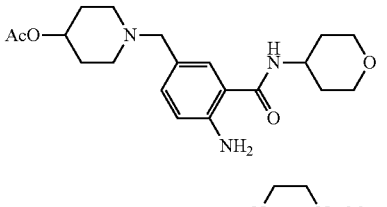 | P13 MS(FAB) m/z: 376([M + H]+) | |
| 184 | 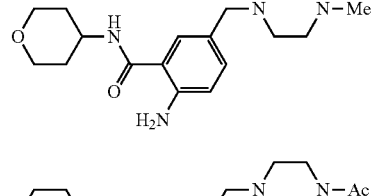 | P13 MS(ESI) m/z: 333([M + H]+) | |
| 185 | 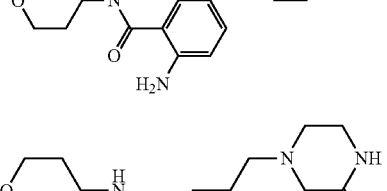 | P13 MS(ESI) m/z: 361([M + H]+) | |
| 186 | 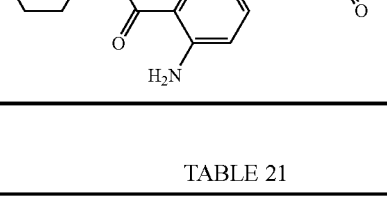 | P13 MS(FAB) m/z: 333([M + H]+) | |
TABLE 21
| | | |
|---|---|---|
| 187 | 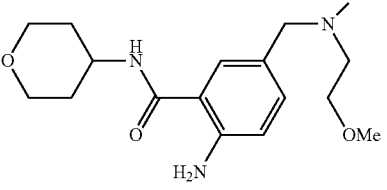 | P13 MS(ESI) m/z: 322([M + H]+) |
| 188 | 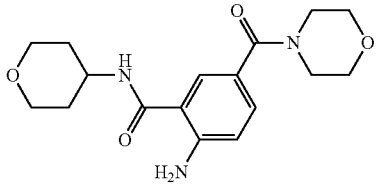 | P13 MS(ESI) m/z: 334([M + H]+) |
TABLE 21-continued
| | | |
|---|---|---|
| 189 | 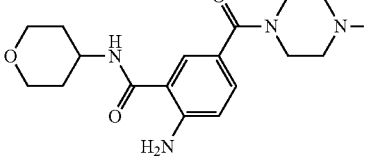 | P13 MS(ESI) m/z: 347([M + H]+) |
| 40 | 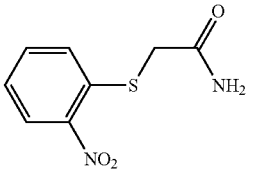 | P40 MS(FAB) m/z: 213([M + H]+) |
| 190 | 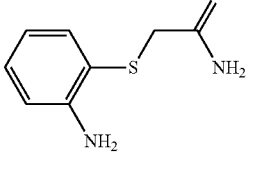 | P32 MS(FAB) m/z: 183([M + H]+) |
| 44 | 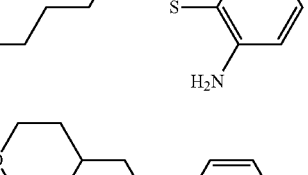 | P44 MS(EI) m/z: 211([M]+) |
| 191 | 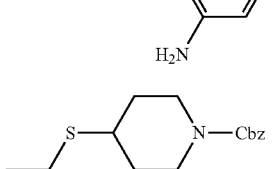 | P43 MS(ESI) m/z: 224([M + H]+) |
| 192 | 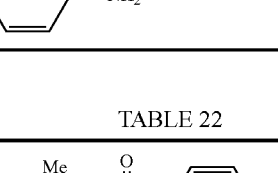 | P43 MS(FAB) m/z: 343([M + H]+) |
TABLE 22
| | | |
|---|---|---|
| 193 | 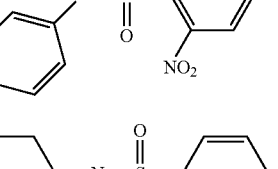 | P47 MS(ESI) m/z: 294([M + H]+) |
| 47 | 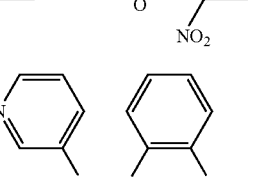 | P47 MS(ESI) m/z: 285([M − H]−) |
| 194 | 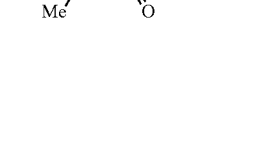 | P32 MS(ESI) m/z: 264([M + H]+) |

TABLE 22-continued

| 195 | (tetrahydropyran-4-yl sulfonamide with 2-aminophenyl) | P32 MS(ESI) m/z: 257([M + H]+) |
| 41 | Boc-pyrrolidin-3-yl-CH2OMe * | P41 MS(ESI) m/z: 216([M + H]+) |
| 196 | * Boc-N pyrrolidine, 4-OMe, 2-CO2Me | P20 MS(FAB) m/z: 260([M + H]+) |
| 18 | * Boc-N pyrrolidine, 4-OMe, 2-CH2OH | P18 MS(FAB) m/z: 232([M + H]+) |
| 197 | * TBSO-, OMe Boc-N pyrrolidine | P20 MS(FAB) m/z: 346([M + H]+) |
| 198 | * pyrrolidin-3-yl-CH2OMe, NH | P65 (HCl) MS(ESI) m/z: 116([M + H]+) |

TABLE 23

| 199 | * HN pyrrolidine 4-OMe, 2-CH2OH | P65 (HCl) MS(ESI) m/z: 132([M + H]+) |
| 200 | * HO-, pyrrolidine 2-CH2OMe, NH | P65 (HCl) MS(ESI) m/z: 132([M + H]+) |
| 201 | * F-pyrrolidine 2-CH2OH, NH | P65 (HCl) MS(ESI) m/z: 120([M + H]+) |

TABLE 23-continued

| 202 | * F3C-C(O)-N pyrrolidine 3-NHMe | P41→P65 (HCl) MS(FAB) m/z: 197([M + H]+) |
| 203 | * F3C-C(O)-N pyrrolidine 3-NHMe | P41→P65 (HCl) MS(EI) m/z: 196([M]+) |
| 31 | Boc-N piperidine 4-O-CH=CH2 | P31 MS(EI) m/z: 227([M]+) |
| 8 | Boc-N piperidine 4-O-cyclopropyl | P8 MS(FAB) m/z: 242([M + H]+) |
| 28 | Cbz-N piperidine 4-OCHF2 | P28 MS(ESI) m/z: 286([M + H]+) |
| 204 | OEt-CH2-piperidine-3-yl N-Boc * | P41 MS(ESI) m/z: 244([M + H]+) |
| 205 | OEt-CH2-piperidine-3-yl N-Boc * | P41 MS(EI) m/z: 243([M]+) |
| 43 | Boc-N piperidine 4-SEt | P43 MS(EI) m/z: 245([M]+) |

TABLE 24

| 19 | Boc-N piperidine 4-SO2Et | P19 MS(FAB) m/z: 278([M + H]+) |
| 206 | CONMe2-CH2-N(Me)-piperidine-4-yl-N-Boc | P2 MS(ESI) m/z: 200([M + H]+) |
| 33 | HN-piperidine 4-OCHF2 | P33 MS(ESI) m/z: 152([M + H]+) |

TABLE 24-continued

| | | |
|---|---|---|
| 207 | 4-cyclopropoxypiperidine | P65 (HCl) MS(ESI) m/z: 142([M + H]+) |
| 208 | * 3-(ethoxymethyl)piperidine | P65 (HCl) MS(ESI) m/z: 144([M + H]+) |
| 209 | * 3-(ethoxymethyl)piperidine | P65 (HCl) MS(ESI) m/z: 144([M + H]+) |
| 65 | 4-(ethylsulfonyl)piperidine | P65 (HCl) MS(ESI) m/z: 178([M + H]+) |
| 210 | Me₂NOC-CH₂-N(Me)-piperidin-4-yl | P65 (2HCl) MS(ESI) m/z: 200([M + H]+) |
| 211 | Cbz-N piperidine 4-OMe 3-F | P41 MS(ESI) m/z: 290([M + Na]+) |
| 212 | Cbz-N piperidine 4-OMe 3-F | P41 MS(ESI) m/z: 290([M + Na]+) |
| 213 | Cbz-N piperidine 4-OEt 3-F | P41 MS(ESI) m/z: 304([M + Na]+) |

TABLE 25

| | | |
|---|---|---|
| 214 | Cbz-N piperidine 4-OEt 3-F | P41 MS(ESI) m/z: 304([M + Na]+) |
| 215 | HN piperidine 4-OMe 3-F | P33 (HCl) MS(ESI) m/z: 134([M + H]+) |
| 216 | HN piperidine 4-OMe 3-F | P33 (HCl) MS(ESI) m/z: 134([M + H]+) |

TABLE 25-continued

| | | |
|---|---|---|
| 217 | HN piperidine 4-OEt 3-F | P33 (HCl) MS(ESI) m/z: 148([M + H]+) |
| 218 | HN piperidine 4-OEt 3-F | P33 (HCl) MS(ESI) m/z: 148([M + H]+) |
| 39 | Cbz-N piperidine 3-F 4-O-pyrimidinyl | P39 MS(ESI) m/z: 332([M + H]+) |
| 219 | HN piperidine 3-F 4-O-pyrimidinyl | P33 MS(ESI) m/z: 198([M + H]+) |
| 29 | 3-(2-fluoropyridin-3-ylmethyl)-4-hydroxy-piperidine-1-Boc | P29 MS(ESI) m/z: 254([M + H − C4H9]+) |
| 220 | Boc-N spiro furopyridine | P39 MS(ESI) m/z: 291([M + H]+) |
| 221 | HN spiro furopyridine | P65 (2HCl) MS(ESI) m/z: 191([M + H]+) |
| 222 | * Boc-N piperidine 3-CH₂O-pyrimidinyl | P39 MS(CI) m/z: 294([M + H]+) |

TABLE 26

| | | |
|---|---|---|
| 223 | * HN piperidine 3-CH₂O-pyrimidinyl | P65 (HCl) MS(ESI) m/z: 194([M + H]+) |
| 224 | HN piperidine 3-F 4-OH | P33 MS(ESI) m/z: 120([M + H]+) |

TABLE 26-continued

| | | |
|---|---|---|
| 20 | [Boc-NH-CH(Me)-CH2-OMe, (S)-config, *] | P20 MS(CI) m/z: 190([M + H]+) |
| 25 | [EtO2C-NH-CH(Me)-CH2-OMe, (R)-config, *] | P25 MS(CI) m/z: 162([M + H]+) |
| 225 | [Boc-morpholine-CH2OMe] | P20 MS(FAB) m/z: 232([M + H]+) |
| 226 | [H-morpholine-CH2OMe] | P65 (HCl) MS(ESI) m/z: 132([M + H]+) |
| 16 | [MeNH-CH(Me)-CH2-OMe, *] | P16 (HCl) MS(FAB) m/z: 104([M + H]+) |
| 227 | [MeNH-CH(Me)-CH2-OMe, *] | P16 (HCl) MS(FAB) m/z: 104([M + H]+) |
| 27 | [BnO-cyclopentyl-CO2Bn] | P27 MS(ESI) m/z: 311([M + H]+) |
| 228 | [BnO-cyclopentyl-COOH] | P51 MS(ESI) m/z: 219([M − H]−) |
| 229 | [BnO-cyclopentyl-CONH2] | P61 MS(ESI) m/z: 220([M + H]+) |

TABLE 27

| | | |
|---|---|---|
| 230 | [Ph-C(O)-NH-C(S)-pyrrolidine-OMe, *] | P5 MS(ESI) m/z: 265([M + H]+) |
| 231 | [Ph-C(O)-NH-C(S)-pyrrolidine(F)(CH2OH), *] | P5 MS(ESI) m/z: 281([M − H]−) |
| 232 | [Ph-C(O)-NH-C(S)-pyrrolidine(OH)(CH2OMe), *] | P5 MS(ESI) m/z: 295([M + H]+) |
| 5 | [Ph-C(O)-NH-C(S)-piperidine-F] | P5 MS(ESI) m/z: 265([M − H]−) |
| 233 | [Ph-C(O)-NH-C(S)-piperidine-CF2] | P5 MS(ESI) m/z: 285([M + H]+) |
| 234 | [Ph-C(O)-NH-C(S)-piperidine-O-CH2CH2-OMe] | P5 MS(ESI) m/z: 323([M + H]+) |
| 235 | [Ph-C(O)-NH-C(S)-azepane-CH2OH] | P5 MS(ESI) m/z: 293([M + H]+) |
| 236 | [Ph-C(O)-NH-C(S)-morpholine-Me, *] | P5 MS(FAB) m/z: 265([M + H]+) |
| 237 | [Ph-C(O)-NH-C(S)-morpholine-CH2OMe] | P5 MS(ESI) m/z: 293([M − H]−) |

TABLE 28

| No. | Structure | Ref | MS |
|---|---|---|---|
| 238 | Ph-C(=O)-NH-C(=S)-N(morpholine with CH2OMe)* | P5 | MS(FAB) m/z: 295([M+H]+) |
| 239 | Ph-C(=O)-NH-C(=S)-N(Me)-CH(Me)-CH2OMe * | P5 | MS(FAB) m/z: 267([M+H]+) |
| 240 | Ph-C(=O)-NH-C(=S)-N(Me)-CH(Me)-CH2OMe * | P5 | MS(FAB) m/z: 267([M+H]+) |
| 241 | Ph-C(=O)-NH-C(=S)-N(Me)-CH2CH2OEt | P5 | MS(ESI) m/z: 267([M+H]+) |
| 242 | Ph-C(=O)-NH-C(=S)-N(Me)-CH2CH2-O-CH(Me)2 | P5 | MS(ESI) m/z: 281([M+H]+) |
| 243 | Ph-C(=O)-NH-C(=S)-N(Me)-CH2CH2-O-C(Me)3 | P5 | MS(ESI) m/z: 295([M+H]+) |
| 244 | MeO-pyrrolidine-C(=S)NH2 * | P55 | MS(ESI) m/z: 161([M+H]+) |
| 245 | H2N-C(=S)-pyrrolidine(CH2OMe)(OH) * | P55 | MS(ESI) m/z: 191([M+H]+) |
| 246 | H2N-C(=S)-pyrrolidine(CH2OH)(F) * | P55 | MS(ESI) m/z: 177([M−H]−) |
| 55 | H2N-C(=S)-piperidine-F | P55 | MS(ESI) m/z: 163([M+H]+) |

TABLE 29

| No. | Structure | Ref | MS |
|---|---|---|---|
| 247 | H2N-C(=S)-piperidine-3,3-F2 | P55 | MS(ESI) m/z: 181([M+H]+) |
| 248 | H2N-C(=S)-piperidine-O-CH2CH2-OMe | P55 | MS(ESI) m/z: 219([M+H]+) |
| 249 | H2N-C(=S)-azepane-CH2OH | P55 | MS(ESI) m/z: 189([M+H]+) |
| 250 | H2N-C(=S)-morpholine-Me * | P55 | MS(FAB) m/z: 161([M+H]+) |
| 251 | H2N-C(=S)-morpholine-CH2OMe | P55 | MS(API) m/z: 191([M+H]+) |
| 252 | H2N-C(=S)-morpholine-CH2OMe * | P55 | MS(EI) m/z: 190([M]+) |
| 253 | H2N-C(=S)-N(Me)-CH(Me)-CH2OMe * | P55 | MS(FAB) m/z: 163([M+H]+) |
| 254 | H2N-C(=S)-N(Me)-CH(Me)-CH2OMe * | P55 | MS(FAB) m/z: 163([M+H]+) |
| 255 | H2N-C(=S)-N(Me)-CH2CH2OEt | P55 | MS(API) m/z: 161([M−H]−) |

| | | |
|---|---|---|
| 256 | 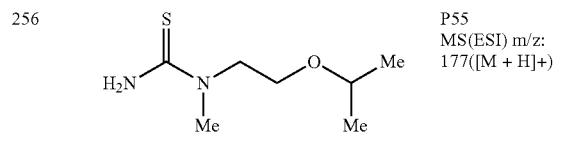 | P55<br>MS(ESI) m/z:<br>177([M + H]+) |

TABLE 30

| | | |
|---|---|---|
| 257 | 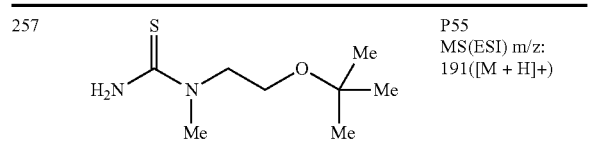 | P55<br>MS(ESI) m/z:<br>191([M + H]+) |
| 258 | 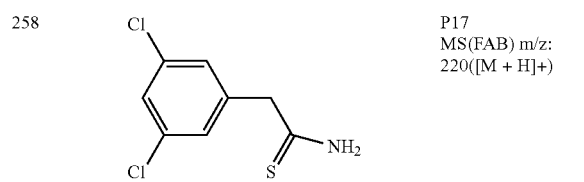 | P17<br>MS(FAB) m/z:<br>220([M + H]+) |
| 17 | 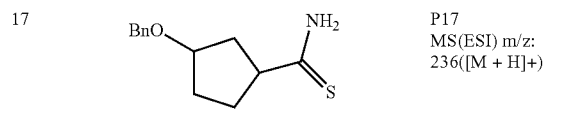 | P17<br>MS(ESI) m/z:<br>236([M + H]+) |
| 259 | 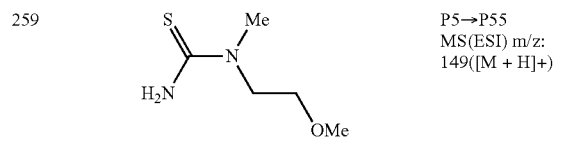 | P5→P55<br>MS(ESI) m/z:<br>149([M + H]+) |
| 260 | 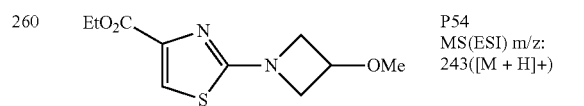 | P54<br>MS(ESI) m/z:<br>243([M + H]+) |
| 261 | 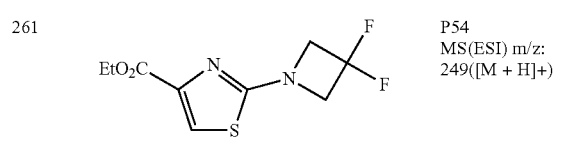 | P54<br>MS(ESI) m/z:<br>249([M + H]+) |
| 262 | 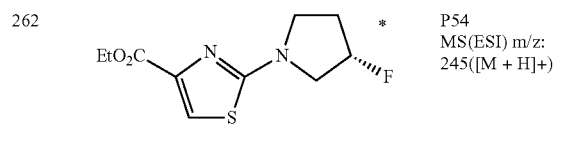 | P54<br>MS(ESI) m/z:<br>245([M + H]+) |
| 263 | 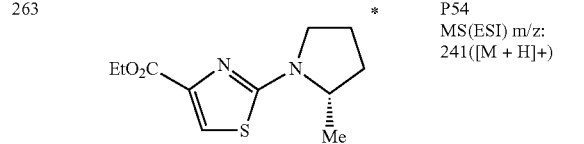 | P54<br>MS(ESI) m/z:<br>241([M + H]+) |
| 264 | 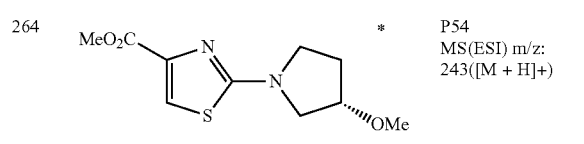 | P54<br>MS(ESI) m/z:<br>243([M + H]+) |
| 265 | 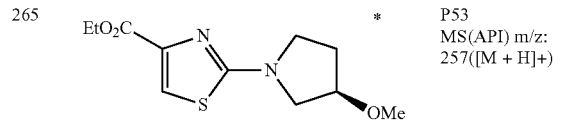 | P53<br>MS(API) m/z:<br>257([M + H]+) |

TABLE 30-continued

| | | |
|---|---|---|
| 266 | 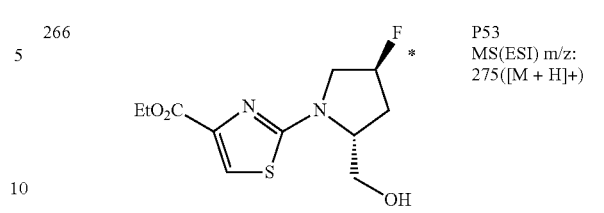 | P53<br>MS(ESI) m/z:<br>275([M + H]+) |

TABLE 31

| | | |
|---|---|---|
| 267 | 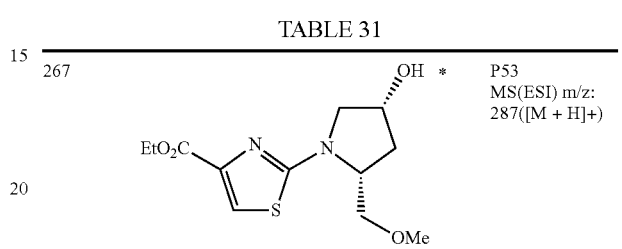 | P53<br>MS(ESI) m/z:<br>287([M + H]+) |
| 268 | 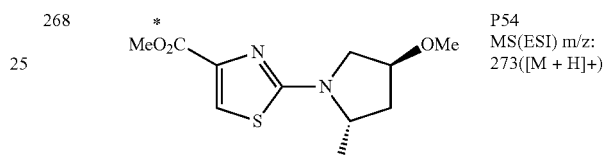 | P54<br>MS(ESI) m/z:<br>273([M + H]+) |
| 9 | 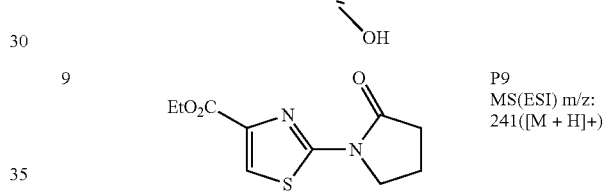 | P9<br>MS(ESI) m/z:<br>241([M + H]+) |
| 269 | 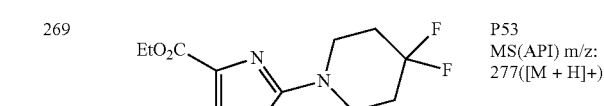 | P53<br>MS(API) m/z:<br>277([M + H]+) |
| 53 | 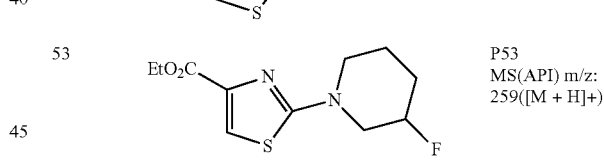 | P53<br>MS(API) m/z:<br>259([M + H]+) |
| 270 | 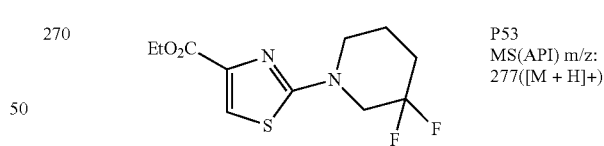 | P53<br>MS(API) m/z:<br>277([M + H]+) |
| 271 | 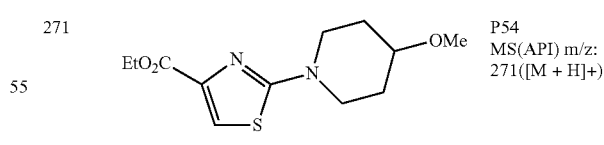 | P54<br>MS(API) m/z:<br>271([M + H]+) |
| 272 | 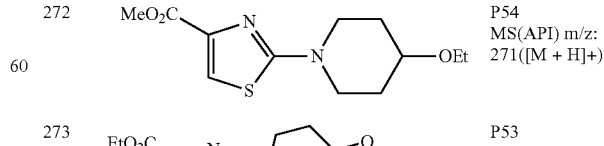 | P54<br>MS(API) m/z:<br>271([M + H]+) |
| 273 | 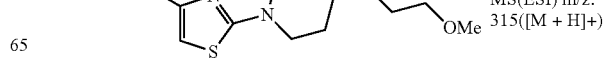 | P53<br>MS(ESI) m/z:<br>315([M + H]+) |

TABLE 31-continued

| | | | |
|---|---|---|---|
| 274 | [structure: EtO2C-thiazole-N-piperidine with OMe, *] | | P54 MS(EI) m/z: 270([M]+) |
| 275 | [structure: EtO2C-thiazole-N-piperidine-CH2OMe] | | P54 MS(API) m/z: 285([M + H]+) |

TABLE 32

| | | | |
|---|---|---|---|
| 276 | [structure: MeO2C-thiazole-N-spiro oxolane piperidine] | | P54 MS(ESI) m/z: 283([M + H]+) |
| 277 | [structure: EtO2C-thiazole-N-azepane-CH2OH] | | P53 MS(ESI) m/z: 285([M + H]+) |
| 278 | [structure: EtO2C-thiazole-N-morpholine-Me, *] | | P53 MS(FAB) m/z: 257([M + H]+) |
| 279 | [structure: EtO2C-thiazole-N-morpholine-CH2OMe] | | P53 MS(ESI) m/z: 287([M + H]+) |
| 280 | [structure: EtO2C-thiazole-N-morpholine-CH2OMe, *] | | P53 MS(FAB) m/z: 287([M + H]+) |
| 281 | [structure: EtO2C-thiazole-N(Me)-CH2CH2OEt] | | P53 MS(API) m/z: 259([M + H]+) |
| 282 | [structure: EtO2C-thiazole-N(Me)-CH2CH2OCH(Me)2] | | P53 MS(API) m/z: 273([M + H]+) |

TABLE 32-continued

| | | | |
|---|---|---|---|
| 283 | [structure: EtO2C-thiazole-N(Me)-CH2CH2-O-C(Me)2Me] | | P53 MS(ESI) m/z: 287([M + H]+) |
| 284 | [structure: MeO2C-thiazole-N(Me)-CH2-tetrahydropyran] | | P54 MS(ESI) m/z: 271([M + H]+) |
| 285 | [structure: EtO2C-thiazole-N(Me)-CH(Me)CH2OMe, *] | | P53 MS(FAB) m/z: 259([M + H]+) |

TABLE 33

| | | | |
|---|---|---|---|
| 286 | [structure: EtO2C-thiazole-N(Me)-CH(Me)CH2OMe, *] | | P53 MS(EI) m/z: 258([M]+) |
| 287 | [structure: MeO2C-thiazole-N(Me)-CH2C(O)NH2] | | P54 MS(FAB) m/z: 230([M + H]+) |
| 288 | [structure: MeO2C-thiazole-N(Me)-CH2C(O)NMe2] | | P54 MS(FAB) m/z: 258([M + H]+) |
| 289 | [structure: MeO2C-thiazole-N(Me)-CH2CH2NMe2] | | P54 MS(CI) m/z: 244([M + H]+) |
| 290 | [structure: EtO2C-thiazole-CH2-NH-CO2Me] | | P25 MS(EI) m/z: 244([M]+) |
| 37 | [structure: EtO2C-thiazole-piperidine-N-Me] | | P37 MS(API) m/z: 255([M + H]+) |
| 291 | [structure: EtO2C-thiazole-piperidine-N-CH2CH2Me] | | P37 MS(ESI) m/z: 283([M + H]+) |
| 22 | [structure: EtO2C-thiazole-piperidine-N-C(O)Et] | | P22 MS(ESI) m/z: 297([M + H]+) |

TABLE 33-continued
| 42 | 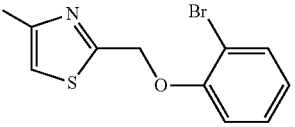 | P42 MS(FAB) m/z: 342([M + H]+) |
| --- | --- | --- |
| 292 | 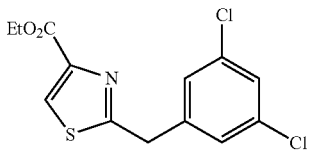 | P53 MS(FAB) m/z: 316([M + H]+) |
| 293 | 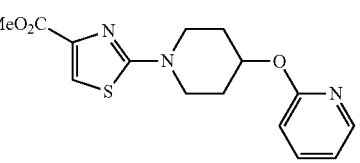 | P54 MS(API) m/z: 320([M + H]+) |
TABLE 34
| 54 | 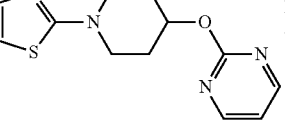 | P54 MS(ESI) m/z: 321([M + H]+) |
| --- | --- | --- |
| 294 | 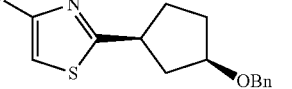 | P53 MS(ESI) m/z: 332([M + H]+) |
| 295 | 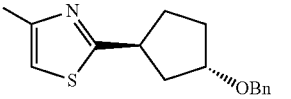 | P53 MS(ESI) m/z: 332([M + H]+) |
| 296 | 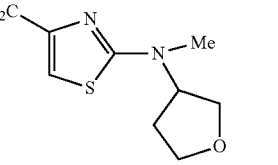 | P54 MS(ESI) m/z: 257([M + H]+) |
| 297 | 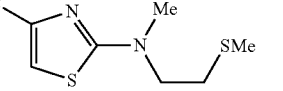 | P5→P55→P53 MS(API) m/z: 261([M + H]+) |
| 298 | 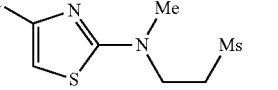 | P19 MS(API) m/z: 293([M + H]+) |
| 299 | 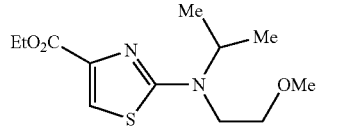 | P5→P55→P53 MS(API) m/z: 273([M + H]+) |
TABLE 34-continued
| 300 | 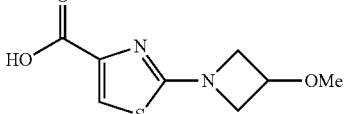 | P3 MS(ESI) m/z: 215([M + H]+) |
| --- | --- | --- |
| 301 | 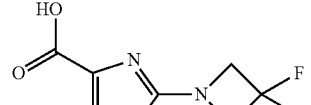 | P3 MS(ESI) m/z: 221([M + H]+) |
| 302 | 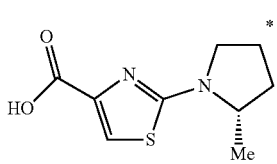 | P3 MS(ESI) m/z: 213([M + H]+) |
TABLE 35
| 303 | 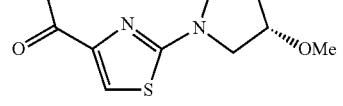 | P3 MS(ESI) m/z: 229([M + H]+) |
| --- | --- | --- |
| 304 | 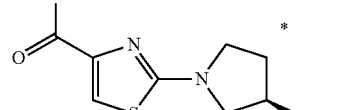 | P3 MS(ESI) m/z: 229([M + H]+) |
| 305 | 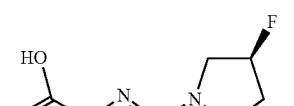 | P3 MS(ESI) m/z: 247([M + H]+) |
| 306 | 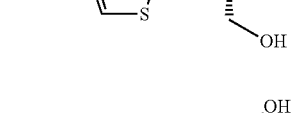 | P3 MS(ESI) m/z: 259([M + H]+) |
| 307 | 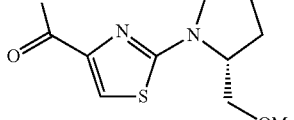 | P3 MS(ESI) m/z: 259([M + H]+) |

TABLE 35-continued

| No. | Structure | Notes |
|---|---|---|
| 308 | 2-(2-oxopyrrolidin-1-yl)thiazole-4-carboxylic acid | P3 MS(ESI) m/z: 213([M + H]+) |
| 309 | 2-(4,4-difluoropiperidin-1-yl)thiazole-4-carboxylic acid | P3 MS(ESI) m/z: 249([M + H]+) |
| 310 | 2-(3-fluoropiperidin-1-yl)thiazole-4-carboxylic acid | P3 MS(ESI) m/z: 231([M + H]+) |
| 311 | 2-(3,3-difluoropiperidin-1-yl)thiazole-4-carboxylic acid | P3 MS(ESI) m/z: 249([M + H]+) |

TABLE 36

| No. | Structure | Notes |
|---|---|---|
| 312 | 2-(4-hydroxypiperidin-1-yl)thiazole-4-carboxylic acid | P3 MS(ESI) m/z: 229([M + H]+) |
| 313 | 2-(4-methoxypiperidin-1-yl)thiazole-4-carboxylic acid | P3 MS(ESI) m/z: 243([M + H]+) |
| 314 | 2-(4-ethoxypiperidin-1-yl)thiazole-4-carboxylic acid | P3 MS(ESI) m/z: 255([M – H]–) |
| 315 | 2-(4-(2-methoxyethoxy)piperidin-1-yl)thiazole-4-carboxylic acid | P3 MS(ESI) m/z: 287([M + H]+) |
| 316 | 2-(4-(methoxymethyl)piperidin-1-yl)thiazole-4-carboxylic acid | P3 MS(ESI) m/z: 257([M + H]+) |

TABLE 36-continued

| No. | Structure | Notes |
|---|---|---|
| 317 | (S)-2-(3-methoxypiperidin-1-yl)thiazole-4-carboxylic acid * | P3 MS(FAB) m/z: 243([M + H]+) |
| 318 | 2-(1-oxa-8-azaspiro[4.5]decan-8-yl)thiazole-4-carboxylic acid | P3 (Na) MS(ESI) m/z: 269([M + H]+) |
| 319 | 2-(2-(hydroxymethyl)azepan-1-yl)thiazole-4-carboxylic acid | P3 MS(ESI) m/z: 257([M + H]+) |
| 320 | 2-morpholinothiazole-4-carboxylic acid | P3 MS(ESI) m/z: 215([M + H]+) |
| 321 | (S)-2-(3-methylmorpholino)thiazole-4-carboxylic acid * | P3 MS(ESI) m/z: 229([M + H]+) |

TABLE 37

| No. | Structure | Notes |
|---|---|---|
| 322 | 2-(3-(methoxymethyl)morpholino)thiazole-4-carboxylic acid | P3 MS(ESI) m/z: 259([M + H]+) |
| 323 | (S)-2-(3-(methoxymethyl)morpholino)thiazole-4-carboxylic acid * | P3 MS(FAB) m/z: 259([M + H]+) |
| 324 | 2-((2-ethoxyethyl)(methyl)amino)thiazole-4-carboxylic acid | P3 MS(API) m/z: 231([M + H]+) |
| 325 | 2-((2-(isopropoxy)ethyl)(methyl)amino)thiazole-4-carboxylic acid | P3 MS(ESI) m/z: 245([M + H]+) |

TABLE 37-continued

| 326 | [carboxythiazole with N(Me)CH2CH2OC(Me)3] | P3 MS(ESI) m/z: 259([M + H]+) |
|---|---|---|
| 327 | [carboxythiazole with N(Me)CH2-tetrahydropyran] | P3 MS(ESI) m/z: 257([M + H]+) |
| 328 | [carboxythiazole with N(Me)CH(Me)CH2OMe]* | P3 MS(FAB) m/z: 231([M + H]+) |
| 329 | [carboxythiazole with N(Me)CH(Me)CH2OMe]* | P3 MS(EI) m/z: 230([M]+) |
| 330 | [carboxythiazole with N(Me)CH2C(O)NH2] | P3 MS(FAB) m/z: 216([M + H]+) |

TABLE 38

| 331 | [carboxythiazole with N(Me)CH2C(O)NMe2] | P3 MS(FAB) m/z: 242([M − H]−) |
|---|---|---|
| 332 | [carboxythiazole with N(Me)CH2CH2NMe2] | P3 MS(ESI) m/z: 230([M + H]+) |
| 333 | [MeO2C-NH-CH2-thiazole-COOH] | P3 MS(FAB) m/z: 217([M + H]+) |
| 334 | [Ac-NH-CH2-thiazole-COOH] | P3 MS(FAB) m/z: 199([M − H]−) |

TABLE 38-continued

| 335 | [carboxythiazole-2-yl-(1-methylpiperidin-4-yl)] | P3 MS(ESI) m/z: 227([M + H]+) |
|---|---|---|
| 336 | [carboxythiazole-2-yl-(1-propylpiperidin-4-yl)] | P3 MS(ESI) m/z: 255([M + H]+) |
| 337 | [carboxythiazole-2-yl-(1-propanoylpiperidin-4-yl)] | P3 MS(ESI) m/z: 269([M + H]+) |
| 338 | [carboxythiazole-2-yl-CH2-O-(2-bromophenyl)] | P3 MS(FAB) m/z: 314([M + H]+) |
| 339 | [carboxythiazole-2-yl-CH2-(3,5-dichlorophenyl)] | P3 MS(FAB) m/z: 288([M + H]+) |
| 340 | [carboxythiazole-2-yl-(3-fluoropyrrolidin-1-yl)]* | P3 MS(ESI) m/z: 217([M + H]+) |

TABLE 39

| 341 | [carboxythiazole-2-yl-(4-(pyridin-2-yloxy)piperidin-1-yl)] | P3 MS(ESI) m/z: 306([M + H]+) |
|---|---|---|
| 3 | [carboxythiazole-2-yl-(4-(pyrimidin-2-yloxy)piperidin-1-yl)] | P3 MS(ESI) m/z: 307([M + H]+) |
| 342 | [carboxythiazole-2-yl-(3-(benzyloxy)cyclopentyl)] | P3 MS(ESI) m/z: 304([M + H]+) |

TABLE 39-continued

| # | Structure | Notes |
|---|---|---|
| 343 | (cyclopentane with OBn substituent)-thiazole-4-carboxylic acid | P3<br>MS(ESI) m/z: 304([M + H]+) |
| 344 | 2-(N-methyl-N-(tetrahydrofuran-3-yl)amino)thiazole-4-carboxylic acid | P3<br>MS(EI) m/z: 228([M]+) |
| 345 | 2-(N-methyl-N-(2-(methylsulfonyl)ethyl)amino)thiazole-4-carboxylic acid | P3<br>MS(ESI) m/z: 263([M − H]−) |
| 346 | 2-(N-methyl-N-(2-methoxyethyl)amino)thiazole-4-carboxylic acid | P53→P3<br>MS(ESI) m/z: 217([M + H]+) |
| 347 | 2-(N-isopropyl-N-(2-methoxyethyl)amino)thiazole-4-carboxylic acid | P3<br>MS(API) m/z: 245([M + H]+) |
| 56 | 3-methoxyazetidine-1-carboxamide | P56<br>MS(FAB) m/z: 131([M + H]+) |
| 348 | 3,3-difluoropiperidine-1-carboxamide | P56<br>MS(ESI) m/z: 165([M + H]+) |

TABLE 40

| # | Structure | Notes |
|---|---|---|
| 349 | 4-(cyclopropylmethoxy)piperidine-1-carboxamide | P56<br>MS(ESI) m/z: 199([M + H]+) |
| 350 | (S)-3-(methoxymethyl)morpholine-4-carboxamide * | P56<br>MS(FAB) m/z: 175([M + H]+) |
| 351 | (S)-N-methyl-N-(1-methoxy-2-methylpropan-2-yl)urea * | P56<br>MS(FAB) m/z: 147([M + H]+) |

TABLE 40-continued

| # | Structure | Notes |
|---|---|---|
| 352 | N-methyl-N-(2-ethoxyethyl)urea | P56<br>MS(ESI) m/z: 147([M + H]+) |
| 353 | N-methyl-N-(2-(1-methoxyethoxy)ethyl)urea | P56<br>MS(ESI) m/z: 161([M + H]+) |
| 354 | N-methyl-N-(2-(dimethylamino)-2-oxoethyl)urea | P56<br>MS(EI) m/z: 159([M]+) |
| 355 | 4-ethoxypiperidine-1-carboxamide | P56<br>MS(ESI) m/z: 173([M + H]+) |
| 356 | (S)-methyl 2-(tetrahydro-2H-pyran-4-carboxamido)-3-hydroxypropanoate * | P46<br>MS(ESI) m/z: 232([M + H]+) |
| 46 | (S)-methyl 2-(2-(Boc-amino)isonicotinamido)-3-hydroxypropanoate * | P46<br>MS(FAB) m/z: 340([M + H]+) |

TABLE 41

| # | Structure | Notes |
|---|---|---|
| 357 | (S)-methyl 2-(2-(2-bromophenoxy)acetamido)-3-hydroxypropanoate * | P46<br>MS(FAB) m/z: 332([M + H]+) |
| 358 | (S)-methyl 2-(2-methoxyacetamido)-3-hydroxypropanoate * | P46<br>MS(FAB) m/z: 192([M + H]+) |
| 359 | (S)-methyl 2-(2-(isopropoxy)acetamido)-3-hydroxypropanoate * | P46<br>MS(FAB) m/z: 220([M + H]+) |

TABLE 41-continued

| | | |
|---|---|---|
| 360 | 3,5-dichlorophenylacetamide (H2N-C(O)-CH2-C6H3Cl2) | P61<br>MS(EI) m/z: 203([M]+) |
| 361 | EtO2C-oxazole-N-azetidine-OH | P56→P58<br>MS(ESI) m/z: 213([M + H]+) |
| 362 | EtO2C-oxazole-N-azetidine-OMe | P58<br>MS(EI) m/z: 226([M]) |
| 363 | EtO2C-oxazole-N-azetidine-O-pyrimidine | P39<br>MS(ESI) m/z: 291([M + H]+) |
| 10 | EtO2C-oxazole-N-pyrrolidine-F * | P10<br>MS(ESI) m/z: 229([M + H]+) |
| 364 | EtO2C-oxazole-N-pyrrolidine-OH * | P56→P58<br>MS(ESI) m/z: 227([M + H]+) |
| 365 | EtO2C-oxazole-N-pyrrolidine-OMe * | P56→P58<br>MS(FAB) m/z: 241([M + H]+) |

TABLE 42

| | | |
|---|---|---|
| 366 | EtO2C-oxazole-N-pyrrolidine-OEt * | P41<br>MS(ESI) m/z: 225([M + H]+) |
| 367 | EtO2C-oxazole-N-pyrrolidine-O-CH2CH2-OMe * | P41<br>MS(ESI) m/z: 285([M + H]+) |
| 368 | EtO2C-oxazole-N-pyrrolidine-O-pyridine * | P39<br>MS(ESI) m/z: 304([M + H]+) |

TABLE 42-continued

| | | |
|---|---|---|
| 369 | EtO2C-oxazole-N-pyrrolidine-O-pyrimidine * | P39<br>MS(ESI) m/z: 305([M + H]+) |
| 370 | EtO2C-oxazole-N-piperidine-F | P10<br>MS(ESI) m/z: 243([M + H]+) |
| 371 | EtO2C-oxazole-N-piperidine-CF2 | P58<br>MS(ESI) m/z: 261([M + H]+) |
| 372 | EtO2C-oxazole-N-piperidine-OH | P58<br>MS(ESI) m/z: 241([M + H]+) |
| 373 | EtO2C-oxazole-N-piperidine-O-CH2-cyclopropyl | P58<br>MS(API) m/z: 295([M + H]+) |
| 374 | EtO2C-oxazole-N-piperidine-O-pyridine | P39<br>MS(ESI) m/z: 318([M + H]+) |
| 375 | EtO2C-oxazole-N-piperidine-O-pyridine-CN | P39<br>MS(ESI) m/z: 343([M + H]+) |

TABLE 43

| | | |
|---|---|---|
| 376 | EtO2C-oxazole-N-piperidine-O-pyrimidine | P39<br>MS(ESI) m/z: 319([M + H]+) |
| 377 | EtO2C-oxazole-N-piperidine-O-pyrazine | P39<br>MS(ESI) m/z: 319([M + H]+) |
| 57 | EtO2C-oxazole-N-piperidine-O-pyridazinone | P57<br>MS(ESI) m/z: 335([M + H]+) |

TABLE 43-continued

| # | Structure | Notes |
|---|---|---|
| 378 | EtO2C-oxazole-morpholine | P56→P58 MS(ESI) m/z: 227([M + H]+) |
| 379 | EtO2C-oxazole-morpholine with CH2OMe * | P58 MS(FAB) m/z: 271([M + H]+) |
| 380 | EtO2C-oxazole-N(Me)CH2CH2OEt | P58 MS(API) m/z: 243([M + H]+) |
| 381 | EtO2C-oxazole-N(Me)CH2CH2OCH(Me)2 | P58 MS(ESI) m/z: 257([M + H]+) |
| 382 | EtO2C-oxazole-N(Me)CH2-tetrahydropyran | P56→P58 MS(ESI) m/z: 269([M + H]+) |
| 383 | EtO2C-oxazole-N(Me)CH(Me)CH2OMe * | P58 MS(EI) m/z: 242([M]+) |

TABLE 44

| # | Structure | Notes |
|---|---|---|
| 384 | EtO2C-oxazole-N(Me)CH2C(O)NMe2 | P58 MS(FAB) m/z: 256([M + H]+) |
| 385 | tetrahydropyran-oxazole-CO2Me | P45 MS(ESI) m/z: 212([M + H]+) |
| 386 | MeO2C-oxazole-CH2OMe | P45 MS(FAB) m/z: 172([M + H]+) |
| 387 | MeO2C-oxazole-CH2OCH(Me)2 | P45 MS(CI) m/z: 200([M + H]+) |

TABLE 44-continued

| # | Structure | Notes |
|---|---|---|
| 388 | MeO2C-oxazole-CH2O-(2-bromophenyl) | P45 MS(EI) m/z: 311([M]+) |
| 45 | MeO2C-oxazole-pyridine-NHBoc | P45 MS(FAB) m/z: 320([M + H]+) |
| 389 | EtO2C-oxazole-(3-F,4-OH-piperidine) | P56→P58 MS(ESI) m/z: 259([M + H]+) |
| 390 | EtO2C-oxazole-(3-F,4-O-pyrimidinyl-piperidine) | P56→P58 MS(ESI) m/z: 337([M + H]+) |
| 58 | EtO2C-oxazole-N(Me)CH2CH2OMe | P58 MS(ESI) m/z: 229([M + H]+) |
| 391 | HOOC-oxazole-(3-OMe-azetidine) | P3 (Na) MS(FAB) m/z: 199([M + H]+) |

TABLE 45

| # | Structure | Notes |
|---|---|---|
| 392 | HOOC-oxazole-azetidine-O-pyrimidine | P3 (Na) MS(ESI) m/z: 263([M + H]+) |
| 393 | HOOC-oxazole-(3-F-pyrrolidine) * | P3 (Na) MS(ESI) m/z: 201([M + H]+) |
| 394 | HOOC-oxazole-(3-OMe-pyrrolidine) * | P3 MS(FAB) m/z: 213([M + H]+) |

TABLE 45-continued

| | | |
|---|---|---|
| 395 | [structure] | P3 (Na) MS(ESI) m/z: 227([M + H]+) |
| 396 | [structure] | P3 (Na) MS(ESI) m/z: 277([M + H]+) |
| 397 | [structure] | P3 (Na) MS(ESI) m/z: 215([M + H]+) |
| 398 | [structure] | P3 (Na) MS(ESI) m/z: 231([M − H]−) |
| 399 | [structure] | P3 (Na) MS(ESI) m/z: 213([M + H]+) |
| 400 | [structure] | P3 (Na) MS(ESI) m/z: 231([M + H]+) |
| 401 | [structure] | P3 (Na) MS(ESI) m/z: 241([M + H]+) |

TABLE 46

| | | |
|---|---|---|
| 402 | [structure] | P3 (Na) MS(ESI) m/z: 265([M − H]−) |
| 403 | [structure] | P3 (Na) MS(ESI) m/z: 290([M + H]+) |

TABLE 46-continued

| | | |
|---|---|---|
| 404 | [structure] | P3 (Na) MS(ESI) m/z: 315([M + H]+) |
| 405 | [structure] | P3 (Na) MS(ESI) m/z: 291([M + H]+) |
| 406 | [structure] | P3 (Na) MS(ESI) m/z: 309([M + H]+) |
| 407 | [structure] | P3 (Na) MS(ESI) m/z: 291([M + H]+) |
| 408 | [structure] | P3 (Na) MS(ESI) m/z: 307([M + H]+) |
| 409 | [structure] | P3 MS(ESI) m/z: 199([M + H]+) |
| 410 | [structure] | P3 (Na) MS(ESI) m/z: 243([M + H]+) |
| 411 | [structure] | P3 (Na) MS(ESI) m/z: 215([M + H]+) |

TABLE 47

| | | |
|---|---|---|
| 412 | [structure] | P3 (Na) MS(ESI) m/z: 227([M − H]−) |
| 413 | [structure] | P3 (Na) MS(ESI) m/z: 241([M + H]+) |

TABLE 47-continued

| # | Structure | Notes |
|---|---|---|
| 414 | carboxy-oxazole-N(Me)-CH(Me)CH2OMe * | P3 (Na) MS(FAB) m/z: 213([M − H]−) |
| 415 | carboxy-oxazole-N(Me)-CH2C(O)NMe2 | P3 (Na) MS(FAB) m/z: 228([M + H]+) |
| 416 | carboxy-oxazole-(tetrahydropyran-4-yl) | P3 MS(ESI) m/z: 198([M + H]+) |
| 417 | carboxy-oxazole-CH2OMe | P3 MS(FAB) m/z: 158([M + H]+) |
| 418 | carboxy-oxazole-CH2OCH(Me)2 | P3 MS(FAB) m/z: 186([M + H]+) |
| 419 | carboxy-oxazole-CH2O-(2-bromophenyl) | P3 MS(FAB) m/z: 298([M + H]+) |
| 420 | carboxy-oxazole-(2-(NHBoc)pyridin-4-yl) | P3 MS(FAB) m/z: 306([M + H]+) |

TABLE 48

| # | Structure | Notes |
|---|---|---|
| 421 | carboxy-oxazole-N-pyrrolidin-3-yl-O-(pyridin-2-yl) * | P3 (Na) MS(ESI) m/z: 276([M + H]+) |
| 422 | carboxy-oxazole-N-pyrrolidin-3-yl-O-CH2CH2OMe * | P3 (Na) MS(ESI) m/z: 257([M + H]+) |
| 423 | carboxy-oxazole-N(Me)CH2CH2OMe | P3 MS(ESI) m/z: 201([M + H]+) |
| 67 | morpholinomethyl-benzoxazinone-thiazole-N(Me)CH2-(tetrahydropyran-4-yl) | P67 MS(ESI) m/z: 457([M + H]+) |

TABLE 48-continued

| | | |
|---|---|---|
| 424 | [structure] | P67 MS(ESI) m/z: 358([M + H]+) |
| 60 | [structure] | P60 MS(API) m/z: 348([M + H]+) |
| 70 | [structure] | P70 MS(FAB) m/z: 324([M]+) |
| 425 | [structure] | P4 MS(FAB) m/z: 424([M]+) |

TABLE 49

| | | |
|---|---|---|
| 426 | [structure] | P3 MS(ESI) m/z: 269([M + H]+) |
| 427 | [structure] * | P39 MS(FAB) m/z: 294([M + H]+) |
| 428 | [structure] * | P65 (HCl) MS(ESI) m/z: 194([M + H]+) |
| 429 | [structure] | P54 MS(API) m/z: 283([M + H]+) |

TABLE 49-continued

| | | |
|---|---|---|
| 69 | [structure] | P69 MS(FAB) m/z: 338([M + H]+) |
| 430 | [structure] | P62 MS(ESI) m/z: 353([M + H]+) |
| 68 | [structure] | P68 MS(ESI) m/z: 408([M + H]+) |

TABLE 49-continued
| | | |
|---|---|---|
| 431 | 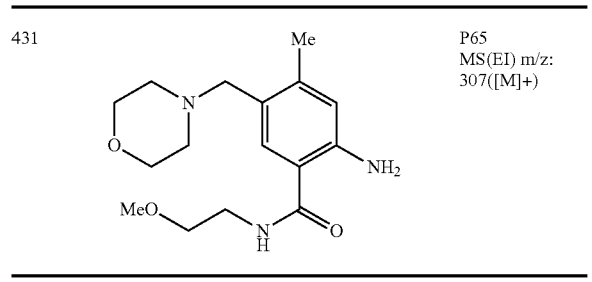 | P65 MS(EI) m/z: 307([M]+) |
TABLE 50
| | | |
|---|---|---|
| 432 | 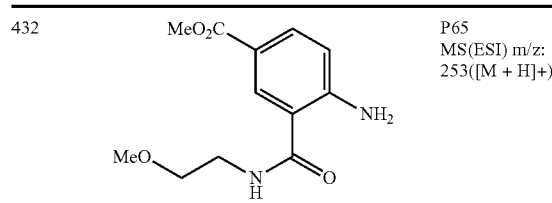 | P65 MS(ESI) m/z: 253([M + H]+) |
| 433 | 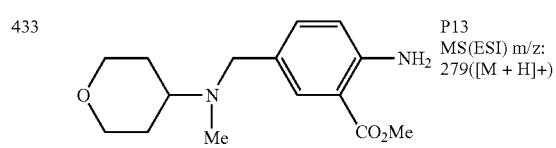 | P13 MS(ESI) m/z: 279([M + H]+) |
| 434 | 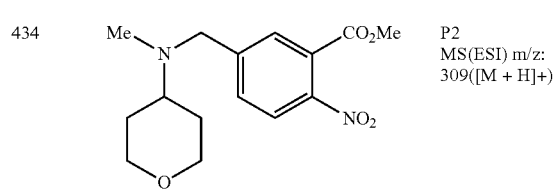 | P2 MS(ESI) m/z: 309([M + H]+) |
| 440 | 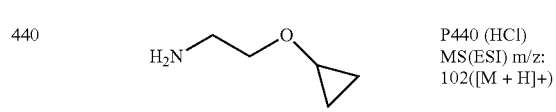 | P440 (HCl) MS(ESI) m/z: 102([M + H]+) |
| 449 | 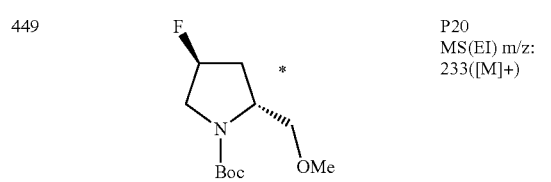 | P20 MS(EI) m/z: 233([M]+) |
| 438 | 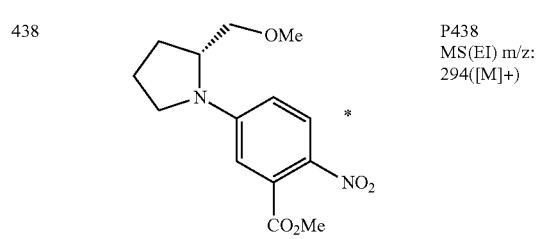 | P438 MS(EI) m/z: 294([M]+) |
| 450 | 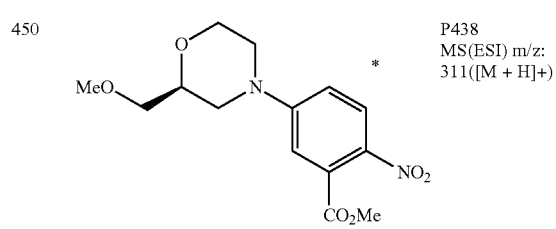 | P438 MS(ESI) m/z: 311([M + H]+) |
TABLE 50-continued
| | | |
|---|---|---|
| 451 | 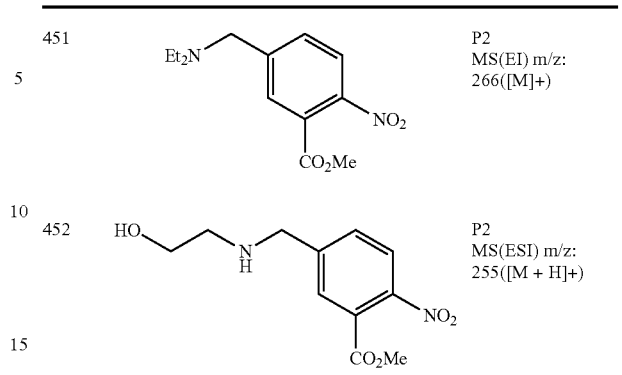 | P2 MS(EI) m/z: 266([M]+) |
| 452 | 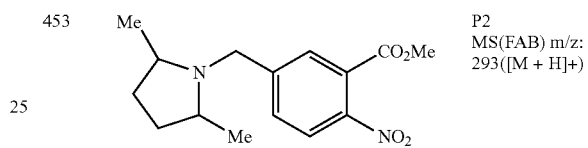 | P2 MS(ESI) m/z: 255([M + H]+) |
TABLE 51
| | | |
|---|---|---|
| 453 | 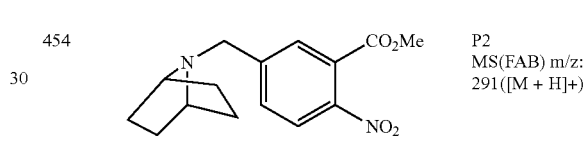 | P2 MS(FAB) m/z: 293([M + H]+) |
| 454 | 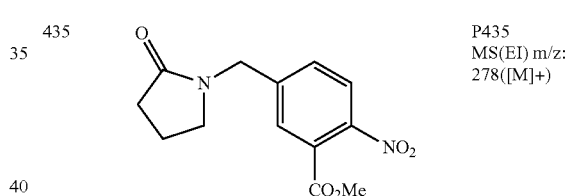 | P2 MS(FAB) m/z: 291([M + H]+) |
| 435 | 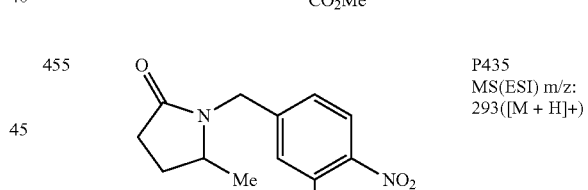 | P435 MS(EI) m/z: 278([M]+) |
| 455 | 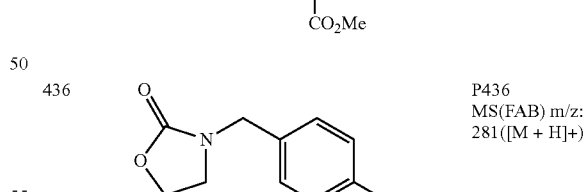 | P435 MS(ESI) m/z: 293([M + H]+) |
| 436 | 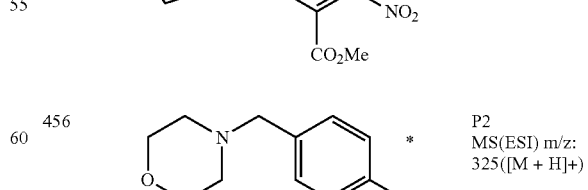 | P436 MS(FAB) m/z: 281([M + H]+) |
| 456 | 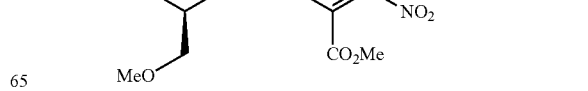 | P2 MS(ESI) m/z: 325([M + H]+) |

TABLE 51-continued

| | | |
|---|---|---|
| 439 | [structure: MeO2C, O2N-phenyl, pyrrolidine-N-Bn] | P439<br>MS(ESI) m/z:<br>341([M + H]+) |
| 457 | [structure: MeO2C, O2N-phenyl-vinyl] | P48<br>MS(ESI) m/z:<br>208([M + H]+) |
| 458 | [structure: 3,3-dimethylmorpholine-CH2-phenyl(CO2H)(NO2)] | P51<br>MS(ESI) m/z:<br>295([M + H]+) |

TABLE 52

| | | |
|---|---|---|
| 459 | [structure: morpholine-CH2CH2-phenyl(NO2)(CO2H)] | P51<br>MS(ESI) m/z:<br>281([M + H]+) |
| 460 | [structure: morpholine-CH2-phenyl(NO2)-C(O)NH-CH2CH2OMe] | P62<br>MS(ESI) m/z:<br>324([M + H]+) |
| 461 | [structure: 3,3-dimethylmorpholine-CH2-phenyl(NO2)-C(O)NH-CH2CH2OMe] | P62<br>MS(ESI) m/z:<br>352([M + H]+) |
| 462 | [structure: morpholine-CH2CH2-phenyl(NO2)-C(O)NH-CH2CH2OMe] | P62<br>MS(ESI) m/z:<br>338([M + H]+) |

TABLE 52-continued

| | | |
|---|---|---|
| 463 | [structure: morpholine-CH2CH2-phenyl(NO2)-C(O)NH-CH2CH2CH2F] | P62<br>MS(ESI) m/z:<br>340([M + H]+) |
| 464 | [structure: benzodioxine-NO2-C(O)NH-pyridyl] | P62<br>MS(ESI) m/z:<br>300([M − H]−) |
| 465 | [structure: pyridyl-NH-C(O)-phenyl(NO2)-CH2OMe] | P61<br>MS(ESI) m/z:<br>286([M − H]−) |

TABLE 53

| | | |
|---|---|---|
| 466 | [structure: 3,3-dimethylmorpholine-CH2-phenyl(NO2)-C(O)NH-pyridyl] | P62<br>MS(ESI) m/z:<br>371([M + H]+) |
| 467 | [structure: 2-(methoxymethyl)pyrrolidine-N-phenyl(NH2)(CO2Me)] * | P32<br>MS(EI) m/z:<br>264([M]+) |
| 468 | [structure: 2-(methoxymethyl)morpholine-N-phenyl(NH2)(CO2Me)] * | P32<br>MS(EI) m/z:<br>280([M]+) |
| 469 | [structure: Et2N-CH2-phenyl(NH2)(CO2Me)] | P13<br>MS(EI) m/z:<br>236([M]+) |

TABLE 53-continued

| # | Structure | Ref / MS |
|---|---|---|
| 470 | (2,5-dimethylpyrrolidin-1-yl)methyl on 4-amino-3-methoxycarbonylphenyl | P13 MS(ESI) m/z: 263([M + H]+) |
| 471 | (8-azabicyclo)methyl on 4-amino-3-methoxycarbonylphenyl | P13 MS(ESI) m/z: 261([M + H]+) |
| 472 | (2-methoxymethylmorpholin-4-yl)methyl on 4-amino-3-methoxycarbonylphenyl * | P13 MS(EI) m/z: 294([M]+) |
| 473 | (2-oxopyrrolidin-1-yl)methyl on 4-amino-3-methoxycarbonylphenyl | P13 MS(ESI) m/z: 249([M + H]+) |

TABLE 54

| # | Structure | Ref / MS |
|---|---|---|
| 474 | (5-oxo-2-methylpyrrolidin-1-yl)methyl on 4-amino-3-methoxycarbonylphenyl | P13 MS(ESI) m/z: 263([M + H]+) |
| 475 | (2-oxo-oxazolidin-3-yl)methyl on 4-amino-3-methoxycarbonylphenyl | P13 MS(ESI) m/z: 251([M + H]+) |
| 476 | 1-benzylpyrrolidin-3-yl on 2-amino-methoxycarbonylphenyl | P13 MS(ESI) m/z: 311([M + H]+) |
| 477 | morpholinomethyl on 3-amino-4-methoxycarbonylphenyl | P13 MS(EI) m/z: 250([M]+) |
| 441 | methyl 2-methyl-5-(Boc-amino)pyridine-4-carboxylate | P441 MS(ESI) m/z: 267([M + H]+) |

TABLE 54-continued

| # | Structure | Ref / MS |
|---|---|---|
| 478 | methyl 2-(morpholinomethyl)-5-(Boc-amino)pyridine-4-carboxylate | P24→P2 MS(FAB) m/z: 352([M + H]+) |
| 479 | methyl 2-(morpholinomethyl)-5-aminopyridine-4-carboxylate | P65 MS(FAB) m/z: 252([M + H]+) |
| 480 | 2-amino-5-(morpholinomethyl)-N-(2-methoxyethyl)benzamide | P13 MS(ESI) m/z: 294([M + H]+) |
| 481 | 2-amino-5-((3,3-dimethylmorpholino)methyl)-N-(2-methoxyethyl)benzamide | P13 MS(EI) m/z: 321([M]+) |

TABLE 55

| # | Structure | Ref / MS |
|---|---|---|
| 482 | 2-amino-5-(2-morpholinoethyl)-N-(2-methoxyethyl)benzamide | P13 MS(ESI) m/z: 308([M + H]+) |
| 483 | 2-amino-5-(2-morpholinoethyl)-N-(3-fluoropropyl)benzamide | P13 MS(ESI) m/z: 310([M + H]+) |
| 484 | 2-amino-5-((2-(methoxymethyl)pyrrolidin-1-yl)methyl)-N-(tetrahydro-2H-pyran-4-yl)benzamide * | P51→P62 MS(ESI) m/z: 348([M + H]+) |

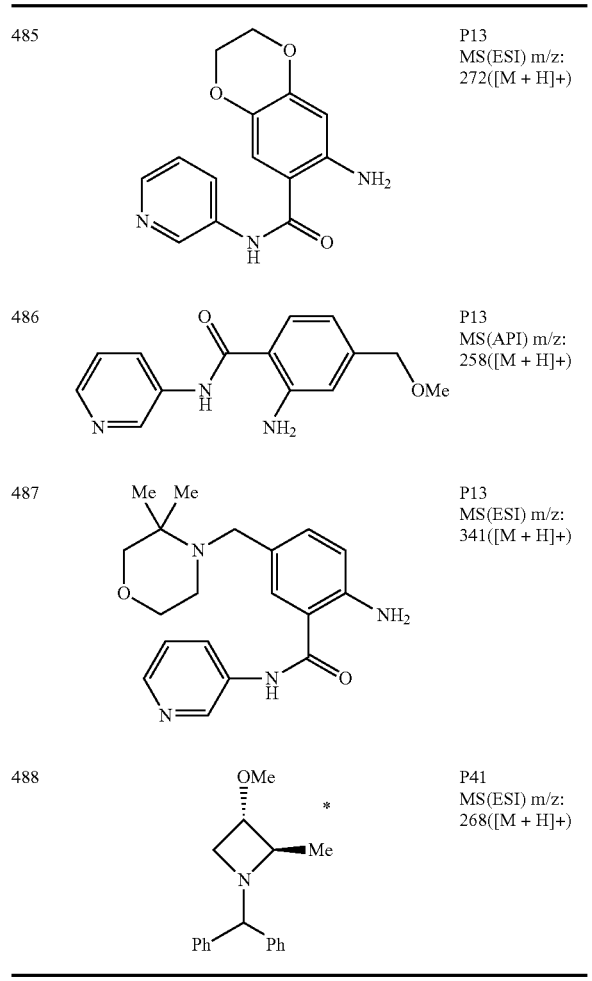
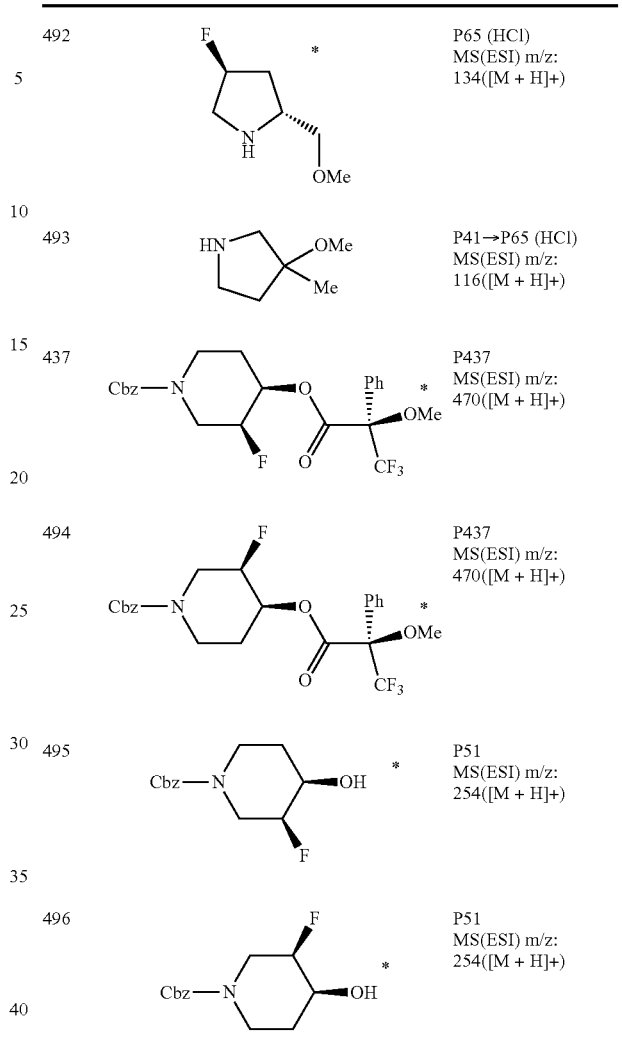

TABLE 57-continued

| | | |
|---|---|---|
| 500 | (structure) | P33 MS(ESI) m/z: 198([M + H]+) |
| 501 | (structure) | P33 MS(ESI) m/z: 198([M + H]+) |
| 502 | (structure) | P65 (2HCl) MS(ESI) m/z: 194([M + H]+) |
| 443 | (structure) | P443 MS(ESI) m/z: 206([M + H]+) |
| 503 | (structure) | P37 MS(API) m/z: 192([M + H]+) |
| 504 | (structure) | P37 MS(API) m/z: 192([M + H]+) |

TABLE 58

| | | |
|---|---|---|
| 505 | (structure) | P12 MS(EI) m/z: 231([M]+) |

TABLE 58-continued

| | | |
|---|---|---|
| 506 | (structure) | P12 MS(EI) m/z: 231([M]+) |
| 507 | (structure) | P16 MS(EI) m/z: 217([M]+) |
| 508 | (structure) | P16 MS(EI) m/z: 217([M]+) |
| 442 | (structure) | P442 (HCl) MS(ESI) m/z: 128([M + H]+) |
| 509 | (structure) | P442 (HCl) MS(ESI) m/z: 128([M + H]+) |
| 510 | (structure) | P39 MS(ESI) m/z: 313([M + H]+) |
| 511 | (structure) | P442 MS(ESI) m/z: 223([M + H]+) |
| 512 | (structure) | P46 MS(ESI) m/z: 324([M + H]+) |
| 513 | (structure) | P54 MS(ESI) m/z: 229([M + H]+) |

TABLE 59

| | | |
|---|---|---|
| 514 | (structure) | P41 MS(EI) m/z: 256([M]+) |

TABLE 59-continued

| # | Structure | Method / MS |
|---|---|---|
| 515 | MeO₂C-thiazole-N(azetidine-OEt) | P54<br>MS(ESI) m/z:<br>243([M + H]+) |
| 516 | MeO₂C-thiazole-N(Me)(CH₂)₃OH | P54<br>MS(EI) m/z:<br>230([M]+) |
| 517 | MeO₂C-thiazole-N(Me)CH₂CH₂CH₂O-pyrimidine | P39<br>MS(ESI) m/z:<br>309([M + H]+) |
| 518 | EtO₂C-oxazole-piperidine-O-(4-Me-pyrimidine) | P39<br>MS(ESI) m/z:<br>333([M + H]+) |
| 519 | EtO₂C-oxazole-(bicyclic amine)-O-pyrimidine | P56→P58<br>MS(ESI) m/z:<br>345([M + H]+) |
| 520 | EtO₂C-oxazole-piperidine(F)-O-pyrimidine * | P56→P58<br>MS(ESI) m/z:<br>337([M + H]+) |
| 521 | EtO₂C-oxazole-piperidine(F)-O-pyrimidine * | P56→P58<br>MS(ESI) m/z:<br>337([M + H]+) |
| 522 | MeO₂C-oxazole-cyclohexyl-O-pyrimidine | P45<br>MS(ESI) m/z:<br>304([M + H]+) |
| 523 | HO₂C-thiazole-N(pyrrolidine-OEt) * | P3<br>MS(ESI) m/z:<br>243([M + H]+) |
| 524 | HO₂C-thiazole-N(azetidine-OEt) | P3<br>MS(ESI) m/z:<br>229([M + H]+) |

TABLE 60
| 525 | 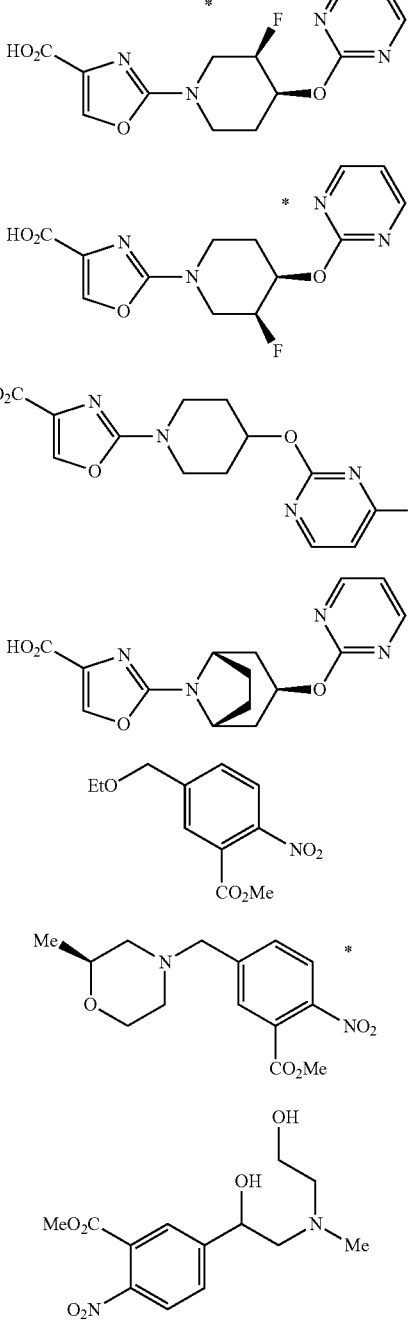 | P3 MS(ESI) m/z: 295([M + H]+) |
| 526 |  | P3 MS(ESI) m/z: 309([M + H]+) |
| 527 |  | P3 MS(ESI) m/z: 309([M + H]+) |
| 528 |  | P3 (Na) MS(ESI) m/z: 303([M − H]−) |
| 529 | 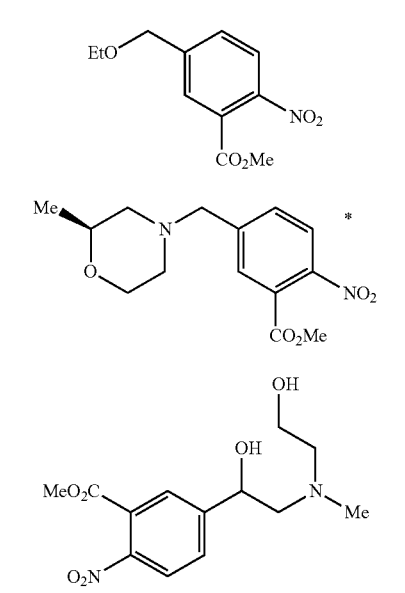 | P3 (Na) MS(ESI) m/z: 317([M + H]+) |
| 445 | 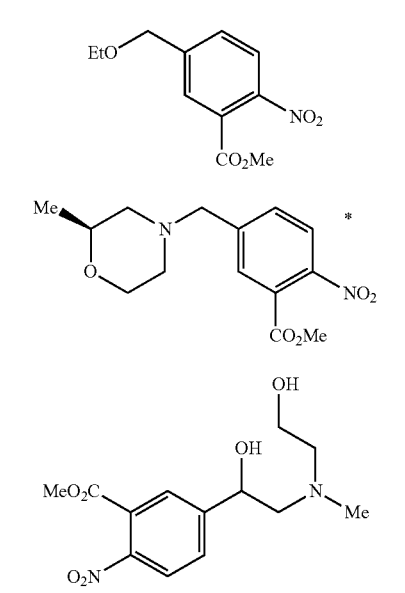 | P445 MS(ESI) m/z: 240([M + H]+) |
| 530 | 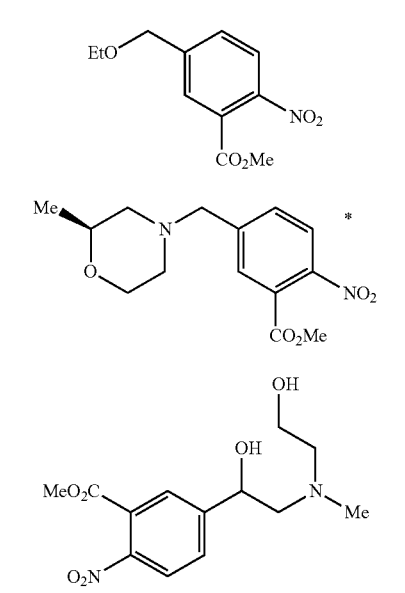 | P2 MS(ESI) m/z: 295([M + H]+) |
| 446 | 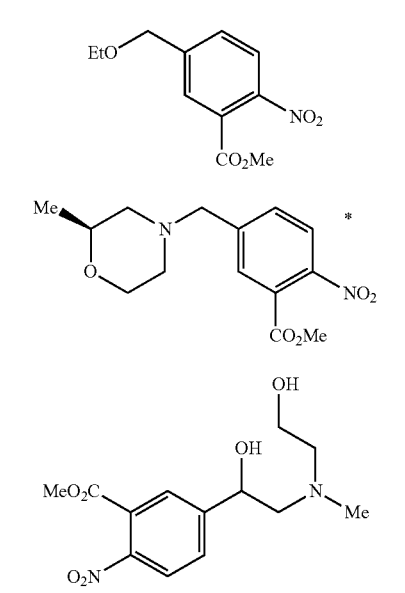 | P446 MS(ESI) m/z: 299([M + H]+) |
| 447 | 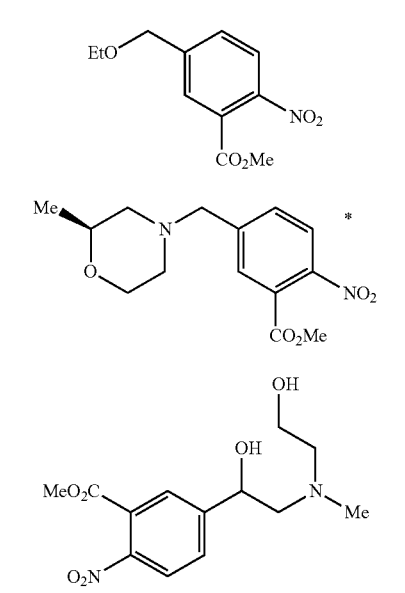 | P447 MS(ESI) m/z: 281([M + H]+) |

TABLE 61

| | | |
|---|---|---|
| 448 | morpholine-C(=O)-CHCl-(phenyl with 4-NO2, 3-CO2Me) | P448<br>MS(ESI) m/z:<br>343([M + H]+) |
| 531 | (2-Me-morpholine)-CH2-(phenyl with 2-NH2, 3-CO2Me) * | P13<br>MS(ESI) m/z:<br>265([M + H]+) |
| 532 | EtO-CH2-(phenyl with 2-NH2, 3-CO2Me) | P13<br>MS(EI) m/z:<br>209([M]+) |
| 533 | (4-Me-morpholin-2-yl)-(phenyl with 4-NH2, 2-CO2Me) | P13<br>MS(ESI) m/z:<br>251([M + H]+) |
| 534 | morpholine-C(=O)-CH2-(phenyl with 2-NH2, 3-CO2Me) | P32<br>MS(ESI) m/z:<br>279([M + H]+) |

TABLE 62

[Core structure: pyridin-3-yl-NH-C(=O)-phenyl-NH-C(=O)-thiazole-R¹]

| Ex | R¹ | Syn (Sal)<br>Dat |
|---|---|---|
| 44 | 1-methylpiperidin-4-yl with OH | E11 (HCl)<br>MS(ESI) m/z:<br>424([M + H]+) |
| 45 | (1-methylpiperidin-4-yl)-CH2-OH | E28<br>MS(ESI) m/z:<br>438([M + H]+) |
| 46 | (1-methylpiperidin-4-yl)-CH2CH2-OH | E28<br>MS(ESI) m/z:<br>452([M + H]+) |

TABLE 62-continued

[Core structure: pyridin-3-yl-NH-C(=O)-phenyl-NH-C(=O)-thiazole-R¹]

| Ex | R¹ | Syn (Sal)<br>Dat |
|---|---|---|
| 47 | 1-methylpiperidin-4-yl-O-Me | E11<br>MS(ESI) m/z:<br>438([M + H]+) |
| 48 | (1-methylpiperidin-4-yl)-CH2-O-Me | E28<br>MS(FAB) m/z:<br>452([M + H]+) |
| 49 | 1-methylpiperidin-4-yl-O-Et | E28<br>MS(ESI) m/z:<br>450([M − H]−) |
| 50 | 1-methylpiperidin-4-yl-O-CH2-CH(Me)2 | E28<br>MS(ESI) m/z:<br>480([M + H]+) |
| 51 | 1-methylpiperidin-4-yl-O-CH2-cyclopropyl | E28<br>MS(ESI) m/z:<br>478([M + H]+) |
| 52 | 1-methylpiperidin-4-yl-O-CHF2 | E28<br>MS(ESI) m/z:<br>474([M + H]+) |
| 53 | 1-methylpiperidin-4-yl-O-CH2CH2-O-Me | E9<br>MS(ESI) m/z:<br>480([M − H]−) |
| 54 | 1-methylpiperidin-4-yl-O-(pyridin-2-yl) | E9 (HCl)<br>MS(FAB) m/z:<br>501([M + H]+) |
| 55 | 1-methylpiperidin-4-yl-O-(pyrimidin-2-yl) | E9 (HCl)<br>MS(FAB) m/z:<br>502([M + H]+) |
| 56 | 1-methylpiperidin-3-yl-O-Me * | E11<br>MS(ESI) m/z:<br>438([M + H]+) |

TABLE 62-continued

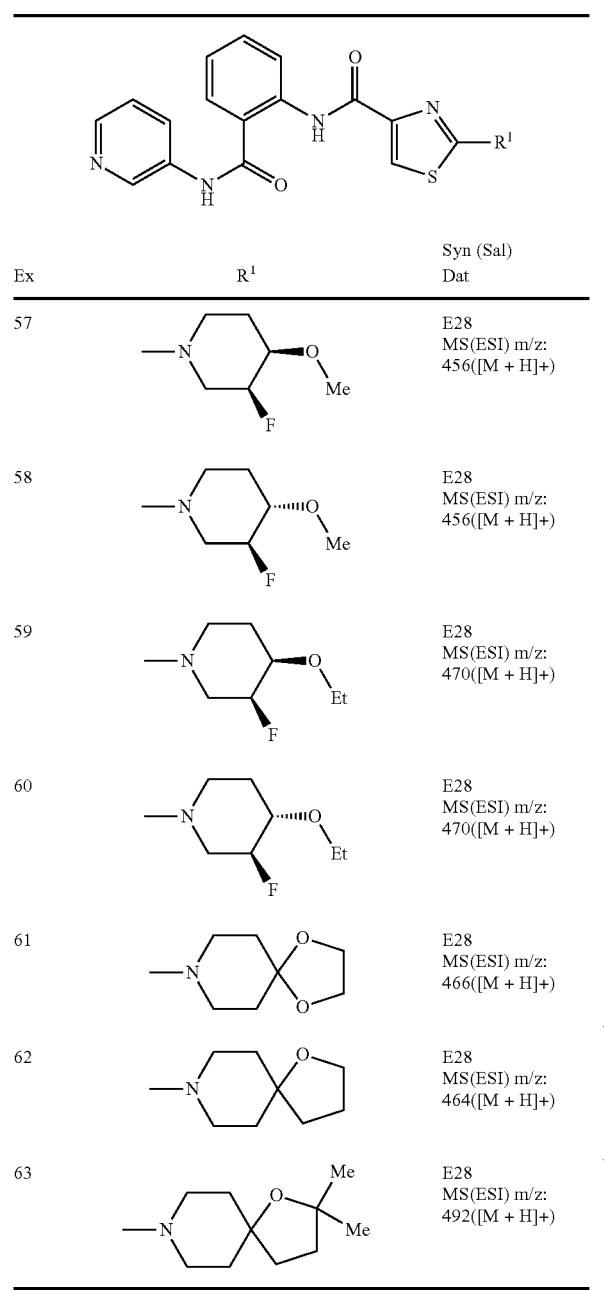

| Ex | R¹ | Syn (Sal) Dat |
|---|---|---|
| 57 | | E28 MS(ESI) m/z: 456([M + H]+) |
| 58 | | E28 MS(ESI) m/z: 456([M + H]+) |
| 59 | | E28 MS(ESI) m/z: 470([M + H]+) |
| 60 | | E28 MS(ESI) m/z: 470([M + H]+) |
| 61 | | E28 MS(ESI) m/z: 466([M + H]+) |
| 62 | | E28 MS(ESI) m/z: 464([M + H]+) |
| 63 | | E28 MS(ESI) m/z: 492([M + H]+) |

TABLE 63

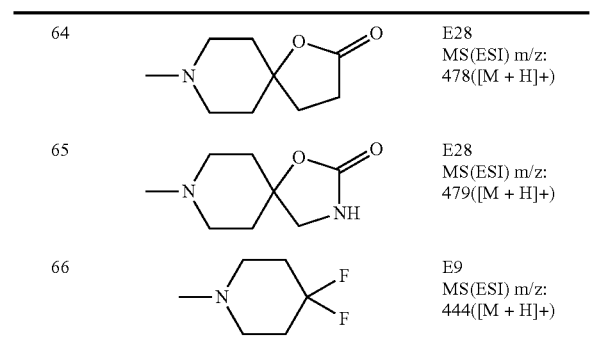

| 64 | | E28 MS(ESI) m/z: 478([M + H]+) |
|---|---|---|
| 65 | | E28 MS(ESI) m/z: 479([M + H]+) |
| 66 | | E9 MS(ESI) m/z: 444([M + H]+) |

TABLE 63-continued

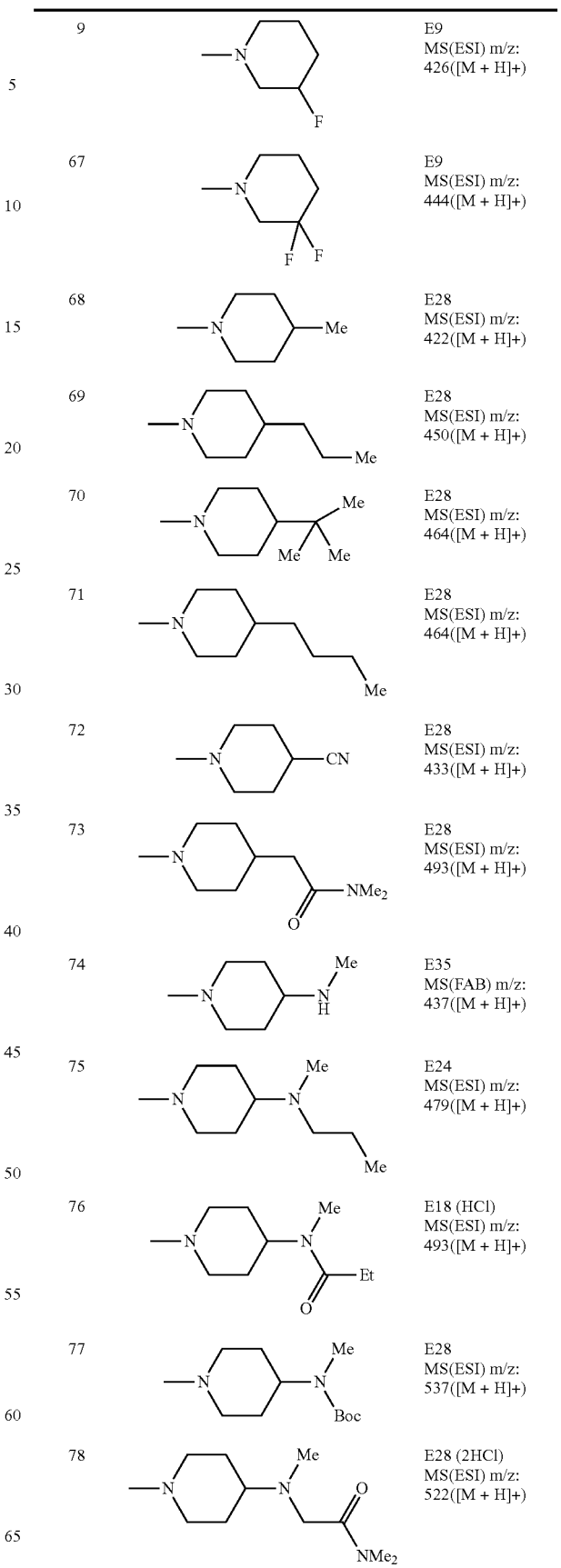

| 9 | | E9 MS(ESI) m/z: 426([M + H]+) |
|---|---|---|
| 67 | | E9 MS(ESI) m/z: 444([M + H]+) |
| 68 | | E28 MS(ESI) m/z: 422([M + H]+) |
| 69 | | E28 MS(ESI) m/z: 450([M + H]+) |
| 70 | | E28 MS(ESI) m/z: 464([M + H]+) |
| 71 | | E28 MS(ESI) m/z: 464([M + H]+) |
| 72 | | E28 MS(ESI) m/z: 433([M + H]+) |
| 73 | | E28 MS(ESI) m/z: 493([M + H]+) |
| 74 | | E35 MS(FAB) m/z: 437([M + H]+) |
| 75 | | E24 MS(ESI) m/z: 479([M + H]+) |
| 76 | | E18 (HCl) MS(ESI) m/z: 493([M + H]+) |
| 77 | | E28 MS(ESI) m/z: 537([M + H]+) |
| 78 | | E28 (2HCl) MS(ESI) m/z: 522([M + H]+) |

TABLE 63-continued

| # | Structure | Notes |
|---|---|---|
| 79 | (1-methylpiperidin-4-yl)amino-pyrimidine | E28 (2HCl) MS(ESI) m/z: 501([M + H]+) |
| 80 | (1-methylpiperidin-4-yl)(methyl)amino-pyrimidine | E28 (2HCl) MS(ESI) m/z: 515([M + H]+) |
| 81 | 1-methylpiperidine-4-sulfonamide | E28 MS(ESI) m/z: 487([M + H]+) |
| 82 | 4-(ethylsulfonyl)-1-methylpiperidine | E28 MS(ESI) m/z: 500([M + H]+) |
| 83 | (3-methoxy)-1-methylpyrrolidine * | E28 MS(ESI) m/z: 424([M + H]+) |
| 84 | (3-methoxy)-1-methylpyrrolidine * | E11 MS(ESI) m/z: 424([M + H]+) |
| 85 | (1-methylpyrrolidin-2-yl)methanol * | E28 MS(ESI) m/z: 424([M + H]+) |
| 86 | 2-(methoxymethyl)-1-methylpyrrolidine * | E28 MS(ESI) m/z: 438([M + H]+) |

TABLE 64

| # | Structure | Notes |
|---|---|---|
| 87 | 4-methoxy-2-(hydroxymethyl)-1-methylpyrrolidine * | E11 MS(ESI) m/z: 454([M + H]+) |
| 88 | 4-hydroxy-2-(methoxymethyl)-1-methylpyrrolidine * | E30 MS(ESI) m/z: 454([M + H]+) |

TABLE 64-continued

| # | Structure | Notes |
|---|---|---|
| 89 | 4-fluoro-2-(hydroxymethyl)-1-methylpyrrolidine * | E11 MS(ESI) m/z: 442([M + H]+) |
| 90 | 2-methyl-1-methylpyrrolidine * | E11 MS(ESI) m/z: 408([M + H]+) |
| 91 | 3-fluoro-1-methylpyrrolidine * | E11 MS(ESI) m/z: 412([M + H]+) |
| 92 | 1-methylpyrrolidin-2-one | E30 (HCl) MS(ESI) m/z: 406([M − H]−) |
| 93 | 3-methoxy-1-methylazetidine | E28 MS(ESI) m/z: 410([M + H]+) |
| 94 | 3,3-difluoro-1-methylazetidine | E11 MS(ESI) m/z: 416([M + H]+) |
| 95 | 1-methylazetidine-3-carbonitrile | E28 MS(ESI) m/z: 405([M + H]+) |
| 96 | 1-methylazepan-4-ol | E28 MS(ESI) m/z: 438([M + H]+) |
| 97 | (1-methylazepan-2-yl)methanol | E11 MS(ESI) m/z: 452([M + H]+) |
| 98 | 3,4-dimethylmorpholine * | E11 MS(ESI) m/z: 424([M + H]+) |
| 99 | 2,4,6-trimethylmorpholine | E28 (HCl) MS(FAB) m/z: 438([M + H]+) |
| 100 | 3-(methoxymethyl)-4-methylmorpholine | E11 (HCl) MS(FAB) m/z: 454([M + H]+) |

TABLE 64-continued

| # | Structure | Data |
|---|---|---|
| 101 | (S)-3-(methoxymethyl)-4-methylmorpholine * | E11 MS(ESI) m/z: 454([M + H]+) |
| 102 | 1-methylpiperazine | E28 (2HCl) MS(FAB) m/z: 409([M + H]+) |
| 103 | N-(2-methoxyethyl)-N-methylamine | E30 (HCl) MS(FAB) m/z: 412([M + H]+) |
| 104 | (S)-N-(1-methoxypropan-2-yl)-N-methylamine * | E11 MS(ESI) m/z: 426([M + H]+) |
| 105 | (R)-N-(1-methoxypropan-2-yl)-N-methylamine * | E11 MS(ESI) m/z: 426([M + H]+) |
| 106 | N-(2-ethoxyethyl)-N-methylamine | E9 MS(ESI) m/z: 426([M + H]+) |
| 107 | N-(2-isopropoxyethyl)-N-methylamine | E9 MS(API) m/z: 440([M + H]+) |

TABLE 65

| # | Structure | Data |
|---|---|---|
| 108 | N-(2-tert-butoxyethyl)-N-methylamine | E9 MS(ESI) m/z: 452([M − H]−) |
| 109 | N-methyl-tetrahydrofuran-3-amine | E28 (HCl) MS(ESI) m/z: 424([M + H]+) |
| 30 | N-methyl-1-(tetrahydro-2H-pyran-4-yl)methanamine | E30 MS(ESI) m/z: 452([M + H]+) |

TABLE 65-continued

| # | Structure | Data |
|---|---|---|
| 110 | N-methyl-1-(3-methyloxetan-3-yl)methanamine | E28 MS(ESI) m/z: 438([M + H]+) |
| 111 | 2-(methylamino)acetamide | E30 MS(FAB) m/z: 411([M + H]+) |
| 112 | N,N-dimethyl-2-(methylamino)acetamide | E30 MS(ESI) m/z: 437([M − H]−) |
| 113 | N-methyl-N-(2-(methylsulfonyl)ethyl)amine | E6 (HCl) MS(ESI) m/z: 458([M − H]−) |
| 114 | N1,N1,N2-trimethylethane-1,2-diamine | E30 (2HCl) MS(ESI) m/z: 425([M + H]+) |
| 115 | N1,N1,N3-trimethylpropane-1,3-diamine | E28 (2HCl) MS(ESI) m/z: 439([M + H]+) |
| 13 | N-methyl-2-(pyrrolidin-1-yl)ethanamine | E13 MS(ESI) m/z: 451([M + H]+) |
| 116 | N-methyl-2-(piperidin-1-yl)ethanamine | E13 MS(ESI) m/z: 465([M + H]+) |
| 117 | 1-(2-(methylamino)ethyl)piperidin-4-ol | E13 (2HCl) MS(ESI) m/z: 481([M + H]+) |
| 118 | N-methyl-1-(1-methylpiperidin-4-yl)methanamine | E28 MS(ESI) m/z: 465([M + H]+) |

TABLE 65-continued

| | | | |
|---|---|---|---|
| 119 | 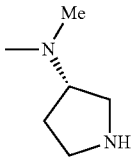 | * | E29 MS(ESI) m/z: 421([M − H]−) |
| 120 | 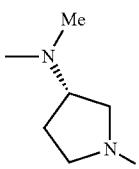 | * | E24 (2HCl) MS(FAB) m/z: 437([M + H]+) |
| 24 | 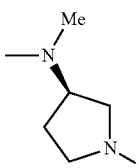 | * | E24 (2HCl) MS(ESI) m/z: 437([M + H]+) |
| 121 | 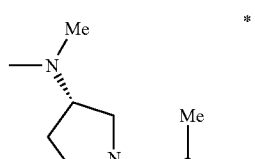 | * | E24 (2HCl) MS(FAB) m/z: 479([M + H]+) |
| 122 | 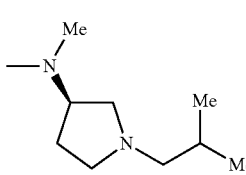 | * | E24 (2HCl) MS(ESI) m/z: 479([M + H]+) |
| 123 | 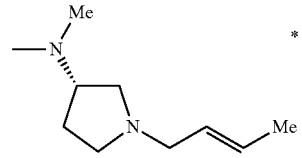 | * | E24 (2HCl) MS(FAB) m/z: 477([M + H]+) |

TABLE 66

| | | | |
|---|---|---|---|
| 124 | 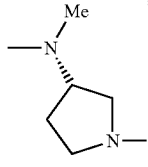 | * | E28 (2HCl) MS(ESI) m/z: 513([M + H]+) |
| 125 | 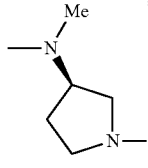 | * | E28 (2HCl) MS(ESI) m/z: 513([M + H]+) |
| 1 | 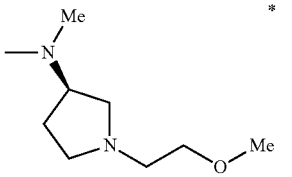 | * | E1 (2HCl) MS(ESI) m/z: 481([M + H]+) |
| 126 | —Ph | | E6 (HCl) MS(FAB) m/z: 401([M + H]+) |
| 127 | 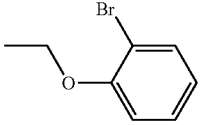 | | E11 (HCl) MS(FAB) m/z: 511([M + H]+) |
| 128 | 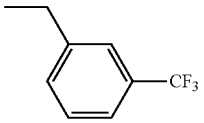 | | E11 (HCl) MS(FAB) m/z: 483([M + H]+) |
| 129 | 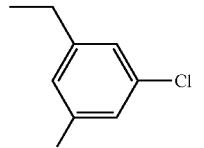 | | E11 (HCl) MS(FAB) m/z: 483([M + H]+) |
| 130 | 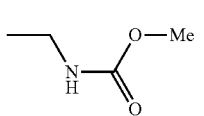 | | E30 (HCl) MS(ESI) m/z: 412([M + H]+) |
| 131 | 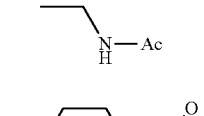 | | E30 MS(ESI) m/z: 396([M + H]+) |
| 132 | 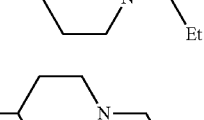 | | E9 MS(API) m/z: 464([M + H]+) |
| 133 | 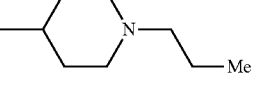 | | E9 MS(ESI) m/z: 450([M + H]+) |
| 134 | 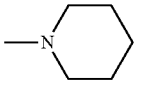 | | E40 MS(ESI) m/z: 408([M + H]+) |
| 135 | 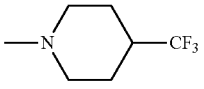 | | E40 MS(ESI) m/z: 476([M + H]+) |
| 136 | 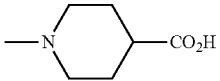 | | E40 MS(ESI) m/z: 452([M + H]+) |
| 137 | 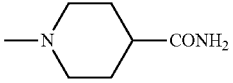 | | E40 MS(ESI) m/z: 451([M + H]+) |

TABLE 66-continued

| # | Structure | Data |
|---|---|---|
| 138 | [piperidine-N-Me, 4-C(O)NHMe] | E40 MS(ESI) m/z: 465([M + H]+) |
| 139 | [piperidine-N-Me, 4-C(O)NHCH2CH2OH] | E40 MS(ESI) m/z: 495([M + H]+) |
| 140 | [piperidine-N-Me, 4-NMe2] | E40 MS(ESI) m/z: 451([M + H]+) |
| 141 | [piperidine-N-Me, 4-CH2OEt] | E40 MS(ESI) m/z: 466([M + H]+) |
| 142 | [piperidine-N-Me, 3-OH *] | E40 MS(ESI) m/z: 424([M + H]+) |
| 143 | [piperidine-N-Me, 3-CO2H] | E40 MS(ESI) m/z: 452([M + H]+) |
| 144 | [piperidine-N-Me, 3-CONH2] | E40 MS(ESI) m/z: 451([M + H]+) |
| 145 | [piperidine-N-Me, 3-C(O)NHCH2CH2OH] | E40 MS(ESI) m/z: 495([M + H]+) |
| 146 | [piperidine-N-Me, 3-CH2CH2OH] | E40 MS(ESI) m/z: 452([M + H]+) |

TABLE 67

| # | Structure | Data |
|---|---|---|
| 147 | [piperidine-N-Me, 2-CH2OMe] | E40 MS(ESI) m/z: 452([M + H]+) |
| 148 | [piperidine-N-Me, 2-CH2CH2OH] | E40 MS(ESI) m/z: 452([M + H]+) |

TABLE 67-continued

| # | Structure | Data |
|---|---|---|
| 149 | [piperidine-N-Me, 4-Ph] | E40 MS(ESI) m/z: 484([M + H]+) |
| 150 | [piperidine-N-Me, 4-OH, 4-Ph] | E40 MS(ESI) m/z: 500([M + H]+) |
| 151 | [piperidine-N-Me, 4-OH, 4-Bn] | E40 MS(ESI) m/z: 514([M + H]+) |
| 152 | [piperidine-N-Me, 4-CH(Ph)OH] | E40 MS(ESI) m/z: 514([M + H]+) |
| 153 | [spiro piperidine-benzofuran, N-Me] | E40 MS(ESI) m/z: 512([M + H]+) |
| 154 | [piperidine-N-Me, 3-OPh] | E40 MS(ESI) m/z: 500([M + H]+) |
| 155 | [pyrrolidine-N-Me] | E40 MS(ESI) m/z: 394([M + H]+) |
| 156 | [pyrrolidine-N-Me, 2-CH2OH *] | E40 MS(ESI) m/z: 424([M + H]+) |
| 157 | [pyrrolidine-N-Me, 2-CH2OMe *] | E40 MS(ESI) m/z: 438([M + H]+) |
| 158 | [pyrrolidine-N-Me, 2,5-bis(CH2OMe) *] | E40 MS(ESI) m/z: 482([M + H]+) |
| 159 | [pyrrolidine-N-Me, 2-CONH2 *] | E40 MS(ESI) m/z: 437([M + H]+) |

TABLE 67-continued

| | | |
|---|---|---|
| 160 | [N-methyl pyrrolidine with CONH2, stereo *] | E40 MS(ESI) m/z: 437([M + H]+) |
| 161 | [N-methyl pyrrolidine with CF3] | E40 MS(ESI) m/z: 462([M + H]+) |
| 162 | [N-methyl pyrrolidine with NMe2, stereo *] | E40 MS(ESI) m/z: 437([M + H]+) |
| 163 | [N-methyl pyrrolidine with NMe2, stereo *] | E40 MS(ESI) m/z: 437([M + H]+) |
| 164 | [N-methyl pyrrolidine with NHAc, stereo *] | E40 MS(ESI) m/z: 451([M + H]+) |
| 165 | [N-methyl pyrrolidine with NHAc, stereo *] | E40 MS(ESI) m/z: 451([M + H]+) |
| 166 | [N-methyl pyrrolidine with Ms] | E40 MS(ESI) m/z: 472([M + H]+) |
| 167 | [N-methyl spiro pyrrolidine-cyclohexane] | E40 MS(ESI) m/z: 462([M + H]+) |
| 168 | [N-methyl azetidine with OPh] | E40 MS(ESI) m/z: 472([M + H]+) |
| 169 | [N-methyl azepane] | E40 MS(ESI) m/z: 422([M + H]+) |
| 170 | [N-methyl morpholine] | E40 MS(ESI) m/z: 410([M + H]+) |
| 171 | [N-methyl oxa-bridged bicyclic, stereo *] | E40 MS(ESI) m/z: 422([M + H]+) |

TABLE 68

| | | |
|---|---|---|
| 172 | [N-methyl morpholine with CH2OH] | E40 MS(ESI) m/z: 440([M + H]+) |
| 173 | [N-methyl thiomorpholine] | E40 MS(ESI) m/z: 426([M + H]+) |
| 174 | [N-methyl piperazine with CH2CH2OH] | E40 MS(ESI) m/z: 453([M + H]+) |
| 175 | [N-methyl piperazine with CH2CH2CH2OMe] | E40 MS(ESI) m/z: 481([M + H]+) |
| 176 | [N-methyl piperazine with (CH2)4OMe] | E40 MS(ESI) m/z: 495([M + H]+) |
| 177 | [N-methyl piperazine N-Ac] | E40 MS(ESI) m/z: 451([M + H]+) |
| 178 | [N-methyl piperazine N-Ms] | E40 MS(ESI) m/z: 487([M + H]+) |
| 179 | [N-methyl piperazine N-SO2-NMe] | E40 MS(ESI) m/z: 516([M + H]+) |
| 180 | [N-methyl piperazinone N-Me] | E40 MS(ESI) m/z: 437([M + H]+) |
| 181 | [N-methyl diazepane N-Me] | E40 MS(ESI) m/z: 437([M + H]+) |
| 182 | [N-methyl diazepane N-CH2CH2OH] | E40 MS(ESI) m/z: 467([M + H]+) |
| 183 | [N-methyl diazepanone NH] | E40 MS(ESI) m/z: 437([M + H]+) |
| 184 | [N-Me-CH2-tetrahydropyran] | E40 MS(ESI) m/z: 452([M + H]+) |

TABLE 68-continued

| | | |
|---|---|---|
| 185 | Me-N(CH2CH(Me))-CH2CH2OMe | E40 MS(ESI) m/z: 440([M + H]+) |
| 186 | Bn-N-CH2CH2OMe | E40 MS(ESI) m/z: 488([M + H]+) |
| 187 | Me-N-CH2CH2OH | E40 MS(ESI) m/z: 398([M + H]+) |
| 188 | Me-N-CH2CH(Me)OH | E40 MS(ESI) m/z: 412([M + H]+) |
| 189 | Me-N-CH2CH(OH)CH2OH | E40 MS(ESI) m/z: 428([M + H]+) |
| 190 | Me-N-CH2C(O)-morpholine | E40 MS(ESI) m/z: 481([M + H]+) |
| 191 | Me-N-(1-Me-pyrrolidin-3-yl) | E40 MS(ESI) m/z: 437([M + H]+) |
| 192 | Me-N-(1-Me-piperidin-4-yl) | E40 MS(ESI) m/z: 451([M + H]+) |
| 193 | Me-N-(1,1-dioxo-tetrahydrothiophen-3-yl) | E40 MS(ESI) m/z: 472([M + H]+) |
| 194 | —NHPh | E40 MS(ESI) m/z: 416([M + H]+) |

TABLE 69

| | | |
|---|---|---|
| 40 | Me-N-Bn | E40 MS(ESI) m/z: 444([M + H]+) |
| 195 | Me-N-CH2CH2Ph | E40 MS(ESI) m/z: 458([M + H]+) |
| 196 | Me-N-CH2CH2OPh | E40 MS(ESI) m/z: 474([M + H]+) |
| 197 | Me-N-CH2-(pyridin-3-yl) | E40 MS(ESI) m/z: 445([M + H]+) |
| 29 | Me-N-((3S)-pyrrolidin-3-yl)* | E29 MS(FAB) m/z: 423([M + H]+) |
| 22 | Me-N-CH2CH2OMs | E22 MS(ESI) m/z: 476([M + H]+) |

TABLE 70

[Structure: 2-(pyridin-3-ylaminocarbonyl)-N-(2-R¹-oxazole-4-carbonyl)aniline]

| Ex | R¹ | Syn (Sal) Dat |
|---|---|---|
| 199 | 1-Me-piperidin-4-yl-OH | E30 MS(ESI) m/z: 408([M + H]+) |
| 200 | 1-Me-piperidin-4-yl-OEt | E9 MS(ESI) m/z: 436([M + H]+) |
| 201 | 1-Me-piperidin-4-yl-OCH2-cyclopropyl | E9 MS(ESI) m/z: 462([M + H]+) |

TABLE 70-continued

[Structure: 2-(pyridin-3-ylcarbamoyl)-N-(2-R¹-oxazole-4-carbonyl)aniline scaffold with R¹ variable]

| Ex | R¹ | Syn (Sal) Dat |
|---|---|---|
| 202 | 1-methylpiperidin-4-yloxy-pyrimidin-2-yl | E30 MS(ESI) m/z: 486([M + H]+) |
| 203 | 4-fluoro-1-methylpiperidin-4-yl | E30 MS(ESI) m/z: 410([M + H]+) |
| 204 | 3,3-difluoro-1-methylpiperidin-4-yl | E9 MS(ESI) m/z: 428([M + H]+) |
| 11 | 4-methylmorpholin-3-yl | E11 (HCl) MS(ESI) m/z: 392([M − H]−) |
| 205 | (4-methylmorpholin-3-yl)methoxymethyl * | E30 MS(FAB) m/z: 438([M + H]+) |
| 206 | (3-methoxy-1-methylpyrrolidin-3-yl) * | E30 MS(FAB) m/z: 408([M + H]+) |
| 207 | (3-ethoxy-1-methylpyrrolidin-3-yl) * | E30 MS(ESI) m/z: 422([M + H]+) |
| 208 | (1-methylpyrrolidin-3-yl)oxy-pyridin-2-yl * | E30 MS(ESI) m/z: 471([M + H]+) |

TABLE 71

| Ex | R¹ | Syn (Sal) Dat |
|---|---|---|
| 209 | (1-methylpyrrolidin-3-yl)oxy-pyrimidin-2-yl * | E30 MS(ESI) m/z: 472([M + H]+) |
| 210 | (3-fluoro-1-methylpyrrolidin-3-yl) * | E30 MS(ESI) m/z: 396([M + H]+) |
| 211 | 3-methoxy-1-methylazetidin-3-yl | E30 MS(FAB) m/z: 394([M + H]+) |
| 212 | N,N-dimethyl-2-methoxyethylamino | E11 (HCl) MS(ESI) m/z: 394([M − H]−) |
| 213 | N-methyl-N-(2-ethoxyethyl)amino | E9 MS(ESI) m/z: 410([M + H]+) |
| 214 | N-methyl-N-(2-isopropoxyethyl)amino | E9 MS(ESI) m/z: 424([M + H]+) |
| 215 | N-methyl-N-(N,N-dimethylcarbamoylmethyl)amino | E30 MS(ESI) m/z: 421([M − H]−) |
| 216 | tetrahydropyran-4-yl | E11 MS(ESI) m/z: 393([M + H]+) |
| 217 | methoxymethyl (Et-O-Me) | E11 (HCl) MS(FAB) m/z: 353([M + H]+) |
| 218 | 1-ethoxyethyl | E11 (HCl) MS(FAB) m/z: 381([M + H]+) |
| 219 | 2-bromophenoxyethyl | E11 (HCl) MS(FAB) m/z: 495([M + H]+) |
| 220 | 2-amino-4-methylpyridin-... | E35 (2HCl) MS(FAB) m/z: 401([M + H]+) |
| 221 | 2-(NHBoc)-4-methylpyridin-... | E30 MS(ESI) m/z: 501([M + H]+) |

TABLE 72

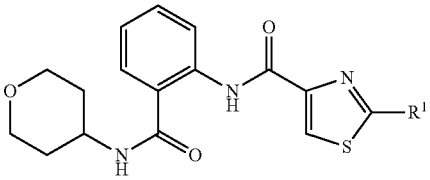

| Ex | R¹ | Syn (Sal) Dat |
|---|---|---|
| 222 | 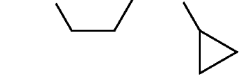 | E11 MS(ESI) m/z: 431([M + H]+) |
| 223 | 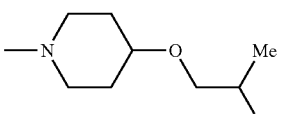 | E28 MS(ESI) m/z: 445([M + H]+) |
| 224 | 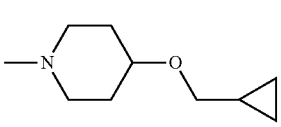 | E28 MS(ESI) m/z: 459([M + H]+) |
| 225 | 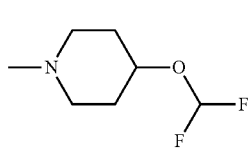 | E11 MS(ESI) m/z: 445([M + H]+) |
| 28 | 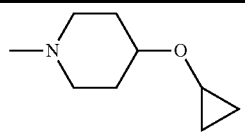 | E28 MS(ESI) m/z: 459([M + H]+) |
| 226 | | E28 MS(ESI) m/z: 473([M + H]+) |

TABLE 73

| 227 | | E28 MS(ESI) m/z: 471([M + H]+) |
|---|---|---|
| 228 | | E28 MS(ESI) m/z: 487([M + H]+) |
| 229 | | E28 MS(ESI) m/z: 485([M + H]+) |
| 230 | | E28 MS(ESI) m/z: 481([M + H]+) |

TABLE 73-continued

| 231 | 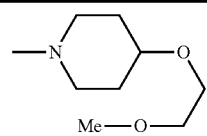 | E9 MS(ESI) m/z: 489([M + H]+) |
|---|---|---|
| 232 | 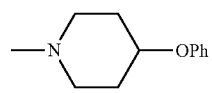 | E28 MS(ESI) m/z: 507([M + H]+) |
| 233 | 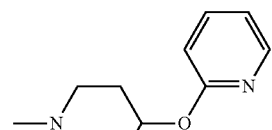 | E28 MS(FAB) m/z: 508([M + H]+) |
| 234 | 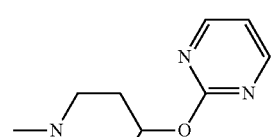 | E28 MS(FAB) m/z: 509([M + H]+) |
| 235 | 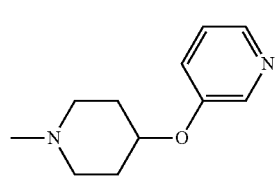 | E28 MS(ESI) m/z: 508([M + H]+) |
| 236 | 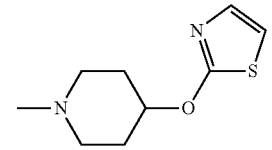 | E28 MS(ESI) m/z: 514([M + H]+) |
| 237 | 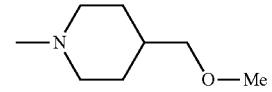 | E11 MS(ESI) m/z: 459([M + H]+) |
| 238 | 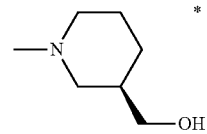 | E28 MS(ESI) m/z: 445([M + H]+) |
| 239 | 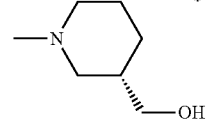 | E28 MS(ESI) m/z: 445([M + H]+) |
| 240 | 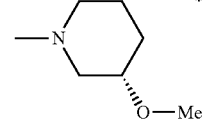 | E11 MS(ESI) m/z: 445([M + H]+) |
| 241 | 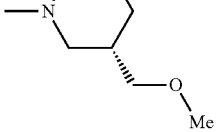 | E28 MS(ESI) m/z: 457([M − H]−) |

TABLE 73-continued

| | | | |
|---|---|---|---|
| 242 | 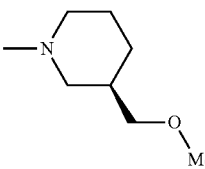 * | | E28<br>MS(ESI) m/z:<br>459([M + H]+) |
| 243 | 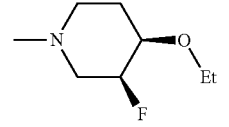 * | | E28<br>MS(ESI) m/z:<br>473([M + H]+) |
| 244 | 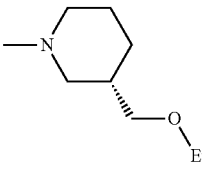 * | | E28<br>MS(ESI) m/z:<br>473([M + H]+) |
| 245 | 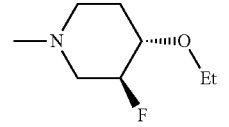 * | | E28<br>MS(ESI) m/z:<br>523([M + H]+) |
| 246 | 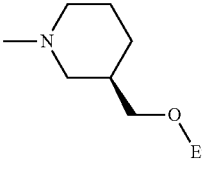 | | P33→E28<br>MS(ESI) m/z:<br>449([M + H]+) |
| 247 | 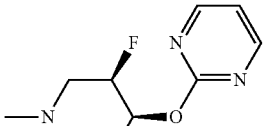 | | E28<br>MS(ESI) m/z:<br>449([M + H]+) |

TABLE 74

| | | | |
|---|---|---|---|
| 14 | 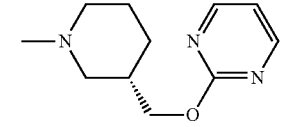 * | | E14<br>MS(ESI) m/z:<br>449([M + H]+) |
| 15 | 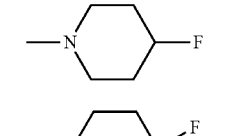 * | | E15<br>MS(ESI) m/z:<br>449([M + H]+) |
| 248 | 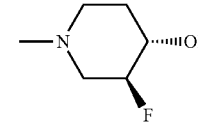 | | E28<br>MS(ESI) m/z:<br>463([M + H]+) |
| 249 | 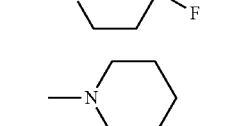 | | E28<br>MS(ESI) m/z:<br>463([M + H]+) |

TABLE 74-continued

| | | | |
|---|---|---|---|
| 250 | 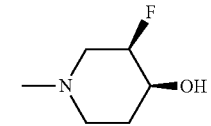 | | E28<br>MS(ESI) m/z:<br>477([M + H]+) |
| 251 | 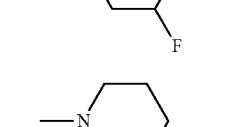 | | E28<br>MS(ESI) m/z:<br>477([M + H]+) |
| 252 | 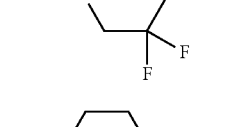 | | E28<br>MS(ESI) m/z:<br>527([M + H]+) |
| 253 | 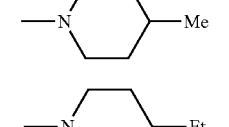 | | E28<br>MS(ESI) m/z:<br>433([M + H]+) |
| 254 | 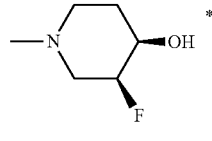 | | E9<br>MS(API) m/z:<br>451([M + H]+) |
| 255 | 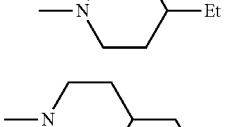 | | E9<br>MS(ESI) m/z:<br>433([M + H]+) |
| 256 | 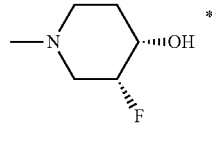 | | E9<br>MS(ESI) m/z:<br>451([M + H]+) |
| 257 | 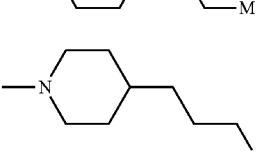 | | E28<br>MS(ESI) m/z:<br>429([M + H]+) |
| 258 | 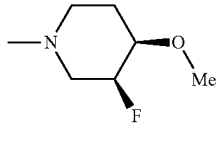 | | E28<br>MS(ESI) m/z:<br>443([M + H]+) |
| 259 | 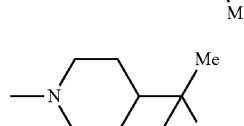 | | E28<br>MS(ESI) m/z:<br>457([M + H]+) |
| 260 | 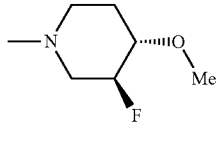 | | E28<br>MS(ESI) m/z:<br>471([M + H]+) |
| 261 | 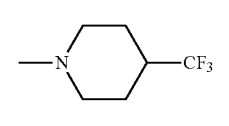 | | E28<br>MS(ESI) m/z:<br>471([M + H]+) |
| 262 |  | | E28<br>MS(ESI) m/z:<br>483([M + H]+) |

TABLE 74-continued

| 263 | 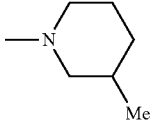 | E28 MS(ESI) m/z: 429([M + H]+) |
|---|---|---|
| 264 | 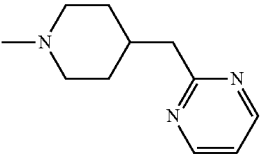 | E28 MS(ESI) m/z: 440([M + H]+) |
| 265 |  | E28 MS(FAB) m/z: 440([M + H]+) |
| 266 | 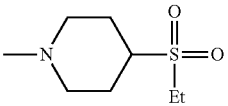 | E28 MS(ESI) m/z: 500([M + H]+) |
| 267 | 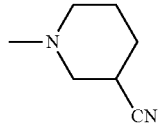 | E28 MS(ESI) m/z: 469([M + H]+) |
| 268 | 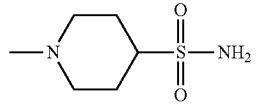 | E28 MS(ESI) m/z: 553([M + H]+) |
| 269 | 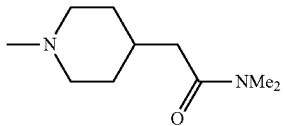 | E28 MS(ESI) m/z: 563([M + H]+) |

TABLE 75

| 270 | 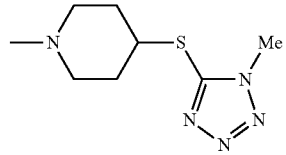 | E33 MS(ESI) m/z: 549([M + H]+) |
|---|---|---|
| 271 | 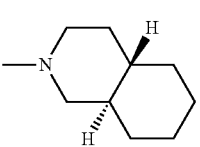 | E28 MS(ESI) m/z: 506([M + H]+) |

TABLE 75-continued

| 272 | 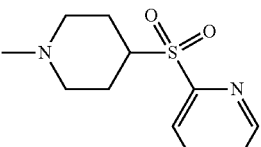 | E28 MS(ESI) m/z: 507([M + H]+) |
|---|---|---|
| 273 | 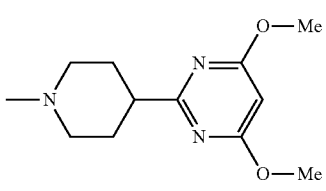 | E28 MS(ESI) m/z: 507([M + H]+) |
| 274 | 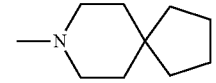 | E28 MS(ESI) m/z: 494([M + H]+) |
| 275 | 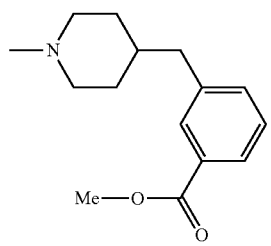 | E28 MS(ESI) m/z: 529([M + H]+) |
| 276 | 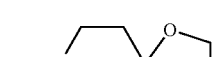 | E28 MS(ESI) m/z: 556([M + H]+) |
| 277 | 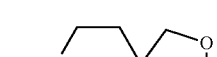 | E28 MS(ESI) m/z: 469([M + H]+) |
| 278 | 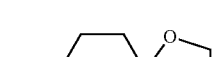 | E28 MS(ESI) m/z: 471([M + H]+) |
| 279 | 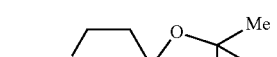 | E28 MS(ESI) m/z: 471([M + H]+) |
| 280 | 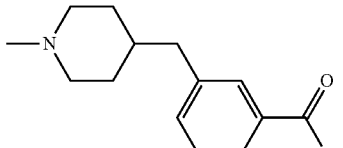 | E28 MS(ESI) m/z: 473([M + H]+) |
| 281 | 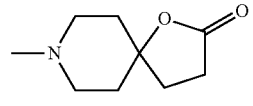 | E28 MS(ESI) m/z: 499([M + H]+) |
| 282 | 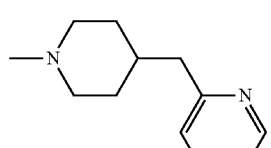 | E28 MS(ESI) m/z: 485([M + H]+) |
| 283 | 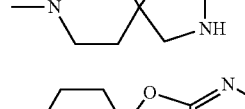 | E28 MS(ESI) m/z: 486([M + H]+) |
| 284 | 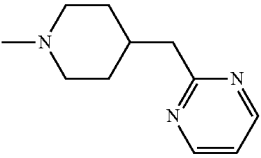 | E28 MS(ESI) m/z: 520([M + H]+) |

TABLE 75-continued

| 285 | (1-methylpyrrolidin-3-yl)oxy, * | E28 MS(ESI) m/z: 417([M + H]+) |
| 286 | (1-methylpyrrolidin-3-yl)OMe, * | E11 MS(ESI) m/z: 431([M + H]+) |
| 287 | (1-methylpyrrolidin-3-yl)OMe, * | E11 MS(ESI) m/z: 431([M + H]+) |
| 288 | (1-methylpyrrolidin-3-yl)CH2OMe, * | E28 MS(ESI) m/z: 443([M − H]−) |
| 289 | (1-methylpyrrolidin-3-yl)F, * | E11 MS(FAB) m/z: 419([M + H]+) |
| 290 | (1-methylpyrrolidin-3-yl)F, * | E28 MS(ESI) m/z: 419([M + H]+) |
| 291 | (1-methyl-2-methylpyrrolidinyl), * | E11 MS(FAB) m/z: 415([M + H]+) |
| 292 | (4-fluoro-2-hydroxymethyl-1-methylpyrrolidinyl), * | E11 MS(ESI) m/z: 449([M + H]+) |
| 293 | (4-hydroxy-2-methoxymethyl-1-methylpyrrolidinyl), * | E30 MS(ESI) m/z: 461([M + H]+) |

TABLE 76

| 294 | 1-methylazetidin-3-ol | E28 MS(ESI) m/z: 403([M + H]+) |
| 295 | 3-methoxy-1-methylazetidine | E11 MS(ESI) m/z: 417([M + H]+) |
| 296 | 3-fluoro-1-methylazetidine | E28 MS(ESI) m/z: 405([M + H]+) |
| 297 | 3,3-difluoro-1-methylazetidine | E11 MS(ESI) m/z: 421([M − H]−) |
| 298 | 1-methylazetidine-3-carbonitrile | E28 MS(ESI) m/z: 412([M + H]+) |

TABLE 76-continued

| 299 | 1-methylazepan-4-ol | E28 MS(ESI) m/z: 445([M + H]+) |
| 300 | (1-methylazepan-2-yl)methanol | E11 MS(ESI) m/z: 459([M + H]+) |
| 301 | 4-methylmorpholine | E26 MS(FAB) m/z: 417([M + H]+) |
| 302 | (3-methyl-4-methylmorpholine), * | E11 MS(FAB) m/z: 431([M + H]+) |
| 303 | 1,4-dimethylpiperazine | E28 MS(ESI) m/z: 430([M + H]+) |
| 304 | 1-ethyl-4-methylpiperazine | E28 MS(ESI) m/z: 458([M + H]+) |
| 305 | 1-acetyl-4-methylpiperazine | E28 MS(ESI) m/z: 458([M + H]+) |
| 306 | 4-methylpiperazin-2-one | E28 MS(ESI) m/z: 430([M + H]+) |
| 307 | 2-(1-methyl-1,2,3,6-tetrahydropyridin-4-yl)pyrimidine | E28 MS(ESI) m/z: 491([M + H]+) |
| 308 | 2-methyl-1,2,3,4-tetrahydroisoquinoline | E28 MS(ESI) m/z: 463([M + H]+) |
| 309 | 5-methyl-4,5,6,7-tetrahydrothieno[3,2-c]pyridine | E28 MS(ESI) m/z: 469([M + H]+) |
| 310 | 2,5-dimethyl-4,5,6,7-tetrahydrothiazolo[5,4-c]pyridine | E28 MS(ESI) m/z: 484([M + H]+) |
| 311 | N-(2-methoxyethyl)-N-methylamine | E6 (HCl) MS(FAB) m/z: 419([M + H]+) |

TABLE 76-continued

| | | | |
|---|---|---|---|
| 312 | [structure: Me-N(Me)-CH(Me)-CH2-O-Me] * | E11 MS(ESI) m/z: 433([M + H]+) | |
| 313 | [structure: Me-N(Me)-CH(Me)-CH2-O-Me] * | E11 MS(ESI) m/z: 433([M + H]+) | |
| 314 | [structure: Me-N(Me)-CH2CH2-O-CH(Me)2] | E9 MS(API) m/z: 447([M + H]+) | |
| 315 | [structure: Me-N(Me)-CH2CH2-O-C(Me)3] | E9 MS(ESI) m/z: 461([M + H]+) | |
| 316 | [structure: Me-CH(Me)-N-CH2CH2-O-Me] | E30 MS(FAB) m/z: 447([M + H]+) | |
| 317 | [structure: Me-N(Me)-tetrahydrofuran-3-yl] | E11 MS(ESI) m/z: 431([M + H]+) | |

TABLE 77

| | | | |
|---|---|---|---|
| 318 | [structure: Me-N(Me)-CH2-tetrahydropyran-4-yl] | E30 MS(ESI) m/z: 459([M + H]+) | |
| 319 | [structure: Me-N(Me)-CH2-tetrahydrofuran-2-yl] * | E28 MS(ESI) m/z: 445([M + H]+) | |
| 320 | [structure: Me-N(Me)-CH2-tetrahydrofuran-2-yl] * | E28 MS(ESI) m/z: 445([M + H]+) | |

TABLE 77-continued

| | | | |
|---|---|---|---|
| 321 | [structure: Me-N(Me)-CH2-(3-Me-oxetan-3-yl)] | E28 MS(ESI) m/z: 445([M + H]+) | |
| 322 | [structure: Me-N(Me)-CH2-C(=O)-NMe2] | E30 MS(FAB) m/z: 446([M + H]+) | |
| 323 | [structure: Me-N(Me)-CH2CH2-Ms] | E30 MS(ESI) m/z: 465([M − H]−) | |
| 324 | [structure: Me-N(Me)-CH2CH2-NMe2] | E30 (HCl) MS(ESI) m/z: 432([M + H]+) | |
| 325 | [structure: Me-N(Me)-(1-Me-pyrrolidin-3-yl)] * | E24 (HCl) MS(ESI) m/z: 444([M + H]+) | |
| 326 | [structure: Me-N(Me)-(1-Me-pyrrolidin-3-yl)] * | E24 (HCl) MS(ESI) m/z: 444([M + H]+) | |
| 327 | [structure: 4-(N-Me-piperidinyl)] | E9 MS(ESI) m/z: 429([M + H]+) | |
| 328 | [structure: 4-(N-Et-piperidinyl)] | E9 MS(ESI) m/z: 457([M + H]+) | |
| 329 | [structure: 4-(N-Boc-piperidinyl)] | E9 MS(ESI) m/z: 515([M + H]+) | |
| 330 | [structure: cis-3-OBn-cyclopentyl] | E11 MS(FAB) m/z: 506([M + H]+) | |
| 331 | [structure: cis-3-OBn-cyclopentyl] | E11 MS(FAB) m/z: 506([M + H]+) | |
| 332 | —Ph | E26 MS(FAB) m/z: 408([M + H]+) | |
| 333 | [structure: 4-pyridyl] | E33→E26 (HCl) MS(ESI) m/z: 409([M + H]+) | |

TABLE 77-continued

| Ex | R¹ | Syn (Sal) Dat |
|---|---|---|
| 334 | (3)-N-methyl-N-methylaminopyrrolidine * | E29 MS(ESI) m/z: 430([M + H]+) |
| 335 | (3)-N-methyl-N-methylaminopyrrolidine * | E29 MS(ESI) m/z: 430([M + H]+) |
| 336 | 4-methyl-1-propanoylpiperidine | E9 MS(ESI) m/z: 471([M + H]+) |
| 337 | N-methyl-decahydroisoquinoline (trans, H,H) | E28 MS(ESI) m/z: 469([M + H]+) |
| 338 | (1-methylpiperidin-3-yl)methoxy-pyrimidine * | E28 MS(ESI) m/z: 523([M + H]+) |

TABLE 78

Structure: tetrahydropyran-4-yl-NH-C(O)-[2-substituted phenyl]-NH-C(O)-oxazole-R¹

| Ex | R¹ | Syn (Sal) Dat |
|---|---|---|
| 339 | 1-methyl-4-hydroxypiperidine | E9 MS(ESI) m/z: 415([M + H]+) |
| 340 | 1-methyl-4-ethoxypiperidine | E9 MS(ESI) m/z: 443([M + H]+) |
| 341 | 1-methyl-4-(cyclopropylmethoxy)piperidine | E9 MS(ESI) m/z: 469([M + H]+) |
| 342 | 1-methyl-4-(pyridin-2-yloxy)piperidine | E30 MS(ESI) m/z: 492([M + H]+) |

TABLE 78-continued

| Ex | R¹ | Syn (Sal) Dat |
|---|---|---|
| 343 | 1-methyl-4-(pyrimidin-2-yloxy)piperidine | E30 MS(ESI) m/z: 493([M + H]+) |
| 344 | 1-methyl-4-(pyrazin-2-yloxy)piperidine | E30 MS(ESI) m/z: 493([M + H]+) |
| 345 | 1-methyl-4-[(5-cyanopyridin-2-yl)oxy]piperidine | E30 MS(ESI) m/z: 517([M + H]+) |
| 346 | 1-methyl-4-[(6-oxo-1,6-dihydropyridazin-3-yl)oxy]piperidine | E30 MS(ESI) m/z: 509([M + H]+) |
| 347 | 1-methyl-4-fluoropiperidine | E30 MS(ESI) m/z: 417([M + H]+) |
| 348 | 1-methyl-3,3-difluoropiperidine | E9 MS(ESI) m/z: 435([M + H]+) |
| 349 | 1-methyl-3-fluoro-4-hydroxypiperidine | E30 MS(ESI) m/z: 433([M + H]+) |
| 350 | 1-methyl-3-fluoro-4-(pyrimidin-2-yloxy)piperidine | E30 MS(ESI) m/z: 511([M + H]+) |

TABLE 78-continued

| Ex | R¹ | Syn (Sal) Dat |
|---|---|---|
| 351 | (1-methylpyrrolidin-3-yl)-OMe * | E30 MS(FAB) m/z: 415([M + H]+) |
| 352 | (1-methylpyrrolidin-3-yl)-OEt * | E30 MS(ESI) m/z: 429([M + H]+) |
| 353 | (1-methylpyrrolidin-3-yl)-OCH2CH2OMe * | E30 MS(ESI) m/z: 459([M + H]+) |
| 354 | (1-methylpyrrolidin-3-yl)-O-(pyridin-2-yl) * | E30 MS(ESI) m/z: 478([M + H]+) |
| 355 | (1-methylpyrrolidin-3-yl)-O-(pyrimidin-2-yl) * | E30 MS(ESI) m/z: 479([M + H]+) |
| 356 | (1-methylpyrrolidin-3-yl)-F * | E30 MS(ESI) m/z: 403([M + H]+) |
| 357 | 1-methyl-3-methoxyazetidine | E30 MS(FAB) m/z: 401([M + H]+) |

TABLE 79

| Ex | R¹ | Syn (Sal) Dat |
|---|---|---|
| 358 | 1-methylazetidin-3-yl-O-(pyrimidin-2-yl) | E30 MS(ESI) m/z: 465([M + H]+) |
| 359 | 4-methylmorpholine | E30 MS(FAB) m/z: 401([M + H]+) |
| 360 | (3-methoxymethyl-4-methylmorpholine) * | E30 MS(FAB) m/z: 445([M + H]+) |

TABLE 79-continued

| Ex | R¹ | Syn (Sal) Dat |
|---|---|---|
| 361 | Me-N(Me)-CH2CH2-O-Me | E30 MS(FAB) m/z: 403([M + H]+) |
| 362 | Me-N(Me)-CH(Me)-CH2-O-Me * | E30 MS(FAB) m/z: 417([M + H]+) |
| 363 | Me-N(Me)-CH2CH2-O-CH(Me)2 | E9 MS(ESI) m/z: 431([M + H]+) |
| 364 | Me-N(Me)-CH2-(tetrahydropyran-4-yl) | E30 MS(ESI) m/z: 443([M + H]+) |
| 365 | Me-N(Me)-CH2-C(=O)-NMe2 | E30 MS(FAB) m/z: 430([M + H]+) |

TABLE 80

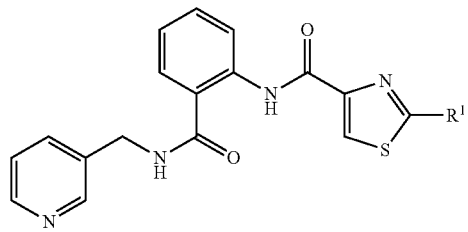

| Ex | R¹ | Syn (Sal) Dat |
|---|---|---|
| 366 | 1-methyl-3,3-difluoropiperidine | E9 MS(ESI) m/z: 458([M + H]+) |
| 367 | Me-N(Me)-CH2-C(=O)-NMe2 | E30 MS(ESI) m/z: 451([M − H]−) |
| 368 | Me-N(Me)-CH2CH2-NMe2 | E30 (2 HCl) MS(ESI) m/z: 439([M + H]+) |

TABLE 80-continued

Structure: 2-({[(pyridin-3-yl)methyl]carbamoyl}phenyl)-NH-C(=O)-thiazole-R¹

| Ex | R¹ | Syn (Sal) Dat |
|---|---|---|
| 369 | Me-N(*)-pyrrolidine-N-Me | E24 (2 HCl) MS(ESI) m/z: 451([M + H]+) |
| 370 | Me-N(*)-pyrrolidine-N-Me | E24 (2 HCl) MS(ESI) m/z: 451([M + H]+) |
| 371 | Me-N(*)-pyrrolidine-NH | E29 MS(ESI) m/z: 437([M + H]+) |
| 372 | Me-N(*)-pyrrolidine-NH | E29 MS(ESI) m/z: 437([M + H]+) |

TABLE 81

Structure: 2-({[(pyridin-3-yl)methyl]carbamoyl}phenyl)-NH-C(=O)-oxazole-R¹

| Ex | R¹ | Syn (Sal) Dat |
|---|---|---|
| 373 | N-methylpiperidine-4-F | E30 MS(ESI) m/z: 424([M + H]+) |
| 374 | N-methylpyrrolidine-3-F (*) | E30 MS(ESI) m/z: 410([M + H]+) |

TABLE 81-continued

| Ex | R¹ | Syn (Sal) Dat |
|---|---|---|
| 375 | N-methylpyrrolidine-3-OEt (*) | E30 MS(ESI) m/z: 436([M + H]+) |
| 376 | N-methylpyrrolidine-3-O-pyridin-2-yl (*) | E30 MS(ESI) m/z: 485([M + H]+) |
| 377 | N-methylpyrrolidine-3-O-pyrimidin-2-yl (*) | E30 MS(ESI) m/z: 486([M + H]+) |
| 378 | morpholine | E30 MS(ESI) m/z: 406([M − H]−) |
| 379 | Me-N(Me)-CH2CH2-O-Me | E30 MS(FAB) m/z: 410([M + H]+) |

TABLE 82

Structure with ring A, R², thiazole-2-morpholine

| Ex | (R²-A group) | Syn (Sal) Dat |
|---|---|---|
| 380 | cyclobutyl-NH-C(=O)-(2-methylphenyl) | E6 MS(FAB) m/z: 387([M + H]+) |
| 381 | cyclopentyl-NH-C(=O)-(2-methylphenyl) | E26 MS(FAB) m/z: 401([M + H]+) |

TABLE 82-continued

| Ex | | Syn (Sal) Dat |
|---|---|---|
| 382 | cyclohexyl-NH-C(O)-(2-methylphenyl) | E26 MS(FAB) m/z: 413([M − H]−) |
| 383 | cyclopentylmethyl-NH-C(O)-(2-methylphenyl) | E26 MS(FAB) m/z: 415([M + H]+) |
| 384 | cyclohexylmethyl-NH-C(O)-(2-methylphenyl) | E26 MS(FAB) m/z: 429([M + H]+) |
| 385 | 3-cyclohexylpropyl-NH-C(O)-(2-methylphenyl) | E26 MS(FAB) m/z: 457([M + H]+) |
| 386 | HO-CH2CH2-NH-C(O)-(2-methylphenyl) | E6 MS(FAB) m/z: 377([M + H]+) |
| 387 | HOCH2-C(Me)2-CH2-NH-C(O)-(2-methylphenyl) | E26 MS(FAB) m/z: 419([M + H]+) |
| 388 | 1-(hydroxymethyl)cyclopropylmethyl-NH-C(O)-(2-methylphenyl) | E26 MS(ESI) m/z: 415([M − H]−) |
| 389 | (2-hydroxycyclopentyl)methyl-NH-C(O)-(2-methylphenyl) | E26 MS(ESI) m/z: 429([M − H]−) |
| 390 | trans-4-hydroxycyclohexyl-NH-C(O)-(2-methylphenyl) | E26 MS(ESI) m/z: 431([M + H]+) |
| 391 | cis-4-hydroxycyclohexyl-NH-C(O)-(2-methylphenyl) | E26 MS(ESI) m/z: 431([M + H]+) |
| 392 | MeO-N(Me)-C(O)-(2-methylphenyl) | E26 MS(ESI) m/z: 377([M + H]+) |
| 393 | MeO-CH2CH2-NH-C(O)-(2-methylphenyl) | E6 MS(FAB) m/z: 391([M + H]+) |
| 394 | MeO-CH2CH2-N(Me)-C(O)-(2-methylphenyl) | E26 MS(FAB) m/z: 405([M + H]+) |
| 395 | MeOCH2-C(Me)2-CH2-NH-C(O)-(2-methylphenyl) | E26 MS(FAB) m/z: 433([M + H]+) |
| 396 | oxetan-3-yl-NH-C(O)-(2-methylphenyl) | E26 MS(FAB) m/z: 389([M + H]+) |
| 397 | (S)-tetrahydrofuran-3-yl-NH-C(O)-(2-methylphenyl) * | E26 MS(FAB) m/z: 403([M + H]+) |

TABLE 83

| | | |
|---|---|---|
| 398 | [tetrahydrofuran-2-ylmethyl N-H C(O) 2-methylphenyl] | E6<br>MS(FAB) m/z:<br>417([M + H]+) |
| 399 | [tetrahydrofuran-3-ylmethyl N-H C(O) 2-methylphenyl] | E26<br>MS(FAB) m/z:<br>417([M + H]+) |
| 400 | [tetrahydropyran-3-ylmethyl N-H C(O) 2-methylphenyl] | E26<br>MS(FAB) m/z:<br>431([M + H]+) |
| 401 | [(3-methyloxetan-3-yl)methyl N-H C(O) 2-methylphenyl] | E26<br>MS(FAB) m/z:<br>417([M + H]+) |
| 402 | [H2N-C(O)-CH2-NH-C(O) 2-methylphenyl] | E30<br>MS(ESI) m/z:<br>388([M − H]−) |
| 403 | [H2N-C(O)-CH2CH2-CH2-NH-C(O) 2-methylphenyl] | E26<br>MS(ESI) m/z:<br>416([M − H]−) |
| 404 | [4-carboxycyclohexyl-NH-C(O) 2-methylphenyl] | E33 (Na)<br>MS(ESI) m/z:<br>459([M + H]+) |

TABLE 83-continued

| | | |
|---|---|---|
| 405 | [methyl 4-(2-methylbenzamido)cyclohexanecarboxylate] | E6<br>MS(FAB) m/z:<br>473([M + H]+) |
| 406 | [4-carbamoylcyclohexyl-NH-C(O) 2-methylphenyl] | E6<br>MS(FAB) m/z:<br>458([M + H]+) |
| 407 | [cis-3-carbamoylcyclohexyl-NH-C(O) 2-methylphenyl] | E26<br>MS(ESI) m/z:<br>456([M − H]−) |
| 408 | [trans-3-carbamoylcyclohexyl-NH-C(O) 2-methylphenyl] | E26<br>MS(ESI) m/z:<br>456([M − H]−) |
| 409 | [1-acetylpyrrolidin-3-yl-NH-C(O) 2-methylphenyl] | E26<br>MS(ESI) m/z:<br>442([M − H]−) |
| 410 | [3-(2-oxopyrrolidin-1-yl)propyl-NH-C(O) 2-methylphenyl] | E26<br>MS(FAB) m/z:<br>458([M + H]+) |
| 411 | [3-aminocyclohexyl-NH-C(O) 2-methylphenyl] | E26→E35 (HCl)<br>MS(ESI) m/z:<br>430([M + H]+) |

TABLE 83-continued

| 5 | (structure: N-(3-cyanocyclohexyl)-2-methylbenzamide, stereochemistry shown) | E5 MS(FAB) m/z: 440([M + H]+) |
|---|---|---|
| 412 | (structure: N-(3-cyanocyclohexyl)-2-methylbenzamide, stereochemistry shown) | E5 MS(FAB) m/z: 440([M + H]+) |

TABLE 84

| 413 | (morpholin-2-ylmethyl)-2-methylbenzamide | E35 (HCl) MS(ESI) m/z: 432([M + H]+) |
| 414 | (4-methylmorpholin-2-yl)methyl benzamide | E1 (HCl) MS(ESI) m/z: 446([M + H]+) |
| 415 | (4,4-dimethylmorpholinium-2-yl)methyl benzamide, I⁻ | E1 MS(ESI) m/z: 586([M − H]−) |
| 416 | (4-(2-hydroxyethyl)morpholin-2-yl)methyl benzamide | E1 (HCl) MS(ESI) m/z: 476([M + H]+) |
| 417 | (4-(2-methoxyethyl)morpholin-2-yl)methyl benzamide | E1 (HCl) MS(ESI) m/z: 490([M + H]+) |

TABLE 84-continued

| 418 | (4-benzylmorpholin-2-yl)methyl benzamide | E26 MS(FAB) m/z: 522([M + H]+) |
| 419 | (pyridin-3-ylmethyl) benzamide | E30 MS(ESI) m/z: 422([M − H]−) |
| 420 | (1,1-dioxidotetrahydrothiophen-3-yl) benzamide | E26 MS(ESI) m/z: 449([M − H]−) |
| 421 | (tetrahydro-2H-pyran-4-yl)-5-fluoro-2-methylbenzamide | E6 MS(ESI) m/z: 435([M + H]+) |
| 422 | (tetrahydro-2H-pyran-4-yl)-4-fluoro-2-methylbenzamide | E6 MS(FAB) m/z: 435([M + H]+) |
| 423 | (tetrahydro-2H-pyran-4-yl)-2,4-difluoro-6-methylbenzamide | E33→E26 MS(FAB) m/z: 453([M + H]+) |
| 424 | (tetrahydro-2H-pyran-4-yl)-2-chloro-6-methylbenzamide | E26 MS(FAB) m/z: 451([M + H]+) |
| 425 | H₂N-carbamoyl-4-chloro-2-methylbenzamide | E26 MS(FAB) m/z: 367([M + H]+) |
| 426 | (tetrahydro-2H-pyran-4-yl)-4-chloro-2-methylbenzamide | E26 MS(FAB) m/z: 451([M + H]+) |

TABLE 84-continued

| | | | |
|---|---|---|---|
| 427 | *N-(tetrahydropyran-4-yl)-2-methyl-4-methylbenzamide* | E11 MS(FAB) M/Z: 431([M + H]+) | |
| 36 | *N-(tetrahydropyran-4-yl)-2-methyl-4-hydroxybenzamide* | E36 MS(FAB) m/z: 433([M + H]+) | |
| 428 | *N-(tetrahydropyran-4-yl)-2-methoxy-6-methylbenzamide* | E26 MS(FAB) m/z: 447([M + H]+) | |
| 429 | *N-(tetrahydropyran-4-yl)-5-methoxy-2-methylbenzamide* | E6 MS(ESI) m/z: 447([M + H]+) | |
| 430 | *N-(tetrahydropyran-4-yl)-4-methoxy-2-methylbenzamide* | E6 MS(ESI) m/z: 447([M + H]+) | |

TABLE 85

| | | |
|---|---|---|
| 431 | | E26 MS(FAB) m/z: 461([M + H]+) |
| 432 | | E26 MS(FAB) m/z: 523([M + H]+) |
| 433 | | E35 (HCl) MS(FAB) m/z: 476([M + H]+) |
| 434 | | E11 (HCl) MS(FAB) m/z: 428([M + H]+) |
| 435 | | E11 (HCl) MS(FAB) m/z: 428([M + H]+) |
| 436 | | E11 (HCl) MS(ESI) m/z: 428([M + H]+) |
| 437 | | E11 (HCl) MS(FAB) m/z: 424([M + H]+) |
| 438 | | E11 (HCl) MS(ESI) m/z: 440([M + H]+) |
| 439 | | E11 (HCl) MS(ESI) m/z: 440([M + H]+) |
| 25 | | E25 (HCl) MS(FAB) m/z: 435([M + H]+) |

TABLE 85-continued
| 440 | 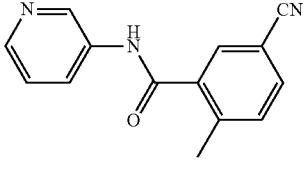 | E6 (HCl) MS(ESI) m/z: 435([M + H]+) |
| 441 | 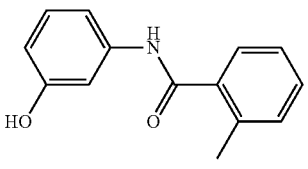 | E6 MS(ESI) m/z: 423([M − H]−) |
| 442 | 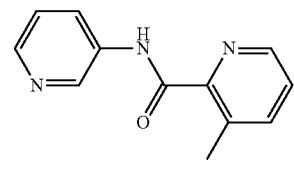 | E26 (2 HCl) MS(FAB) m/z: 411([M + H]+) |
| 443 | 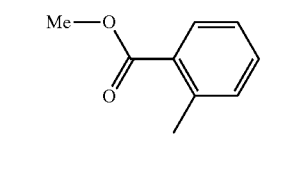 | E30 MS(FAB) m/z: 348([M + H]+) |
| 444 | 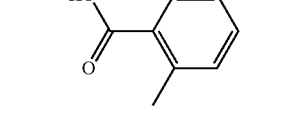 | E33 MS(FAB) m/z: 334([M + H]+) |
| 445 | 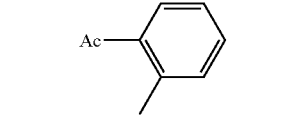 | E23 MS(FAB) m/z: 332([M + H]+) |
| 446 | 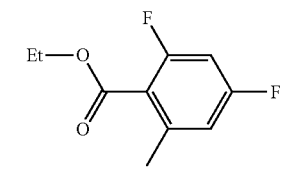 | E6 MS(FAB) m/z: 398([M + H]+) |
| 447 | 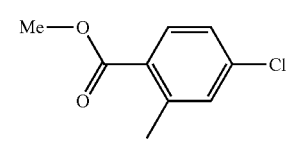 | E6 MS(FAB) m/z: 382([M + H]+) |
TABLE 86
| 448 | 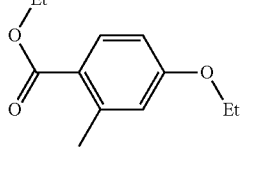 | E11 MS(FAB) m/z: 378([M + H]+) |
| 449 | 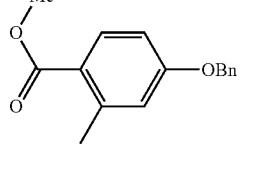 | E6 MS(FAB) m/z: 406([M + H]+) |
| 450 | 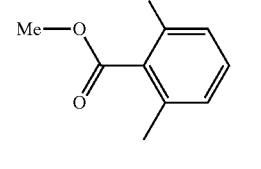 | E6 MS(FAB) m/z: 454([M + H]+) |
| 451 | 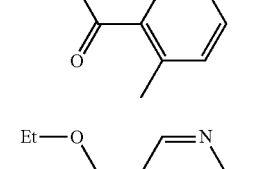 | E6 MS(FAB) m/z: 373([M + H]+) |
| 452 | 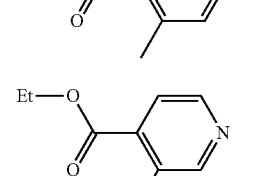 | E11 MS(FAB) m/z: 363([M + H]+) |
| 453 | 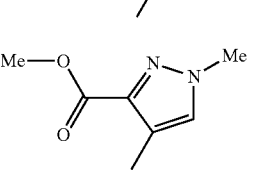 | E6 MS(FAB) m/z: 363([M + H]+) |
| 454 | 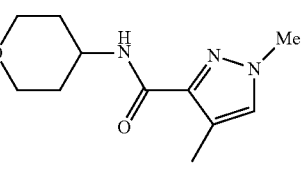 | E6 MS(FAB) m/z: 363([M + H]+) |
| 455 | 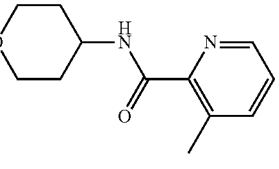 | E6 MS(FAB) m/z: 352([M + H]+) |
| 456 | 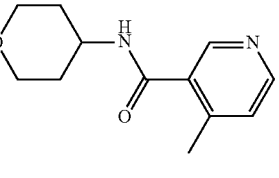 | E26 MS(FAB) m/z: 421([M + H]+) |
| 457 |  | E26 (HCl) MS(FAB) m/z: 418([M + H]+) |
| 458 | 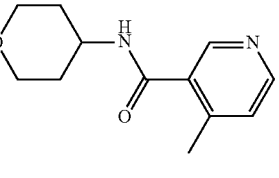 | E26 (HCl) MS(FAB) m/z: 418([M + H]+) |

TABLE 86-continued

| | | |
|---|---|---|
| 459 | tetrahydropyran-CH2-NH-C(O)-pyridine-Me | E26 (HCl) MS(FAB) m/z: 418([M + H]+) |
| 460 | O=C(NH2)-CH2-SO2-C6H4-Me | E12 MS(FAB) m/z: 411([M + H]+) |
| 12 | HO-(CH2)4-SO2-C6H4-Me | E12 MS(ESI) m/z: 440([M + H]+) |
| 21 | AcO-(CH2)5-SO2-C6H4-Me | E21 MS(ESI) m/z: 482([M + H]+) |
| 461 | NC-(CH2)4-SO2-C6H4-Me | E4 MS(ESI) m/z: 449([M + H]+) |
| 462 | AcHN-(CH2)5-SO2-C6H4-Me | E18 MS(FAB) m/z: 481([M + H]+) |
| 463 | Me2N-(CH2)5-SO2-C6H4-Me | E24 (HCl) MS(ESI) m/z: 467([M + H]+) |
| 38 | HN-piperidine-SO2-C6H4-Me | E38 MS(FAB) m/z: 437([M + H]+) |

TABLE 87

| | | |
|---|---|---|
| 464 | Cbz-piperidine-SO2-C6H4-Me | E12 MS(FAB) m/z: 571([M + H]+) |
| 465 | tetrahydropyran-CH2-SO2-C6H4-Me | E12 MS(ESI) m/z: 452([M + H]+) |
| 466 | pyridine-CH2-SO2-C6H4-Me | E12 MS(ESI) m/z: 445([M + H]+) |
| 467 | EtO-C(O)-C6H3(Cl)-Me | E6 MS(FAB) m/z: 396([M + H]+) |
| 468 | MeO-C(O)-C6H3(Me)-O-CH2CH2-NHBoc | E6 MS(FAB) m/z: 507([M + H]+) |
| 469 | HOOC-C6H3(Cl)-Me | E33 MS(FAB) m/z: 368([M + H]+) |
| 470 | HOOC-C6H3(Cl)-Me | E33 MS(ESI) m/z: 366([M − H]−) |
| 471 | HOOC-C6H3(OMe)-Me | E33 MS(FAB) m/z: 364([M + H]+) |
| 472 | HOOC-C6H3(CN)-Me | E33 MS(ESI) m/z: 357([M − H]−) |

TABLE 87-continued

| | | | |
|---|---|---|---|
| 473 | 4-ethoxy-2-methylbenzoic acid | E33 | MS(ESI) m/z: 376([M − H]−) |
| 474 | 4-(benzyloxy)-2-methylbenzoic acid | E33 | MS(FAB) m/z: 440([M + H]+) |
| 475 | 4-(2-(Boc-amino)ethoxy)-2-methylbenzoic acid | E33 | MS(FAB) m/z: 493([M + H]+) |
| 476 | 3-methylpicolinic acid | E33 | MS(FAB) m/z: 335([M + H]+) |
| 477 | 4-methylnicotinic acid | E33 | MS(FAB) m/z: 335([M + H]+) |
| 478 | 3-methylisonicotinic acid | E33 | MS(FAB) m/z: 335([M + H]+) |
| 479 | 1,4-dimethyl-1H-pyrazole-3-carboxylic acid | E33 | MS(FAB) m/z: 338([M + H]+) |
| 480 | methyl (1S,3R)-3-(2-methylbenzamido)cyclohexanecarboxylate | E26 | MS(ESI) m/z: 473([M + H]+) |
| 481 | methyl (1R,3S)-3-(2-methylbenzamido)cyclohexanecarboxylate | E26 | MS(ESI) m/z: 473([M + H]+) |
| 482 | (1S,3R)-3-(2-methylbenzamido)cyclohexanecarboxylic acid | E33 | MS(ESI) m/z: 459([M + H]+) |

TABLE 88

| | | | |
|---|---|---|---|
| 483 | (1R,3S)-3-(2-methylbenzamido)cyclohexanecarboxylic acid | E33 | MS(ESI) m/z: 457([M − H]−) |
| 484 | 4-(2-methylbenzamido)butanoic acid | E33 | MS(ESI) m/z: 417([M − H]−) |
| 485 | tert-butyl 2-((2-methylbenzamido)methyl)morpholine-4-carboxylate | E26 | MS(ESI) m/z: 530([M − H]−) |
| 486 | Boc-protected compound with tetrahydropyran | E26 | MS(FAB) m/z: 576([M + H]+) |
| 487 | 2-((2-methylphenyl)thio)acetamide | E30 | MS(ESI) m/z: 379([M + H]+) |
| 488 | benzyl 4-((2-methylphenyl)thio)piperidine-1-carboxylate | E30 | MS(FAB) m/z: 539([M + H]+) |

TABLE 88-continued

| 489 | [structure: HO-(CH2)4-S-(2-methylphenyl)] | E30 MS(FAB) m/z: 408([M + H]+) |
| 490 | [structure: pyridin-3-yl-CH2-S-(2-methylphenyl)] | E30 MS(ESI) m/z: 413([M + H]+) |
| 491 | [structure: 2-methylbenzamide-NH-(CH2)3-C(=O)-O-Et] | E26 MS(ESI) m/z: 447([M + H]+) |
| 492 | [structure: MsO-(CH2)4-SO2-(2-methylphenyl)] | E22 MS(FAB) m/z: 518([M + H]+) |
| 16 | [structure: N3-(CH2)4-SO2-(2-methylphenyl)] | E16 MS(FAB) m/z: 465([M + H]+) |
| 17 | [structure: H2N-(CH2)4-SO2-(2-methylphenyl)] | E17 MS(ESI) m/z: 439([M + H]+) |
| 493 | [structure: tetrahydropyran-4-yl-CH2-S-(2-methylphenyl)] | E23 MS(ESI) m/z: 420([M + H]+) |

TABLE 89

[General structure: A-NH-C(=O)-(thiazole)-N(piperidine-OEt), with R² on ring A]

| Ex | [structure] | Syn (Sal) Dat |
|---|---|---|
| 494 | HO-CH2CH2-NH-C(=O)-(2-methylphenyl) | E6 MS(ESI) m/z: 419([M + H]+) |
| 495 | HO-CH2-C(Me)2-CH2-NH-C(=O)-(2-methylphenyl) | E11 MS(ESI) m/z: 461([M + H]+) |
| 496 | MeO-CH2CH2-NH-C(=O)-(2-methylphenyl) | E11 MS(FAB) m/z: 433([M + H]+) |
| 497 | H2N-C(=O)-CH2-NH-C(=O)-(2-methylphenyl) | E6 MS(ESI) m/z: 430([M − H]−) |
| 498 | Me2N-CH2-C(Me)2-CH2-NH-C(=O)-(2-methylphenyl) | E11 (Fum) MS(ESI) m/z: 488([M + H]+) |
| 499 | morpholinyl-CH2-(phenyl)-C(=O)-NH-(tetrahydropyran-4-yl), with Me on phenyl | E26 (HCl) MS(ESI) m/z: 558([M + H]+) |
| 500 | * [bicyclic oxa-aza structure]-CH2-(phenyl)-C(=O)-NH-(tetrahydropyran-4-yl), with Me on phenyl | E26 (HCl) MS(ESI) m/z: 570([M + H]+) |

| | | |
|---|---|---|
| 501 | 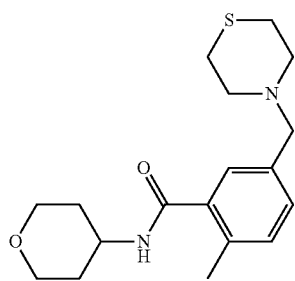 | E26 (HCl) MS(ESI) m/z: 574([M + H]+) |
| 502 | 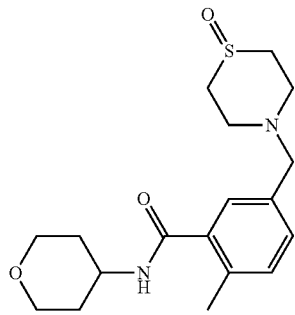 | E12 (HCl) MS(ESI) m/z: 590([M + H]+) |
| 503 | 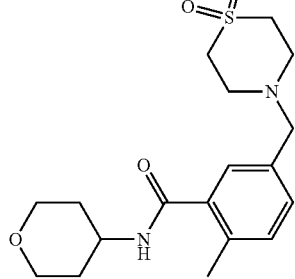 | E12 (HCl) MS(FAB) m/z: 606([M + H]+) |
| 504 | 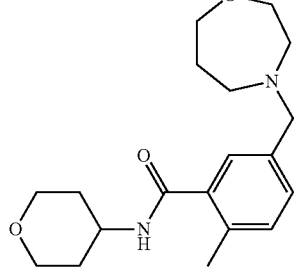 | E26 (HCl) MS(ESI) m/z: 572([M + H]+) |
| 505 | 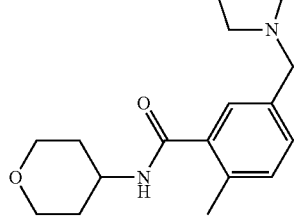 | P13→E9→E33→E26 (HCl) MS(ESI) m/z: 542([M + H]+) |
TABLE 90
| | | |
|---|---|---|
| 506 | 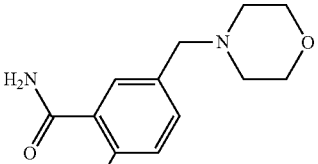 | E26 (Fum) MS(FAB) m/z: 474([M + H]+) |
| 507 | 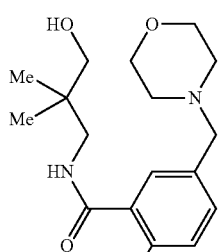 | E26 (HCl) MS(ESI) m/z: 560([M + H]+) |
| 508 | 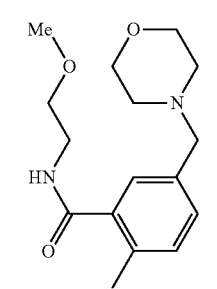 | E26 (HCl) MS(ESI) m/z: 532([M + H]+) |
| 509 | 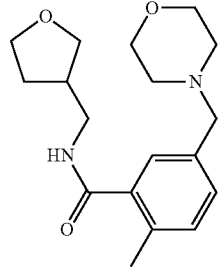 | E26 (Fum) MS(FAB) m/z: 558([M + H]+) |
| 510 | 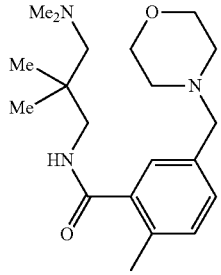 | E26 (2 HCl) MS(FAB) m/z: 587([M + H]+) |
| 511 | 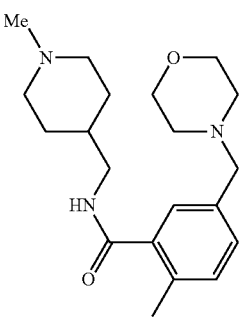 | E26 (3 Fum) MS(ESI) m/z: 585([M + H]+) |

TABLE 90-continued

| | | |
|---|---|---|
| 512 | [tetrahydropyran-NH-C(=O)-pyridine with 4-Me] | E26 (HCl) MS(FAB) m/z: 460([M + H]+) |
| 513 | [tetrahydropyran-NH-C(=O)-pyridine with 3-Me] | E26 (HCl) MS(FAB) m/z: 460([M + H]+) |
| 514 | [morpholine-CH2-Ar(Me)(CO2Me)] | E30 MS(ESI) m/z: 489([M + H]+) |
| 515 | [homomorpholine-CH2-Ar(Me)(CO2Me)] | E9 MS(ESI) m/z: 503([M + H]+) |
| 516 | [oxabicyclic-N-CH2-Ar(Me)(CO2Me)] * | E6 MS(ESI) m/z: 501([M + H]+) |
| 517 | [thiomorpholine-CH2-Ar(Me)(CO2Me)] | E6 MS(ESI) m/z: 505([M + H]+) |
| 518 | [Et ester of 3-methylpyridine-2-carboxylate] | E6 MS(FAB) m/z: 405([M + H]+) |

TABLE 91

| | | |
|---|---|---|
| 519 | [Et ester of 3-methylpyridine-4-carboxylate] | E6 MS(FAB) m/z: 405([M + H]+) |
| 520 | [morpholine-CH2-Ar(Me)(CO2H)] | E33 MS(ESI) m/z: 475([M + H]+) |
| 521 | [homomorpholine-CH2-Ar(Me)(CO2H)] | E33 MS(FAB) m/z: 489([M + H]+) |
| 522 | [oxabicyclic-N-CH2-Ar(Me)(CO2H)] * | E33 MS(FAB) m/z: 487([M + H]+) |
| 523 | [thiomorpholine-CH2-Ar(Me)(CO2H)] | E33 MS(FAB) m/z: 491([M + H]+) |
| 524 | [3-methylpyridine-2-carboxylic acid] | E33 MS(FAB) m/z: 377([M + H]+) |

TABLE 91-continued

| | | |
|---|---|---|
| 525 | 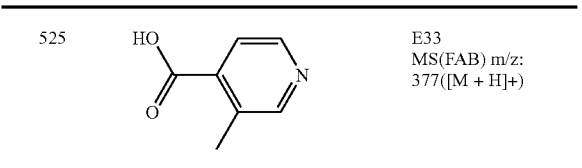 | E33<br>MS(FAB) m/z:<br>377([M + H]+) |

TABLE 92

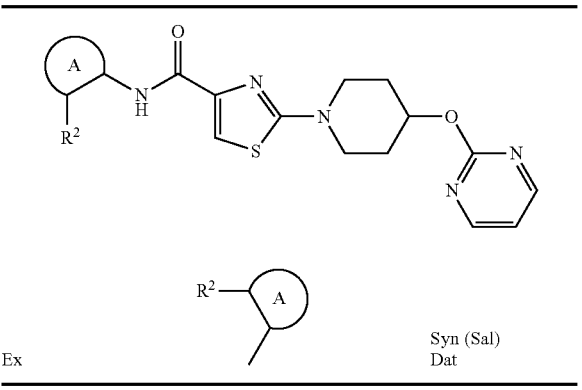

| Ex | 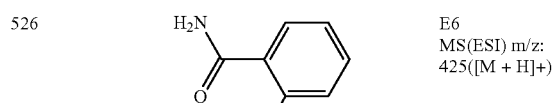 | Syn (Sal)<br>Dat |
|---|---|---|
| 526 | 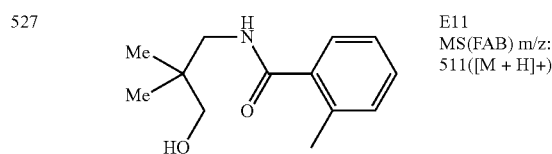 | E6<br>MS(ESI) m/z:<br>425([M + H]+) |
| 527 | 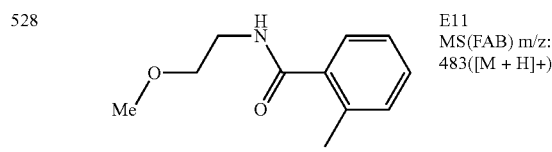 | E11<br>MS(FAB) m/z:<br>511([M + H]+) |
| 528 | 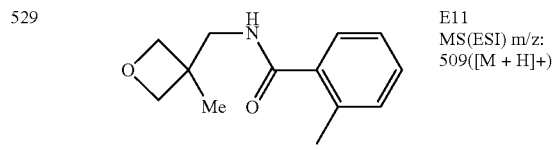 | E11<br>MS(FAB) m/z:<br>483([M + H]+) |
| 529 | 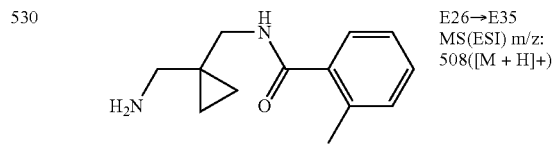 | E11<br>MS(ESI) m/z:<br>509([M + H]+) |
| 530 | 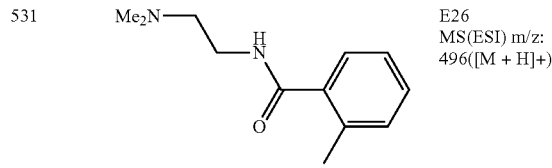 | E26→E35<br>MS(ESI) m/z:<br>508([M + H]+) |
| 531 | 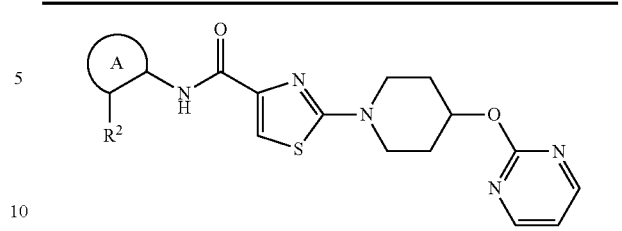 | E26<br>MS(ESI) m/z:<br>496([M + H]+) |

TABLE 92-continued

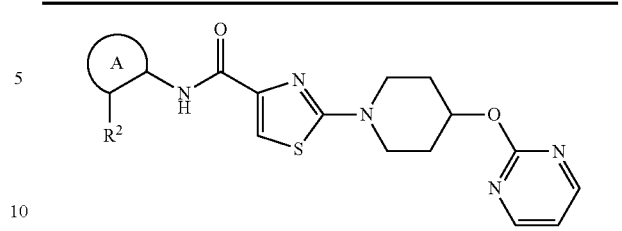

| Ex | 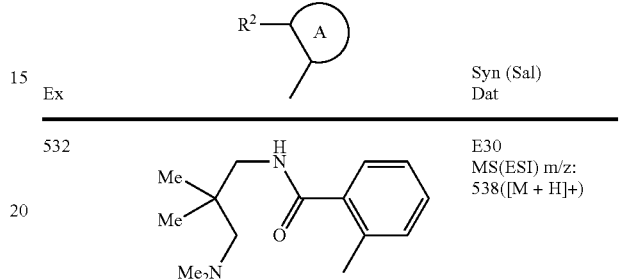 | Syn (Sal)<br>Dat |
|---|---|---|
| 532 | 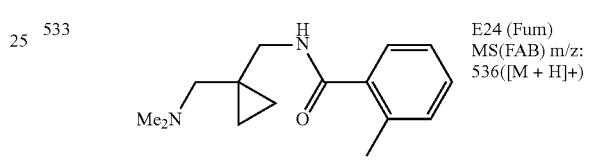 | E30<br>MS(ESI) m/z:<br>538([M + H]+) |
| 533 | 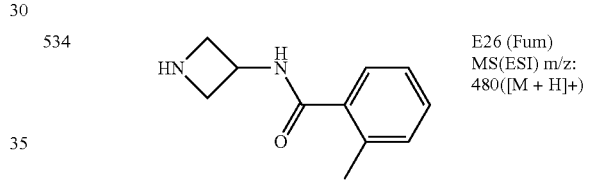 | E24 (Fum)<br>MS(FAB) m/z:<br>536([M + H]+) |
| 534 | 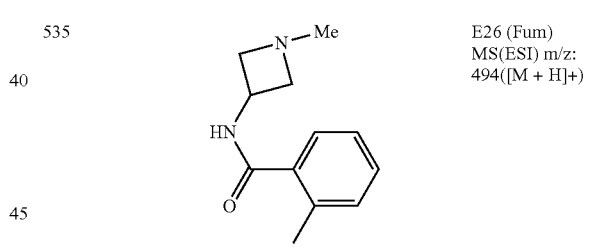 | E26 (Fum)<br>MS(ESI) m/z:<br>480([M + H]+) |
| 535 | 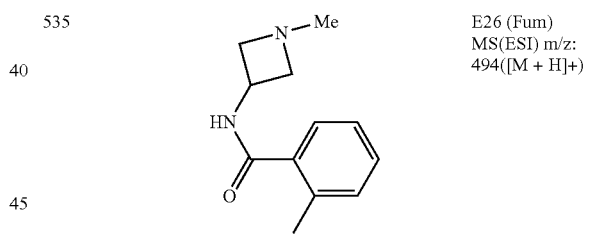 | E26 (Fum)<br>MS(ESI) m/z:<br>494([M + H]+) |
| 536 | 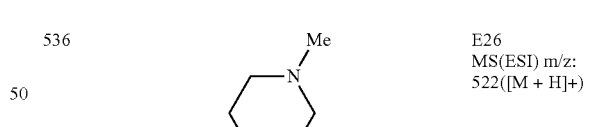 | E26<br>MS(ESI) m/z:<br>522([M + H]+) |
| 537 | 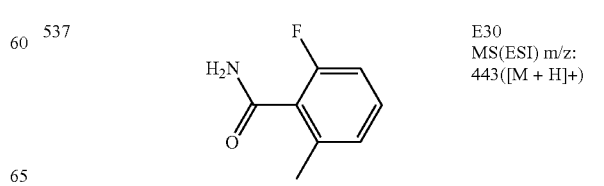 | E30<br>MS(ESI) m/z:<br>443([M + H]+) |

TABLE 92-continued

| Ex | R²–A structure | Syn (Sal) Dat |
|---|---|---|
| 538 | 2-Me, 6-CONH₂ phenyl | E6 MS(ESI) m/z: 439([M + H]+) |
| 539 | (3-methoxypyrrolidin-1-yl)methyl on 3-carbamoyl-4-methylphenyl * | E26 (HCl) MS(ESI) m/z: 538([M + H]+) |

TABLE 93

| Ex | Structure | Syn (Sal) Dat |
|---|---|---|
| 540 | (2-(methoxymethyl)pyrrolidin-1-yl)methyl on 3-carbamoyl-4-methylphenyl * | E26 MS(FAB) m/z: 552([M + H]+) |
| 541 | morpholinomethyl on 3-carbamoyl-4-methylphenyl | E26 (HCl) MS(ESI) m/z: 524([M + H]+) |
| 542 | 1-morpholinoethyl on 3-carbamoyl-4-methylphenyl | E26 MS(FAB) m/z: 538([M + H]+) |
| 543 | 1-(N-(2-methoxyethyl)-N-methylamino)ethyl on 3-carbamoyl-4-methylphenyl | E26 MS(FAB) m/z: 540([M + H]+) |
| 544 | pyrrolidin-1-ylmethyl on N-(tetrahydropyran-4-yl)-3-carbamoyl-4-methylphenyl | E9 (HCl) MS(FAB) m/z: 592([M + H]+) |
| 545 | (3-methoxypyrrolidin-1-yl)methyl on N-(tetrahydropyran-4-yl)-3-carbamoyl-4-methylphenyl * | E26 (HCl) MS(ESI) m/z: 622([M + H]+) |
| 546 | (2-(methoxymethyl)pyrrolidin-1-yl)methyl on N-(tetrahydropyran-4-yl)-3-carbamoyl-4-methylphenyl * | E26 MS(FAB) m/z: 636([M + H]+) |

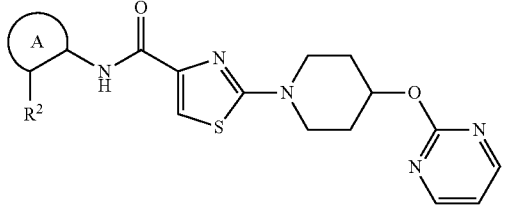

TABLE 93-continued
| | | |
|---|---|---|
| 34 | 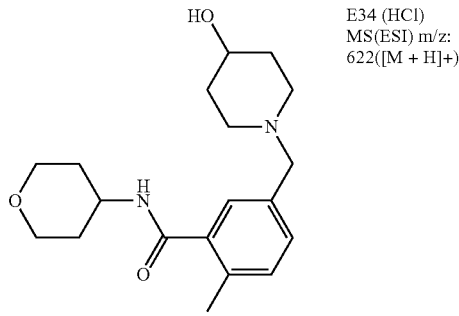 | E34 (HCl)<br>MS(ESI) m/z:<br>622([M + H]+) |
| 547 | 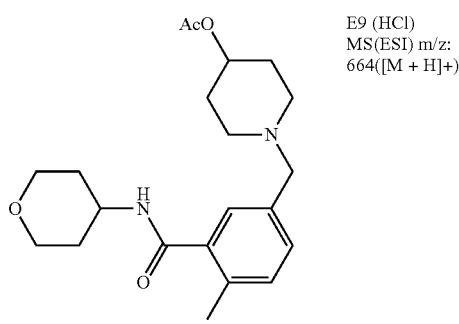 | E9 (HCl)<br>MS(ESI) m/z:<br>664([M + H]+) |
| 548 | 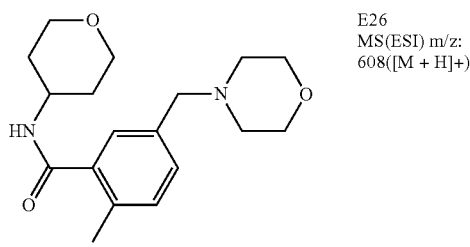 | E26<br>MS(ESI) m/z:<br>608([M + H]+) |
| 549 | 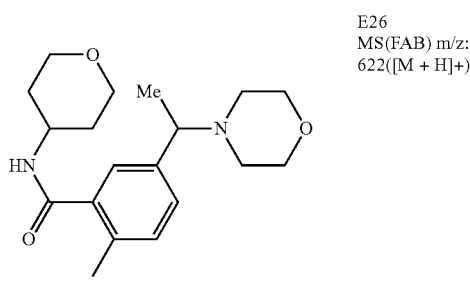 | E26<br>MS(FAB) m/z:<br>622([M + H]+) |
| 550 | 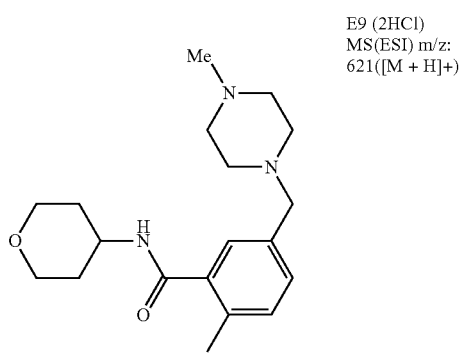 | E9 (2HCl)<br>MS(ESI) m/z:<br>621([M + H]+) |
TABLE 94
| | | |
|---|---|---|
| 551 | 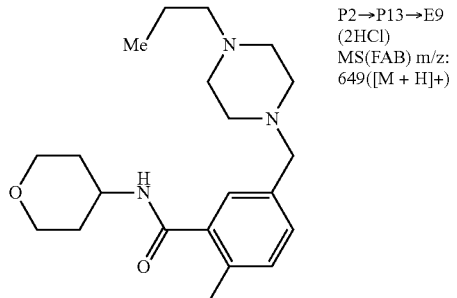 | P2→P13→E9<br>(2HCl)<br>MS(FAB) m/z:<br>649([M + H]+) |
| 552 | 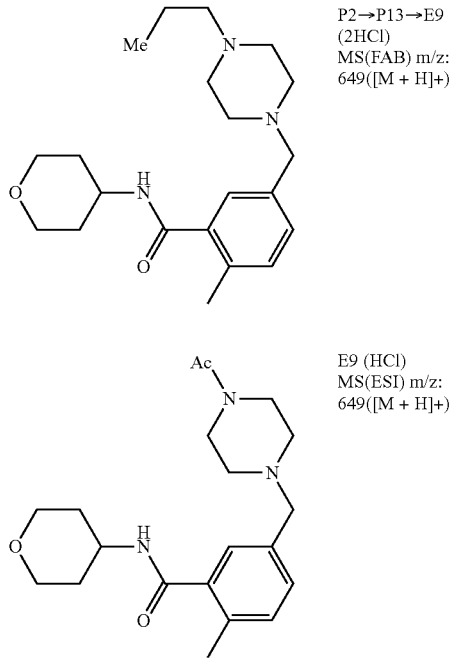 | E9 (HCl)<br>MS(ESI) m/z:<br>649([M + H]+) |
| 553 | 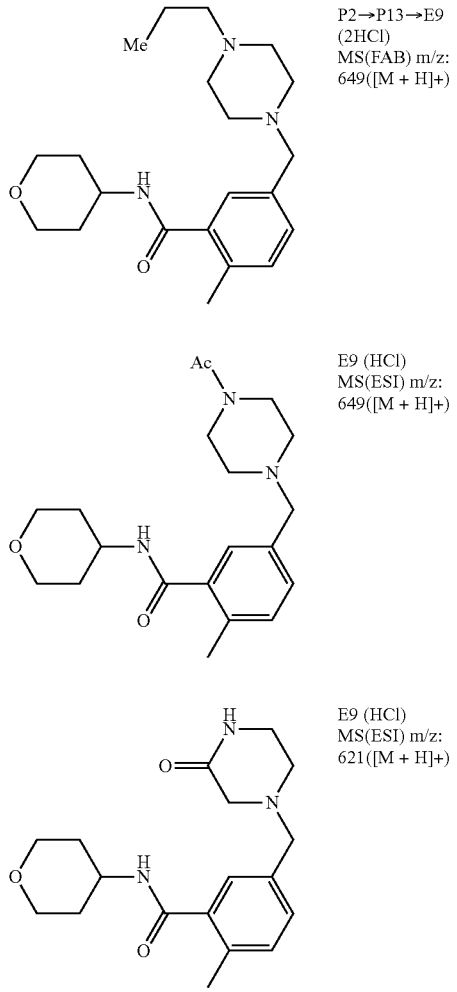 | E9 (HCl)<br>MS(ESI) m/z:<br>621([M + H]+) |
| 554 | 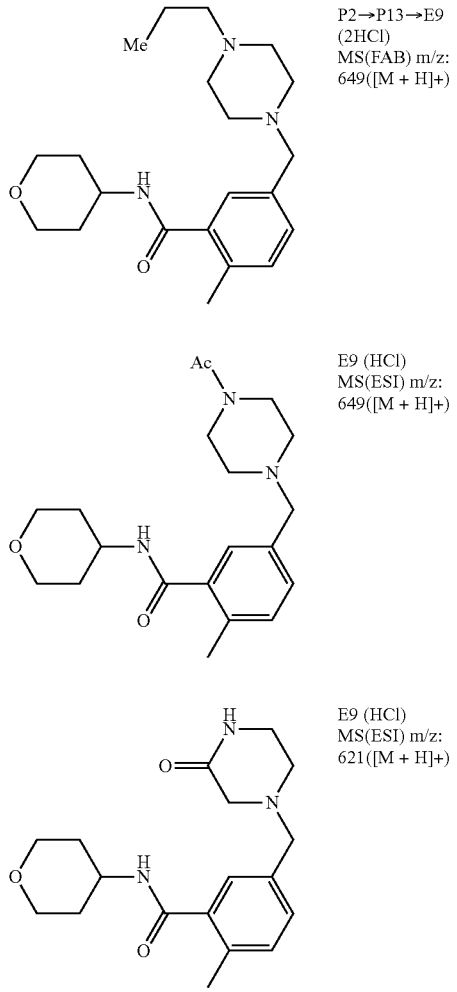 | E9 (HCl)<br>MS(ESI) m/z:<br>610([M + H]+) |
| 555 | 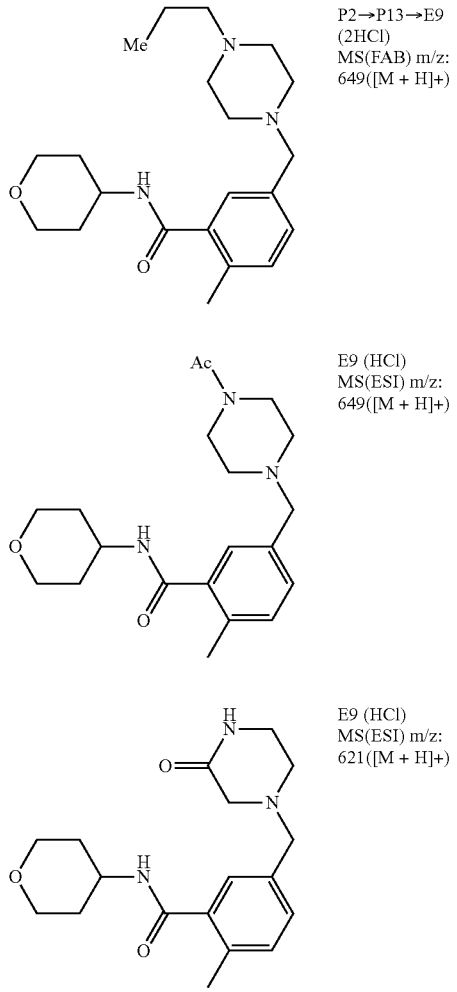 | P2→P13→E9<br>(2HCl)<br>MS(FAB) m/z:<br>623([M + H]+) |

TABLE 94-continued

| 556 | [structure] | E26 (Fum) MS(FAB) m/z: 624([M + H]+) |
| 557 | [structure] | E9 (HCl) MS(FAB) m/z: 606([M + H]+) |
| 558 | [structure] | E26 MS(ESI) m/z: 622([M + H]+) |
| 559 | [structure] | E33→E26 (HCl) MS(FAB) m/z: 606([M + H]+) |
| 560 | [structure] | E9 MS(FAB) m/z: 622([M + H]+) |
| 561 | [structure] | E9 (HCl) MS(ESI) m/z: 635([M + H]+) |
| 562 | [structure] * | E26 (HCl) MS(ESI) m/z: 596([M + H]+) |

TABLE 95

| 563 | [structure] | E26 MS(ESI) m/z: 610([M + H]+) |
| 564 | [structure] | E26 MS(ESI) m/z: 582([M + H]+) |
| 565 | [structure] | E26 (HCl) MS(FAB) m/z: 596([M + H]+) |
| 566 | [structure] | E26 MS(ESI) m/z: 610([M + H]+) |

TABLE 95-continued
| | | |
|---|---|---|
| 567 | 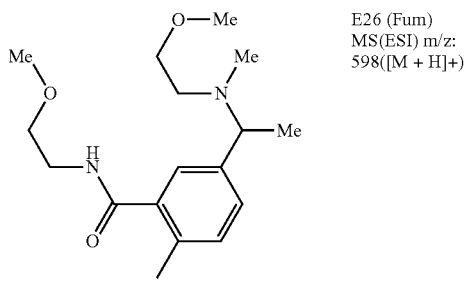 | E26 (Fum)<br>MS(ESI) m/z:<br>598([M + H]+) |
| 568 | 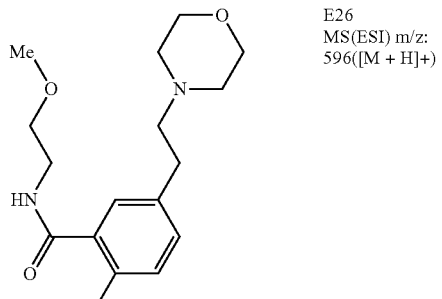 | E26<br>MS(ESI) m/z:<br>596([M + H]+) |
| 2 | 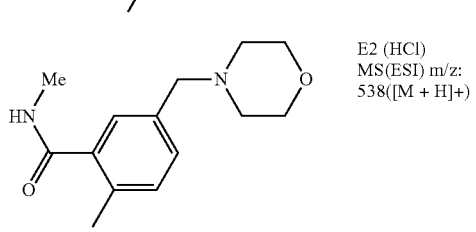 | E2 (HCl)<br>MS(ESI) m/z:<br>538([M + H]+) |
| 26 | 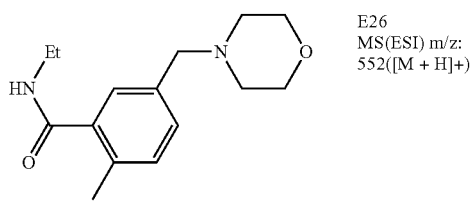 | E26<br>MS(ESI) m/z:<br>552([M + H]+) |
| 569 | 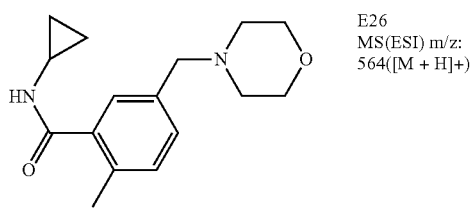 | E26<br>MS(ESI) m/z:<br>564([M + H]+) |
| 570 | 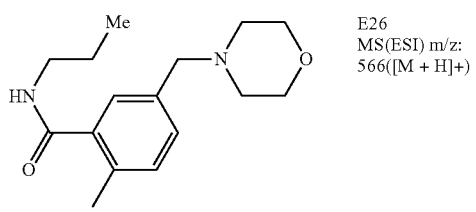 | E26<br>MS(ESI) m/z:<br>566([M + H]+) |
| 571 | 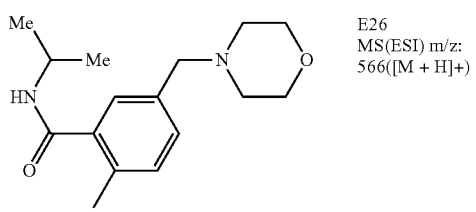 | E26<br>MS(ESI) m/z:<br>566([M + H]+) |
TABLE 95-continued
| | | |
|---|---|---|
| 572 | 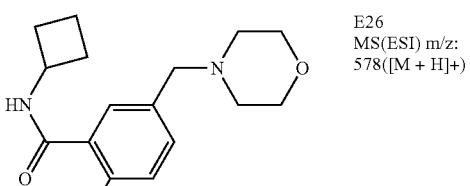 | E26<br>MS(ESI) m/z:<br>578([M + H]+) |
| 573 | 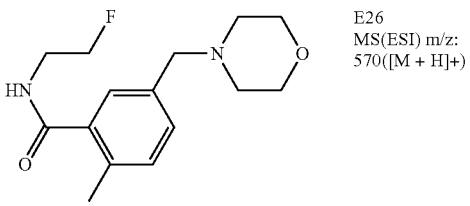 | E26<br>MS(ESI) m/z:<br>570([M + H]+) |
| 574 | 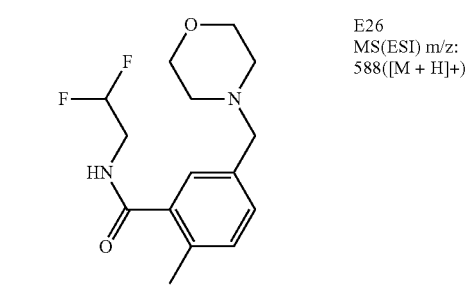 | E26<br>MS(ESI) m/z:<br>588([M + H]+) |
TABLE 96
| | | |
|---|---|---|
| 575 | 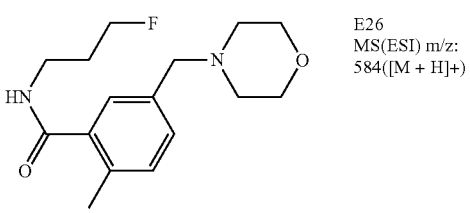 | E26<br>MS(ESI) m/z:<br>584([M + H]+) |
| 576 | 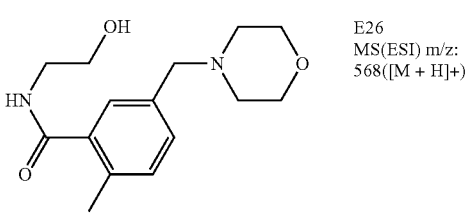 | E26<br>MS(ESI) m/z:<br>568([M + H]+) |
| 577 | 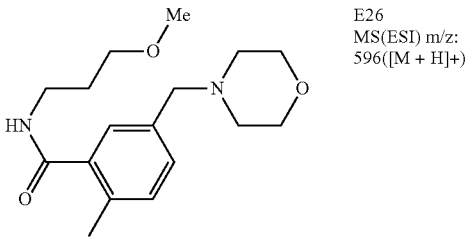 | E26<br>MS(ESI) m/z:<br>596([M + H]+) |

TABLE 96-continued

| | | |
|---|---|---|
| 578 | | E26 MS(ESI) m/z: 596([M + H]+) |
| 579 | | E26 MS(ESI) m/z: 580([M + H]+) |
| 580 | | E26 MS(ESI) m/z: 594([M + H]+) |
| 581 | | E26 MS(ESI) m/z: 594([M + H]+) |
| 582 | | E26 (HCl) MS(ESI) m/z: 608([M + H]+) |
| 583 | | E26 (HCl) MS(ESI) m/z: 608([M + H]+) |
| 584 | | E26 MS(ESI) m/z: 608([M + H]+) |
| 585 | | E26 (HCl) MS(ESI) m/z: 624([M + H]+) |
| 586 | | E26 (2Fum) MS(FAB) m/z: 595([M + H]+) |
| 587 | | E26 (2Fum) MS(ESI) m/z: 637([M + H]+) |

TABLE 97

| | | |
|---|---|---|
| 588 | | E26 (2Fum) MS(ESI) m/z: 593([M + H]+) |

TABLE 97-continued
| | | | |
|---|---|---|---|
| 589 | 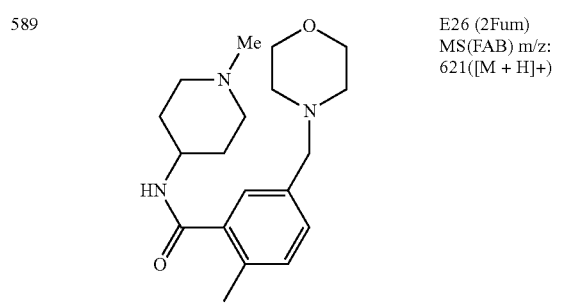 | | E26 (2Fum) MS(FAB) m/z: 621([M + H]+) |
| 590 | 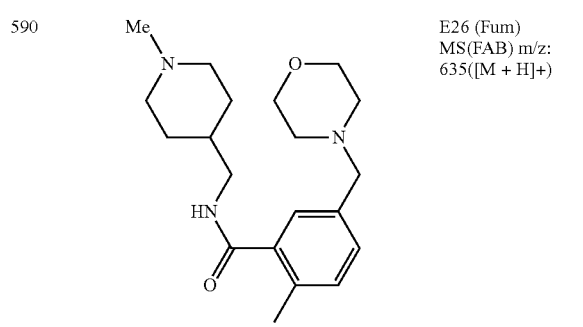 | | E26 (Fum) MS(FAB) m/z: 635([M + H]+) |
| 591 | 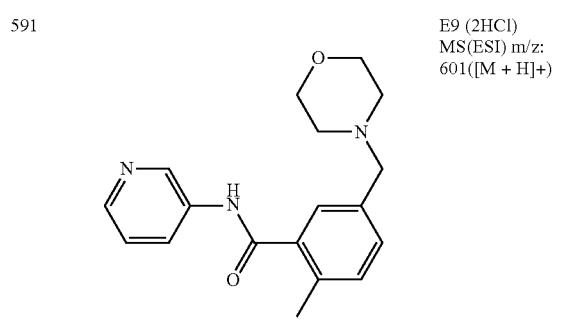 | | E9 (2HCl) MS(ESI) m/z: 601([M + H]+) |
| 592 | 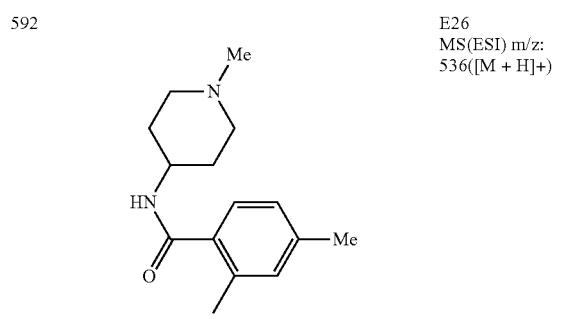 | | E26 MS(ESI) m/z: 536([M + H]+) |
| 593 | 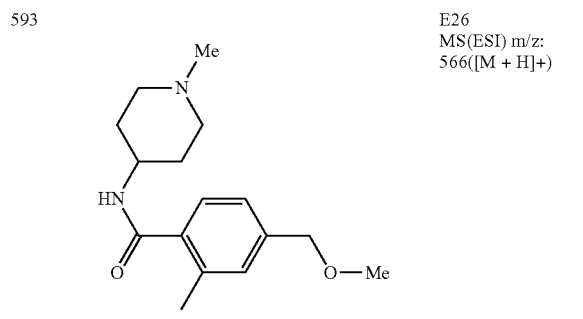 | | E26 MS(ESI) m/z: 566([M + H]+) |
TABLE 97-continued
| | | | |
|---|---|---|---|
| 593 | 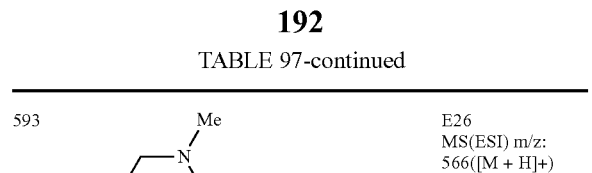 | | E26 MS(ESI) m/z: 566([M + H]+) |
| 594 | 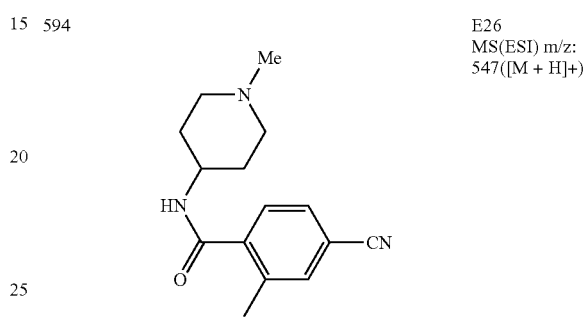 | | E26 MS(ESI) m/z: 547([M + H]+) |
| 595 | 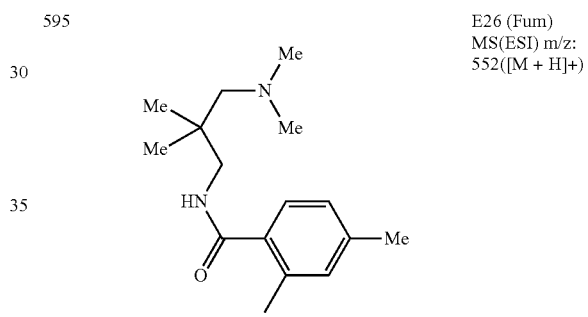 | | E26 (Fum) MS(ESI) m/z: 552([M + H]+) |
| 596 | 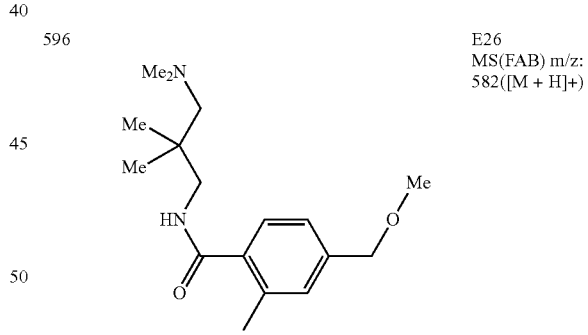 | | E26 MS(FAB) m/z: 582([M + H]+) |
| 597 | 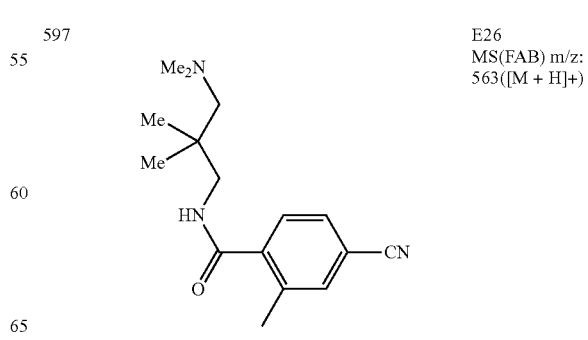 | | E26 MS(FAB) m/z: 563([M + H]+) |

TABLE 97-continued

| | | |
|---|---|---|
| 598 | [structure: 4-cyano-2-methyl-N-(2,2-dimethyl-3-methoxypropyl)benzamide] | E26 MS(ESI) m/z: 548([M − H]−) |
| 599 | [structure: 3-methylpyridine-2-carboxamide] | E6 MS(FAB) m/z: 426([M + H]+) |
| 600 | [structure: 4-methylpyridine-3-carboxamide] | E6 MS(FAB) m/z: 426([M + H]+) |
| 601 | [structure: 3-methylisonicotinamide] | E6 MS(ESI) m/z: 426([M + H]+) |

TABLE 98

| | | |
|---|---|---|
| 602 | [structure: N-(tetrahydropyran-4-yl)-4-methylnicotinamide] | E26 MS(FAB) m/z: 510([M + H]+) |
| 603 | [structure: N-(tetrahydropyran-4-yl)-3-methylisonicotinamide] | E26 MS(FAB) m/z: 510([M + H]+) |
| 604 | [structure: N-(tetrahydropyran-4-yl)-2,5-dimethylisonicotinamide] | E26 MS(ESI) m/z: 524([M + H]+) |
| 605 | [structure: N-(tetrahydropyran-4-yl)-4-methylpyridazine-3-carboxamide] | E26 MS(ESI) m/z: 511([M + H]+) |
| 606 | [structure: 1,4-dimethyl-1H-pyrazole-3-carboxamide] | E26 MS(ESI) m/z: 429([M + H]+) |

TABLE 98-continued

| | | |
|---|---|---|
| 607 | [structure: N-(2-methoxyethyl)-1,4-dimethyl-1H-pyrazole-3-carboxamide] | E26 MS(ESI) m/z: 487([M + H]+) |
| 608 | [structure: 2-methylbenzoic acid] | E33 MS(ESI) m/z: 424([M − H]−) |
| 609 | [structure: 2'-methylacetophenone] | E6 MS(ESI) m/z: 424([M + H]+) |
| 610 | [structure: 2-methylphenyl methyl sulfone] | E6 MS(ESI) m/z: 460([M + H]+) |
| 611 | [structure: 2-methylphenyl difluoromethyl sulfone] | E6 MS(ESI) m/z: 496([M + H]+) |
| 612 | [structure: (2-methylphenyl)(pyridin-2-yl)methanone] | E30 MS(ESI) m/z: 487([M + H]+) |
| 613 | [structure: 2,4-dimethylbenzoic acid] | E33 MS(FAB) m/z: 440([M + H]+) |
| 614 | [structure: 4-cyano-2-methylbenzoic acid] | E33 MS(FAB) m/z: 451([M + H]+) |
| 615 | [structure: 4-(methoxymethyl)-2-methylbenzoic acid] | E33 MS(FAB) m/z: 470([M + H]+) |
| 616 | [structure: (S)-3-methoxypyrrolidine with methyl 3-methylbenzoate substituent] | E23 MS(ESI) m/z: 553([M + H]+) |

TABLE 98-continued

| 617 | (structure: (3-methoxypyrrolidin-1-yl)methyl on 2-methyl-benzoic acid) | E33 MS(ESI) m/z: 539([M + H]+) |
| 618 | (structure: 2-(methoxymethyl)pyrrolidin-1-yl methyl on methyl 2-methyl-benzoate) | E23 MS(FAB) m/z: 567([M + H]+) |
| 619 | (structure: 2-(methoxymethyl)pyrrolidin-1-yl methyl on 2-methyl-benzoic acid) | E33 MS(FAB) m/z: 553([M + H]+) |

TABLE 99

| 620 | (structure: 4-methoxypiperidin-1-yl methyl on methyl 2-methyl-benzoate) | E23 MS(ESI) m/z: 567([M + H]+) |
| 6 | (structure: morpholinomethyl on methyl 2-methyl-benzoate) | E6 MS(ESI) m/z: 539([M + H]+) |
| 33 | (structure: morpholinomethyl on 2-methyl-benzoic acid) | E33 MS(ESI) m/z: 525([M + H]+) |
| 621 | (structure: morpholinomethyl on 3-acetyl-4-methyl-phenyl) | E6 MS(ESI) m/z: 523([M + H]+) |
| 622 | (structure: 1-morpholinoethyl on methyl 2-methyl-benzoate) | E23 MS(ESI) m/z: 553([M + H]+) |
| 623 | (structure: 1-morpholinoethyl on 2-methyl-benzoic acid) | E33 MS(ESI) m/z: 539([M + H]+) |
| 624 | (structure: (3,3-dimethylmorpholino)methyl on methyl 2-methyl-benzoate) | E23 MS(ESI) m/z: 567([M + H]+) |
| 625 | (structure: N-(2-methoxyethyl)-N-methyl-1-arylethylamine on methyl 2-methyl-benzoate) | E23 (HCl) MS(ESI) m/z: 555([M + H]+) |

TABLE 99-continued

| | | |
|---|---|---|
| 626 | [structure: 3-methyl-5-(1-(N-methyl-N-(2-methoxyethyl)amino)ethyl)benzoic acid] | E33 MS(ESI) m/z: 541([M + H]+) |
| 627 | [structure: methyl 5-(2-morpholinoethyl)-3-methylbenzoate] | E6 MS(ESI) m/z: 553([M + H]+) |
| 628 | [structure: 1-(3-acetyl-4-methylphenyl)cyclopropanecarbonitrile] | E6 MS(ESI) m/z: 489([M + H]+) |
| 629 | [structure: 2-acetyl-3-methylpyridine] | E6 MS(ESI) m/z: 425([M + H]+) |
| 630 | [structure: methyl 2-methylnicotinate] | E6 MS(ESI) m/z: 441([M + H]+) |
| 631 | [structure: ethyl 2,5-dimethylisonicotinate] | E23 MS(ESI) m/z: 469([M + H]+) |

TABLE 100

| | | |
|---|---|---|
| 632 | [structure: methyl 1,4-dimethyl-1H-pyrazole-3-carboxylate] | E6 MS(ESI) m/z: 444([M + H]+) |
| 633 | [structure: 1,4-dimethyl-1H-pyrazole-3-carboxylic acid] | E33 MS(ESI) m/z: 430([M + H]+) |

TABLE 100-continued

| | | |
|---|---|---|
| 634 | [structure: ethyl 1,3-dimethyl-1H-pyrazole-4-carboxylate] | E30 MS(ESI) m/z: 458([M + H]+) |
| 635 | [structure: ethyl 1,5-dimethyl-1H-pyrazole-4-carboxylate] | E30 MS(ESI) m/z: 458([M + H]+) |
| 636 | [structure: benzyl] | E30 MS(ESI) m/z: 382([M + H]+) |
| 637 | [structure: 2-fluoro-6-methylphenyl] | E30 MS(ESI) m/z: 400([M + H]+) |
| 638 | [structure: 2-chloro-6-methylphenyl] | E30 MS(ESI) m/z: 416([M + H]+) |
| 639 | [structure: 2,6-dimethylphenyl] | E30 MS(ESI) m/z: 396([M + H]+) |
| 640 | [structure: 2-ethyl-6-methylphenyl] | E30 MS(ESI) m/z: 410([M + H]+) |
| 641 | [structure: 2-trifluoromethyl-6-methylphenyl] | E30 MS(ESI) m/z: 450([M + H]+) |
| 642 | [structure: 2-methoxy-6-methylphenyl] | E30 MS(ESI) m/z: 412([M + H]+) |
| 643 | [structure: 2-cyano-6-methylphenyl] | E30 MS(ESI) m/z: 407([M + H]+) |
| 644 | [structure: 3-(2-methylphenyl)propanamide] | E30 MS(ESI) m/z: 453([M + H]+) |
| 645 | [structure: 1-(2-methylbenzyl)piperidine] | E30 MS(ESI) m/z: 479([M + H]+) |

TABLE 100-continued
| | | |
|---|---|---|
| 646 | 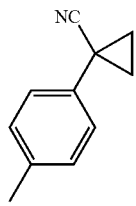 | E28<br>MS(ESI) m/z:<br>447([M + H]+) |
| 647 | 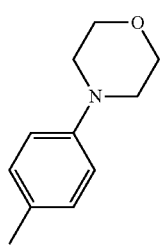 | E30<br>MS(ESI) m/z:<br>467([M + H]+) |
| 648 | 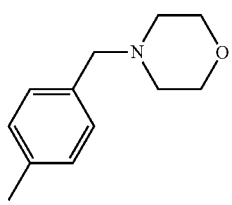 | E30<br>MS(ESI) m/z:<br>481([M + H]+) |
| 649 | 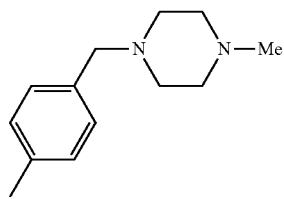 | E30 (2HCl)<br>MS(ESI) m/z:<br>494([M + H]+) |
| 650 | 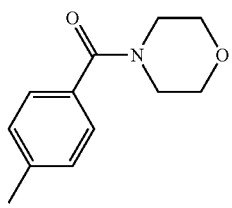 | E30<br>MS(ESI) m/z:<br>495([M + H]+) |
| 651 | 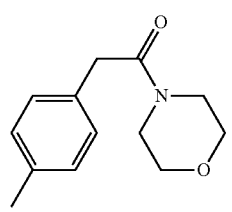 | E30<br>MS(ESI) m/z:<br>509([M + H]+) |
TABLE 101
| | | |
|---|---|---|
| 652 | 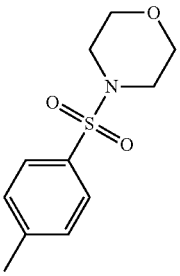 | E30<br>MS(ESI) m/z:<br>531([M + H]+) |
| 3 | 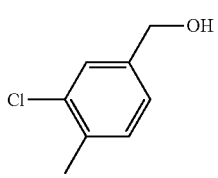 | E3<br>MS(ESI) m/z:<br>446([M + H]+) |
| 653 | 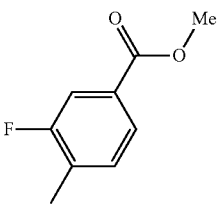 | E6<br>MS(ESI) m/z:<br>458([M + H]+) |
| 654 | 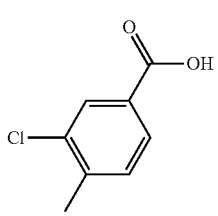 | E33<br>MS(ESI) m/z:<br>460([M + H]+) |
| 655 | 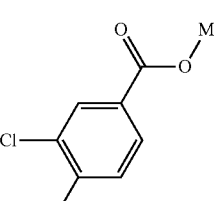 | E30<br>MS(ESI) m/z:<br>474([M + H]+) |
| 656 | 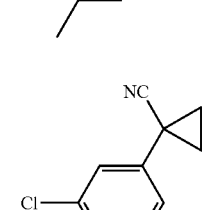 | E30<br>MS(ESI) m/z:<br>481([M + H]+) |
| 657 | 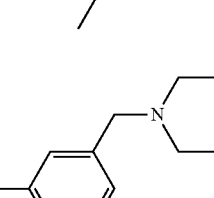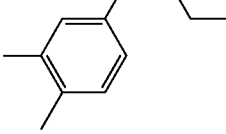 | E22→E13<br>MS(ESI) m/z:<br>515([M + H]+) |

TABLE 101-continued

| | | |
|---|---|---|
| 658 | (3-chloro-4-methylphenyl)(morpholino)methanone structure | E26 MS(ESI) m/z: 429([M + H]+) |
| 7 | 2-(3-(morpholinomethyl)-4-methylphenyl)propan-2-ol structure | E7 (HCl) MS(ESI) m/z: 539([M + H]+) |
| 659 | 2,3-dimethylpyridine structure | E6 MS(ESI) m/z: 397([M + H]+) |
| 660 | 3-methyl-2(1H)-pyridinone structure | E6 MS(ESI) m/z: 399([M + H]+) |
| 661 | methyl 6-methylnicotinate structure | E6 MS(ESI) m/z: 441([M + H]+) |
| 662 | 4-((5-methylpyridin-2-yl)methyl)morpholine structure | E30 MS(ESI) m/z: 482([M + H]+) |
| 663 | ethyl 2-methylbenzoate structure | E6 MS(ESI) m/z: 452([M − H]−) |
| 664 | methyl 2-methyl-5-(1-methylpiperidin-2-yl)benzoate structure | E6 MS(ESI) m/z: 537([M + H]+) |
| 665 | methyl 2,4-dimethylbenzoate structure | E6 MS(ESI) m/z: 454([M + H]+) |

TABLE 101-continued

| | | |
|---|---|---|
| 666 | methyl 4-(methoxymethyl)-2-methylbenzoate structure | E6 MS(ESI) m/z: 485([M + 2H]+) |

TABLE 102

| | | |
|---|---|---|
| 667 | methyl 4-cyano-2-methylbenzoate structure | E6 MS(ESI) m/z: 465([M + H]+) |
| 668 | ethyl 5-methylnicotinate structure | E11 MS(FAB) m/z: 455([M + H]+) |
| 669 | methyl 5-methylpyridazine-4-carboxylate structure | E6 MS(ESI) m/z: 442([M + H]+) |
| 670 | 5-((4-methoxypiperidin-1-yl)methyl)-2-methylbenzoic acid structure | E33 MS(ESI) m/z: 553([M + H]+) |
| 671 | 5-((3,3-dimethylmorpholino)methyl)-2-methylbenzoic acid structure | E33 MS(ESI) m/z: 553([M + H]+) |
| 672 | 2-methyl-5-(2-morpholinoethyl)benzoic acid structure | E33 MS(ESI) m/z: 539([M + H]+) |
| 673 | 4-methylnicotinic acid structure | E11→E33 MS(FAB) m/z: 425([M − H]−) |

TABLE 102-continued
| | | |
|---|---|---|
| 674 | 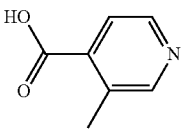 | E33 MS(ESI) m/z: 427([M + H]+) |
| 675 | 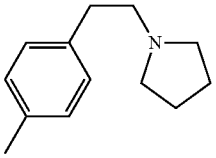 | E33 MS(ESI) m/z: 441([M + H]+) |
| 676 | 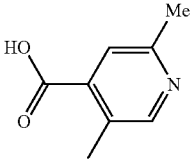 | E33 MS(ESI) m/z: 428([M + H]+) |
| 677 | 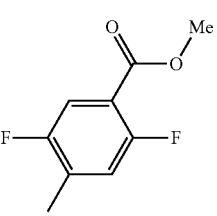 | E6 MS(ESI) m/z: 476([M + H]+) |
| 678 | 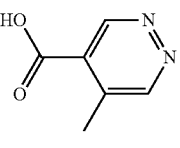 | E33 MS(ESI) m/z: 427([M + H]+) |
| 679 | 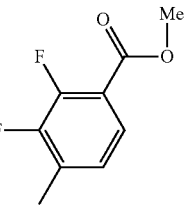 | E30 MS(ESI) m/z: 495([M + H]+) |
| 680 | 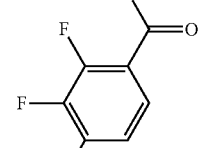 | E33 MS(ESI) m/z: 444([M + H]+) |
| 681 | 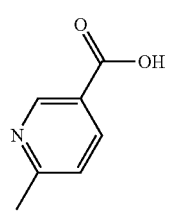 | E9 MS(ESI) m/z: 596([M + H]+) |
| 682 | 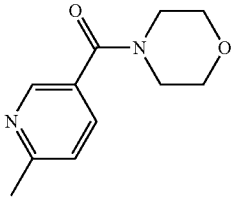 | E30 MS(ESI) m/z: 479([M + H]+) |
| 39 | 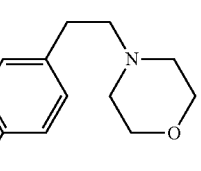 | E39 MS(ESI) m/z: 476([M + H]+) |
TABLE 103
| | | |
|---|---|---|
| 683 | 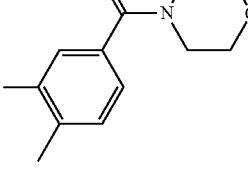 | E33 MS(ESI) m/z: 462([M + H]+) |
| 684 | 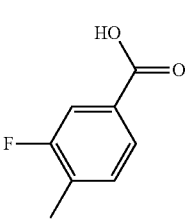 | E30 MS(ESI) m/z: 496([M + H]+) |
| 685 | 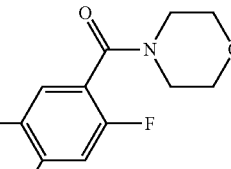 | E30 MS(ESI) m/z: 513([M + H]+) |
| 686 | 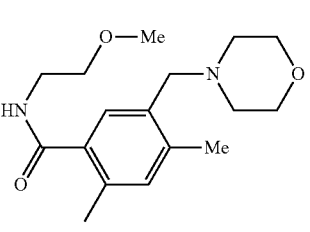 | E30 MS(ESI) m/z: 531([M + H]+) |
| 687 | 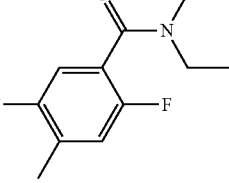 | E9 MS(ESI) m/z: 541([M + H]+) |

TABLE 103-continued
| | | |
|---|---|---|
| 688 | 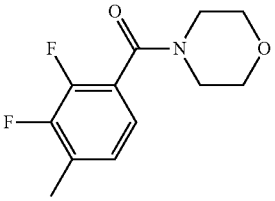 | E30 MS(ESI) m/z: 531([M + H]+) |
| 689 | 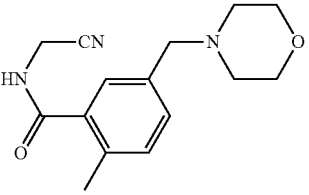 | E30 MS(ESI) m/z: 563([M + H]+) |
| 690 | 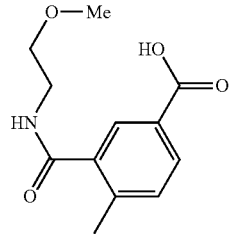 | E33 MS(ESI) m/z: 527([M + H]+) |
| 691 | 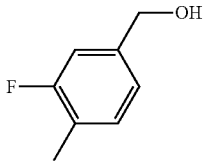 | E3 MS(ESI) m/z: 430([M + H]+) |
| 692 | 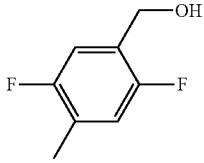 | E3 MS(ESI) m/z: 448([M + H]+) |
| 693 | 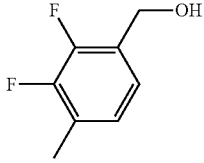 | E3 MS(ESI) m/z: 448([M + H]+) |
| 694 | 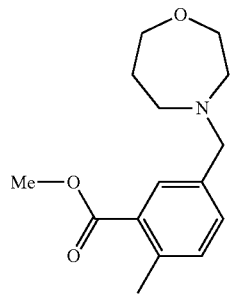 | E23 MS(ESI) m/z: 553([M + H]+) |
TABLE 103-continued
| | | |
|---|---|---|
| 695 | 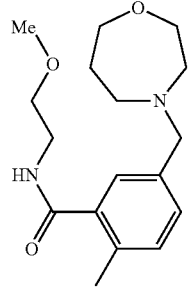 | E30 (Fum) MS(ESI) m/z: 596([M + H]+) |
| 696 | 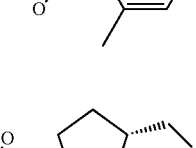 | E3 MS(ESI) m/z: 513([M + H]+) |
| 697 | 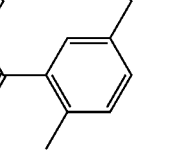 | E30 (Fum) MS(ESI) m/z: 610([M + H]+) |
TABLE 104
| | | |
|---|---|---|
| 698 | 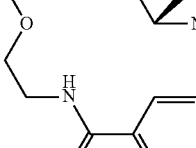 | E30 MS(ESI) m/z: 594([M + H]+) |
| 699 | 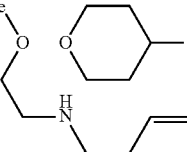 | E30 (Fum) MS(ESI) m/z: 610([M + H]+) |

TABLE 104-continued
| | | |
|---|---|---|
| 700 | 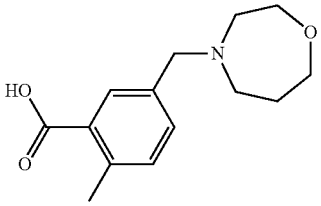 | E33 MS(ESI) m/z: 539([M + H]+) |
| 701 | 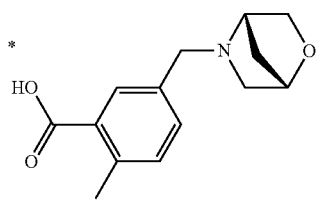 | E33 MS(ESI) m/z: 537([M + H]+) |
| 702 | 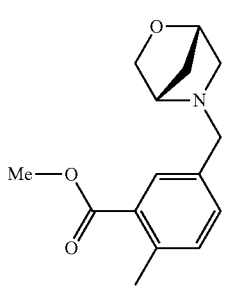 | E23 MS(ESI) m/z: 551([M + H]+) |
| 703 | 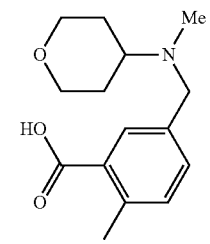 | E33 MS(ESI) m/z: 553([M + H]+) |
| 704 | 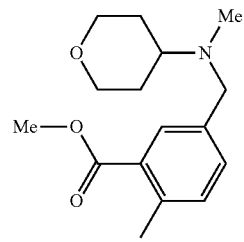 | E23 MS(ESI) m/z: 567([M + H]+) |
| 705 | 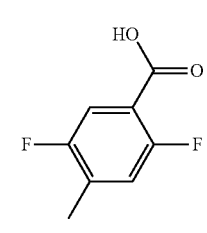 | E6 MS(ESI) m/z: 460([M − H]−) |
TABLE 105
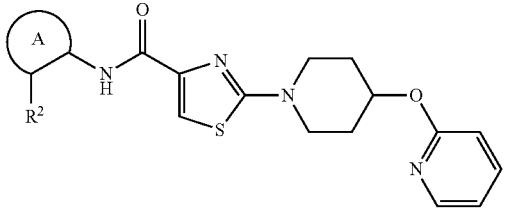
| Ex | $R^2$—A | Syn (Sal) Dat |
|---|---|---|
| 706 | 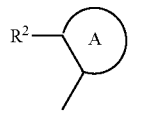 | E33 MS(ESI) m/z: 423([M − H]−) |
| 707 | 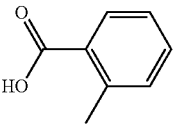 | E6 MS(ESI) m/z: 424([M + H]+) |
| 708 | 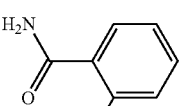 | E6 MS(ESI) m/z: 423([M + H]+) |
| 709 | 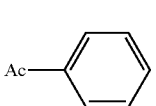 | E6 MS(ESI) m/z: 459([M + H]+) |
| 710 | 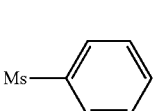 | E11 MS(FAB) m/z: 510([M + H]+) |
| 711 | 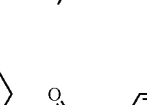 | E11 MS(FAB) m/z: 482([M + H]+) |
| 712 | 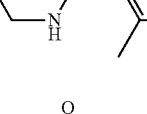 | E26 (Fum) MS(ESI) m/z: 537([M + H]+) |

TABLE 105-continued

| Ex | R²–A (structure) | Syn (Sal) Dat |
|---|---|---|
| 713 | Me₂N-CH₂-C(cyclopropyl)-CH₂-NH-C(O)-(2-methylphenyl) | E24 (Fum) MS(FAB) m/z: 535([M + H]+) |
| 714 | H₂N-CH₂-C(cyclopropyl)-CH₂-NH-C(O)-(2-methylphenyl) | E26→E35 MS(ESI) m/z: 507([M + H]+) |
| 715 | Morpholinomethyl-(2-methyl-5-)benzoic acid | E33 MS(FAB) m/z: 524([M + H]+) |
| 716 | Morpholinomethyl-(2-methyl-5-)benzoic acid methyl ester | E6 MS(FAB) m/z: 538([M + H]+) |
| 717 | 2-methoxyethyl(methyl)aminomethyl-(2-methyl-5-)-N-(tetrahydropyran-4-yl)benzamide | E9 (2HCl) MS(ESI) m/z: 609([M + H]+) |

TABLE 105-continued

| Ex | R²–A (structure) | Syn (Sal) Dat |
|---|---|---|
| 718 | Me₂N-CH₂-C(Me)(Me)-CH₂-NH-C(O)-(2-methyl-5-morpholinomethylphenyl) | E26 MS(ESI) m/z: 636([M + H]+) |

TABLE 106

| Ex | R²–A (structure) | Syn (Sal) Dat |
|---|---|---|
| 719 | N-(1-methylpiperidin-4-yl)-2-methyl-5-(morpholinomethyl)benzamide | E26 MS(ESI) m/z: 620([M + H]+) |
| 720 | N-(pyridin-3-yl)-2-methyl-5-(pyrrolidin-1-ylmethyl)benzamide | E9 (3HCl) MS(ESI) m/z: 584([M + H]+) |
| 721 | N-(pyridin-3-yl)-3-methyl-5-(morpholinomethyl)benzamide | E9 (3HCl) MS(ESI) m/z: 600([M + H]+) |

TABLE 106-continued

| | | |
|---|---|---|
| 722 | [structure: 3-methyl-N-(pyridin-3-yl)-4-{[(2-methoxyethyl)(methyl)amino]methyl}benzamide] | E9 (3HCl)<br>MS(ESI) m/z:<br>602([M + H]+) |
| 723 | [structure: ethyl 2-methylbenzoate derivative] | E6<br>MS(API) m/z:<br>453([M + H]+) |

TABLE 107

[General structure with A ring, R² substituent, amide linker to thiazole-piperidine-OH]

| Ex | | Syn (Sal)<br>Dat |
|---|---|---|
| 724 | [trans-4-hydroxycyclohexyl 2-methylbenzamide] | E30<br>MS(ESI) m/z:<br>443([M − H]−) |
| 725 | [N-(pyridin-4-ylmethyl) 2-methylbenzamide] | E28<br>MS(FAB) m/z:<br>438([M + H]+) |
| 726 | [N-(2-(pyridin-3-yl)ethyl) 2-methylbenzamide] | E28 (HCl)<br>MS(FAB) m/z:<br>452([M + H]+) |

TABLE 108

[General structure with A ring, R² substituent, amide linker to thiazole-piperidine-O-cyclopropyl]

| Ex | | Syn (Sal)<br>Dat |
|---|---|---|
| 727 | [methyl 5-(morpholinomethyl)-2-methylbenzoate] | E9<br>MS(ESI) m/z:<br>501([M + H]+) |
| 728 | [5-(morpholinomethyl)-2-methylbenzoic acid] | E33<br>MS(ESI) m/z:<br>487([M + H]+) |
| 729 | [N-ethyl-5-(morpholinomethyl)-2-methylbenzamide] | E30<br>MS(ESI) m/z:<br>514([M + H]+) |
| 730 | [N-(tetrahydropyran-4-yl)-5-(morpholinomethyl)-2-methylbenzamide] | E30<br>MS(ESI) m/z:<br>570([M + H]+) |

TABLE 109

| Ex | A-R² structure | Syn (Sal) Dat |
|---|---|---|
| 731 | methyl 2-methylbenzoate derivative | E30 MS(FAB) m/z: 362([M + H]+) |
| 732 | HO-CH2-C(Me)2-CH2-NH-C(O)-(2-methylphenyl) | E11 MS(ESI) m/z: 433([M + H]+) |
| 733 | MeO-CH2CH2-NH-C(O)-(2-methylphenyl) | E11 MS(FAB) m/z: 405([M + H]+) |
| 734 | Me2N-CH2-C(Me)2-CH2-NH-C(O)-(2-methylphenyl) | E11 (Fum) MS(ESI) m/z: 460([M + H]+) |
| 735 | 2-pyridyl-CH2-NH-C(O)-(2-methylphenyl) | E26 MS(ESI) m/z: 438([M + H]+) |
| 736 | 3-pyridyl-CH2-NH-C(O)-(2-methylphenyl) | E26 MS(ESI) m/z: 438([M + H]+) |
| 737 | 4-pyridyl-CH2-NH-C(O)-(2-methylphenyl) | E26 MS(ESI) m/z: 438([M + H]+) |
| 738 | 3-pyridyl-CH2CH2-NH-C(O)-(2-methylphenyl) | E26 MS(ESI) m/z: 452([M + H]+) |
| 739 | methyl 5-(cyanomethyl)-2-methylbenzoate | E30 MS(ESI) m/z: 401([M + H]+) |
| 740 | tetrahydropyran-4-yl-NH-C(O)-[3-(cyanomethyl)-6-methylphenyl] | E26 MS(ESI) m/z: 470([M + H]+) |
| 741 | methyl 5-(1-cyanocyclopropyl)-2-methylbenzoate | E30 MS(ESI) m/z: 427([M + H]+) |

TABLE 109-continued

General structure:

A-ring with R² substituent, connected via NH-C(=O) to thiazole (with N, S), thiazole connected to pyrrolidine bearing OMe group. * indicates attachment point.

| Ex | R²—A | Syn (Sal) Dat |
|---|---|---|
| 742 | 3-pyridyl-NH-C(=O)- phenyl with 2-Me and 5-(1-cyanocyclopropyl) * | E26 MS(ESI) m/z: 489([M + H]+) |

TABLE 110

| | | |
|---|---|---|
| 743 | tetrahydropyran-4-yl-NH-C(=O)-phenyl, 2-Me, 4-F * | E30 MS(ESI) m/z: 449([M + H]+) |
| 744 | tetrahydropyran-4-yl-NH-C(=O)-phenyl, 2-Me, 4-Cl * | E11 MS(FAB) m/z: 465([M + H]+) |
| 745 | tetrahydropyran-4-yl-NH-C(=O)-phenyl, 2-Me, 4-Me * | E30 MS(ESI) m/z: 445([M + H]+) |
| 746 | tetrahydropyran-4-yl-NH-C(=O)-phenyl, 2-Me, 4-OMe * | E11 MS(FAB) m/z: 461([M + H]+) |

TABLE 110-continued

| | | |
|---|---|---|
| 747 | 3-pyridyl-NH-C(=O)-phenyl, 2-Me, 4-F * | E11 (HCl) MS(FAB) m/z: 442([M + H]+) |
| 748 | 3-pyridyl-NH-C(=O)-phenyl, 2-Me, 4-Cl * | E11 (HCl) MS(ESI) m/z: 456([M − H]−) |
| 749 | 3-pyridyl-NH-C(=O)-phenyl, 2-Me, 4-Me * | E11 (HCl) MS(FAB) m/z: 438([M + H]+) |
| 750 | 3-pyridyl-NH-C(=O)-phenyl, 2-Me, 4-OMe * | E11 (HCl) MS(FAB) m/z: 454([M + H]+) |
| 751 | 2-methylbenzoic acid * | E33 MS(ESI) m/z: 346([M − H]−) |
| 752 | 2-Me, 5-CH₂CN benzoic acid * | E33 MS(ESI) m/z: 385([M − H]−) |
| 753 | 2-Me, 5-(1-cyanocyclopropyl) benzoic acid * | E33 MS(ESI) m/z: 413([M + H]+) |

TABLE 111
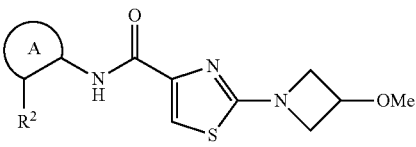
| Ex | R² / A structure | Syn (Sal) Dat |
|---|---|---|
| 27 | 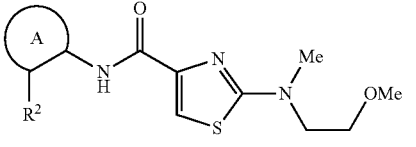 | E27 MS(ESI) m/z: 431([M + H]+) |
| 754 | 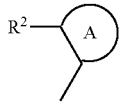 | E11 MS(FAB) m/z: 444([M + H]+) |
| 755 | 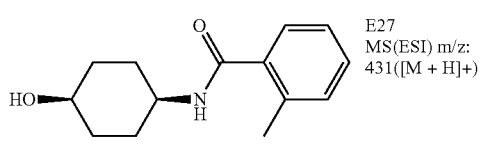 | E30 MS(ESI) m/z: 387([M + H]+) |
| 756 | 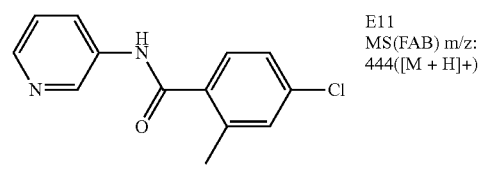 | E26 MS(ESI) m/z: 456([M + H]+) |
| 757 | 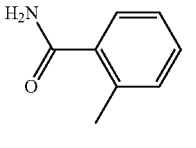 | E11 MS(FAB) m/z: 424([M + H]+) |
| 758 | 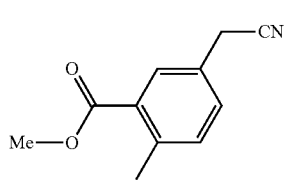 | E33 MS(ESI) m/z: 371([M − H]−) |
TABLE 112
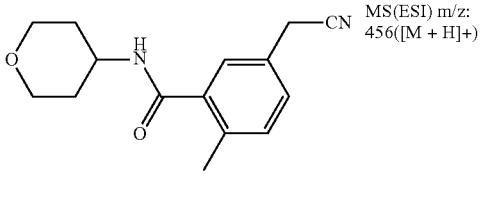
| Ex | R² / A structure | Syn (Sal) Dat |
|---|---|---|
| 759 | 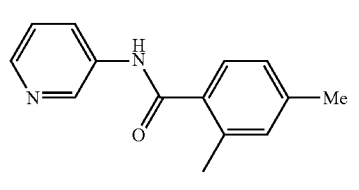 | E26 MS(FAB) m/z: 335([M + H]+) |
| 760 | 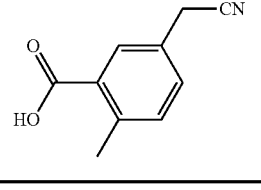 | E6 MS(FAB) m/z: 389([M + H]+) |
| 761 | 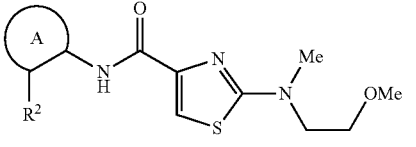 | E30 MS(FAB) m/z: 421([M + H]+) |
| 762 | 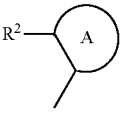 | E26 MS(ESI) m/z: 419([M + H]+) |
| 763 | 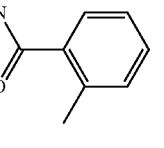 | E26 MS(ESI) m/z: 433([M + H]+) |
| 764 | 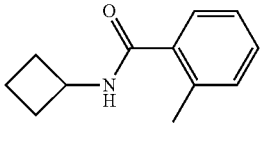 | E26 MS(FAB) m/z: 433([M + H]+) |

TABLE 112-continued

| Ex | R² / A structure | Syn (Sal) Dat |
|---|---|---|
| 765 | 4-hydroxycyclohexyl-NH-C(O)-(2-methylphenyl) | E26 MS(FAB) m/z: 433([M + H]+) |
| 766 | MeO-CH₂CH₂-NH-C(O)-(2-methylphenyl) | E6 MS(FAB) m/z: 393([M + H]+) |
| 767 | MeO-CH₂CH₂-N(Me)-C(O)-(2-methylphenyl) | E26 MS(FAB) m/z: 407([M + H]+) |
| 768 | MeO-CH₂-CH(Me)-NH-C(O)-(2-methylphenyl) * | E26 MS(ESI) m/z: 407([M + H]+) |
| 769 | MeO-CH₂-C(Me)₂-CH₂-NH-C(O)-(2-methylphenyl) | E26 MS(FAB) m/z: 435([M + H]+) |
| 770 | (tetrahydrofuran-3-yl)-NH-C(O)-(2-methylphenyl) * | E26 MS(FAB) m/z: 405([M + H]+) |
| 771 | (3-methyloxetan-3-yl)CH₂-NH-C(O)-(2-methylphenyl) | E6 MS(FAB) m/z: 419([M + H]+) |

TABLE 112-continued

| Ex | R² / A structure | Syn (Sal) Dat |
|---|---|---|
| 772 | H₂N-C(O)-CH₂-NH-C(O)-(2-methylphenyl) | E30 MS(ESI) m/z: 390([M − H]−) |

TABLE 113

| Ex | R² / A structure | Syn (Sal) Dat |
|---|---|---|
| 773 | (2-oxopyrrolidin-1-yl)-(CH₂)₃-NH-C(O)-(2-methylphenyl) | E30 (HCl) MS(FAB) m/z: 460([M + H]+) |
| 774 | (2-oxopyrrolidin-3-yl)-NH-C(O)-(2-methylphenyl) | E26 MS(FAB) m/z: 418([M + H]+) |
| 775 | (2-oxoazepan-3-yl)-NH-C(O)-(2-methylphenyl) | E26 MS(FAB) m/z: 446([M + H]+) |
| 776 | 4-carbamoylcyclohexyl-NH-C(O)-(2-methylphenyl) | E6 MS(FAB) m/z: 460([M + H]+) |

TABLE 113-continued

| | | |
|---|---|---|
| 777 | (cyclopentyl with COOH and NHC(O)-2-methylphenyl) | E33 (Na) MS(ESI) m/z: 447([M + H]+) |
| 778 | H₂N-CH₂CH₂-NH-C(O)-2-methylphenyl | E26→E35 (HCl) MS(FAB) m/z: 392([M + H]+) |
| 779 | Me₂N-(CH₂)₂-NH-C(O)-2-methylphenyl | E26 (HCl) MS(FAB) m/z: 420([M + H]+) |
| 780 | NMe₂-(CH₂)₃-NH-C(O)-2-methylphenyl | E26 (HCl) MS(FAB) m/z: 434([M + H]+) |
| 781 | Me₂C(CH₂NH₂)(CH₂-NHC(O)-2-methylphenyl) | E26→E35 (Fum) MS(ESI) m/z: 420([M + H]+) |
| 782 | cyclopropyl-1,1-bis(CH₂)(NH₂)(NHC(O)-2-methylphenyl) | E26→E35 (HCl) MS(ESI) m/z: 418([M + H]+) |
| 783 | cyclobutyl-1,1-bis(CH₂)(NH₂)(NHC(O)-2-methylphenyl) | E26→E35 (HCl) MS(FAB) m/z: 432([M + H]+) |
| 784 | Me₂N-CH₂-C(Me)₂-CH₂-NH-C(O)-2-methylphenyl | E26 (HCl) MS(FAB) m/z: 448([M + H]+) |

TABLE 113-continued

| | | |
|---|---|---|
| 785 | Me₂N-CH₂-cyclobutyl-CH₂-NH-C(O)-2-methylphenyl | E26→E35→E24 (Fum) MS(ESI) m/z: 460([M + H]+) |
| 786 | 4-aminocyclohexyl-NH-C(O)-2-methylphenyl | E26→E35 (HCl) MS(FAB) m/z: 432([M + H]+) |

TABLE 114

| | | |
|---|---|---|
| 787 | 4-aminocyclohexyl-NH-C(O)-2-methylphenyl | E26→E35 (HCl) MS(FAB) m/z: 432([M + H]+) |
| 788 | 4-(NMe₂)cyclohexyl-NH-C(O)-2-methylphenyl | E24 (HCl) MS(FAB) m/z: 460([M + H]+) |
| 789 | 3-aminocyclohexyl-NH-C(O)-2-methylphenyl | E26→E35 (HCl) MS(FAB) m/z: 432([M + H]+) |
| 790 | piperidin-4-yl-NH-C(O)-2-methylphenyl | E26→E35 (HCl) MS(FAB) m/z: 418([M + H]+) |

TABLE 114-continued
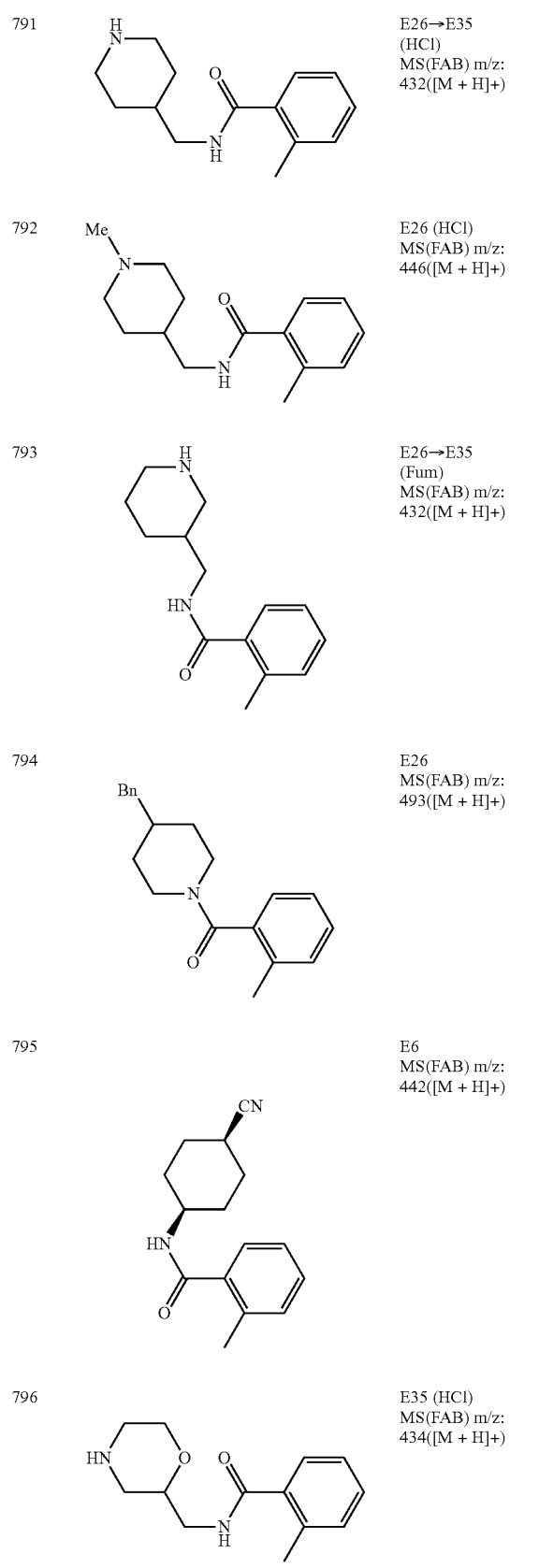
| # | Notes |
|---|---|
| 791 | E26→E35 (HCl) MS(FAB) m/z: 432([M + H]+) |
| 792 | E26 (HCl) MS(FAB) m/z: 446([M + H]+) |
| 793 | E26→E35 (Fum) MS(FAB) m/z: 432([M + H]+) |
| 794 | E26 MS(FAB) m/z: 493([M + H]+) |
| 795 | E6 MS(FAB) m/z: 442([M + H]+) |
| 796 | E35 (HCl) MS(FAB) m/z: 434([M + H]+) |
TABLE 114-continued
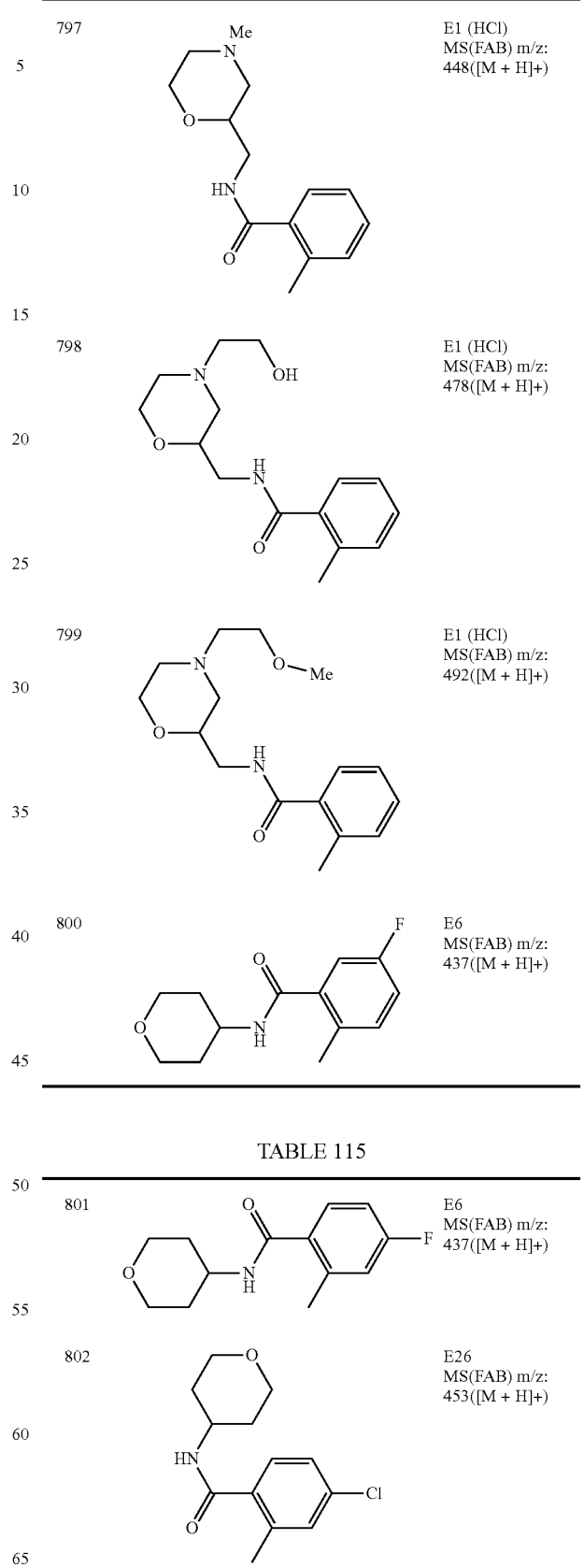
| # | Notes |
|---|---|
| 797 | E1 (HCl) MS(FAB) m/z: 448([M + H]+) |
| 798 | E1 (HCl) MS(FAB) m/z: 478([M + H]+) |
| 799 | E1 (HCl) MS(FAB) m/z: 492([M + H]+) |
| 800 | E6 MS(FAB) m/z: 437([M + H]+) |
TABLE 115
| # | Notes |
|---|---|
| 801 | E6 MS(FAB) m/z: 437([M + H]+) |
| 802 | E26 MS(FAB) m/z: 453([M + H]+) |

TABLE 115-continued

| # | Structure | Method / MS |
|---|---|---|
| 803 | tetrahydropyran-4-yl-NH-C(O)-(2-methyl-4-bromophenyl) | E26<br>MS(FAB) m/z: 497([M + H]+) |
| 804 | tetrahydropyran-4-yl-NH-C(O)-(2-methyl-4-methylphenyl) | E26<br>MS(ESI) m/z: 433([M + H]+) |
| 805 | tetrahydropyran-4-yl-NH-C(O)-(2-methyl-4-hydroxymethylphenyl) | E26<br>MS(ESI) m/z: 449([M + H]+) |
| 806 | tetrahydropyran-4-yl-NH-C(O)-(2-methyl-4-methoxymethylphenyl) | E33→E26<br>MS(FAB) m/z: 463([M + H]+) |
| 807 | tetrahydropyran-4-yl-NH-C(O)-(2-methyl-5-methoxyphenyl) | E6<br>MS(FAB) m/z: 449([M + H]+) |
| 808 | tetrahydropyran-4-yl-NH-C(O)-(2-methyl-4-methoxyphenyl) | E6<br>MS(ESI) m/z: 449([M − H]−) |
| 809 | tetrahydropyran-4-yl-NH-C(O)-(2-methyl-5-ethoxyphenyl) | E26<br>MS(FAB) m/z: 463([M + H]+) |
| 810 | tetrahydropyran-4-yl-NH-C(O)-(2-methyl-5-(n-propoxy)phenyl) | E26<br>MS(FAB) m/z: 491([M + H]+) |
| 811 | tetrahydropyran-4-yl-NH-C(O)-(2-methyl-5-(n-pentyloxy)phenyl) | E26<br>MS(ESI) m/z: 519([M + H]+) |
| 812 | tetrahydropyran-4-yl-NH-C(O)-(2-methyl-5-(3-methylbutoxy)phenyl) | E26<br>MS(ESI) m/z: 505([M + H]+) |
| 813 | tetrahydropyran-4-yl-NH-C(O)-(2-methyl-5-(3-benzyloxypropoxy)phenyl) | E26<br>MS(ESI) m/z: 583([M + H]+) |
| 37 | tetrahydropyran-4-yl-NH-C(O)-(2-methyl-5-(3-hydroxypropoxy)phenyl) | E37<br>MS(FAB) m/z: 493([M + H]+) |
| 814 | tetrahydropyran-4-yl-NH-C(O)-(2-methyl-5-(3-methoxypropoxy)phenyl) | E26<br>MS(FAB) m/z: 507([M + H]+) |

TABLE 116

| # | Structure | Notes |
|---|---|---|
| 815 | (tetrahydropyran-4-yl)NH-C(O)-[2-methyl-5-(O-CH2CH2CH2-NHBoc)phenyl] | E26 MS(FAB) m/z: 592([M + H]+) |
| 816 | (tetrahydropyran-4-yl)NH-C(O)-[2-methyl-5-(O-CH2CH2CH2-SMe)phenyl] | E26 MS(FAB) m/z: 523([M + H]+) |
| 817 | (tetrahydropyran-4-yl)NH-C(O)-[2-methyl-5-(O-tetrahydropyran-4-yl)phenyl] | E26 MS(FAB) m/z: 519([M + H]+) |
| 35 | (tetrahydropyran-4-yl)NH-C(O)-[2-methyl-5-(O-CH2CH2CH2-NH2)phenyl] | E35 (HCl) MS(FAB) m/z: 492([M + H]+) |
| 818 | (tetrahydropyran-4-yl)NH-C(O)-[2-methyl-5-(O-CH2CH2CH2-Ms)phenyl] | E12 MS(FAB) m/z: 555([M + H]+) |
| 18 | (tetrahydropyran-4-yl)NH-C(O)-[2-methyl-5-(O-CH2CH2CH2-NHAc)phenyl] | E18 MS(FAB) m/z: 534([M + H]+) |

TABLE 116-continued

| # | Structure | Notes |
|---|---|---|
| 20 | (tetrahydropyran-4-yl)NH-C(O)-[2-methyl-5-(O-CH2CH2CH2-NHMs)phenyl] | E20 MS(FAB) m/z: 570([M + H]+) |
| 819 | (tetrahydropyran-4-yl)NH-C(O)-[2-methyl-5-(morpholinomethyl)phenyl] | E26 (HCl) MS(FAB) m/z: 518([M + H]+) |
| 820 | (tetrahydropyran-4-yl)NH-C(O)-[2-methyl-5-(CH2CN)phenyl] | E26 MS(ESI) m/z: 458([M + H]+) |
| 821 | (tetrahydropyran-4-yl)NH-C(O)-[2-methyl-5-(1-cyanocyclopropyl)phenyl] | E26 MS(ESI) m/z: 484([M + H]+) |
| 822 | (tetrahydropyran-4-yl)NH-C(O)-[2-methyl-4-cyanophenyl] | E26 MS(FAB) m/z: 444([M + H]+) |
| 823 | (tetrahydropyran-4-yl)NH-C(O)-[2-methyl-4-carbamoylphenyl] | E26 MS(FAB) m/z: 462([M + H]+) |

TABLE 116-continued
| | | |
|---|---|---|
| 824 | 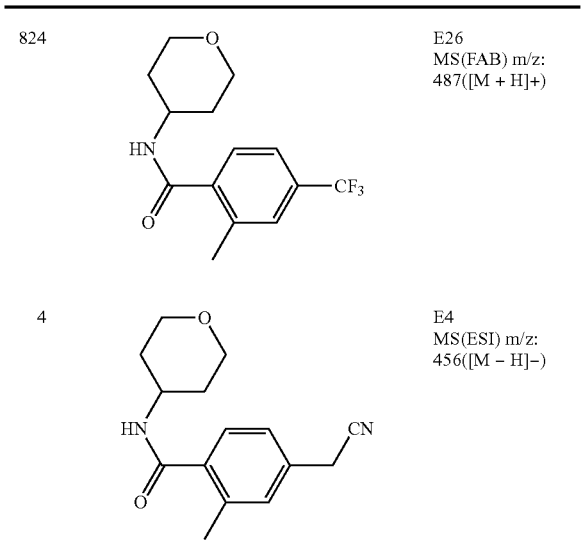 | E26<br>MS(FAB) m/z:<br>487([M + H]+) |
| 4 | | E4<br>MS(ESI) m/z:<br>456([M − H]−) |
TABLE 117
| | | |
|---|---|---|
| 825 | | E26<br>MS(FAB) m/z:<br>369([M + H]+) |
| 826 | 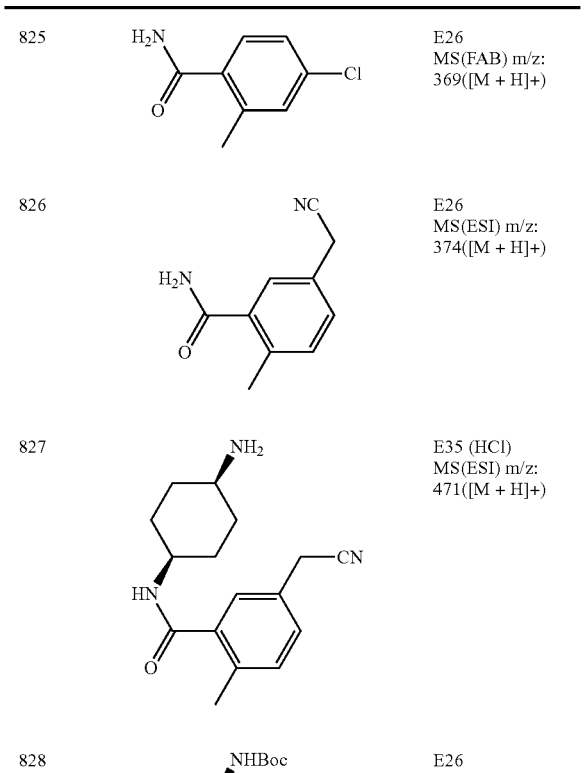 | E26<br>MS(ESI) m/z:<br>374([M + H]+) |
| 827 | | E35 (HCl)<br>MS(ESI) m/z:<br>471([M + H]+) |
| 828 | | E26<br>MS(ESI) m/z:<br>571([M + H]+) |
TABLE 117-continued
| | | |
|---|---|---|
| 829 | 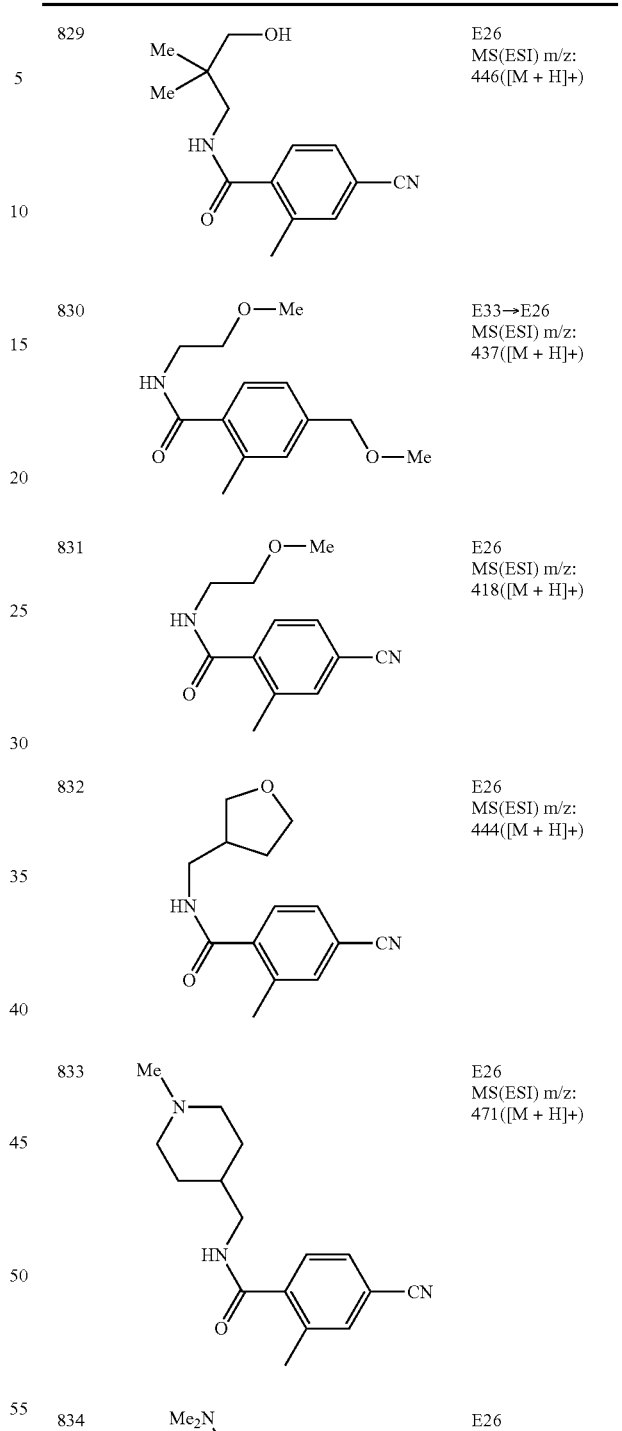 | E26<br>MS(ESI) m/z:<br>446([M + H]+) |
| 830 | | E33→E26<br>MS(ESI) m/z:<br>437([M + H]+) |
| 831 | | E26<br>MS(ESI) m/z:<br>418([M + H]+) |
| 832 | | E26<br>MS(ESI) m/z:<br>444([M + H]+) |
| 833 | | E26<br>MS(ESI) m/z:<br>471([M + H]+) |
| 834 | | E26<br>MS(ESI) m/z:<br>473([M + H]+) |

TABLE 117-continued

| # | Structure | Notes |
|---|---|---|
| 835 | N-(pyridin-3-yl)-2-fluoro-6-methylbenzamide | E6 (HCl) MS(ESI) m/z: 430([M + H]+) |
| 836 | N-(pyridin-3-yl)-5-fluoro-2-methylbenzamide | E30 (HCl) MS(FAB) m/z: 430([M + H]+) |
| 837 | N-(pyridin-3-yl)-4-fluoro-2-methylbenzamide | E30 (HCl) MS(FAB) m/z: 430([M + H]+) |
| 838 | N-(pyridin-3-yl)-3,4-difluoro-2-methylbenzamide | E6 (HCl) MS(FAB) m/z: 448([M + H]+) |

TABLE 118

| # | Structure | Notes |
|---|---|---|
| 839 | N-(pyridin-3-yl)-2-methyl-4-methylbenzamide | E11 (HCl) MS(FAB) m/z: 426([M + H]+) |
| 840 | N-(pyridin-3-yl)-4-cyano-2-methylbenzamide | E26 (HCl) MS(FAB) m/z: 437([M + H]+) |
| 841 | N-(pyridin-3-yl)-5-cyano-2-methylbenzamide | E11 (HCl) MS(FAB) m/z: 437([M + H]+) |
| 842 | N-(pyridin-3-yl)-5-methoxy-2-methylbenzamide | E30 (2 HCl) MS(ESI) m/z: 440([M − H]−) |
| 843 | N-(pyridin-3-yl)-4-methoxy-2-methylbenzamide | E30 (HCl) MS(FAB) m/z: 442([M + H]+) |
| 844 | N-(pyridin-3-yl)-3-methoxy-2-methylbenzamide | E6 (HCl) MS(ESI) m/z: 442([M + H]+) |
| 845 | N-(2-chlorophenyl)-2-methylbenzamide | E6 MS(FAB) m/z: 445([M + H]+) |
| 846 | N-(3-chlorophenyl)-2-methylbenzamide | E6 MS(FAB) m/z 445([M + H]+) |
| 847 | N-(4-chlorophenyl)-2-methylbenzamide | E6 MS(FAB) m/z: 445([M + H]+) |
| 848 | N-(2-cyanophenyl)-2-methylbenzamide | E6 MS(FAB) m/z: 436([M + H]+) |
| 849 | N-(3-cyanophenyl)-2-methylbenzamide | E6 MS(FAB) m/z: 436([M + H]+) |

TABLE 118-continued

| | | |
|---|---|---|
| 850 | (4-cyanophenyl)-2-methylbenzamide structure | E6<br>MS(FAB) m/z:<br>436([M + H]+) |
| 851 | (3-hydroxyphenyl)-2-methylbenzamide structure | E6<br>MS(ESI) m/z:<br>427([M + H]+) |
| 852 | N-(pyridin-3-yl)-3-methylpyridine-2-carboxamide structure | E33→E26<br>(2 HCl)<br>MS(FAB) m/z:<br>413([M + H]+) |
| 853 | N-(pyridin-3-yl)-3-methylthiophene-2-carboxamide structure | E26<br>MS(ESI) m/z:<br>418([M + H]+) |
| 854 | N-(pyridin-3-yl)-4-methylthiophene-3-carboxamide structure | E26 (HCl)<br>MS(ESI) m/z:<br>418([M + H]+) |
| 855 | N-(pyridin-3-yl)-2-methylthiophene-3-carboxamide structure | E26<br>MS(ESI) m/z:<br>418([M + H]+) |

TABLE 119

| | | |
|---|---|---|
| 856 | methyl 2-methylbenzoate | E23<br>MS(FAB) m/z:<br>350([M + H]+) |
| 857 | methyl 2,4-dimethylbenzoate | E30<br>MS(ESI) m/z:<br>364([M + H]+) |
| 858 | methyl 4-(hydroxymethyl)-2-methylbenzoate | E30<br>MS(FAB) m/z:<br>380([M + H]+) |
| 859 | methyl 4-(methoxymethyl)-2-methylbenzoate | E6<br>MS(FAB) m/z:<br>394([M + H]+) |
| 860 | methyl 4-cyano-2-methylbenzoate | E6<br>MS(FAB) m/z:<br>375([M + H]+) |
| 861 | methyl 4-carbamoyl-2-methylbenzoate | E6<br>MS(FAB) m/z:<br>393([M + H]+) |
| 862 | methyl 4-bromo-2-methylbenzoate | E6<br>MS(ESI) m/z:<br>428([M + H]+) |
| 863 | methyl 2-methyl-4-(trifluoromethyl)benzoate | E6<br>MS(FAB) m/z:<br>418([M + H]+) |
| 864 | methyl 5-ethoxy-2-methylbenzoate | P63→E6<br>MS(FAB) m/z:<br>394([M + H]+) |
| 865 | methyl 5-propoxy-2-methylbenzoate | P63→E6<br>MS(FAB) m/z:<br>422([M + H]+) |
| 866 | methyl 5-pentyloxy-2-methylbenzoate | P63→E6<br>MS(FAB) m/z:<br>450([M + H]+) |

TABLE 119-continued

| | | |
|---|---|---|
| 867 | (structure) | E6<br>MS(FAB) m/z:<br>436([M + H]+) |
| 868 | (structure) | E6<br>MS(FAB) m/z:<br>514([M + H]+) |
| 869 | (structure) | E6<br>MS(FAB) m/z:<br>438([M + H]+) |
| 870 | (structure) | E6<br>MS(FAB) m/z:<br>523([M + H]+) |
| 871 | (structure) | E6<br>MS(FAB) m/z:<br>454([M + H]+) |
| 872 | (structure) | E6<br>MS(FAB) m/z:<br>450([M + H]+) |

TABLE 120

| | | |
|---|---|---|
| 873 | (structure) | E30<br>MS(FAB) m/z:<br>389([M + H]+) |
| 874 | (structure) | E30<br>MS(ESI) m/z:<br>415([M + H]+) |
| 875 | (structure) | E23<br>MS(FAB) m/z:<br>356([M + H]+) |
| 876 | (structure) | E23<br>MS(FAB) m/z:<br>356([M + H]+) |
| 877 | (structure) | E23<br>MS(FAB) m/z:<br>356([M + H]+) |
| 878 | (structure) | E26<br>MS(FAB) m/z:<br>425([M + H]+) |
| 879 | (structure) | E33→E26<br>(HCl)<br>MS(FAB) m/z:<br>420([M + H]+) |
| 880 | (structure) | E11<br>MS(ESI) m/z:<br>334([M + H]+) |
| 8 | (structure) | E8 (HCl)<br>MS(FAB) m/z:<br>419([M + H]+) |
| 10 | (structure) | E10<br>MS(FAB) m/z:<br>411([M + H]+) |

TABLE 120-continued

| 881 | [2-methylphenyl with Ms] | E11 MS(ESI) m/z: 370([M + H]+) |
| 882 | [ethyl 2-methylbenzoate] | E6 MS(ESI) m/z: 364([M + H]+) |
| 883 | [methyl 4-chloro-2-methylbenzoate] | E6 MS(FAB) m/z: 384([M + H]+) |
| 884 | [methyl 5-(morpholinomethyl)-2-methylbenzoate] | E6 MS(ESI) m/z: 449([M + H]+) |
| 885 | [ethyl 3-methylpyridine-2-carboxylate] | E6 MS(FAB) m/z: 365([M + H]+) |
| 886 | [2-methylbenzoic acid] | E33 MS(ESI) m/z: 334([M − H]−) |
| 887 | [4-chloro-2-methylbenzoic acid] | E33 MS(FAB) m/z: 370([M + H]+) |
| 888 | [4-bromo-2-methylbenzoic acid] | E33 MS(FAB) m/z: 414([M + H]+) |
| 889 | [2,4-dimethylbenzoic acid] | E33 MS(ESI) m/z: 348([M − H]−) |
| 890 | [4-(hydroxymethyl)-2-methylbenzoic acid] | E33 MS(ESI) m/z: 364([M − H]−) |

TABLE 120-continued

| 891 | [4-carbamoyl-2-methylbenzoic acid] | E33 MS(FAB) m/z: 379([M + H]+) |

TABLE 121

| 892 | [5-ethoxy-2-methylbenzoic acid] | E33 MS(FAB) m/z: 380([M + H]+) |
| 893 | [5-propoxy-2-methylbenzoic acid] | E33 MS(FAB) m/z: 408([M + H]+) |
| 894 | [5-pentyloxy-2-methylbenzoic acid] | E33 MS(ESI) m/z: 436([M + H]+) |
| 895 | [5-(3-methylbutoxy)-2-methylbenzoic acid] | E33 MS(ESI) m/z: 422([M + H]+) |
| 896 | [5-(2-benzyloxyethoxy)-2-methylbenzoic acid] | E33 MS(FAB) m/z: 500([M + H]+) |
| 897 | [5-(tetrahydropyran-4-yloxy)-2-methylbenzoic acid] | E33 MS(FAB) m/z: 436([M + H]+) |

TABLE 121-continued

| | | |
|---|---|---|
| 898 | [tetrahydropyran-4-yl-amino benzoic acid, methyl] | E33 MS(ESI) m/z: 433([M − H]−) |
| 899 | [BocNH-propyl-O- benzoic acid, methyl] | E33 MS(FAB) m/z: 509([M + H]+) |
| 900 | [MeS-propyl-O- benzoic acid, methyl] | E33 MS(FAB) m/z: 440([M + H]+) |
| 901 | [1-cyanocyclopropyl- benzoic acid, methyl] | E33 MS(ESI) m/z: 401([M + H]+) |
| 902 | [3-methylthiophene-2-carboxylic acid] | E33 MS(ESI) m/z: 342([M + H]+) |
| 903 | [4-methylthiophene-3-carboxylic acid] | E33 MS(ESI) m/z: 342([M + H]+) |
| 904 | [2-methylthiophene-3-carboxylic acid] | E33 MS(ESI) m/z: 342([M + H]+) |

TABLE 121-continued

| | | |
|---|---|---|
| 905 | [4-cyano-2-methylbenzoic acid] | E33 MS(FAB) m/z: 361([M + H]+) |
| 906 | [MeO-propyl-O- benzoic acid, methyl] | E33 MS(FAB) m/z: 424([M + H]+) |
| 907 | [4-CF3-2-methylbenzoic acid] | E33 MS(FAB) m/z: 404([M + H]+) |

TABLE 122

| | | |
|---|---|---|
| 908 | [cyanomethyl-benzoic acid, methyl] | E33 MS(ESI) m/z: 375([M + H]+) |
| 909 | [1-(methoxycarbonyl)cyclopentyl-NH-C(O)-benzoic acid, methyl] | E26 MS(ESI) m/z: 461([M + H]+) |
| 910 | [Boc-morpholinyl-CH2-NH-C(O)-benzoic acid, methyl] | E26 MS(ESI) m/z: 534([M + H]+) |

TABLE 123

| Ex | R²-A | Syn (Sal) Dat |
|---|---|---|
| 911 | HO-C(Me)(Me)-CH2-NH- (2-methylphenyl) * | E11 MS(ESI) m/z: 435([M + H]+) |
| 912 | Me2N-CH2-C(Me)(Me)-CH2-NH- (2-methylphenyl) * | E11 (Fum) MS(ESI) m/z: 462([M + H]+) |

TABLE 124

| Ex | R²-A | Syn (Sal) Dat |
|---|---|---|
| 913 | Me-O-C(O)- (2-methylphenyl) | E26 MS(ESI) m/z: 390([M + H]+) |
| 32 | Ac- (2-methylphenyl) | E32 MS(ESI) m/z: 374([M + H]+) |
| 914 | H2N-C(O)- (2-methylphenyl) | E31 MS(ESI) m/z: 375([M + H]+) |
| 915 | HOCH2-C(Me)(Me)-CH2-NH-C(O)- (2-methylphenyl) | E26 MS(ESI) m/z: 461([M + H]+) |
| 916 | MeO-CH2CH2-NH-C(O)- (2-methylphenyl) | E26 MS(ESI) m/z: 433([M + H]+) |
| 917 | (tetrahydrofuran-3-yl)methyl-NH-C(O)- (2-methylphenyl) | E26 MS(ESI) m/z: 459([M + H]+) |
| 918 | Me2N-CH2-C(Me)(Me)-CH2-NH-C(O)- (2-methylphenyl) | E26 (Fum) MS(ESI) m/z: 488([M + H]+) |
| 919 | (1-methylpiperidin-4-yl)methyl-NH-C(O)- (2-methylphenyl) | E26 (Fum) MS(ESI) m/z: 486([M + H]+) |

TABLE 124-continued
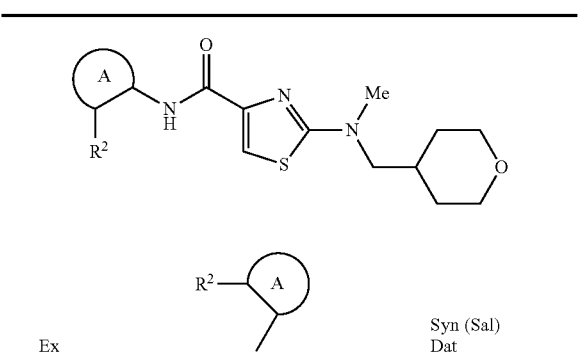
| Ex | | Syn (Sal) Dat |
|---|---|---|
| 920 | | E26→E35 (Fum) MS(ESI) m/z: 474([M + H]+) |
| 921 | | E30 MS(ESI) m/z: 466([M + H]+) |
| 922 | | E33 MS(ESI) m/z: 510([M + H]+) |
| 923 | | E31 MS(ESI) m/z: 524([M + H]+) |
TABLE 125
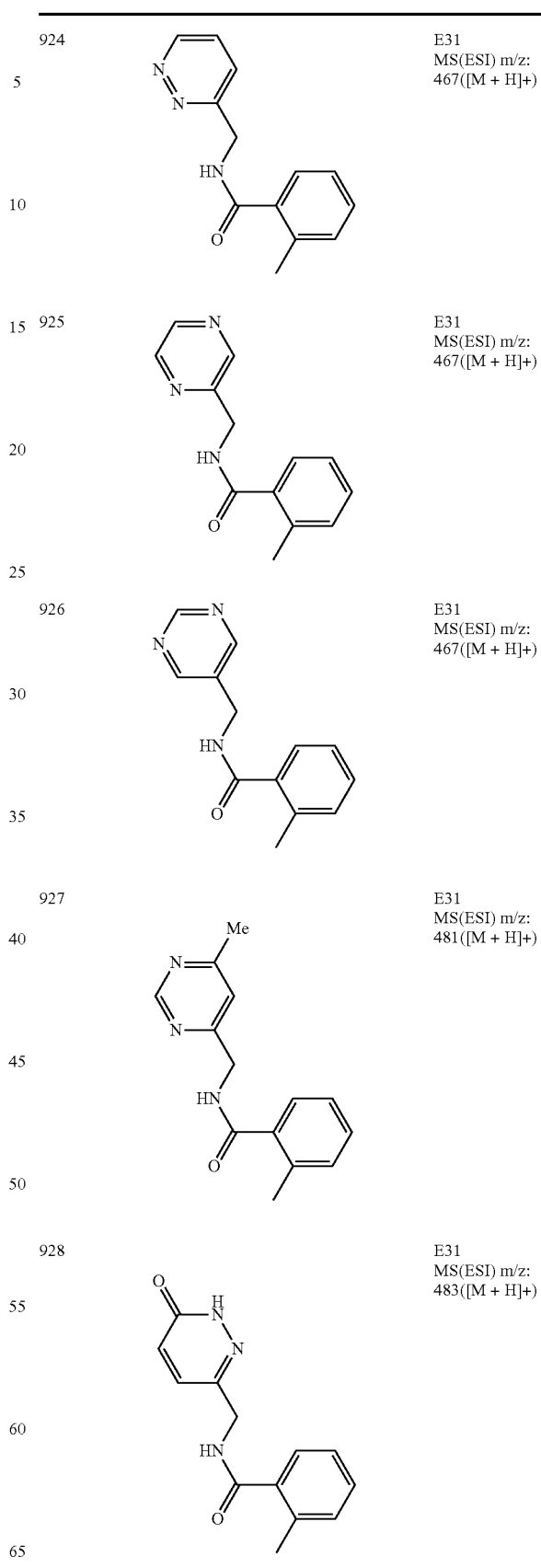
| 924 | | E31 MS(ESI) m/z: 467([M + H]+) |
|---|---|---|
| 925 | | E31 MS(ESI) m/z: 467([M + H]+) |
| 926 | | E31 MS(ESI) m/z: 467([M + H]+) |
| 927 | | E31 MS(ESI) m/z: 481([M + H]+) |
| 928 | | E31 MS(ESI) m/z: 483([M + H]+) |

TABLE 125-continued

| Ex | R² / A structure | Syn (Sal) Dat |
|---|---|---|
| 929 | methyl 5-(morpholinomethyl)-2-methylbenzoate | E30 MS(ESI) m/z: 489([M + H]+) |
| 930 | N-(tetrahydro-2H-pyran-4-yl)-5-(morpholinomethyl)-2-methylbenzamide | E26 MS(ESI) m/z: 558([M + H]+) |
| 31 | N-(pyridin-3-ylmethyl)-5-(morpholinomethyl)-2-methylbenzamide | E31 MS(ESI) m/z: 565([M + H]+) |
| 931 | ethyl 2-methylbenzoate | E6 MS(ESI) m/z: 404([M + H]+) |
| 932 | 2-methylbenzoic acid | E33 MS(ESI) m/z: 374([M − H]−) |
| 933 | 5-(morpholinomethyl)-2-methylbenzoic acid | E33 (HCl) MS(ESI) m/z: 475([M + H]+) |

TABLE 126 general structure: A–NH–C(O)–[thiazole with N(Me)CH₂CH₂SO₂Me at 2-position], with R² on ring A

| Ex | R² / A structure | Syn (Sal) Dat |
|---|---|---|
| 934 | 2-methyl-N-(3-hydroxy-2,2-dimethylpropyl)benzamide | E26 MS(ESI) m/z: 467([M − H]−) |
| 935 | 2-methyl-N-(2-methoxyethyl)benzamide | E26 MS(ESI) m/z: 439([M − H]−) |
| 936 | 2-methyl-N-((tetrahydrofuran-3-yl)methyl)benzamide | E26 MS(ESI) m/z: 467([M + H]+) |
| 937 | 2-methyl-N-(3-(dimethylamino)-2,2-dimethylpropyl)benzamide | E26 MS(ESI) m/z: 496([M + H]+) |
| 938 | 2-methyl-N-(pyridin-3-ylmethyl)benzamide | E11 MS(ESI) m/z: 472([M − H]−) |
| 939 | ethyl 2-methylbenzoate | E11 MS(ESI) m/z: 410([M − H]−) |
| 940 | 2-methylbenzoic acid | E33 MS(ESI) m/z: 384([M + H]+) |

TABLE 127

Structure: A-ring with R² substituent, connected via NH to C(=O)-thiazole-phenyl

| Ex | R²–A group | Syn (Sal) Dat |
|---|---|---|
| 941 | 2-methyl-benzoic acid (HO-C(=O)- on 2-methylphenyl) | E33 MS(FAB) m/z: 325([M + H]+) |
| 942 | ethyl 2-methylbenzoate (Et-O-C(=O)- on 2-methylphenyl) | E6 MS(FAB) m/z: 353([M + H]+) |
| 943 | 2-methylacetophenone (Ac- on 2-methylphenyl) | E30 MS(ESI) m/z: 323([M + H]+) |
| 944 | 2-methylbenzamide (H₂N-C(=O)- on 2-methylphenyl) | E30 MS(FAB) m/z: 324([M + H]+) |
| 945 | (4-methylpiperazin-1-yl)(2-methylphenyl)methanone | E26 (HCl) MS(FAB) m/z: 407([M + H]+) |
| 946 | N-methyl-N-(pyridin-3-yl)-2-methylbenzamide | E6 (HCl) MS(FAB) m/z: 415([M + H]+) |
| 947 | N-(tetrahydropyran-4-yl)-2-methylbenzenesulfonamide | E6 MS(ESI) m/z: 444([M + H]+) |

TABLE 127-continued

| Ex | R²–A group | Syn (Sal) Dat |
|---|---|---|
| 948 | N-(pyridin-3-yl)-2-methylbenzenesulfonamide | E6 (HCl) MS(ESI) m/z: 437([M + H]+) |
| 949 | N-methyl-N-(pyridin-3-yl)-2-methylbenzenesulfonamide | E6 (HCl) MS(FAB) m/z: 451([M + H]+) |
| 19 | 1,4-dimethyl-1H-pyrazole-3-carboxylic acid | E19 MS(ESI) m/z: 327([M – H]–) |
| 950 | 1,4-dimethyl-1H-pyrazole-3-carboxamide | E30 MS(FAB) m/z: 328([M + H]+) |
| 951 | N-(tetrahydropyran-4-yl)-1,4-dimethyl-1H-pyrazole-3-carboxamide | E26 MS(FAB) m/z: 412([M + H]+) |
| 952 | N-[3-(2-oxopyrrolidin-1-yl)propyl]-1,4-dimethyl-1H-pyrazole-3-carboxamide | E26 MS(FAB) m/z: 453([M + H]+) |
| 953 | N-methyl-2-methylbenzamide | E41 MS(ESI) m/z: 338([M + H]+) |

TABLE 127-continued

[Structure: A-ring with R² substituent, NH-C(O)-thiazole-phenyl core]

[R²-A substituent shown]

| Ex | | Syn (Sal) Dat |
|---|---|---|
| 954 | Et-NH-C(O)-(2-methylphenyl) | E41 MS(ESI) m/z: 352([M + H]+) |
| 955 | Me-CH₂-NH-C(O)-(2-methylphenyl) | E41 MS(ESI) m/z: 366([M + H]+) |

TABLE 128

| 956 | n-Bu-NH-C(O)-(2-methylphenyl) | E41 MS(ESI) m/z: 380([M + H]+) |
|---|---|---|
| 957 | iPr-NH-C(O)-(2-methylphenyl) | E41 MS(ESI) m/z: 366([M + H]+) |
| 958 | isobutyl-NH-C(O)-(2-methylphenyl) | E41 MS(ESI) m/z: 380([M + H]+) |
| 959 | neopentyl-NH-C(O)-(2-methylphenyl) | E41 MS(ESI) m/z: 394([M + H]+) |

TABLE 128-continued

| 960 | (3-methylbutyl)-NH-C(O)-(2-methylphenyl) | E41 MS(ESI) m/z: 394([M + H]+) |
|---|---|---|
| 961 | (3,3-dimethylbutyl)-NH-C(O)-(2-methylphenyl) | E41 MS(ESI) m/z: 408([M + H]+) |
| 962 | cyclopropyl-NH-C(O)-(2-methylphenyl) | E41 MS(ESI) m/z: 364([M + H]+) |
| 41 | (2-NMe₂-ethyl)-NH-C(O)-(2-methylphenyl) | E41 MS(ESI) m/z: 395([M + H]+) |
| 963 | cyclopentyl-NH-C(O)-(2-methylphenyl) | E41 MS(ESI) m/z: 392([M + H]+) |
| 964 | cyclohexyl-NH-C(O)-(2-methylphenyl) | E41 MS(ESI) m/z: 406([M + H]+) |
| 965 | cyclopentenyl-NH-C(O)-(2-methylphenyl) | E41 MS(ESI) m/z: 390([M + H]+) |
| 966 | cyclopropylmethyl-NH-C(O)-(2-methylphenyl) | E41 MS(ESI) m/z: 378([M + H]+) |

TABLE 128-continued

| | | |
|---|---|---|
| 967 | cyclohexylmethyl-NH-C(O)-(2-methylphenyl) | E41 MS(ESI) m/z: 420([M + H]+) |
| 968 | (R)-1-cyclohexylethyl-NH-C(O)-(2-methylphenyl) * | E41 MS(ESI) m/z: 434([M + H]+) |
| 969 | (S)-1-cyclohexylethyl-NH-C(O)-(2-methylphenyl) * | E41 MS(ESI) m/z: 434([M + H]+) |
| 970 | norbornyl-NH-C(O)-(2-methylphenyl) | E41 MS(ESI) m/z: 418([M + H]+) |

TABLE 129

| | | |
|---|---|---|
| 971 | adamantyl-NH-C(O)-(2-methylphenyl) | E41 MS(ESI) m/z: 458([M + H]+) |
| 972 | Bn-NH-C(O)-(2-methylphenyl) | E41 MS(ESI) m/z: 414([M + H]+) |
| 973 | Bn-N(Me)-C(O)-(2-methylphenyl) | E41 MS(ESI) m/z: 428([M + H]+) |

TABLE 129-continued

| | | |
|---|---|---|
| 974 | PhCH2CH2-NH-C(O)-(2-methylphenyl) | E41 MS(ESI) m/z: 428([M + H]+) |
| 975 | PhCH2CH2-N(Me)-C(O)-(2-methylphenyl) | E41 MS(ESI) m/z: 442([M + H]+) |
| 976 | azetidinyl-C(O)-(2-methylphenyl) | E41 MS(ESI) m/z: 364([M + H]+) |
| 977 | piperidinyl-C(O)-(2-methylphenyl) | E41 MS(ESI) m/z: 392([M + H]+) |
| 978 | HOCH2CH2-NH-C(O)-(2-methylphenyl) | E41 MS(ESI) m/z: 368([M + H]+) |
| 979 | HOCH2CH(Me)-NH-C(O)-(2-methylphenyl) | E41 MS(ESI) m/z: 382([M + H]+) |
| 980 | HOCH2CH(Et)-NH-C(O)-(2-methylphenyl) | E41 MS(ESI) m/z: 396([M + H]+) |

TABLE 129-continued

| # | Structure | Data |
|---|---|---|
| 981 | HO-CH2-C(Me)(Me)(Me)-NH-C(O)-(2-methylphenyl), * | E41 MS(ESI) m/z: 424([M + H]+) |
| 982 | Me-CH(OH)-CH2-NH-C(O)-(2-methylphenyl) | E41 MS(ESI) m/z: 382([M + H]+) |
| 983 | HO-CH2CH2CH2-NH-C(O)-(2-methylphenyl) | E41 MS(ESI) m/z: 382([M + H]+) |
| 984 | HO-CH2-C(Me)(Me)-CH2-NH-C(O)-(2-methylphenyl) | E41 MS(ESI) m/z: 410([M + H]+) |
| 985 | HO-CH2-CH(OH)-CH2-NH-C(O)-(2-methylphenyl), * | E41 MS(ESI) m/z: 398([M + H]+) |

TABLE 130

| # | Structure | Data |
|---|---|---|
| 986 | 2-hydroxycyclohexyl-NH-C(O)-(2-methylphenyl) | E41 MS(ESI) m/z: 422([M + H]+) |
| 987 | 4-hydroxytetrahydrothiophen-3-yl-NH-C(O)-(2-methylphenyl) | E41 MS(ESI) m/z: 426([M + H]+) |
| 988 | trans-4-hydroxycyclohexyl-NH-C(O)-(2-methylphenyl) | E41 MS(ESI) m/z: 422([M + H]+) |
| 989 | (hydroxymethyl)cyclohex-3-enyl-NH-C(O)-(2-methylphenyl) | E41 MS(ESI) m/z: 434([M + H]+) |
| 990 | (1-hydroxycyclohexyl)methyl-NH-C(O)-(2-methylphenyl) | E41 MS(ESI) m/z: 436([M + H]+) |
| 991 | (2-hydroxycyclohexyl)methyl-NH-C(O)-(2-methylphenyl) | E41 MS(ESI) m/z: 436([M + H]+) |
| 992 | (2-hydroxycyclohexyl)methyl-NH-C(O)-(2-methylphenyl) | E41 MS(ESI) m/z: 436([M + H]+) |

TABLE 130-continued
| 993 | 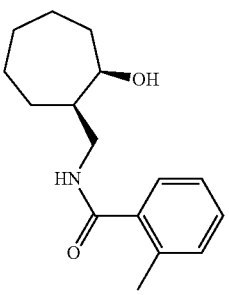 | E41 MS(ESI) m/z: 450([M + H]+) |
| --- | --- | --- |
| 994 | 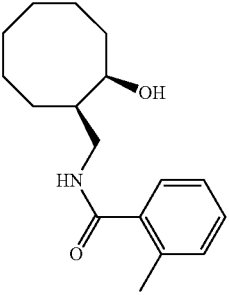 | E41 MS(ESI) m/z: 464([M + H]+) |
| 995 | 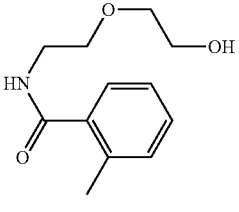 | E41 MS(ESI) m/z: 412([M + H]+) |
| 996 | 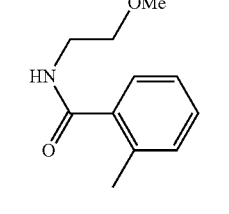 | E41 MS(ESI) m/z: 482([M + H]+) |
| 997 | 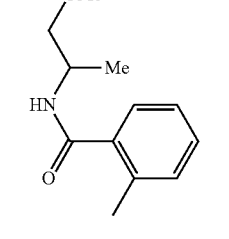 | E41 MS(ESI) m/z: 396([M + H]+) |
| 998 | 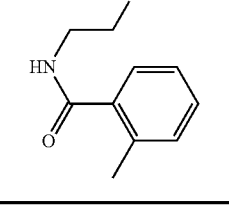 | E41 MS(ESI) m/z: 396([M + H]+) |
TABLE 131
| 999 | 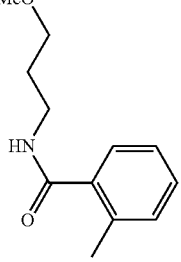 | E41 MS(ESI) m/z: 396([M + H]+) |
| --- | --- | --- |
| 1000 | 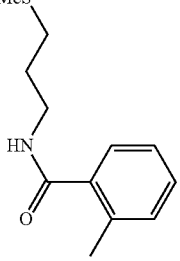 | E41 MS(ESI) m/z: 412([M + H]+) |
| 1001 | 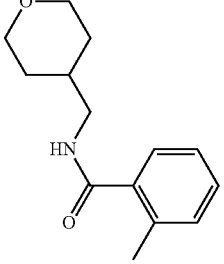 | E41 MS(ESI) m/z: 422([M + H]+) |
| 1002 | 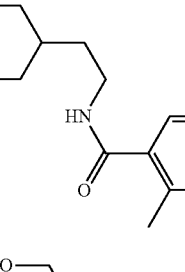 | E41 MS(ESI) m/z: 436([M + H]+) |
| 1003 | 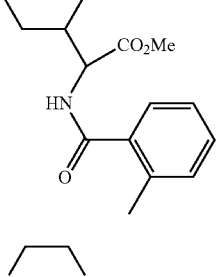 | E41 MS(ESI) m/z: 480([M + H]+) |
| 1004 | 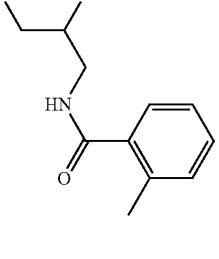 | E41 MS(ESI) m/z: 424([M + H]+) |

TABLE 131-continued
| 1005 | 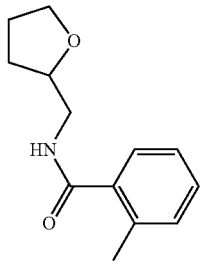 | E41 MS(ESI) m/z: 408([M + H]+) |
| 1006 | 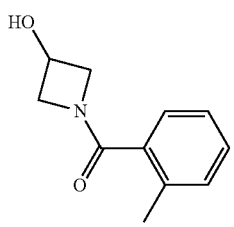 | E41 MS(ESI) m/z: 380([M + H]+) |
| 1007 | 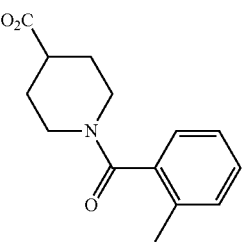 | E41 MS(ESI) m/z: 450([M + H]+) |
| 1008 | 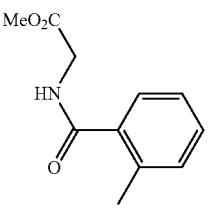 | E41 MS(ESI) m/z: 396([M + H]+) |
| 1009 | 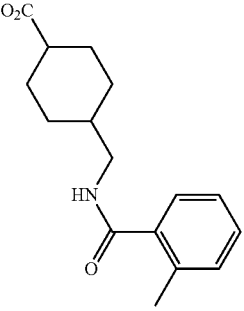 | E41 MS(ESI) m/z: 478([M + H]+) |
| 1010 | 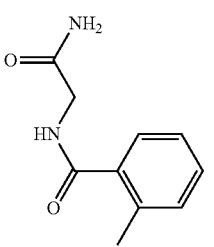 | E41 MS(ESI) m/z: 381([M + H]+) |
TABLE 131-continued
| 1011 | 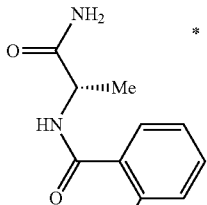 | E41 MS(ESI) m/z: 395([M + H]+) |
TABLE 132
| 1012 | 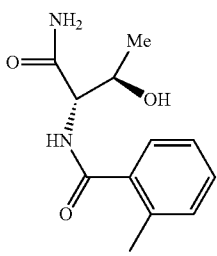 | E41 MS(ESI) m/z: 425([M + H]+) |
| 1013 | 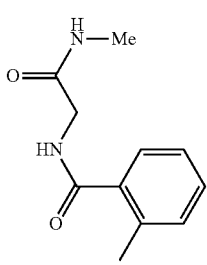 | E41 MS(ESI) m/z: 395([M + H]+) |
| 1014 | 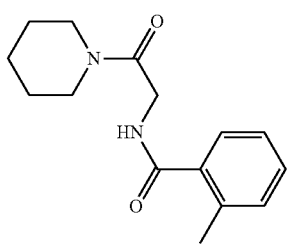 | E41 MS(ESI) m/z: 449([M + H]+) |
| 1015 | 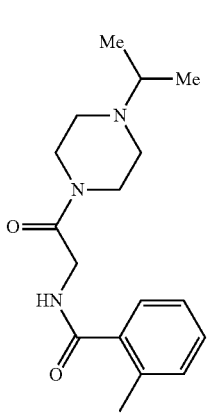 | E41 MS(ESI) m/z: 492([M + H]+) |

TABLE 132-continued
| | | | |
|---|---|---|---|
| 1016 | 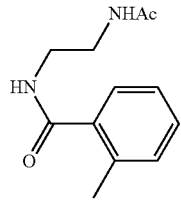 | E41 MS(ESI) m/z: 409([M + H]+) | |
| 1017 | 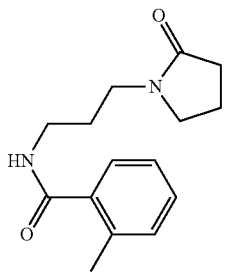 | E41 MS(ESI) m/z: 449([M + H]+) | |
| 1018 | 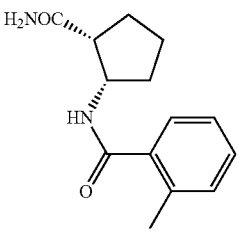 | E41 MS(ESI) m/z: 435([M + H]+) | |
| 1019 | 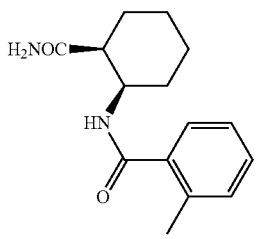 | E41 MS(ESI) m/z: 449([M + H]+) | |
| 1020 | 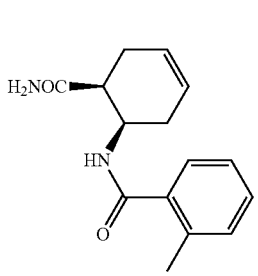 | E41 MS(ESI) m/z: 447([M + H]+) | |
| 1021 | 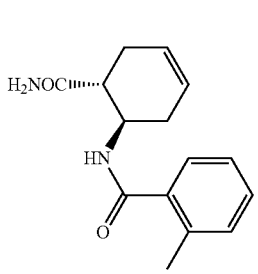 | E41 MS(ESI) m/z: 447([M + H]+) | |
TABLE 132-continued
| | | | |
|---|---|---|---|
| 1022 | 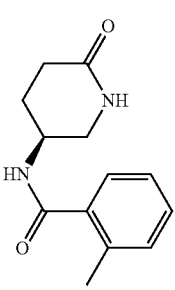 * | E41 MS(ESI) m/z: 421([M + H]+) | |
| 1023 | 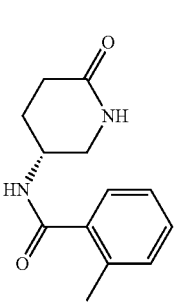 * | E41 MS(ESI) m/z: 421([M + H]+) | |
TABLE 133
| | | | |
|---|---|---|---|
| 1024 | 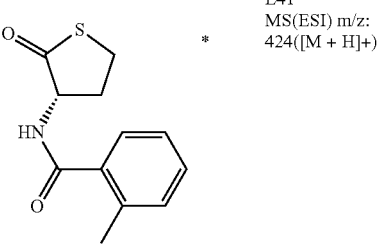 * | E41 MS(ESI) m/z: 424([M + H]+) | |
| 1025 | 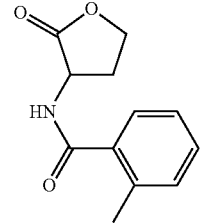 | E41 MS(ESI) m/z: 408([M + H]+) | |
| 1026 | 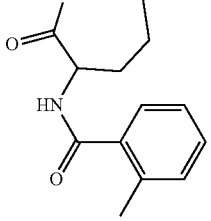 | E41 MS(ESI) m/z: 435([M + H]+) | |

TABLE 133-continued

| 1027 | [structure: 1,1-dioxo-tetrahydrothiophene with OH and NH-C(O)-(2-methylphenyl)] | E41 MS(ESI) m/z: 458([M + H]+) |
| 1028 | [structure: cyclobutyl-CH2-NH-C(O)-(2-methylphenyl)] | E41 MS(ESI) m/z: 378([M + H]+) |
| 1029 | [structure: Me2N-CH2-CH(Me)-NH-C(O)-(2-methylphenyl)] | E41 MS(ESI) m/z: 409([M + H]+) |
| 1030 | [structure: Et2N-CH2CH2-NH-C(O)-(2-methylphenyl)] | E41 MS(ESI) m/z: 423([M + H]+) |
| 1031 | [structure: (iPr)2N-CH2CH2-NH-C(O)-(2-methylphenyl)] | E41 MS(ESI) m/z: 451([M + H]+) |
| 1032 | [structure: tetrahydrothiophene with NMe2 and CH2-NH-C(O)-(2-methylphenyl)] | E41 MS(ESI) m/z: 467([M + H]+) |

TABLE 133-continued

| 1033 | [structure: Me2N-(CH2)3-NH-C(O)-(2-methylphenyl)] | E41 MS(ESI) m/z: 409([M + H]+) |
| 1034 | [structure: Me2N-CH2-C(Me)2-CH2-NH-C(O)-(2-methylphenyl)] | E41 MS(ESI) m/z: 437([M + H]+) |
| 1035 | [structure: Et2N-(CH2)3-NH-C(O)-(2-methylphenyl)] | E41 MS(ESI) m/z: 437([M + H]+) |
| 1036 | [structure: Me2N-(CH2)4-NH-C(O)-(2-methylphenyl)] | E41 MS(ESI) m/z: 423([M + H]+) |

TABLE 134

| 1037 | [structure: pyrrolidin-1-yl-CH2CH2-NH-C(O)-(2-methylphenyl)] | E41 MS(ESI) m/z: 421([M + H]+) |

TABLE 134-continued
| 1038 | 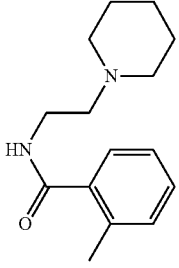 | E41 MS(ESI) m/z: 435([M + H]+) |
| 1039 | 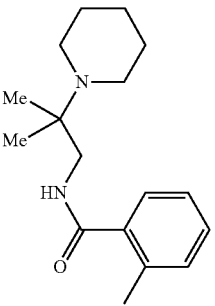 | E41 MS(ESI) m/z: 463([M + H]+) |
| 1040 | 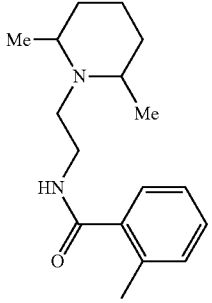 | E41 MS(ESI) m/z: 463([M + H]+) |
| 1041 | 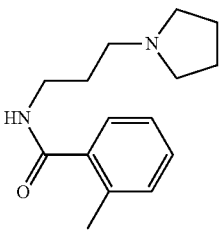 | E41 MS(ESI) m/z: 435([M + H]+) |
| 1042 | 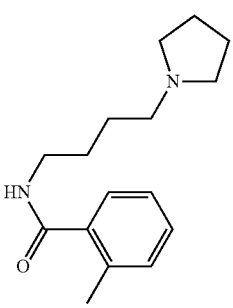 | E41 MS(ESI) m/z: 449([M + H]+) |
TABLE 134-continued
| 1043 | 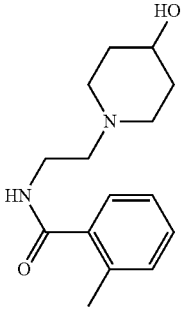 | E41 MS(ESI) m/z: 451([M + H]+) |
| 1044 | 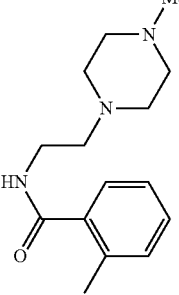 | E41 MS(ESI) m/z: 450([M + H]+) |
| 1045 | 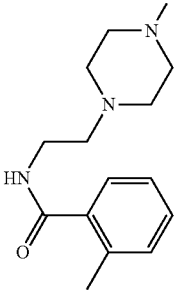 | E41 MS(ESI) m/z: 464([M + H]+) |
| 1046 | 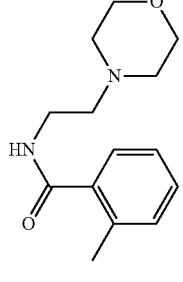 | E41 MS(ESI) m/z: 437([M + H]+) |
| 1047 | 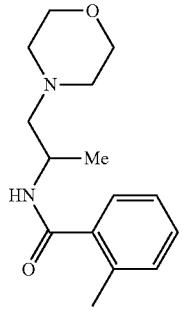 | E41 MS(ESI) m/z: 451([M + H]+) |

TABLE 135

| | | |
|---|---|---|
| 1048 | (morpholine-C(Me)₂-CH₂-NH-C(O)-(2-methylphenyl)) | E41 MS(ESI) m/z: 465([M + H]+) |
| 1049 | ((2R,6S)-2,6-dimethylmorpholine-CH₂CH₂-NH-C(O)-(2-methylphenyl)) | E41 MS(ESI) m/z: 465([M + H]+) |
| 1050 | (morpholine-(CH₂)₃-NH-C(O)-(2-methylphenyl)) | E41 MS(ESI) m/z: 451([M + H]+) |
| 1051 | (1-methylpiperidin-4-yl-NH-C(O)-(2-methylphenyl)) | E41 MS(ESI) m/z: 421([M + H]+) |
| 1052 | (1-ethylpiperidin-3-yl-NH-C(O)-(2-methylphenyl)) | E41 MS(ESI) m/z: 435([M + H]+) |
| 1053 | (1-methylpiperidin-4-yl-CH₂-NH-C(O)-(2-methylphenyl)) | E41 MS(ESI) m/z: 435([M + H]+) |
| 1054 | (1-ethylpiperidin-4-yl-CH₂-NH-C(O)-(2-methylphenyl)) | E41 MS(ESI) m/z: 449([M + H]+) |
| 1055 | (1-isopropylpiperidin-4-yl-NH-C(O)-(2-methylphenyl)) | E41 MS(ESI) m/z: 449([M + H]+) |
| 1056 | (1-(cyclohexylmethyl)piperidin-4-yl-NH-C(O)-(2-methylphenyl)) | E41 MS(ESI) m/z: 503([M + H]+) |
| 1057 | (1-methylpiperidin-2-yl-CH₂-NH-C(O)-(2-methylphenyl)) | E41 MS(ESI) m/z: 435([M + H]+) |

TABLE 135-continued

| | | |
|---|---|---|
| 1058 | [structure] | E41 MS(ESI) m/z: 435([M + H]+) |
| 1059 | [structure] | E41 MS(ESI) m/z: 464([M + H]+) |

TABLE 136

| | | |
|---|---|---|
| 1060 | [structure] | E41 MS(ESI) m/z: 435([M + H]+) |
| 1061 | [structure] | E41 MS(ESI) m/z: 447([M + H]+) |
| 1062 | [structure] | E41 MS(ESI) m/z: 433([M + H]+) |

TABLE 136-continued

| | | |
|---|---|---|
| 1063 | [structure] | E41 MS(ESI) m/z: 504([M + H]+) |
| 1064 | [structure] | E41 MS(ESI) m/z: 503([M + H]+) |
| 1065 | [structure] | E43 MS(ESI) m/z: 339([M + H]+) |
| 1066 | [structure] | E42 MS(ESI) m/z: 355([M + H]+) |
| 1067 | [structure] | E43 MS(ESI) m/z: 330([M + H]+) |
| 1068 | [structure] | E43 MS(ESI) m/z: 330([M + H]+) |
| 1069 | [structure] | E42 MS(ESI) m/z: 344([M + H]+) |
| 1070 | [structure] | E43 MS(ESI) m/z: 345([M + H]+) |

TABLE 136-continued

| | | |
|---|---|---|
| 1071 | 4-methyl-1H-pyrazole-5-carboxamide | E43 MS(ESI) m/z: 314([M + H]+) |
| 1072 | 1,4-dimethyl-1H-pyrazole-5-carboxamide | E43 MS(ESI) m/z: 328([M + H]+) |
| 1073 | 4-carbamoyl-5-methyl-2-(methylthio)-1H-pyrrole-3-carboxamide | E42 MS(ESI) m/z: 402([M + H]+) |
| 43 | 2-methylphenyl methanesulfonyl | E43 MS(ESI) m/z: 359([M + H]+) |
| 1074 | 2-methylphenyl phenylsulfonyl | E43 MS(ESI) m/z: 421([M + H]+) |

TABLE 137

| | | |
|---|---|---|
| 1075 | 4-methyl-3-(phenylsulfonyl)thiophene | E43 MS(ESI) m/z: 427([M + H]+) |

TABLE 138

General structure:

A—NH—C(=O)—(2-bromothiazol-4-yl), with R² on ring A

| Ex | R²—A | Syn (Sal) Dat |
|---|---|---|
| 1076 | 2-methylbenzoic acid | E33 MS(ESI) m/z: 325([M − H]−) |

TABLE 138-continued

| Ex | R²—A | Syn (Sal) Dat |
|---|---|---|
| 1077 | N-(pyridin-2-ylmethyl)-2-methylbenzamide | E26 MS(ESI) m/z: 417([M + H]+) |
| 1078 | N-(pyridin-4-ylmethyl)-2-methylbenzamide | E26 MS(ESI) m/z: 417([M + H]+) |
| 1079 | N-(2-(pyridin-3-yl)ethyl)-2-methylbenzamide | E26 MS(ESI) m/z: 431([M + H]+) |
| 1080 | N-(tetrahydropyran-4-yl)-5-(pyrrolidin-1-ylmethyl)-2-methylbenzamide | E9 MS(FAB) m/z: 493([M + H]+) |
| 1081 | N-(tetrahydropyran-4-yl)-2-methylbenzamide | E30 MS(ESI) m/z: 408([M − H]−) |
| 1082 | N-(pyridin-3-ylmethyl)-2-methylbenzamide | E26 MS(ESI) m/z: 417([M + H]+) |

TABLE 138-continued
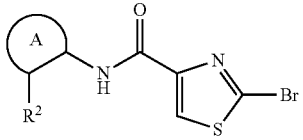
| Ex | | Syn (Sal) Dat |
|---|---|---|
| 1083 | 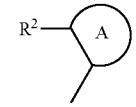 | E30 MS(ESI) m/z: 341([M + H]+) |
| 1084 | 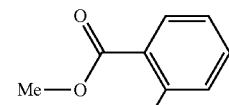 | E11 MS(FAB) m/z: 403([M + H]+) |
TABLE 139
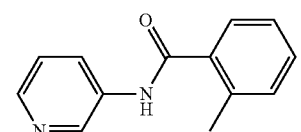
| Ex | | Syn (Sal) Dat |
|---|---|---|
| 1085 | 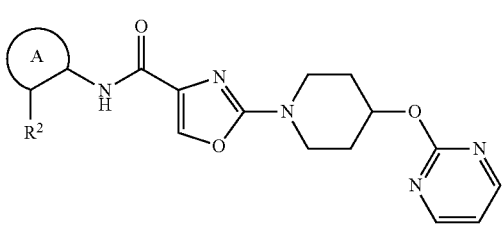 | E30 MS(ESI) m/z: 397([M + H]+) |
| 1086 | 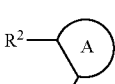 | E26 MS(ESI) m/z: 466([M + H]+) |
| 1087 | 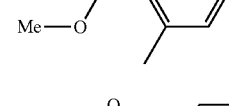 | E33 MS(ESI) m/z: 383([M + H]+) |
TABLE 140
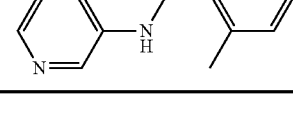
| Ex | | Syn (Sal) Dat |
|---|---|---|
| 1088 | 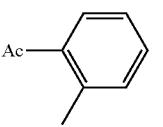 | E30 MS(ESI) m/z: 424([M + H]+) |
| 1089 | 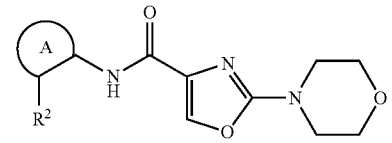 | E30 MS(ESI) m/z: 408([M + H]+) |
| 1090 | 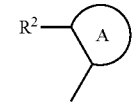 | E30 MS(ESI) m/z: 444([M + H]+) |
| 1091 | 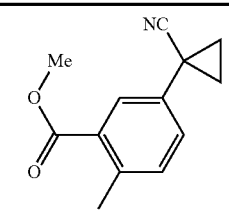 | E30 MS(ESI) m/z: 409([M + H]+) |
| 1092 | 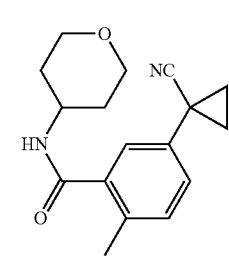 | E30 MS(ESI) m/z: 423([M + H]+) |
| 1093 | 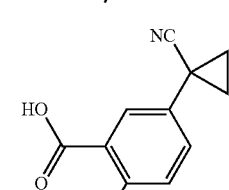 | E30 MS(ESI) m/z: 437([M + H]+) |
| 1094 |  | E30 MS(ESI) m/z: 481([M + H]+) |

TABLE 140-continued
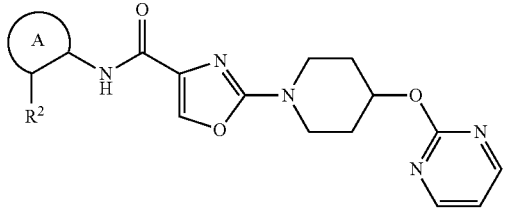
| Ex | R², A | Syn (Sal) Dat |
|---|---|---|
| 1095 | 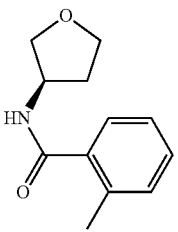 * | E30 MS(ESI) m/z: 479([M + H]+) |
| 1096 | 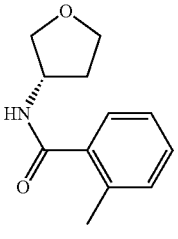 * | E30 MS(ESI) m/z: 479([M + H]+) |
| 1097 | 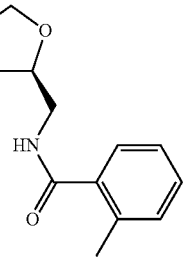 * | E30 MS(ESI) m/z: 493([M + H]+) |
| 1098 | 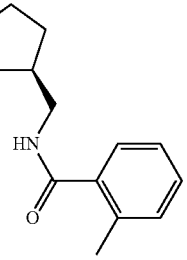 * | E30 MS(ESI) m/z: 493([M + H]+) |
| 1099 | 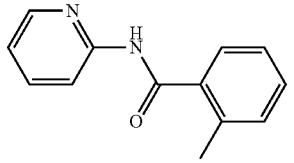 | E30 MS(ESI) m/z: 486([M + H]+) |
TABLE 140-continued
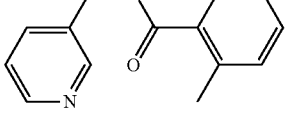
| Ex | R², A | Syn (Sal) Dat |
|---|---|---|
| 1100 | 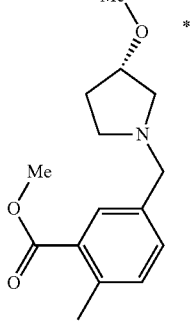 | E30 MS(ESI) m/z: 500([M + H]+) |
| 1101 | 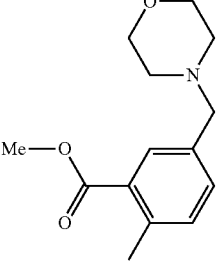 * | E6 MS(ESI) m/z: 537([M + H]+) |
TABLE 141
| 1102 | 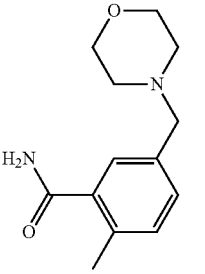 | E30 MS(ESI) m/z: 523([M + H]+) |
| 1103 | | E26 MS(ESI) m/z: 506([M − H]−) |

TABLE 141-continued
| | | |
|---|---|---|
| 1104 | 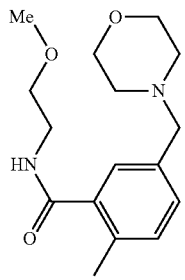 | E26<br>MS(ESI) m/z:<br>564([M − H]−) |
| 1105 | 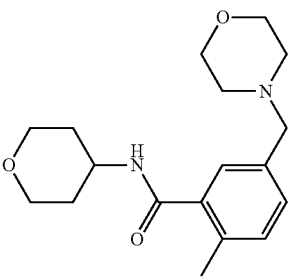 | E26<br>MS(ESI) m/z:<br>590([M − H]−) |
| 1106 | 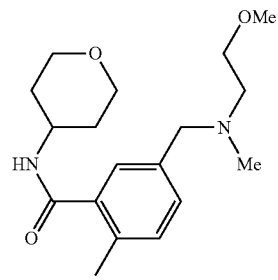 | E30<br>MS(ESI) m/z:<br>594([M + H]+) |
| 1107 | 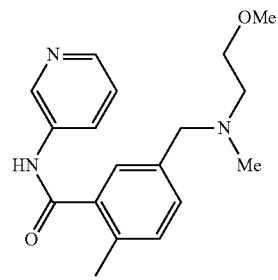 | E30<br>MS(FAB) m/z:<br>587([M + H]+) |
| 1108 | 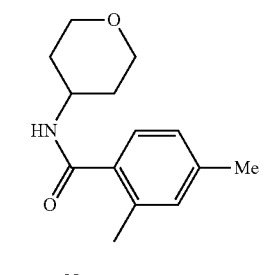 | E30<br>MS(ESI) m/z:<br>507([M + H]+) |
| 1109 | 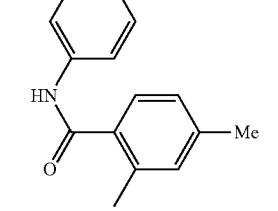 | E30<br>MS(ESI) m/z:<br>500([M + H]+) |
| 1110 | 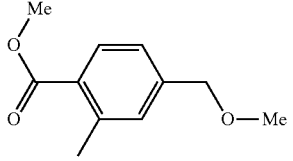 | E6<br>MS(ESI) m/z:<br>468([M + H]+) |
| 1111 | 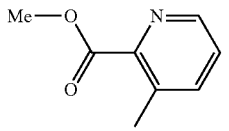 | E6<br>MS(ESI) m/z:<br>425([M + H]+) |
| 1112 | 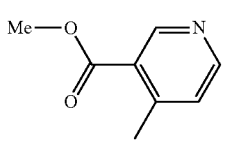 | E6<br>MS(ESI) m/z:<br>425([M + H]+) |
| 1113 | 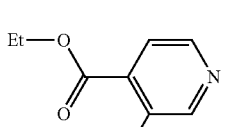 | E6<br>MS(ESI) m/z:<br>439([M + H]+) |
| 1114 | 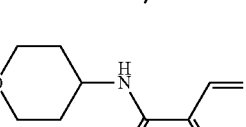 | E33→E26<br>MS(ESI) m/z:<br>494([M + H]+) |
| 1115 | 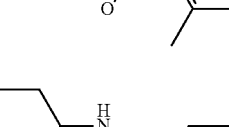 | E33→E26<br>MS(FAB) m/z:<br>494([M + H]+) |
| 1116 | 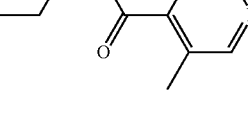 | E33→E26<br>MS(ESI) m/z:<br>523([M + H]+) |
TABLE 142
| | | |
|---|---|---|
| 1117 | 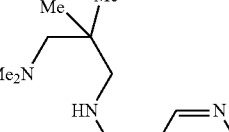 | E30<br>MS(ESI) m/z:<br>596([M + H]+) |

TABLE 142-continued
| 1118 | 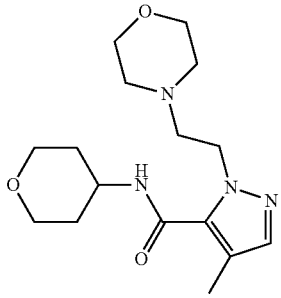 | E30 (Fum) MS(ESI) m/z: 596([M + H]+) |
| 1119 | 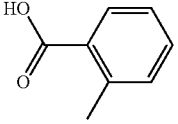 | E33 (Na) MS(ESI) m/z: 410([M + H]+) |
| 1120 | 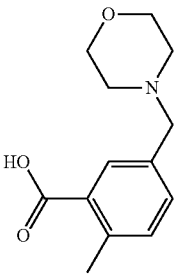 | E33 MS(ESI) m/z: 509([M + H]+) |
| 1121 | 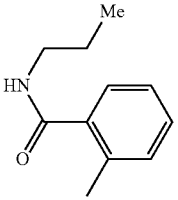 | E30 MS(ESI) m/z: 451([M + H]+) |
| 1122 | 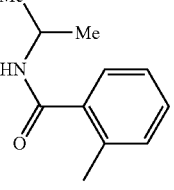 | E30 MS(ESI) m/z: 451([M + H]+) |
| 1123 | 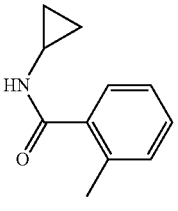 | E30 MS(ESI) m/z: 449([M + H]+) |
| 1124 | 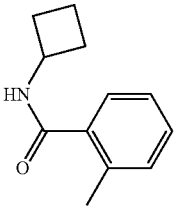 | E30 MS(ESI) m/z: 463([M + H]+) |
TABLE 142-continued
| 1125 |  | E30 MS(ESI) m/z: 455([M + H]+) |
| 1126 | 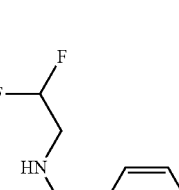 | E30 MS(ESI) m/z: 473([M + H]+) |
| 1127 | 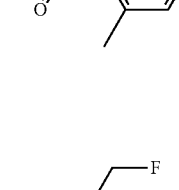 | E30 MS(ESI) m/z: 469([M + H]+) |
| 1128 | 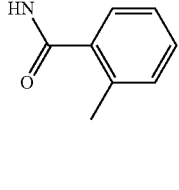 | E30 MS(ESI) m/z: 467([M + H]+) |
| 1129 | 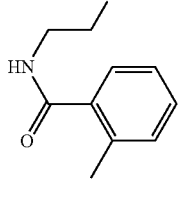 | E30 MS(ESI) m/z: 481([M + H]+) |
| 1130 | 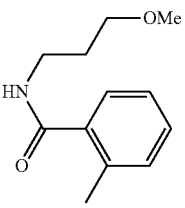 | E30 MS(ESI) m/z: 465([M + H]+) |

TABLE 143

| | | |
|---|---|---|
| 1131 | [tetrahydrofuran-3-ylmethyl-NH-C(O)-(2-methylphenyl)] | E30 MS(ESI) m/z: 493([M + H]+) |
| 1132 | [Me-CH2-CH2-NH-C(O)-(4-methylpyridin-3-yl)] | E30 MS(ESI) m/z: 452([M + H]+) |
| 1133 | [iPr-NH-C(O)-(4-methylpyridin-3-yl)] | E30 MS(ESI) m/z: 452([M + H]+) |
| 1134 | [cyclopropyl-NH-C(O)-(4-methylpyridin-3-yl)] | E30 MS(ESI) m/z: 450([M + H]+) |
| 1135 | [cyclobutyl-NH-C(O)-(4-methylpyridin-3-yl)] | E30 MS(ESI) m/z: 464([M + H]+) |
| 1136 | [F-CH2-CH2-NH-C(O)-(4-methylpyridin-3-yl)] | E30 MS(ESI) m/z: 456([M + H]+) |
| 1137 | [F2CH-CH2-NH-C(O)-(4-methylpyridin-3-yl)] | E30 MS(ESI) m/z: 474([M + H]+) |

TABLE 143-continued

| | | |
|---|---|---|
| 1138 | [F-CH2CH2CH2-NH-C(O)-(4-methylpyridin-3-yl)] | E30 MS(ESI) m/z: 470([M + H]+) |
| 1139 | [HO-CH2CH2-NH-C(O)-(4-methylpyridin-3-yl)] | E30 MS(ESI) m/z: 454([M + H]+) |
| 1140 | [MeO-CH2CH2-NH-C(O)-(4-methylpyridin-3-yl)] | E30 MS(ESI) m/z: 468([M + H]+) |
| 1141 | [MeO-CH2CH2CH2-NH-C(O)-(4-methylpyridin-3-yl)] | E30 MS(ESI) m/z: 482([M + H]+) |
| 1142 | [oxetan-3-yl-NH-C(O)-(4-methylpyridin-3-yl)] | E30 MS(ESI) m/z: 466([M + H]+) |
| 1143 | [Me-NH-C(O)-(4-methylpyridin-3-yl)] | E30 MS(ESI) m/z: 424([M + H]+) |
| 1144 | [Et-NH-C(O)-(4-methylpyridin-3-yl)] | E30 MS(ESI) m/z: 438([M + H]+) |
| 1145 | [EtO-CH2CH2-NH-C(O)-(4-methylpyridin-3-yl)] | E30 MS(ESI) m/z: 482([M + H]+) |

TABLE 144
| | | | |
|---|---|---|---|
| 1146 | 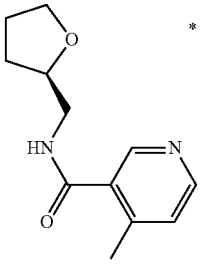 * | | E30 MS(ESI) m/z: 494([M + H]+) |
| 1147 | 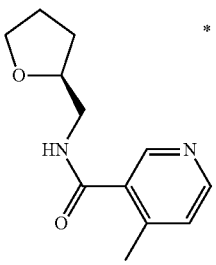 * | | E30 MS(ESI) m/z: 494([M + H]+) |
| 1148 | 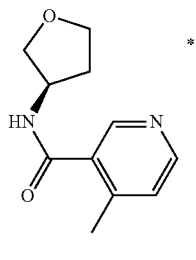 * | | E30 MS(ESI) m/z: 480([M + H]+) |
| 1149 | 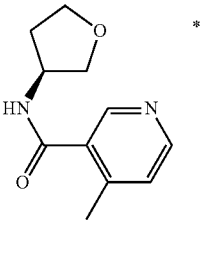 * | | E30 MS(ESI) m/z: 480([M + H]+) |
| 1150 | 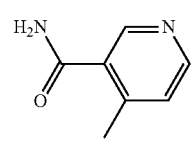 | | E30 MS(ESI) m/z: 410([M + H]+) |
| 1151 | 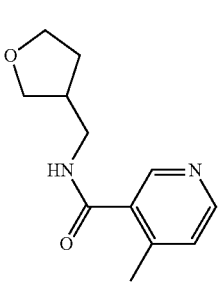 | | E30 MS(ESI) m/z: 494([M + H]+) |
TABLE 144-continued
| | | |
|---|---|---|
| 1152 | 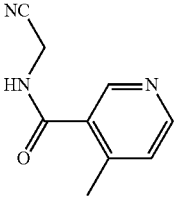 | E30 MS(ESI) m/z: 449([M + H]+) |
| 1153 | 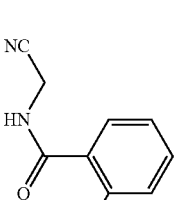 | E30 MS(ESI) m/z: 448([M + H]+) |
TABLE 145
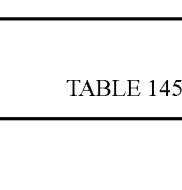
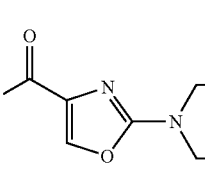
| Ex | | Syn (Sal) Dat |
|---|---|---|
| 1154 | 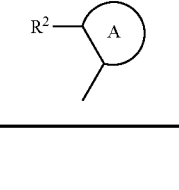 | E23 MS(ESI) m/z: 547([M + H]+) |
| 1155 | 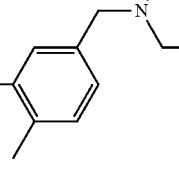 | E23 MS(ESI) m/z: 449([M + H]+) |

TABLE 146

| Ex | R² / A structure | Syn (Sal) Dat |
|---|---|---|
| 1156 | tetrahydropyran-4-yl A; R² = 5-(CH₂N(Me)CH₂CH₂OMe), 2-Me phenyl | E9 MS(ESI) m/z: 536([M + H]+) |
| 1157 | pyridin-3-yl A; R² = 5-(CH₂N(Me)CH₂CH₂OMe), 2-Me phenyl | E9 MS(ESI) m/z: 529([M + H]+) |

TABLE 147

| Ex | R² / A structure | Syn (Sal) Dat |
|---|---|---|
| 1158 | 2-Me, 3-C(O)OMe phenyl | E11 MS(ESI) m/z: 346([M + H]+) |
| 1159 | pyridin-3-ylmethyl-NH-C(O)-, 2-Me phenyl | E26 MS(ESI) m/z: 422([M + H]+) |
| 1160 | pyridin-3-yl-NH-C(O)-, 2-Me, 4-Me phenyl | E11 MS(FAB) m/z: 422([M + H]+) |
| 1161 | pyridin-3-yl-NH-C(O)-, 2-Me, 4-OMe phenyl | E11 MS(FAB) m/z: 438([M + H]+) |
| 1162 | 2-Me, 3-COOH phenyl | E33 MS(ESI) m/z: 332([M + H]+) |

TABLE 148

| Ex | R² / A structure | Syn (Sal) Dat |
|---|---|---|
| 1163 | pyridin-3-ylmethyl-NH-C(O)-, 2-Me phenyl | E30 MS(FAB) m/z: 408([M + H]+) |

TABLE 148-continued

[Structure: A-ring with R² substituent, NH-C(=O)-oxazole-N-azetidine-OMe]

| Ex | | Syn (Sal) Dat |
|---|---|---|
| 1164 | [3-aminopyridine with N-(2-methyl-4-methylphenyl)carboxamide] | E11 MS(FAB) m/z: 408([M + H]+) |
| 1165 | [tetrahydropyran-NH-C(=O)-4-methylpyridine] | E26 MS(FAB) m/z: 402([M + H]+) |
| 1166 | [ethyl 4-methylnicotinate] | E11 MS(FAB) m/z: 347([M + H]+) |
| 1167 | [4-methylnicotinic acid] | E33 MS(FAB) m/z: 319([M + H]+) |

TABLE 149

[Structure: A-ring with R² substituent, NH-C(=O)-oxazole-N(Me)-CH2CH2-OMe]

| Ex | | Syn (Sal) Dat |
|---|---|---|
| 1168 | [HOCH2-C(Me)2-CH2-NH-C(=O)-(3-methyl-4-cyanophenyl)] | E26 MS(ESI) m/z: 430([M + H]+) |

TABLE 149-continued

| Ex | | Syn (Sal) Dat |
|---|---|---|
| 1169 | [morpholinomethyl-benzamide with tetrahydropyran-NH and methyl] | E26 MS(ESI) m/z: 502([M + H]+) |
| 1170 | [3-aminopyridine with 2-methyl-4-methylbenzamide] | E11 MS(FAB) m/z: 410([M + H]+) |
| 1171 | [methyl 2-methyl-4-cyanobenzoate] | E6 MS(ESI) m/z: 357([M − H]−) |
| 23 | [methyl 5-(morpholinomethyl)-4-cyanobenzoate] | E23 MS(FAB) m/z: 433([M + H]+) |
| 1172 | [5-cyano-3-methyl-2-carboxybenzoic acid] | E33 MS(ESI) m/z: 345([M + H]+) |
| 1173 | [3-(morpholinomethyl)-6-methylbenzoic acid] | E33 MS(ESI) m/z: 419([M + H]+) |

TABLE 150

| Ex | Str | Syn (Sal) Dat |
|---|---|---|
| 1174 | | E9<br>MS(ESI) m/z:<br>348([M + H]+) |
| 1175 | | E9<br>MS(ESI) m/z:<br>445([M + H]+) |
| 1176 | | E33→E26 (HCl)<br>MS(ESI) m/z:<br>448([M − H]−) |
| 1177 | | E28 (HCl)<br>MS(FAB) m/z:<br>452([M + H]+) |
| 1178 | | E6<br>MS(ESI) m/z:<br>501([M + H]+) |
| 1179 | | E28 (HCl)<br>MS(ESI) m/z:<br>540([M + H]+) |
| 42 | | E42<br>MS(ESI) m/z:<br>330([M + H]+) |

TABLE 151
| Ex | Str | Syn (Sal) Dat |
|---|---|---|
| 1180 | 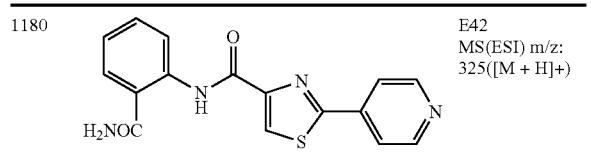 | E42 MS(ESI) m/z: 325([M + H]+) |
| 198 | 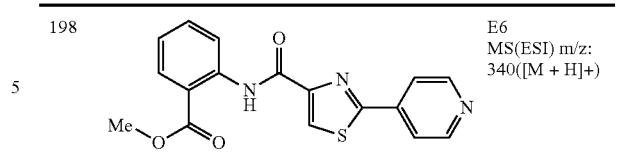 | E6 MS(ESI) m/z: 340([M + H]+) |
TABLE 152
| Ex | Str | Syn (Sal) Dat |
|---|---|---|
| 1196 | 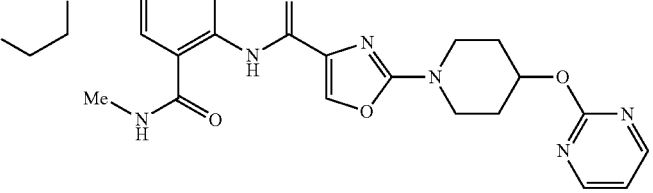 | E26 MS(ESI) m/z: 520([M − H]−) |
| 1197 | 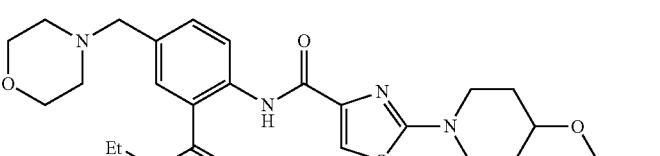 | E26 MS(ESI) m/z: 534([M − H]−) |
| 1198 | 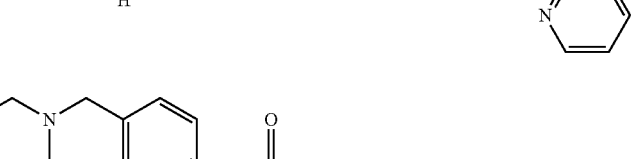 | E26 MS(ESI) m/z: 552([M − H]−) |
| 1199 | 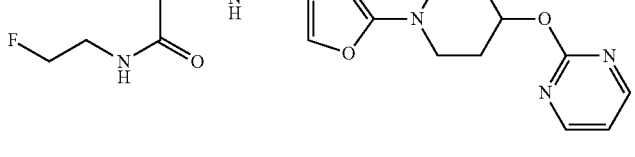 | E26 MS(ESI) m/z: 568([M + H]+) |
| 1200 | 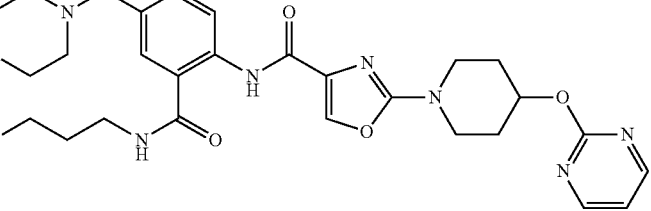 | E26 MS(ESI) m/z: 578([M + H]+) |

TABLE 152-continued

| Ex | Str | Syn (Sal) Dat |
|---|---|---|
| 1201 | | E26<br>MS(ESI) m/z: 590([M − H]−) |
| 1202 | | E26<br>MS(ESI) m/z: 560([M + H]+) |
| 1203 | | E26<br>MS(ESI) m/z: 578([M + H]+) |

TABLE 153

| 1204 | | E26<br>MS(ESI) m/z: 616([M + H]+) |
|---|---|---|
| 1205 | | E26<br>MS(ESI) m/z: 602([M + H]+) |

TABLE 153-continued
| 1206 | 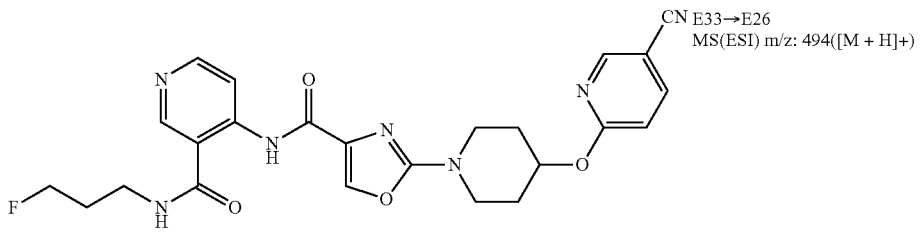 | E33→E26<br>MS(ESI) m/z: 494([M + H]+) |
| 1207 | 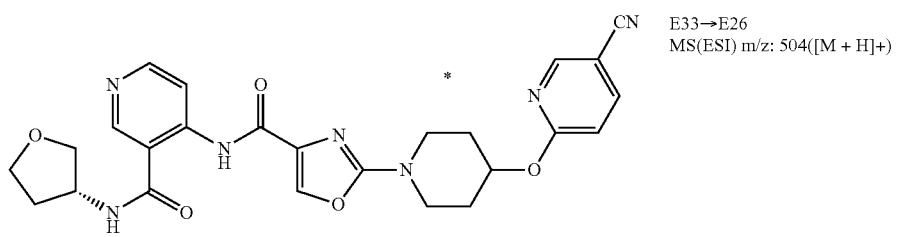 | E33→E26<br>MS(ESI) m/z: 504([M + H]+) |
| 1208 | 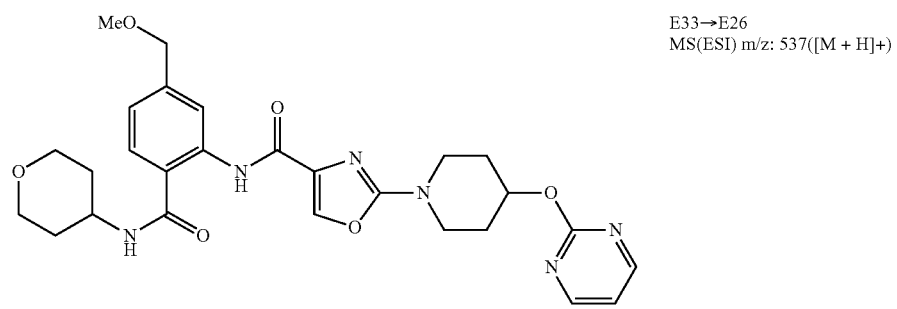 | E33→E26<br>MS(ESI) m/z: 537([M + H]+) |
| 1209 | 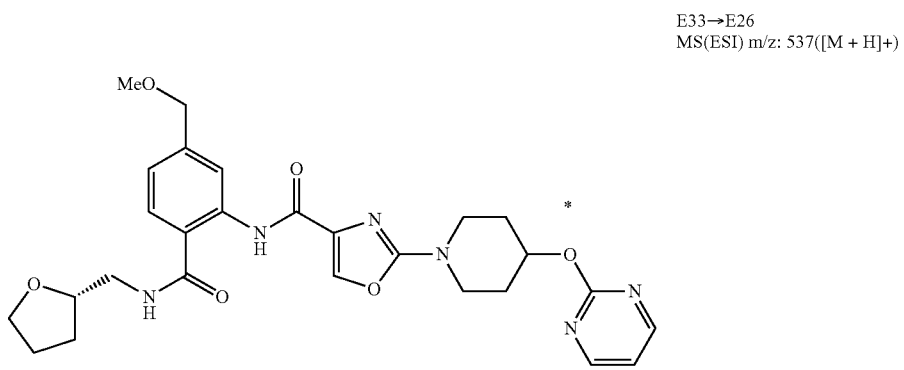 | E33→E26<br>MS(ESI) m/z: 537([M + H]+) |
| 1210 | 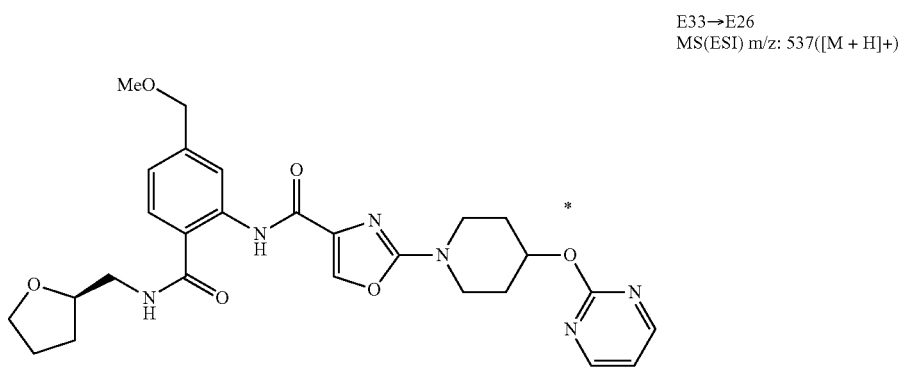 | E33→E26<br>MS(ESI) m/z: 537([M + H]+) |

TABLE 154

| | | |
|---|---|---|
| 1211 | (structure) | E33→E26<br>MS(ESI) m/z: 606([M + H]+) |
| 1212 | (structure) | E33→E26<br>MS(ESI) m/z: 568([M + H]+) |
| 1213 | (structure) | E33→E26<br>MS(ESI) m/z: 544([M + H]+) |
| 1214 | (structure) | E26<br>MS(ESI) m/z: 608([M + H]+) |
| 1215 | (structure) | E26<br>MS(ESI) m/z: 630([M + H]+) |
| 1216 | (structure) | E26<br>MS(ESI) m/z: 480([M + H]+) |

TABLE 154-continued

| | | |
|---|---|---|
| 1217 | | E26<br>MS(ESI) m/z: 452([M + H]+) |
| 1218 | | E26<br>MS(ESI) m/z: 468([M + H]+) |
| 1219 | | E26<br>MS(ESI) m/z: 470([M + H]+) |

TABLE 155

| | | |
|---|---|---|
| 1220 | | E33→E26<br>MS(ESI) m/z: 504([M + H]+) |
| 1221 | | E33→E26<br>MS(ESI) m/z: 518([M + H]+) |
| 1222 | | E26<br>MS(ESI) m/z: 480([M + H]+) |

| | | |
|---|---|---|
| 1223 | 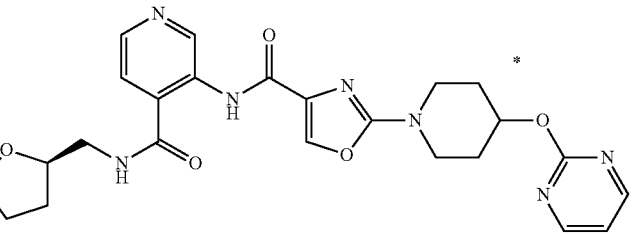 | E26<br>MS(ESI) m/z: 494([M + H]+) |
| 1224 | 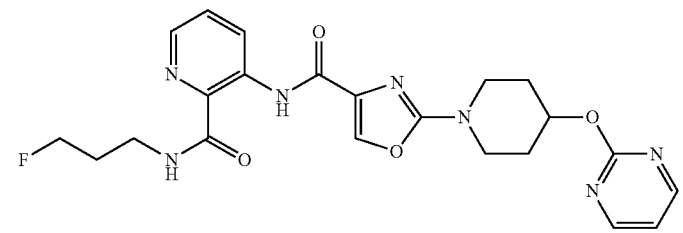 | E33→E26<br>MS(ESI) m/z: 470([M + H]+) |
| 1225 | 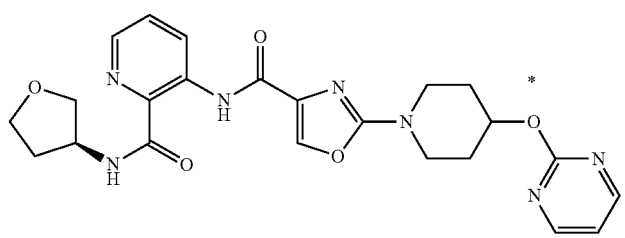 | E33→E26<br>MS(ESI) m/z: 480([M + H]+) |
| 1226 | 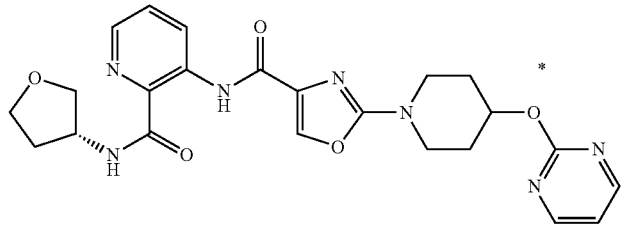 | E33→E26<br>MS(ESI) m/z: 480([M + H]+) |
| 1227 | 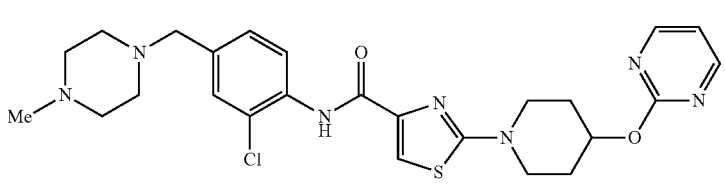 | E13<br>MS(ESI) m/z: 528, 530([M + H]+) |
| 1228 | 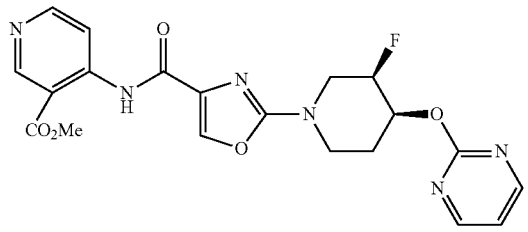 | E30<br>MS(ESI) m/z: 443([M + H]+) |

US 8,304,547 B2
TABLE 156
| | | |
|---|---|---|
| 1229 | 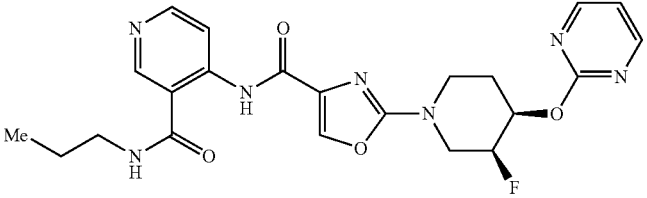 | E26<br>MS(ESI) m/z: 470([M + H]+) |
| 1230 | 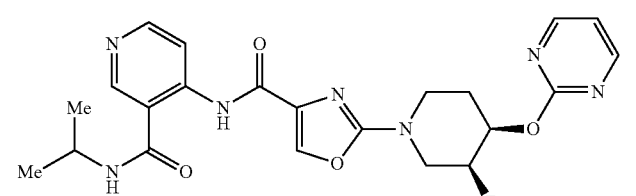 | E26<br>MS(ESI) m/z: 470([M + H]+) |
| 1231 | 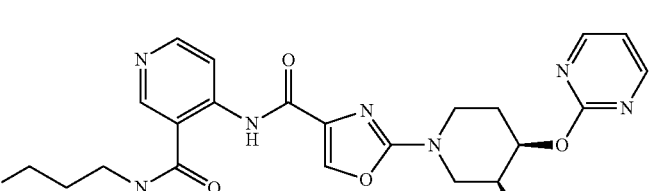 | E26<br>MS(ESI) m/z: 488([M + H]+) |
| 1232 | 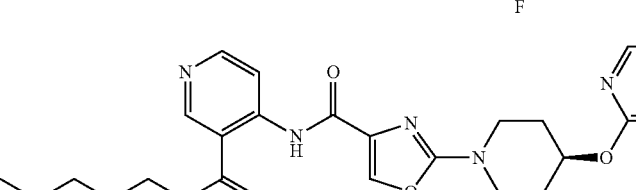 | E26<br>MS(ESI) m/z: 523([M + H]+) |
| 1233 | 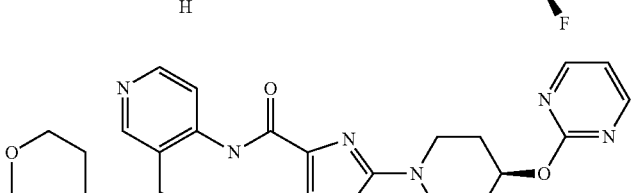 | E26<br>MS(ESI) m/z: 512([M + H]+) |
| 1234 | 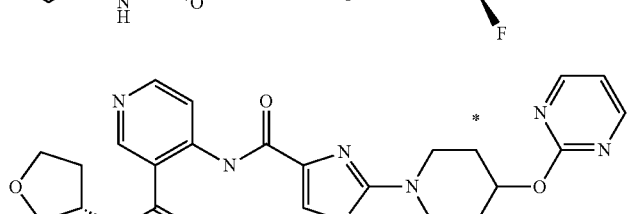 | E26<br>MS(ESI) m/z: 498([M + H]+) |
| 1235 | 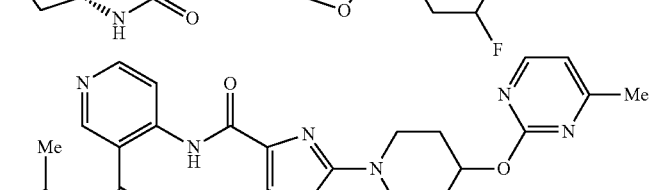 | E26<br>MS(ESI) m/z: 466([M + H]+) |
| 1236 | 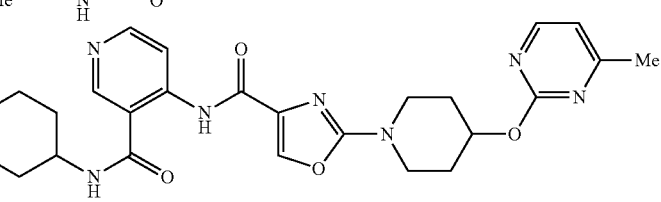 | E26<br>MS(ESI) m/z: 508([M + H]+) |

TABLE 157
| | | |
|---|---|---|
| 1237 | 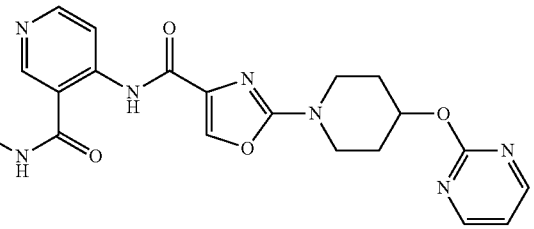 | E26<br>MS(ESI) m/z: 508([M + H]+) |
| 1238 | 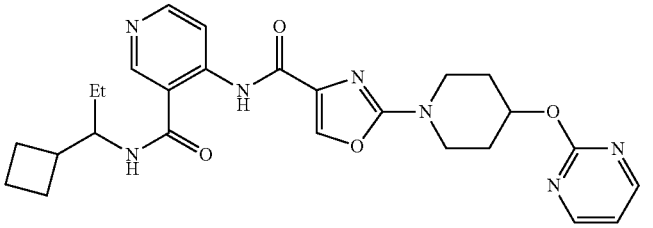 | E26<br>MS(ESI) m/z: 506([M + H]+) |
| 1239 | 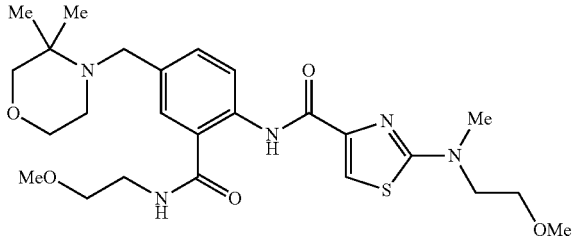 | E30<br>MS(FAB) m/z: 520([M + H]+) |
| 1240 | 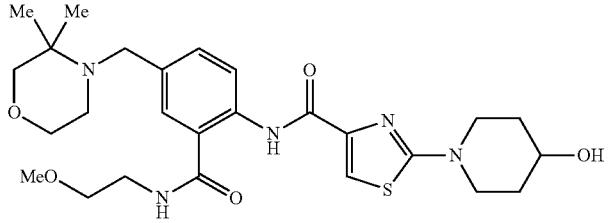 | E30<br>MS(FAB) m/z: 532([M + H]+) |
| 1241 | 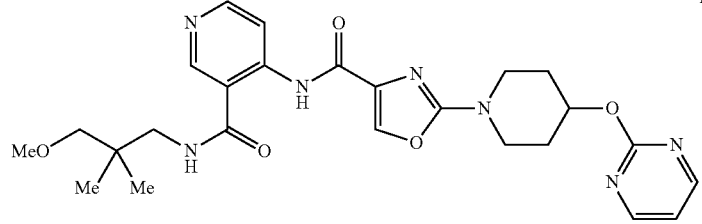 | E26<br>MS(ESI) m/z: 510([M + H]+) |
| 1242 | 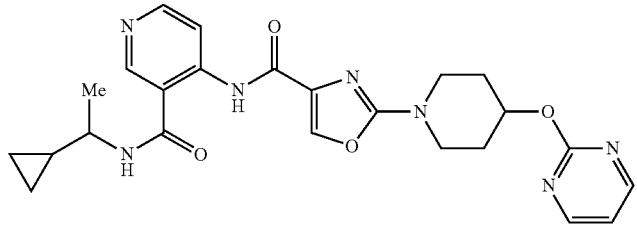 | E26<br>MS(ESI) m/z: 478([M + H]+) |

TABLE 157-continued
| | | |
|---|---|---|
| 1243 | 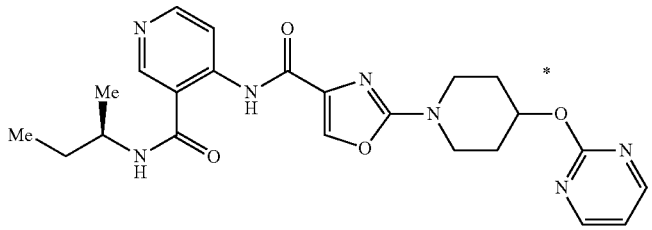 | E26<br>MS(ESI) m/z: 466([M + H]+) |
| 1244 | 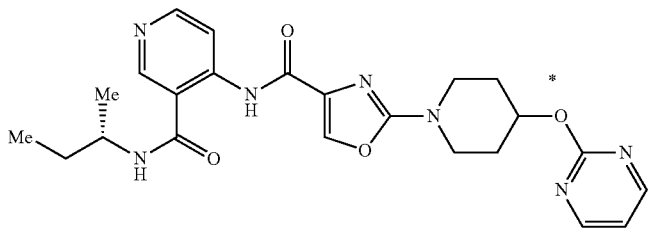 | E26<br>MS(ESI) m/z: 466([M + H]+) |
| 1245 | 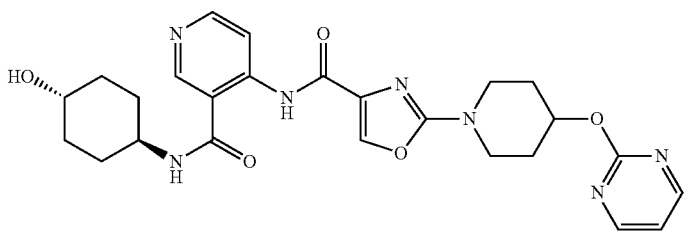 | E26<br>MS(ESI) m/z: 508([M + H]+) |
TABLE 158
| | | |
|---|---|---|
| 1246 | 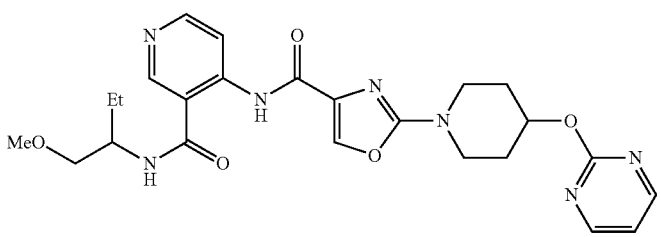 | E26<br>MS(ESI) m/z: 496([M + H]+) |
| 1247 | 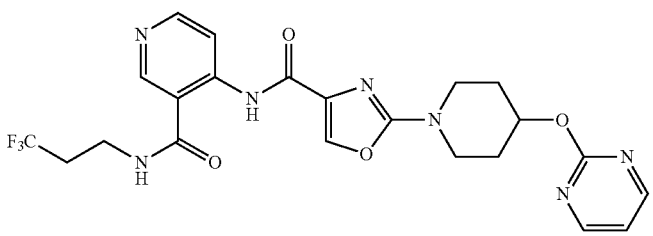 | E26<br>MS(ESI) m/z: 506([M + H]+) |
| 1248 | 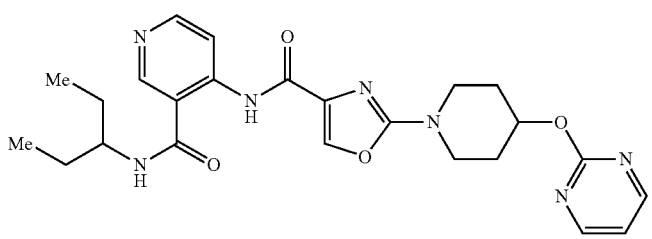 | E26<br>MS(ESI) m/z: 480([M + H]+) |

TABLE 158-continued
| 1249 | 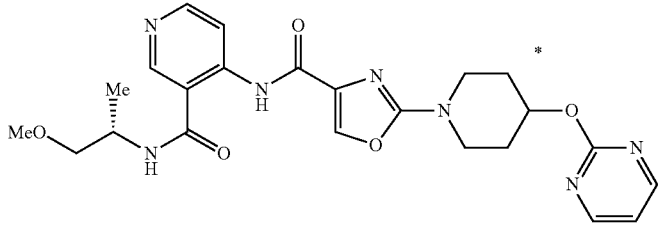 | E26<br>MS(ESI) m/z: 482([M + H]+) |
| --- | --- | --- |
| 1250 | 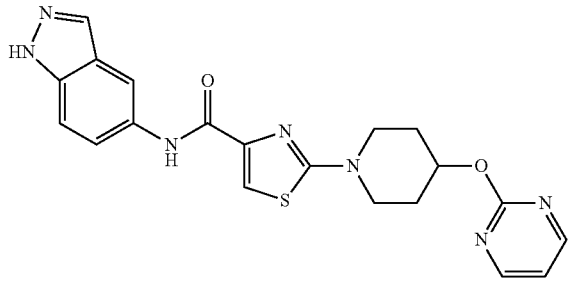 | E30<br>MS(FAB) m/z: 422([M + H]+) |
| 1251 | 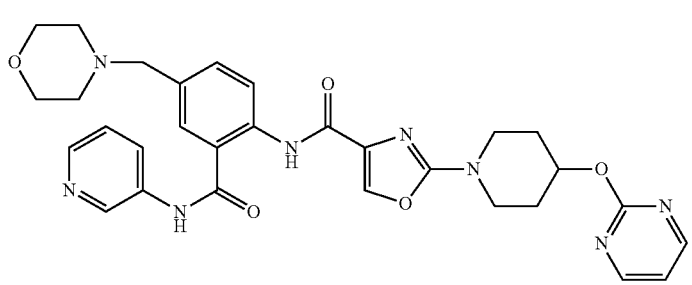 | E6<br>MS(FAB) m/z: 585([M + H]+) |
| 1252 | 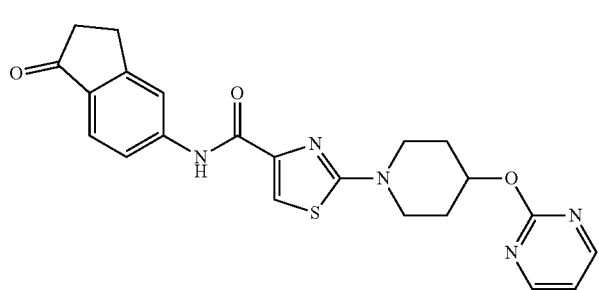 | E30<br>MS(ESI) m/z: 436([M + H]+) |
| 1253 | 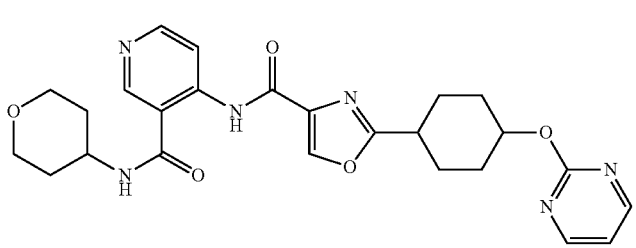 | E26<br>MS(ESI) m/z: 493([M + H]+) |

TABLE 159
| | | |
|---|---|---|
| 1254 | 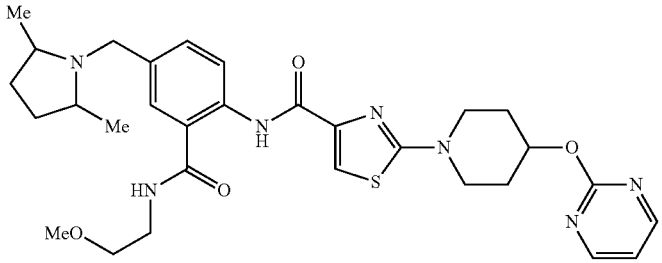 | E26<br>MS(FAB) m/z: 594([M + H]+) |
| 1255 | 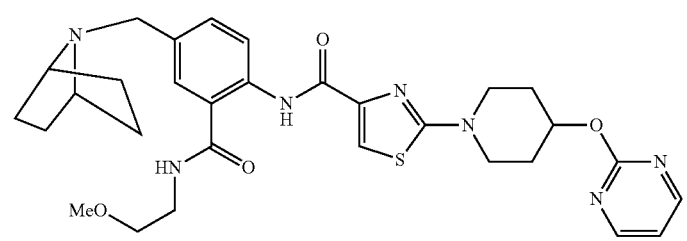 | E26<br>MS(FAB) m/z: 592([M + H]+) |
| 1256 | 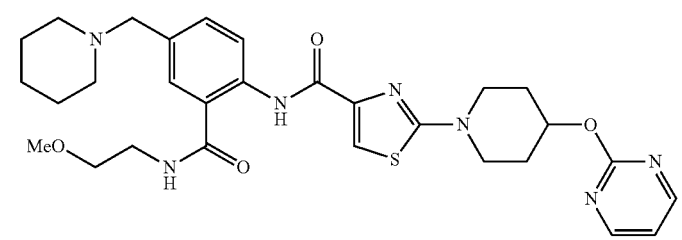 | E1181<br>MS(FAB) m/z: 580([M + H]+) |
| 1257 | 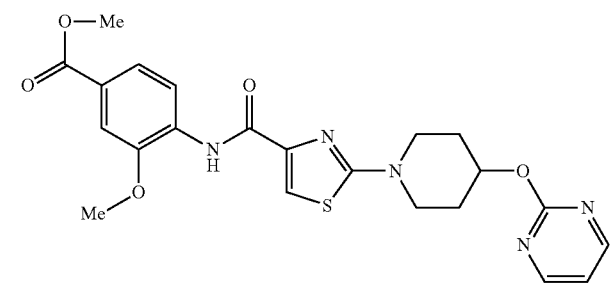 | E30<br>MS(FAB) m/z: 470([M + H]+) |
| 1258 | 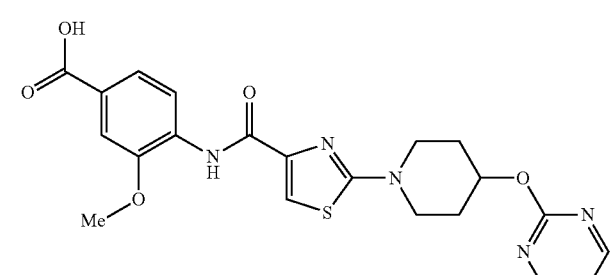 | E33<br>MS(ESI) m/z: 456([M + H]+) |
| 1259 | 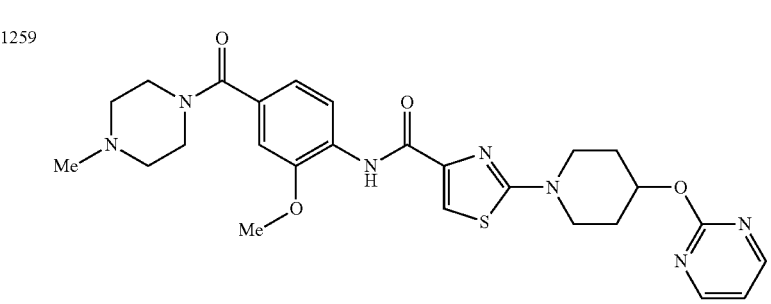 | E26 (HCl)<br>MS(ESI) m/z: 538([M + H]+) |

TABLE 159-continued
| | | |
|---|---|---|
| 1183 | 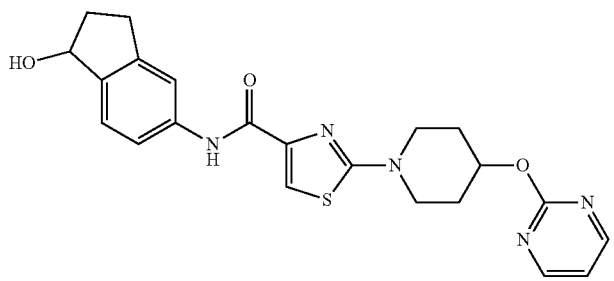 | E1183<br>MS(FAB) m/z: 438([M + H]+) |
| 1260 | 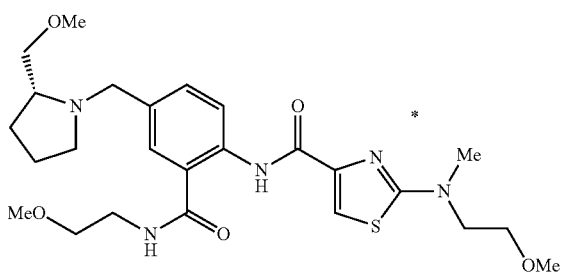 | E26 (HCl)<br>MS(FAB) m/z: 520([M + H]+) |
TABLE 160
| | | |
|---|---|---|
| 1261 | 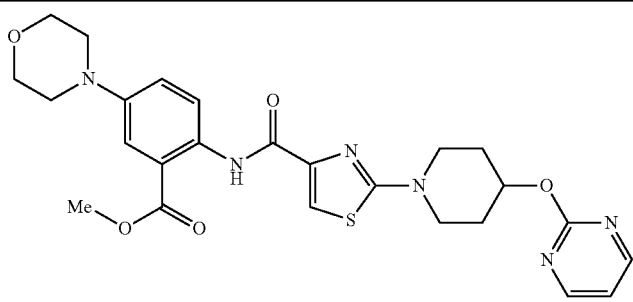 | E6<br>MS(ESI) m/z: 525([M + H]+) |
| 1262 | 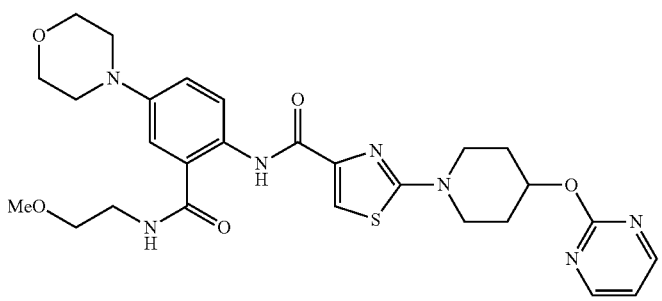 | E26<br>MS(ESI) m/z: 568([M + H]+) |
| 1263 | 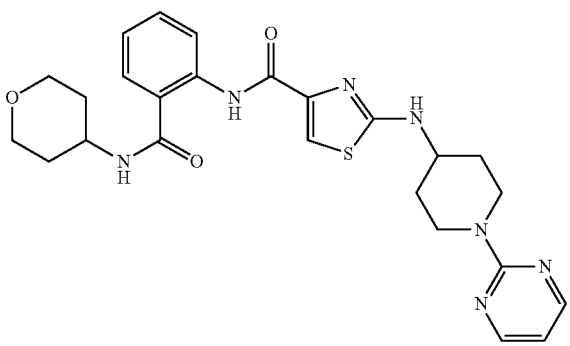 | E28<br>MS(ESI) m/z: 508([M + H]+) |

TABLE 160-continued

| 1264 | (structure) | E6 MS(ESI) m/z: 553([M + H]+) |
| --- | --- | --- |
| 1265 | (structure) | E26 MS(ESI) m/z: 466([M + H]+) |
| 1266 | (structure) | E26 MS(ESI) m/z: 466([M + H]+) |
| 1267 | (structure) | E26 MS(ESI) m/z: 478([M + H]+) |
| 1268 | (structure) | E26 MS(ESI) m/z: 509([M + H]+) |

TABLE 161

| 1269 | (structure) | E26 MS(ESI) m/z: 512([M + H]+) |
| --- | --- | --- |

TABLE 161-continued

| | | |
|---|---|---|
| 1270 | [structure] | E26<br>MS(ESI) m/z: 502([M + H]+) |
| 1271 | [structure] | E26<br>MS(ESI) m/z: 514([M + H]+) |
| 1272 | [structure] | E26<br>MS(ESI) m/z: 464([M + H]+) |
| 1273 | [structure] | E6<br>MS(ESI) m/z: 454([M + H]+) |
| 1274 | [structure] | E6<br>MS(ESI) m/z: 518, 520([M + H]+) |
| 1275 | [structure] | E6<br>MS(ESI) m/z: 508([M + H]+) |
| 1276 | [structure] | E33→E26 (Fum)<br>MS(FAB) m/z: 610([M + H]+) |

TABLE 161-continued

| | | |
|---|---|---|
| 1277 | [structure] | E26<br>MS(ESI) m/z: 596([M + H]+) |

TABLE 162

| | | |
|---|---|---|
| 1278 | [structure] | E26<br>MS(ESI) m/z: 553([M + H]+) |
| 1279 | [structure] | E30<br>MS(ESI) m/z: 380([M + H]+) |
| 1280 | [structure] | E33<br>MS(FAB) m/z: 366([M + H]+) |
| 1281 | [structure] | E1181 (Fum)<br>MS(FAB) m/z: 540([M + H]+) |
| 1282 | [structure] | E1181<br>MS(FAB) m/z: 595([M + H]+) |
| 1283 | [structure] | E1181<br>MS(FAB) m/z: 584([M + H]+) |

TABLE 162-continued

| | | | |
|---|---|---|---|
| 1284 | (structure) | | E1181<br>MS(FAB) m/z: 594([M + H]+) |
| 1285 | (structure) | | E26<br>MS(ESI) m/z: 483, 485([M + H]+) |
| 1286 | (structure) | | E26<br>MS(ESI) m/z: 520([M + H]+) |

TABLE 163

| | | | |
|---|---|---|---|
| 1287 | (structure) | | E26 (HCl)<br>MS(ESI) m/z: 448([M + H]+) |
| 1288 | (structure) | | E6<br>MS(ESI) m/z: 569([M + H]+) |
| 1289 | (structure) | | E26<br>MS(ESI) m/z: 518([M + H]+) |

TABLE 163-continued
| | | |
|---|---|---|
| 1290 | 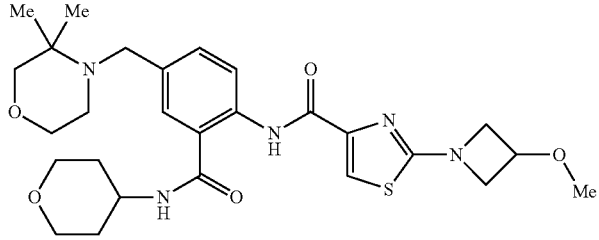 | E26<br>MS(ESI) m/z: 544([M + H]+) |
| 1291 | 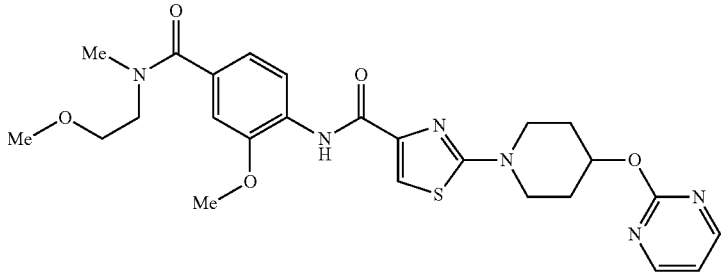 | E26<br>MS(ESI) m/z: 527([M + H]+) |
| 1292 | 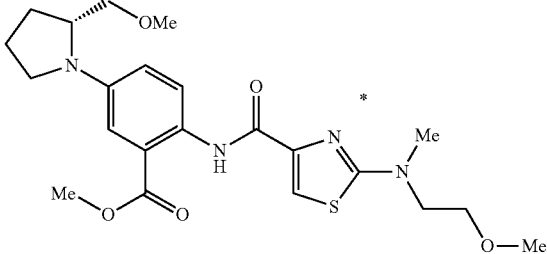 | E6<br>MS(ESI) m/z: 463([M + H]+) |
| 1293 | 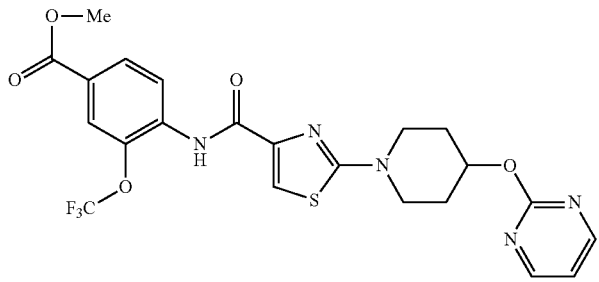 | E23<br>MS(ESI) m/z: 524([M + H]+) |
| 1294 | 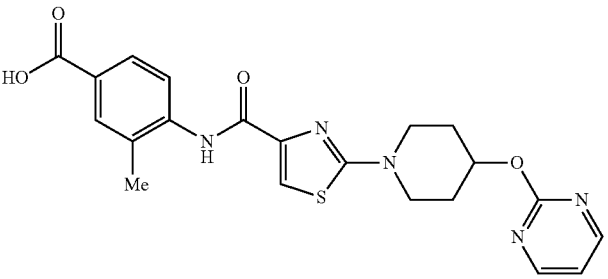 | E33<br>MS(ESI) m/z: 440([M + H]+) |

TABLE 164
| 1295 | 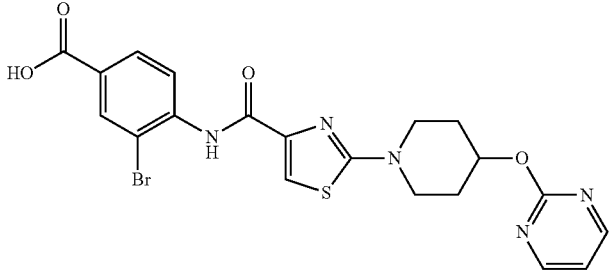 | E33 MS(ESI) m/z: 504, 506([M + H]+) |
| 1296 | 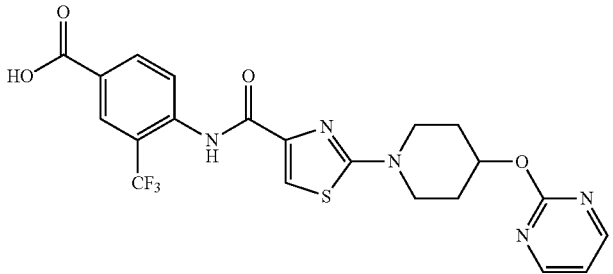 | E33 MS(ESI) m/z: 494([M + H]+) |
| 1297 | | E28 MS(ESI) m/z: 511, 513([M + H]+) |
| | 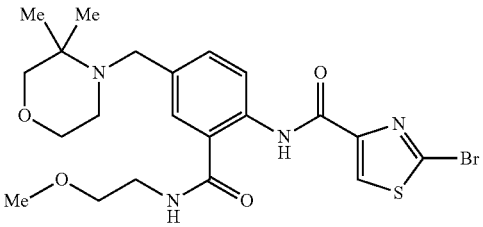 | |
| 1298 | | E33 MS(ESI) m/z: 510([M + H]+) |
| | 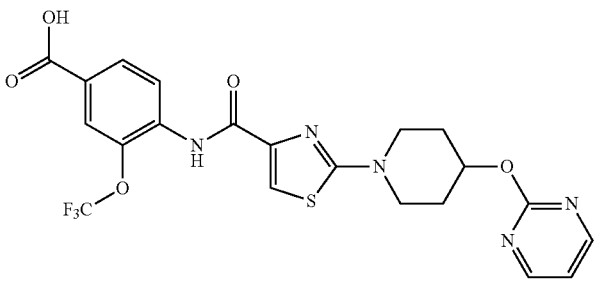 | |
| 1299 | | E26 MS(FAB) m/z: 610([M − H]−) |

TABLE 164-continued

| No. | Structure | Notes |
|---|---|---|
| 1300 | (structure) | E1181<br>MS(ESI) m/z: 610([M + H]+) |
| 1301 | (structure) | E26 (HCl)<br>MS(FAB) m/z: 504([M − H]−) |

TABLE 165

| No. | Structure | Notes |
|---|---|---|
| 1302 | (structure) | E1181 (Fum)<br>MS(ESI) m/z: 582([M + H]+) |
| 1303 | (structure) | E1181<br>MS(ESI) m/z: 568([M + H]+) |
| 1304 | (structure) | E28<br>MS(ESI) m/z: 523([M + H]+) |
| 1305 | (structure) | E28<br>MS(ESI) m/z: 497([M + H]+) |

TABLE 165-continued
| | | |
|---|---|---|
| 1306 | 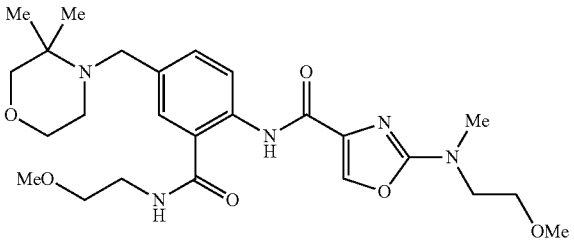 | E26<br>MS(ESI) m/z: 504([M + H]+) |
| 1307 | 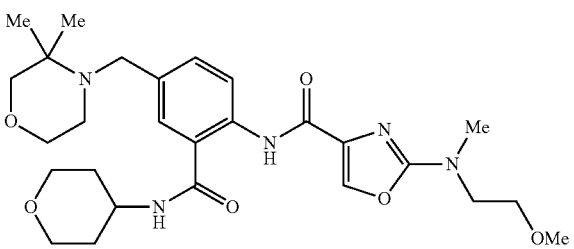 | E26<br>MS(ESI) m/z: 530([M + H]+) |
| 1308 | 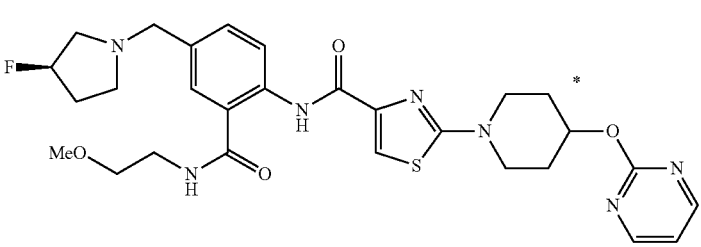 | E1181 (Fum)<br>MS(FAB) m/z: 584([M + H]+) |
| 1309 | 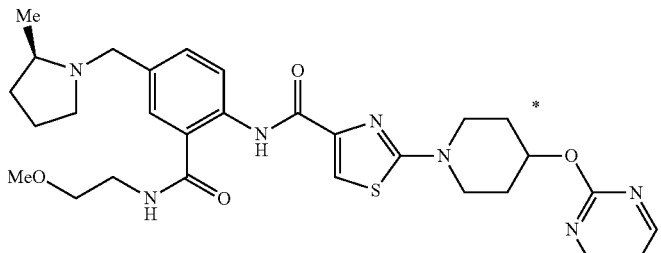 | E1181 (Fum)<br>MS(FAB) m/z: 580([M + H]+) |
TABLE 166
| | | |
|---|---|---|
| 1310 | 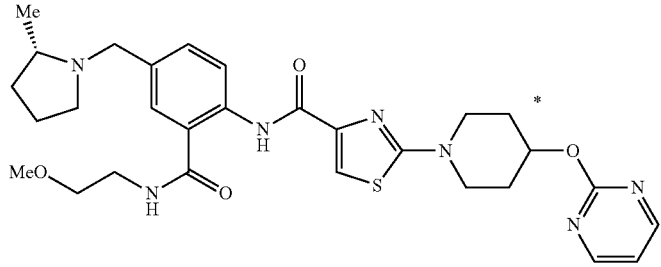 | E1181 (Fum)<br>MS(FAB) m/z: 580([M + H]+) |
| 1311 | 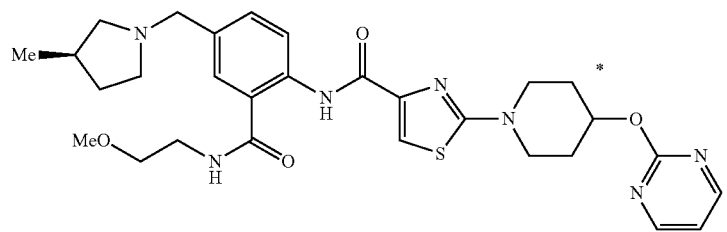 | E1181<br>MS(FAB) m/z: 580([M + H]+) |

TABLE 166-continued

| | | |
|---|---|---|
| 1312 | (structure) | E1181<br>MS(FAB) m/z: 580([M + H]+) |
| 1313 | (structure) | E28<br>MS(ESI) m/z: 550([M + H]+) |
| 1314 | (structure) | E1181<br>MS(ESI) m/z: 636([M + H]+) |
| 1315 | (structure) | E1181 (Fum)<br>MS(ESI) m/z: 626([M + H]+) |
| 1316 | (structure) | E1181<br>MS(ESI) m/z: 610([M + H]+) |
| 1317 | (structure) | E23<br>MS(ESI) m/z: 465([M + H]+) |

TABLE 167
| | | |
|---|---|---|
| 1318 | 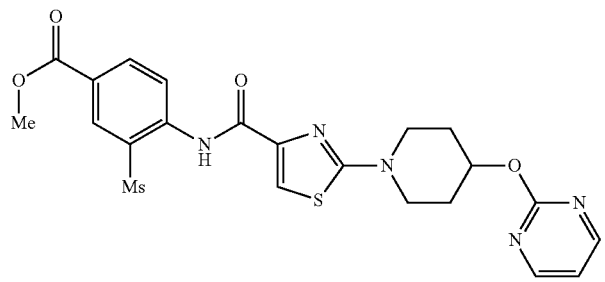 | E23<br>MS(ESI) m/z: 518([M + H]+) |
| 1319 | 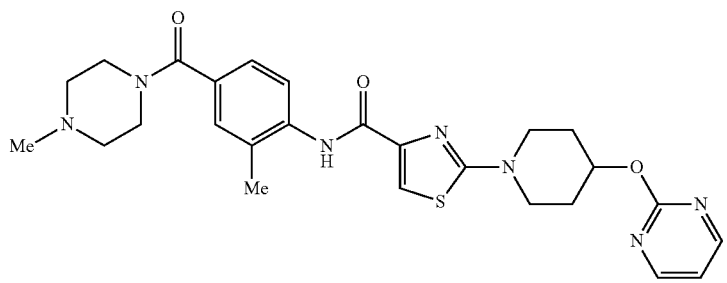 | E26 (HCl)<br>MS(ESI) m/z: 522([M + H]+) |
| 1320 | 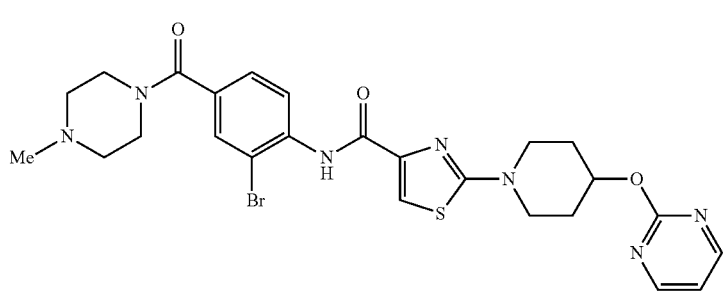 | E26 (HCl)<br>MS(ESI) m/z: 586, 588([M + H]+) |
| 1321 | 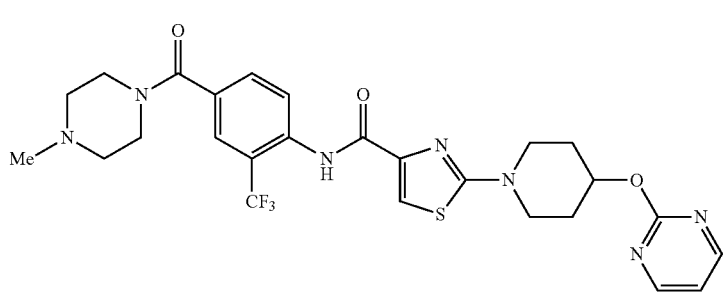 | E26 (HCl)<br>MS(ESI) m/z: 576([M + H]+) |
| 1322 | 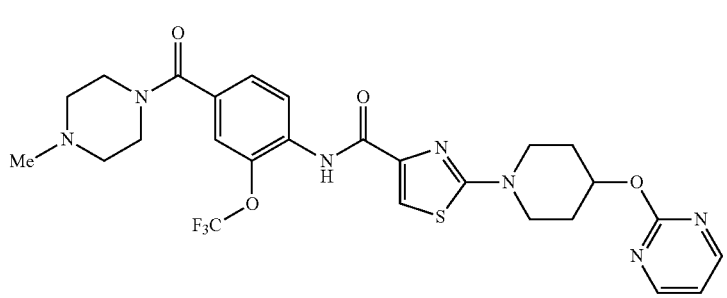 | E26 (HCl)<br>MS(ESI) m/z: 592([M + H]+) |

TABLE 167-continued
| | | |
|---|---|---|
| 1323 | 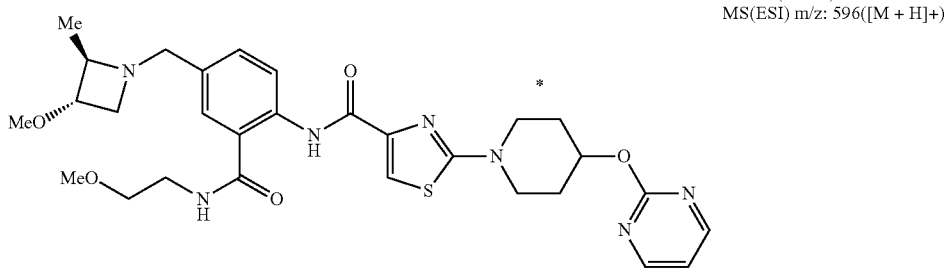 | E1181 (L-Tart)<br>MS(ESI) m/z: 596([M + H]+) |
| 1324 | 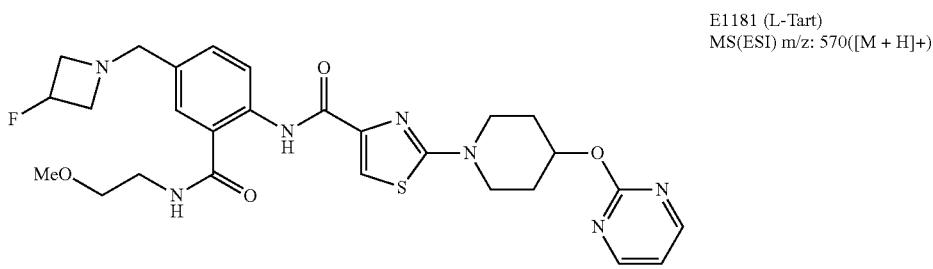 | E1181 (L-Tart)<br>MS(ESI) m/z: 570([M + H]+) |
| 1325 | 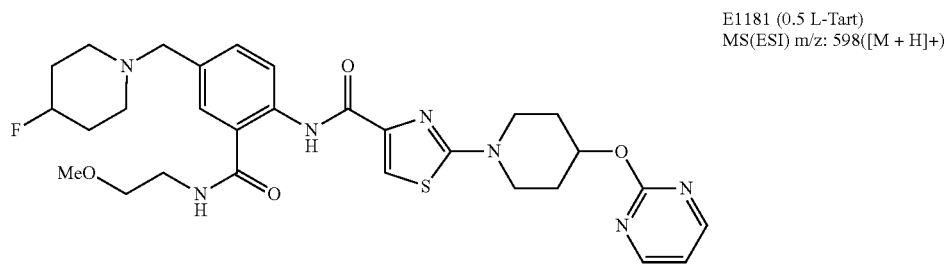 | E1181 (0.5 L-Tart)<br>MS(ESI) m/z: 598([M + H]+) |
| 1326 | 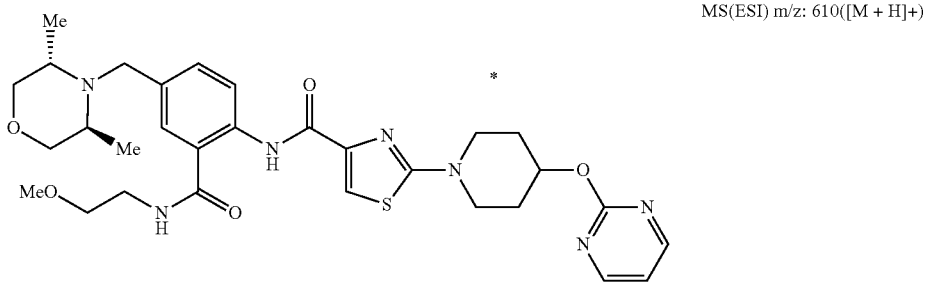 | E1181 (L-Tart)<br>MS(ESI) m/z: 610([M + H]+) |
TABLE 168
| | | |
|---|---|---|
| 1327 | 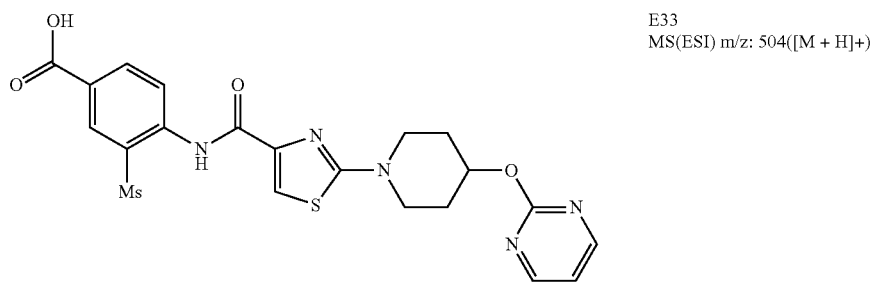 | E33<br>MS(ESI) m/z: 504([M + H]+) |

TABLE 168-continued
| 1186 | 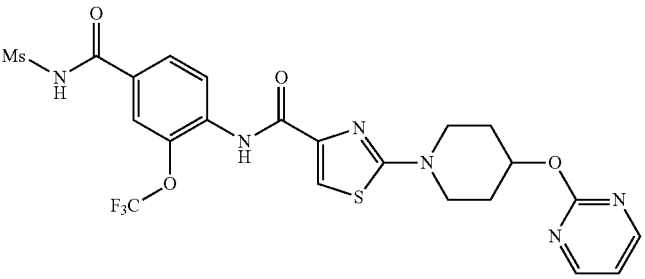 | E1186 MS(ESI) m/z: 587([M + H]+) |
| 1328 | 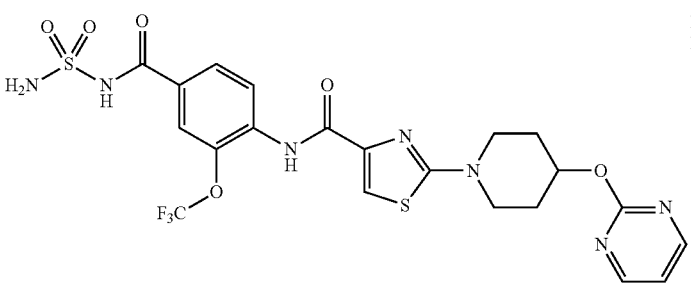 | E1186 MS(ESI) m/z: 588([M + H]+) |
| 1329 | 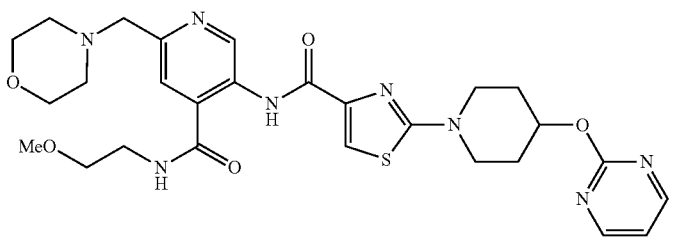 | E25 MS(FAB) m/z: 583([M + H]+) |
| 1330 | 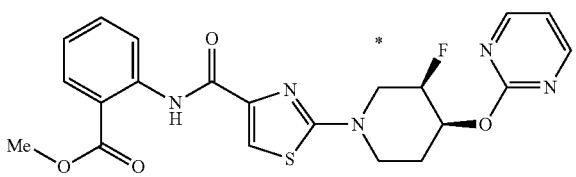 | E23 MS(ESI) m/z: 442([M + H]+) |
| 1331 | 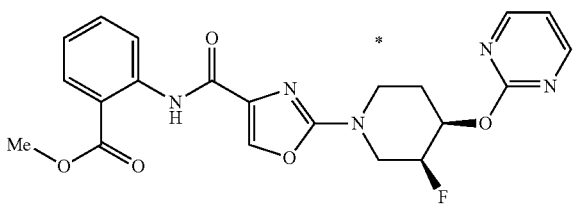 | E23 MS(ESI) m/z: 442([M + H]+) |
| 1332 | 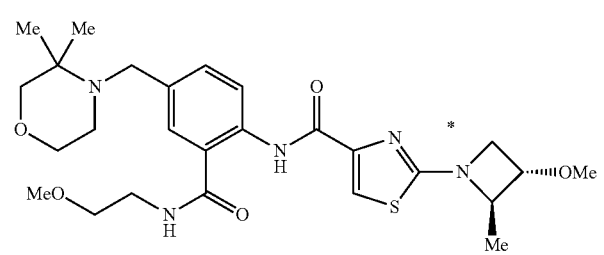 | E28 MS(ESI) m/z: 532([M + H]+) |

TABLE 168-continued
| 1333 | 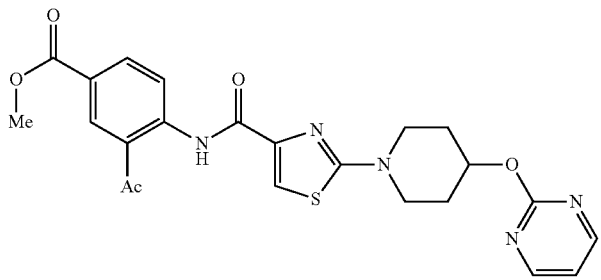 | E23<br>MS(ESI) m/z: 482([M + H]+) |
TABLE 169
| 1334 | 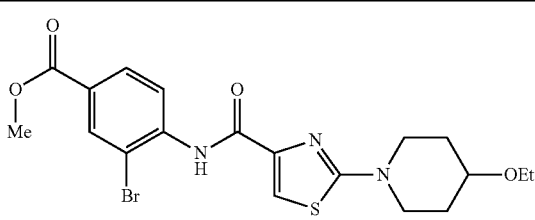 | E23<br>MS(ESI) m/z: 468, 470([M + H]+) |
| 1335 | 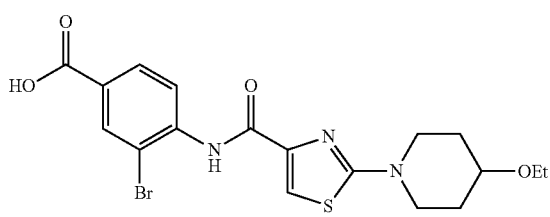 | E33<br>MS(ESI) m/z: 454, 456([M + H]+) |
| 1336 | 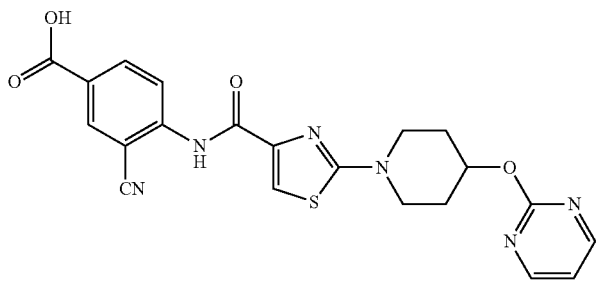 | E23<br>MS(ESI) m/z: 451([M + H]+) |
| 1337 | 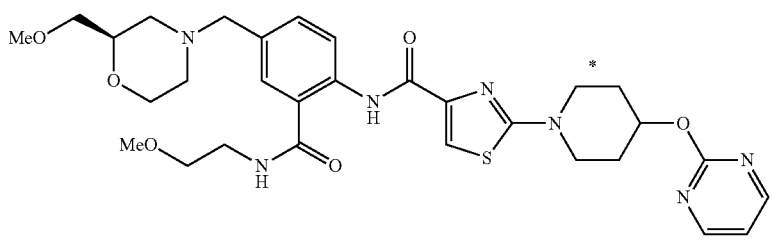 | E1181 (Fum)<br>MS(ESI) m/z: 626([M + H]+) |
| 1338 | 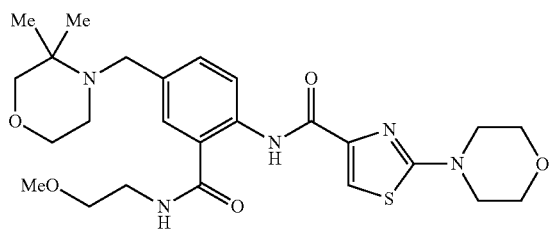 | E23<br>MS(ESI) m/z: 518([M + H]+) |

TABLE 169-continued
| 1339 | 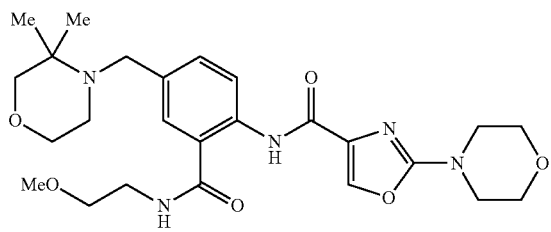 | E23<br>MS(ESI) m/z: 502([M + H]+) |
| --- | --- | --- |
| 1340 | 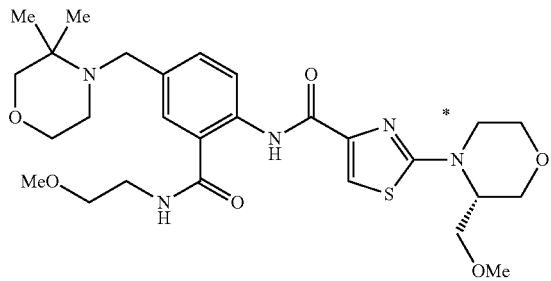 | E23<br>MS(ESI) m/z: 562([M + H]+) |
| 1341 | 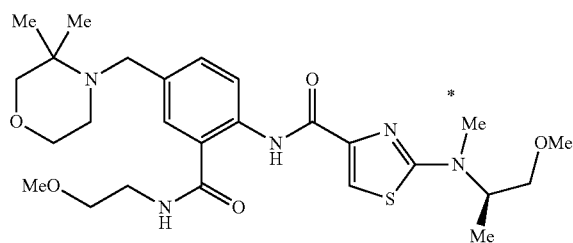 | E23<br>MS(ESI) m/z: 534([M + H]+) |
TABLE 170
| 1342 | 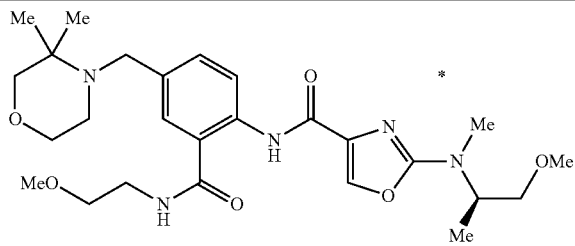 | E23<br>MS(ESI) m/z: 518([M + H]+) |
| --- | --- | --- |
| 1343 | 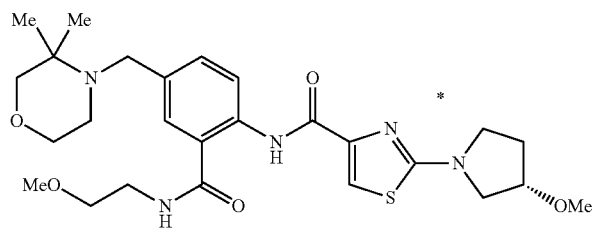 | E23<br>MS(ESI) m/z: 532([M + H]+) |
| 1344 | 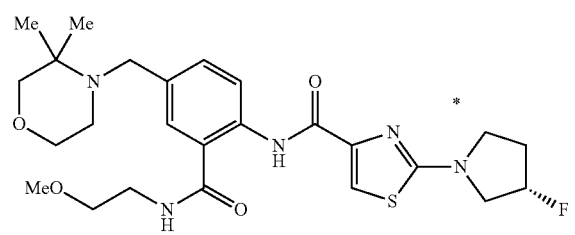 | E23<br>MS(ESI) m/z: 520([M + H]+) |

TABLE 170-continued
| | | |
|---|---|---|
| 1345 | 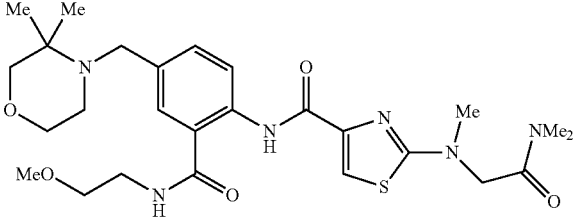 | E23<br>MS(ESI) m/z: 547([M + H]+) |
| 1346 | 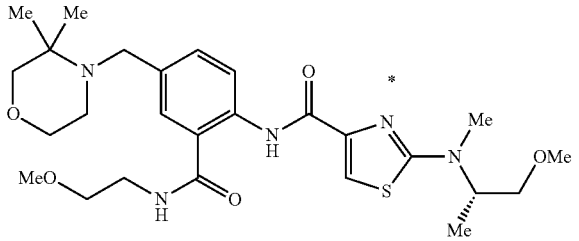 | E23<br>MS(ESI) m/z: 534([M + H]+) |
| 1347 | 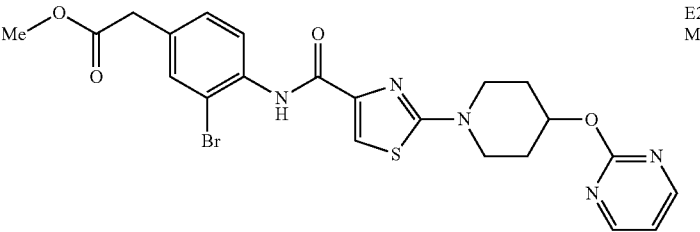 | E23<br>MS(ESI) m/z: 532, 534([M + H]+) |
| 1348 | 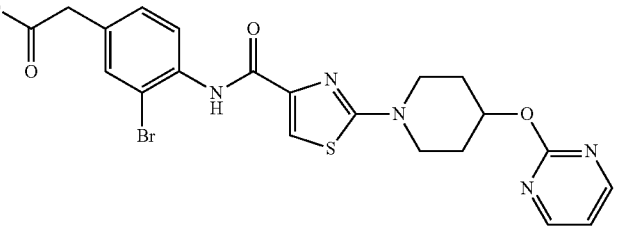 | E23<br>MS(ESI) m/z: 518, 520([M + H]+) |
| 1349 | 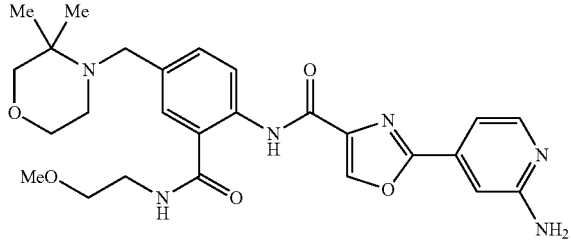 | E35 (2HCl)<br>MS(FAB) m/z: 509([M + H]+) |
TABLE 171
| | | |
|---|---|---|
| 1350 | 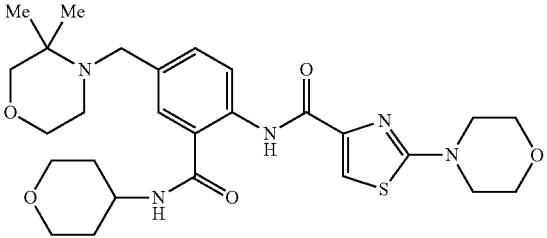 | E26 (0.5 L-Tart)<br>MS(API) m/z: 544([M + H]+) |

TABLE 171-continued
| | | |
|---|---|---|
| 1351 | 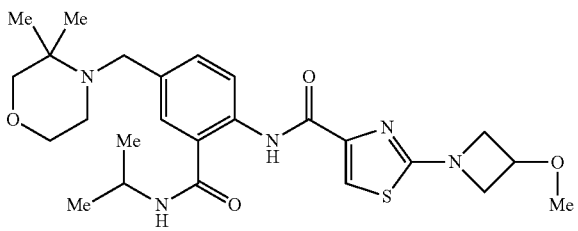 | E26<br>MS(ESI) m/z: 502([M + H]+) |
| 1352 | 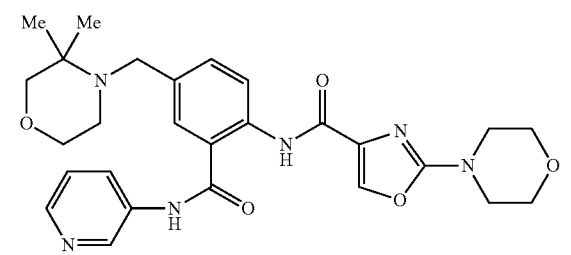 | E23<br>MS(API) m/z: 521([M + H]+) |
| 1353 | 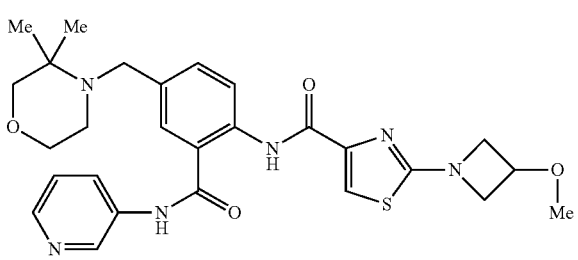 | E6<br>MS(API) m/z: 537([M + H]+) |
| 1354 | 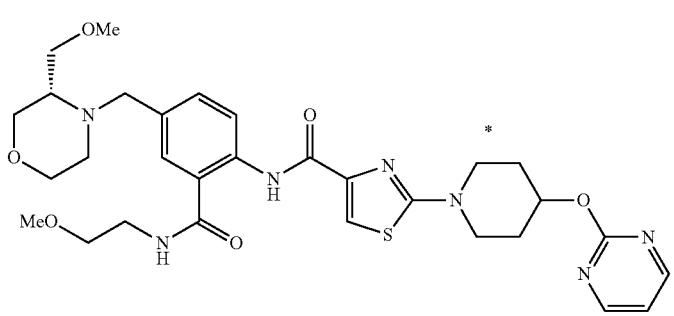 | E1181<br>MS(ESI) m/z: 626([M + H]+) |
| 1355 | 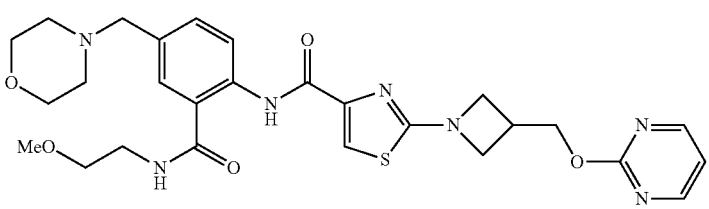 | E28<br>MS(ESI) m/z: 568([M + H]+) |
| 1356 | 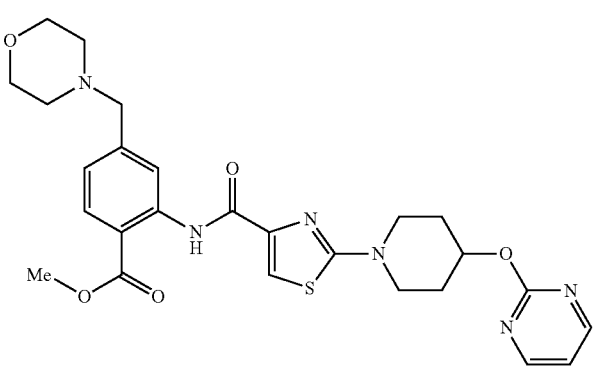 | E6<br>MS(ESI) m/z: 539([M + H]+) |

TABLE 172
| | | |
|---|---|---|
| 1184 | 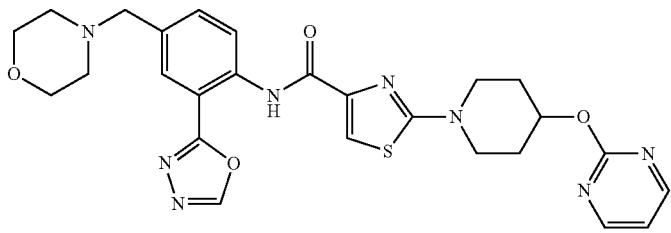 | E1184<br>MS(ESI) m/z: 549([M + H]+) |
| 1357 | 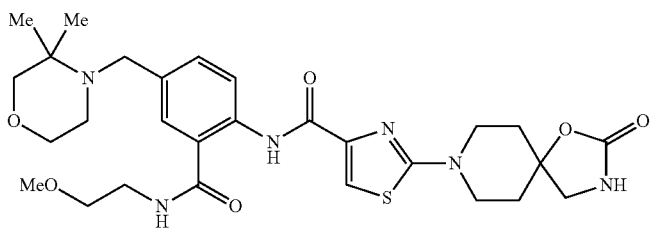 | E28<br>MS(ESI) m/z: 587([M + H]+) |
| 1358 | 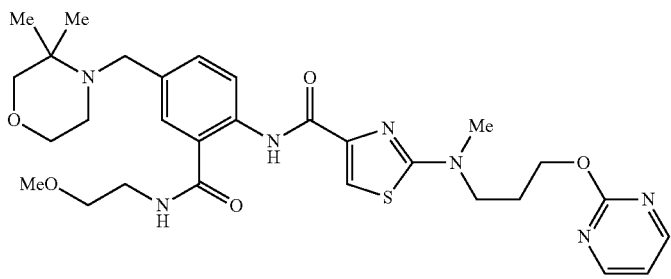 | E23 (L-Tart)<br>MS(ESI) m/z: 598([M + H]+) |
| 1359 | 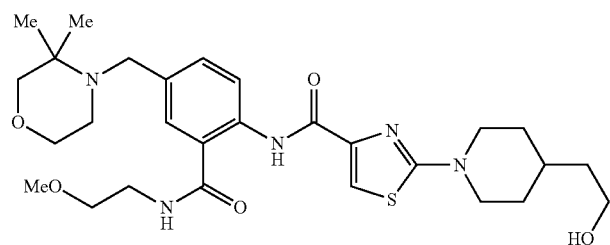 | E28<br>MS(ESI) m/z: 560([M + H]+) |
| 1360 | 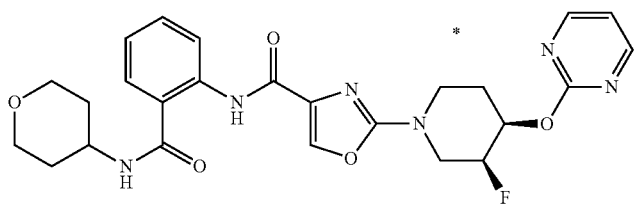 | E26<br>MS(ESI) m/z: 511([M + H]+) |
| 1361 | 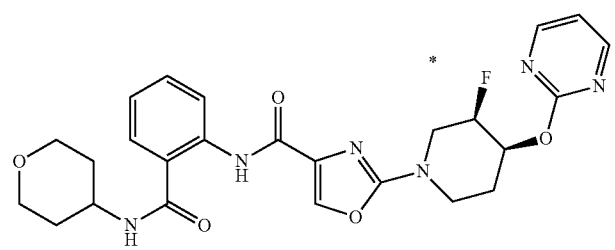 | E26<br>MS(ESI) m/z: 511([M + H]+) |

TABLE 172-continued
| | | |
|---|---|---|
| 1362 | 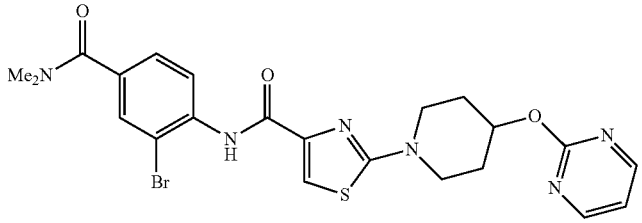 | E26<br>MS(ESI) m/z: 531, 533([M + H]+) |
| 1363 | 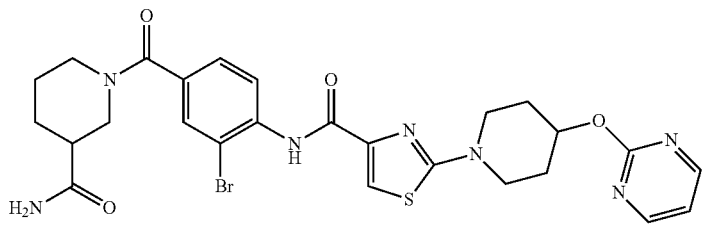 | E26<br>MS(ESI) m/z: 614, 616([M + H]+) |
TABLE 173
| | | |
|---|---|---|
| 1364 | 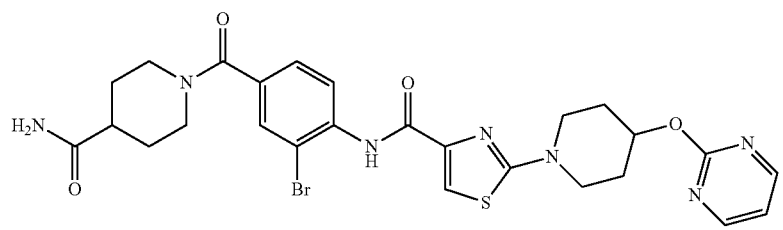 | E26<br>MS(ESI) m/z: 614, 616([M + H]+) |
| 1365 | 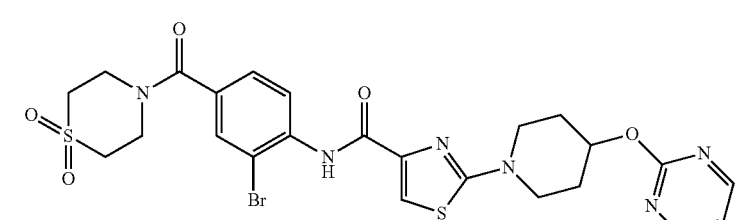 | E26<br>MS(ESI) m/z: 621, 623([M + H]+) |
| 1366 | 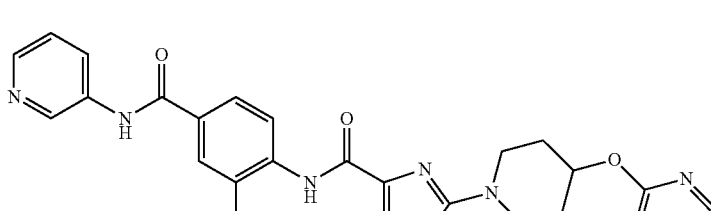 | E26<br>MS(ESI) m/z: 580, 582([M + H]+) |
| 1367 | 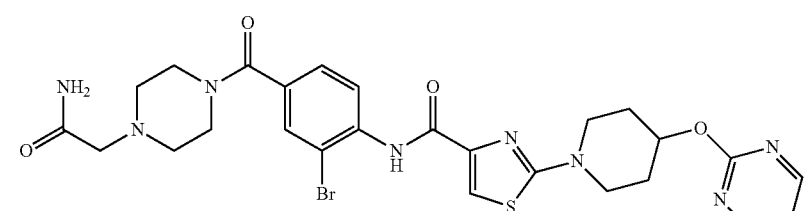 | E26<br>MS(ESI) m/z: 629, 631([M + H]+) |

TABLE 173-continued
| | | |
|---|---|---|
| 1368 | 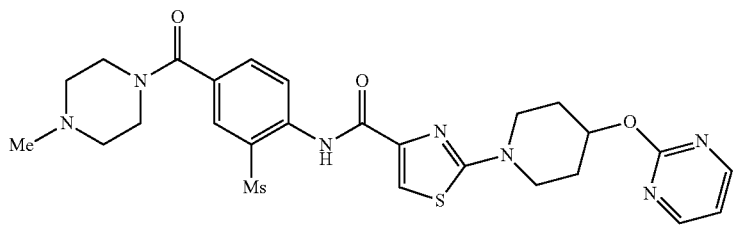 | E26<br>MS(ESI) m/z: 586([M + H]+) |
| 1369 | 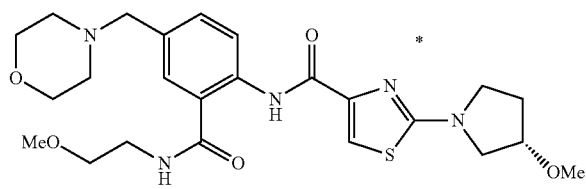 | E28<br>MS(ESI) m/z: 504([M + H]+) |
| 1370 | 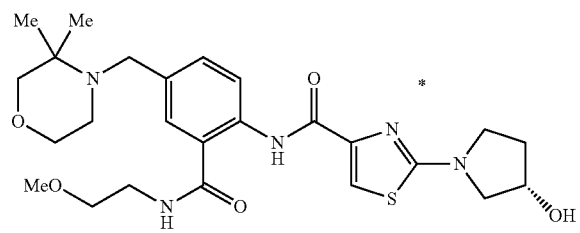 | E23<br>MS(ESI) m/z: 518([M + H]+) |
| 1371 | 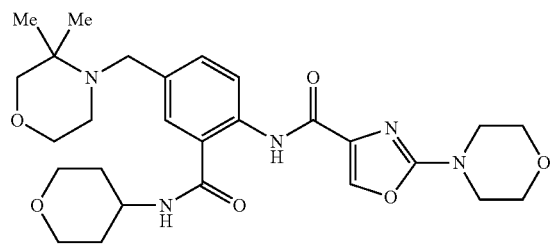 | E26<br>MS(ESI) m/z: 528([M + H]+) |
TABLE 174
| | | |
|---|---|---|
| 1372 | 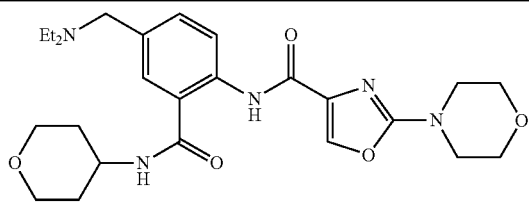 | E26<br>MS(ESI) m/z: 486([M + H]+) |
| 1373 | 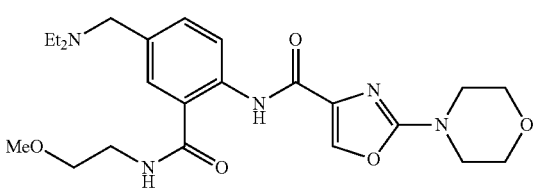 | E26<br>MS(ESI) m/z: 460([M + H]+) |
| 1374 | 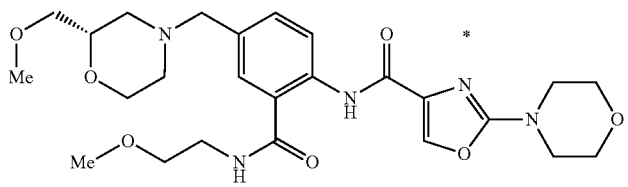 | E26<br>MS(ESI) m/z: 518([M + H]+) |

TABLE 174-continued
| | | |
|---|---|---|
| 1375 | 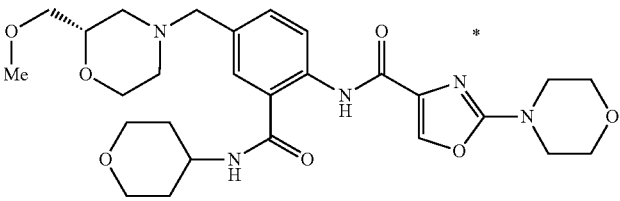 | E26<br>MS(ESI) m/z: 544([M + H]+) |
| 1376 | 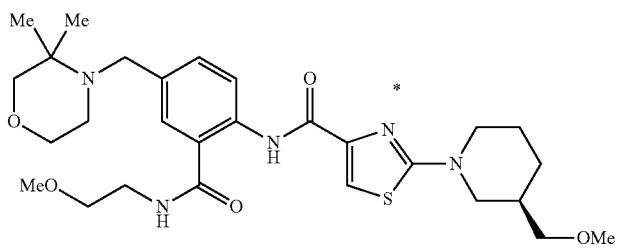 | E28 (HCl)<br>MS(ESI) m/z: 560([M + H]+) |
| 1377 | 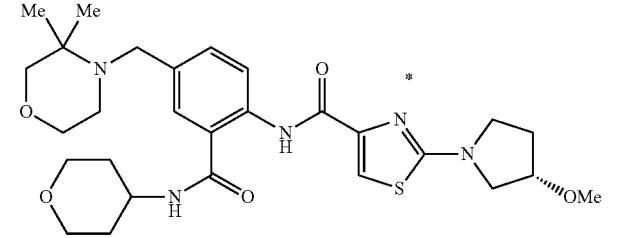 | E26<br>MS(ESI) m/z: 558([M + H]+) |
| 1378 | 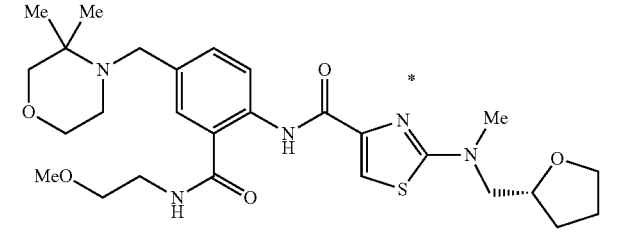 | E28<br>MS(ESI) m/z: 546([M + H]+) |
| 1379 | 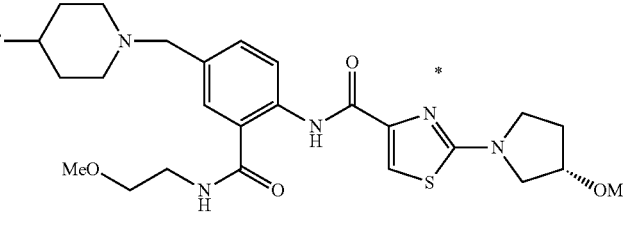 | E1181<br>MS(ESI) m/z: 520([M + H]+) |
TABLE 175
| | | |
|---|---|---|
| 1380 | 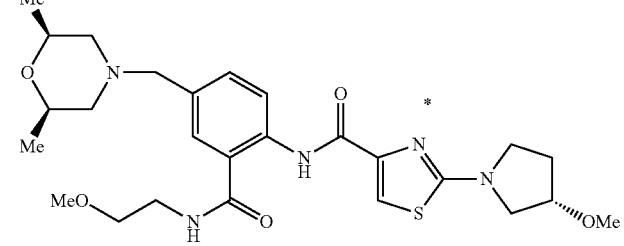 | E1181<br>MS(ESI) m/z: 532([M + H]+) |

TABLE 175-continued

| # | Structure | Notes |
|---|---|---|
| 1381 | 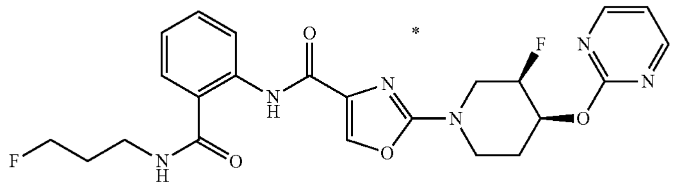 | E26<br>MS(ESI) m/z: 487([M + H]+) |
| 1382 | 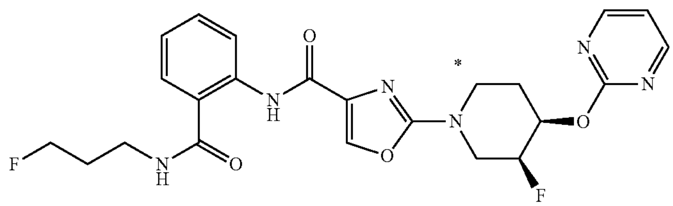 | E26<br>MS(ESI) m/z: 487([M + H]+) |
| 1383 | 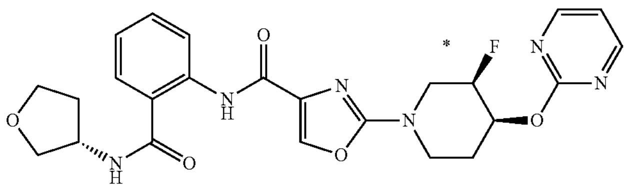 | E26<br>MS(ESI) m/z: 497([M + H]+) |
| 1384 | 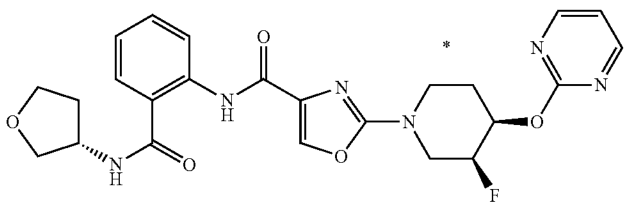 | E26<br>MS(ESI) m/z: 497([M + H]+) |
| 1385 | 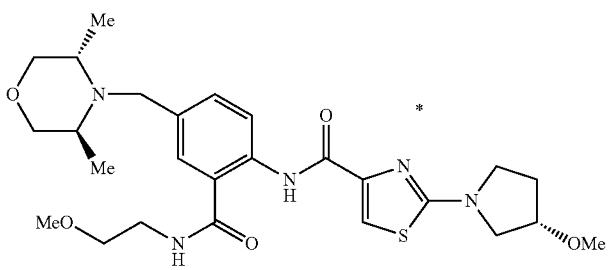 | E1181 (Fum)<br>MS(ESI) m/z: 532([M + H]+) |
| 1386 | 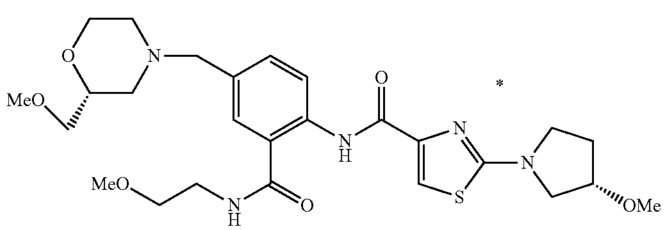 | E1181 (Fum)<br>MS(ESI) m/z: 548([M + H]+) |
| 1387 | 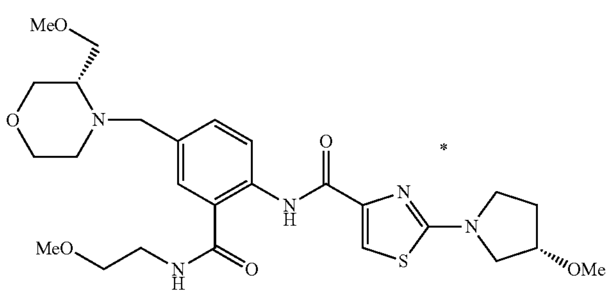 | E1181 (Fum)<br>MS(ESI) m/z: 548([M + H]+) |

TABLE 176
| | | | |
|---|---|---|---|
| 1388 | 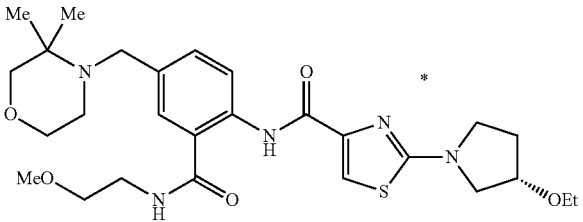 | | E28 (Fum)<br>MS(ESI) m/z: 546([M + H]+) |
| 1389 | 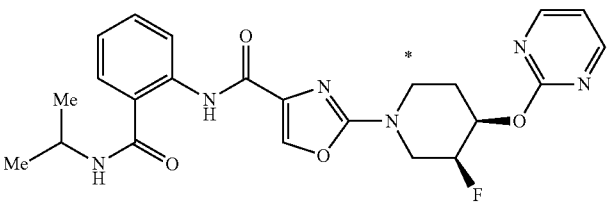 | | E26<br>MS(ESI) m/z: 469([M + H]+) |
| 1390 | 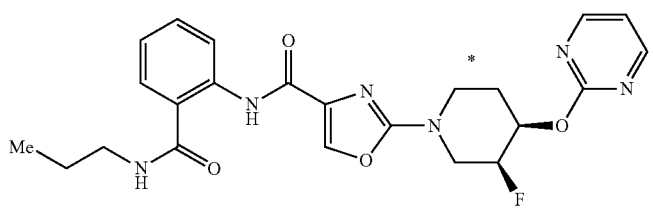 | | E26<br>MS(ESI) m/z: 467([M − H]−) |
| 1391 | 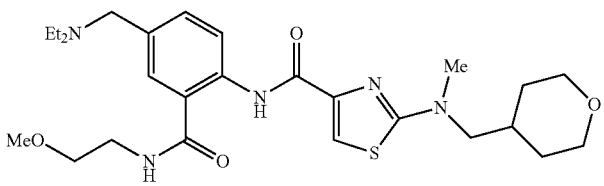 | | E28 (Fum)<br>MS(ESI) m/z: 518([M + H]+) |
| 1392 | 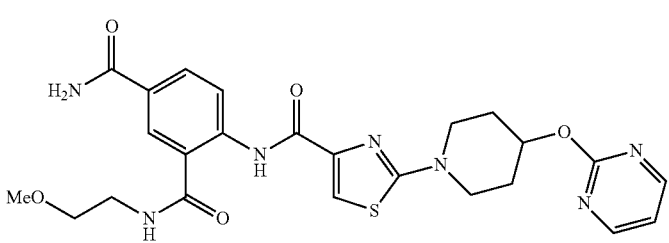 | | E26<br>MS(ESI) m/z: 526([M + H]+) |
| 1393 | 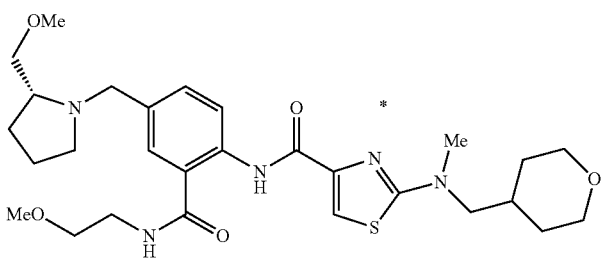 | | E28 (L-Tart)<br>MS(ESI) m/z: 560([M + H]+) |
| 1394 | 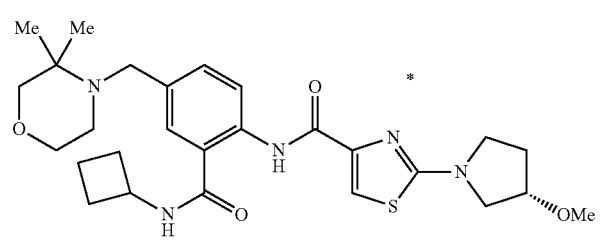 | | E1187 (1.5 Fum)<br>MS(ESI) m/z: 528([M + H]+) |

TABLE 176-continued

| 1187 | [structure] | E1187 (Fum) MS(ESI) m/z: 534([M + H]+) |

TABLE 177

| 1395 | [structure] | E1181 (Fum) MS(ESI) m/z: 518([M + H]+) |
| 1396 | [structure] | E1181 (Fum) MS(ESI) m/z: 532([M + H]+) |
| 1397 | [structure] | E1187 MS(ESI) m/z: 488([M + H]+) |
| 1398 | [structure] | E1187 (Fum) MS(ESI) m/z: 516([M + H]+) |
| 1399 | [structure] | E1187 (Fum) MS(ESI) m/z: 544([M + H]+) |

TABLE 177-continued

| | | |
|---|---|---|
| 1400 | [structure] | E1187 (Fum)<br>MS(ESI) m/z: 544([M + H]+) |
| 1401 | [structure] | E1187 (Fum)<br>MS(ESI) m/z: 520([M + H]+) |
| 1402 | [structure] | E28 (Fum)<br>MS(ESI) m/z: 546([M + H]+) |

TABLE 178

| | | |
|---|---|---|
| 1403 | [structure] | E26 (Fum)<br>MS(ESI) m/z: 506([M + H]+) |
| 1404 | [structure] | E33→E26<br>MS(FAB) m/z: 504([M + H]+) |
| 1405 | [structure] | E30<br>MS(FAB) m/z: 452([M + H]+) |

TABLE 178-continued
| 1406 | | E1181<br>MS(ESI) m/z: 504([M + H]+) |
| 1407 | | E1181<br>MS(ESI) m/z: 550([M + H]+) |
| 1408 | | E1181 (1.5 Fum)<br>MS(ESI) m/z: 520([M + H]+) |
| 1409 | | E1181 (Fum)<br>MS(ESI) m/z: 534([M + H]+) |
| 1410 | | E30<br>MS(FAB) m/z: 516([M + H]+) |
TABLE 179
| 1411 |  | E1181 (1.5 Fum)<br>MS(ESI) m/z: 504([M + H]+) |

TABLE 179-continued

| # | Structure | Notes |
|---|---|---|
| 1412 | (structure) | E1181 (1.5 Fum)<br>MS(ESI) m/z: 520([M + H]+) |
| 1413 | (structure) | E1181 (1.5 Fum)<br>MS(ESI) m/z: 534([M + H]+) |
| 1414 | (structure) | E1181 (Fum)<br>MS(ESI) m/z: 534([M + H]+) |
| 1415 | (structure) | E1181 (Fum)<br>MS(ESI) m/z: 534([M + H]+) |
| 1416 | (structure) | E26 (Fum)<br>MS(ESI) m/z: 502([M + H]+) |
| 1417 | (structure) | E1181 (HCl)<br>MS(ESI) m/z: 552([M + H]+) |
| 1418 | (structure) | E26 (Fum)<br>MS(ESI) m/z: 516([M + H]+) |

TABLE 180
| | | |
|---|---|---|
| 1419 | 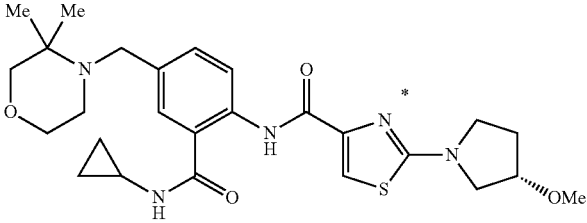 | E26 (Fum)<br>MS(ESI) m/z: 514([M + H]+) |
| 1420 | 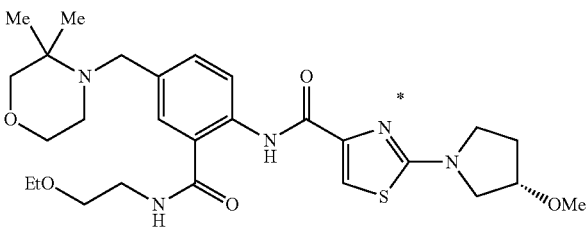 | E26 (1.5 Fum)<br>MS(ESI) m/z: 546([M + H]+) |
| 1421 | 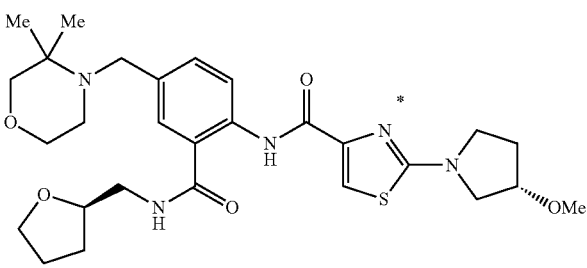 | E26 (1.5 Fum)<br>MS(ESI) m/z: 558([M + H]+) |
| 1422 | 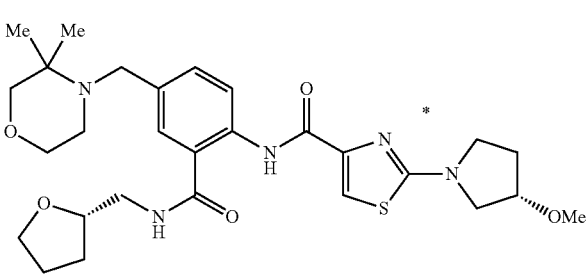 | E26<br>MS(ESI) m/z: 558([M + H]+) |
| 1423 | 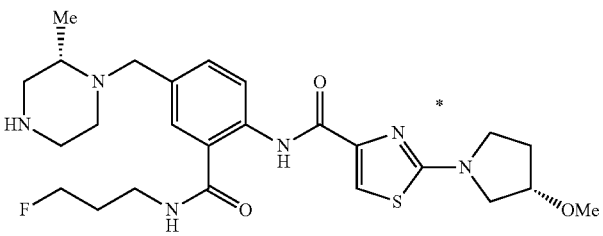 | E35 (3HCl)<br>MS(ESI) m/z: 519([M + H]+) |
| 1424 | 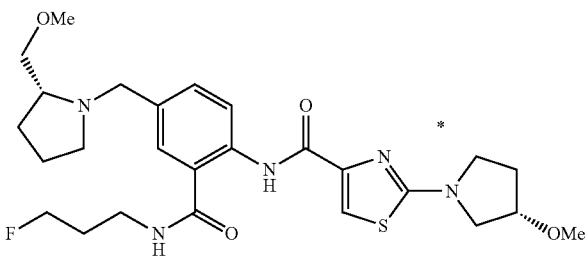 | E1181 (Fum)<br>MS(ESI) m/z: 534([M + H]+) |

TABLE 180-continued

| | | |
|---|---|---|
| 1425 | [structure] | E26<br>MS(ESI) m/z: 516([M + H]+) |
| 1426 | [structure] | E26<br>MS(ESI) m/z: 492([M + H]+) |

TABLE 181

| | | |
|---|---|---|
| 1427 | [structure] | E26 (1.5 Fum)<br>MS(ESI) m/z: 546([M + H]+) |
| 1428 | [structure] | E24 (Fum)<br>MS(ESI) m/z: 520([M + H]+) |
| 1429 | [structure] | E24 (Fum)<br>MS(ESI) m/z: 520([M + H]+) |
| 1430 | [structure] | E26<br>MS(ESI) m/z: 504([M + H]+) |
| 1431 | [structure] | E26<br>MS(ESI) m/z: 474([M + H]+) |

TABLE 181-continued
| | | | |
|---|---|---|---|
| 1432 | 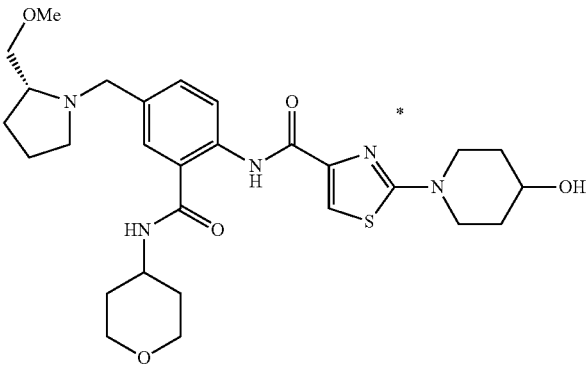 | | E28<br>MS(ESI) m/z: 558([M + H]+) |
| 1433 | 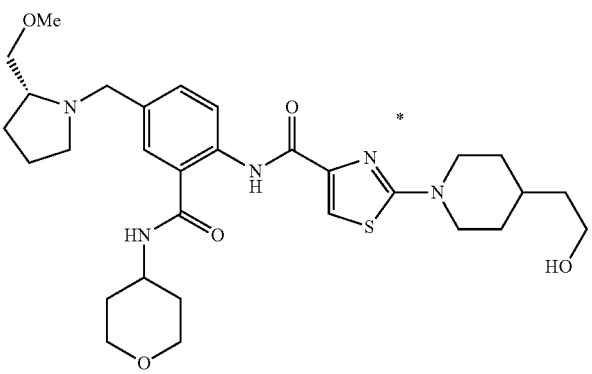 | | E28<br>MS(ESI) m/z: 586([M + H]+) |
| 1434 | 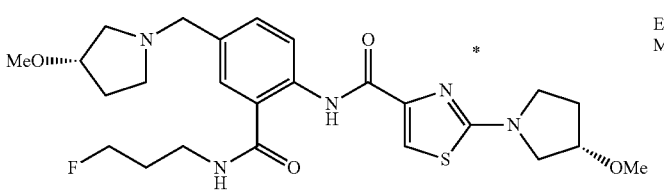 | | E1181 (0.5 L-Tart)<br>MS(ESI) m/z: 520([M + H]+) |
TABLE 182
| | | | |
|---|---|---|---|
| 1435 | 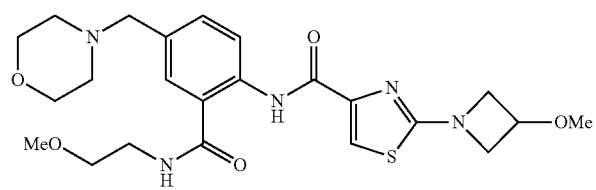 | | E26 (Fum)<br>MS(ESI) m/z: 490([M + H]+) |
| 1436 | 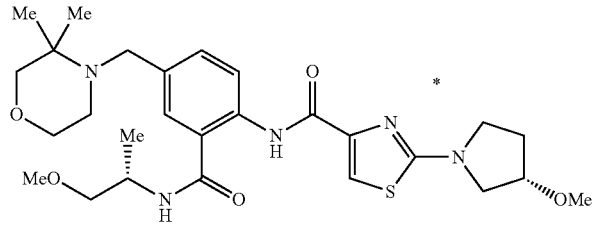 | | E26 (Fum)<br>MS(ESI) m/z: 546([M + H]+) |

TABLE 182-continued

| # | Structure | Ref / MS |
|---|---|---|
| 1185 | (3,3-dimethylmorpholin-4-ylmethyl substituted phenyl with 3-methyl-1,2,4-oxadiazol-5-yl; NH-C(O)-thiazole-2-(3-methoxypyrrolidin-1-yl)) | E1185<br>MS(ESI) m/z: 513([M + H]+) |
| 1437 | (2,3-dihydro-1,4-benzoxazin-4-ylmethyl phenyl; 3-fluoropropyl-NH-C(O); NH-C(O)-thiazole-2-(3-methoxypyrrolidin-1-yl)) | E1181<br>MS(ESI) m/z: 554([M + H]+) |
| 1438 | (morpholinomethyl phenyl; 2-fluoroethyl-NH-C(O); NH-C(O)-thiazole-2-(3-methoxyazetidin-1-yl)) | E26<br>MS(ESI) m/z: 478([M + H]+) |
| 1439 | (morpholinomethyl phenyl; (S)-1-methoxypropan-2-yl-NH-C(O); NH-C(O)-thiazole-2-(3-methoxyazetidin-1-yl)) | E26<br>MS(ESI) m/z: 504([M + H]+) |
| 1440 | (morpholinomethyl phenyl; (S)-tetrahydrofuran-3-yl-NH-C(O); NH-C(O)-thiazole-2-(3-methoxyazetidin-1-yl)) | E26<br>MS(ESI) m/z: 502([M + H]+) |
| 1441 | (2-morpholinoethyl phenyl; 3-fluoropropyl-NH-C(O); NH-C(O)-thiazole-2-(3-methoxypyrrolidin-1-yl)) | E6<br>MS(ESI) m/z: 520([M + H]+) |

TABLE 183
| | | |
|---|---|---|
| 1442 | 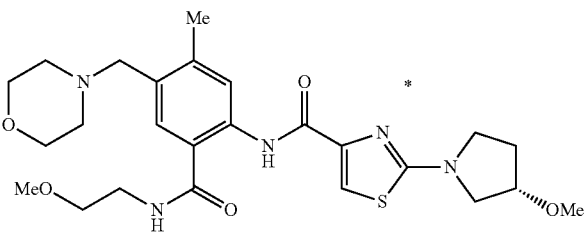 | E6 (Fum)<br>MS(ESI) m/z: 518([M + H]+) |
| 1443 | 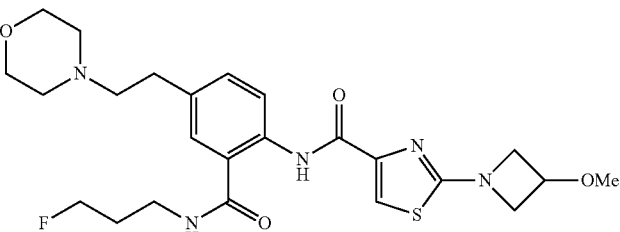 | E6<br>MS(ESI) m/z: 506([M + H]+) |
| 1444 | 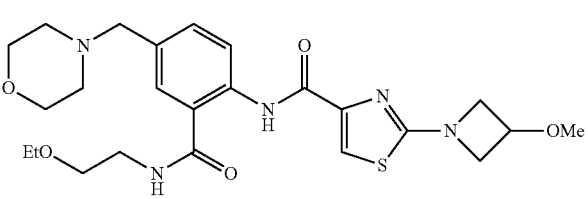 | E26 (Fum)<br>MS(ESI) m/z: 504([M + H]+) |
| 1445 | 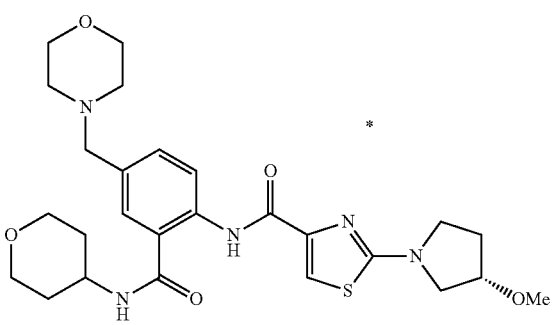 | E26<br>MS(ESI) m/z: 530([M + H]+) |
| 1446 | 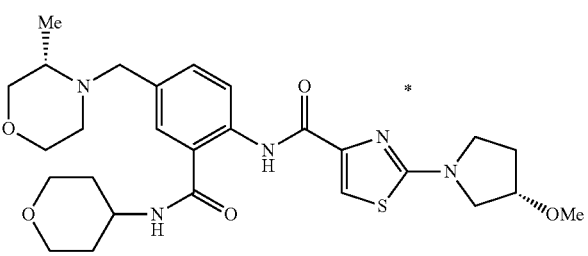 | E1181 (Fum)<br>MS(ESI) m/z: 544([M + H]+) |
| 1447 | 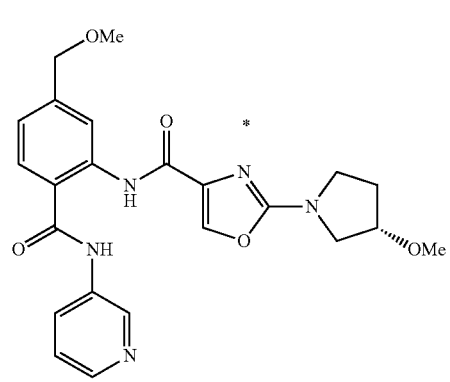 | E9<br>MS(ESI) m/z: 452([M + H]+) |

TABLE 184
| | | |
|---|---|---|
| 1448 | 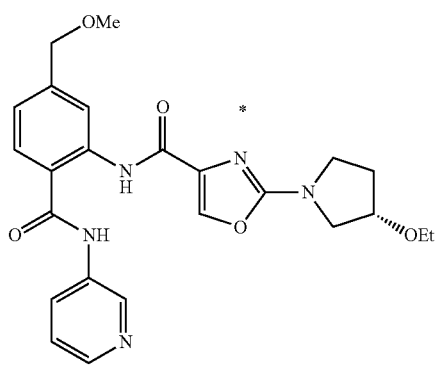 | E9<br>MS(ESI) m/z: 466([M + H]+) |
| 1449 | 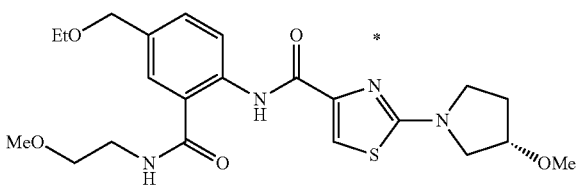 | E1182<br>MS(ESI) m/z: 463([M + H]+) |
| 1450 | 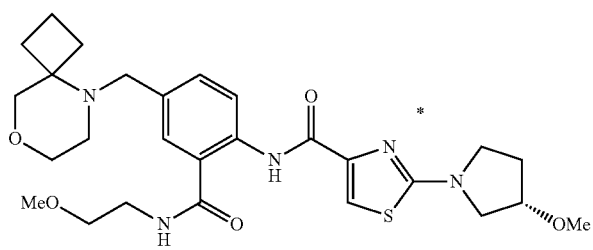 | E1181 (1.5 Fum)<br>MS(ESI) m/z: 544([M + H]+) |
| 1451 | 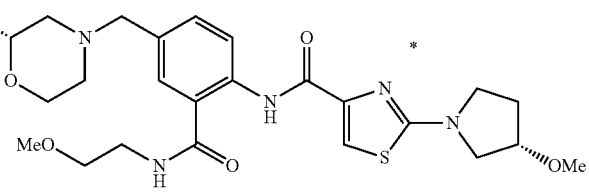 | E1181 (Fum)<br>MS(ESI) m/z: 518([M + H]+) |
| 1181 | 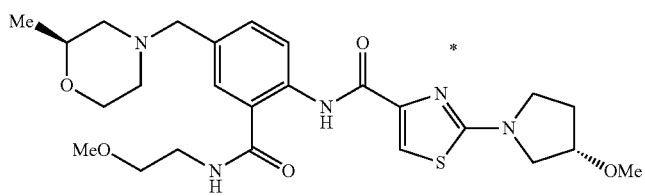 | E1181 (Fum)<br>MS(ESI) m/z: 518([M + H]+) |
| 1452 | 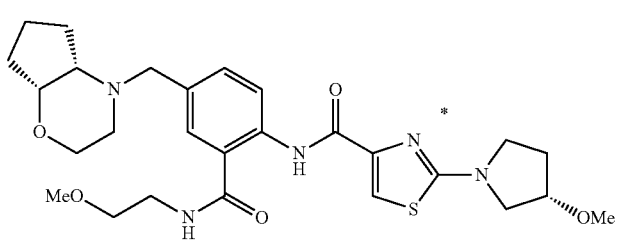 | E1181 (1.5 Fum)<br>MS(ESI) m/z: 544([M + H]+) |

TABLE 184-continued

| | | |
|---|---|---|
| 1453 | [structure] | E1181<br>MS(ESI) m/z: 550([M + H]+) |
| 1454 | [structure] | E1181 (Fum)<br>MS(ESI) m/z: 518([M + H]+) |

TABLE 185

| | | |
|---|---|---|
| 1455 | [structure] | E1181 (1.5 Fum)<br>MS(ESI) m/z: 518([M + H]+) |
| 1456 | [structure] | E24 (3 Fum)<br>MS(ESI) m/z: 533([M + H]+) |
| 1457 | [structure] | E26<br>MS(ESI) m/z: 516([M + H]+) |
| 1458 | [structure] | E26<br>MS(ESI) m/z: 504([M + H]+) |

TABLE 185-continued
| | | |
|---|---|---|
| 1459 | 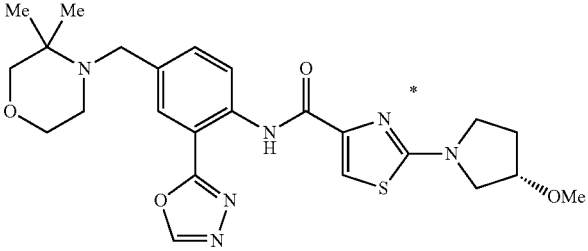 | E1184<br>MS(ESI) m/z: 499([M + H]+) |
| 1460 | 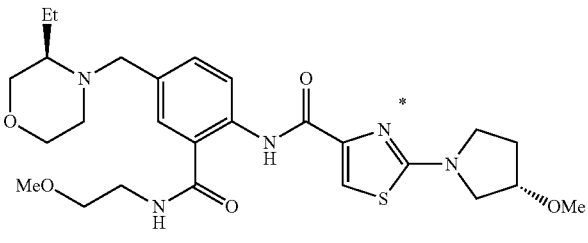 | E1181 (1.5 Fum)<br>MS(ESI) m/z: 532([M + H]+) |
| 1461 | 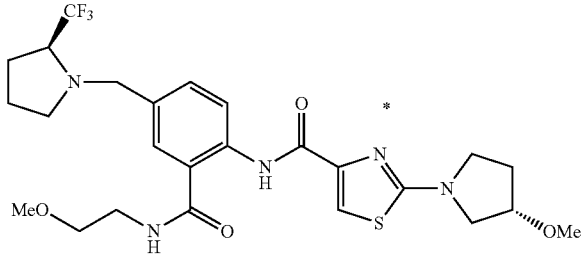 | E1181<br>MS(ESI) m/z: 556([M + H]+) |
| 1462 | 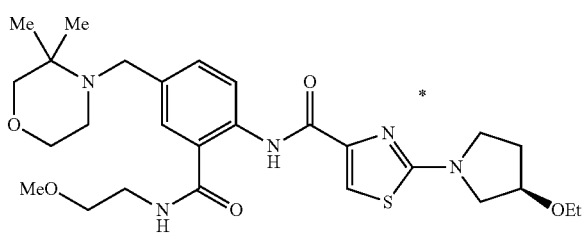 | E6<br>MS(ESI) m/z: 546([M + H]+) |
TABLE 186
| | | |
|---|---|---|
| 1463 | 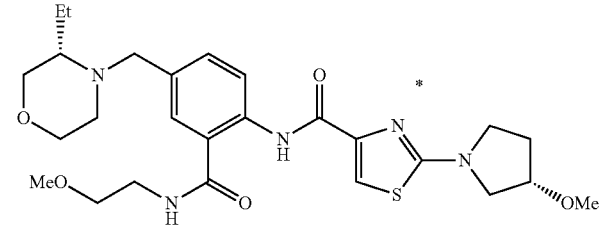 | E1181 (Fum)<br>MS(ESI) m/z: 532([M + H]+) |
| 1464 | 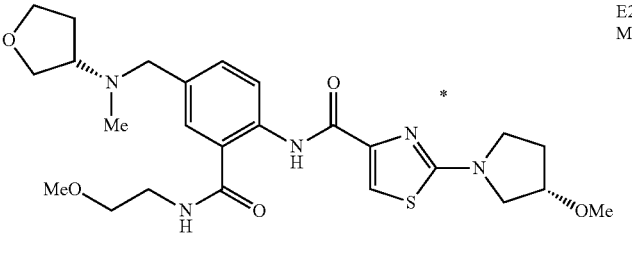 | E24 (Fum)<br>MS(ESI) m/z: 518([M + H]+) |

TABLE 186-continued
| | | |
|---|---|---|
| 1465 |  | E26<br>MS(ESI) m/z: 518([M + H]+) |
| 1466 |  | E26 (Fum)<br>MS(ESI) m/z: 564([M + H]+) |
| 1467 |  | E24 (Fum)<br>MS(ESI) m/z: 488([M + H]+) |
| 1468 |  | E1181<br>MS(ESI) m/z: 548([M + H]+) |
| 1469 |  | E6<br>MS(ESI) m/z: 492([M + H]+) |
| 1470 |  | E6<br>MS(ESI) m/z: 492([M + H]+) |
| 1471 |  | E6 (1.5 Fum)<br>MS(ESI) m/z: 532([M + H]+) |

TABLE 187

| | | | |
|---|---|---|---|
| 1472 | (structure) | E9 | MS(ESI) m/z: 480([M + H]+) |
| 1473 | (structure) | E1181 (Fum) | MS(ESI) m/z: 544([M + H]+) |
| 1474 | (structure) | E6 | MS(ESI) m/z: 488([M − H]−) |
| 1475 | (structure) | E6 | MS(ESI) m/z: 502([M + H]+) |
| 1476 | (structure) | E9 | MS(ESI) m/z: 482([M + H]+) |
| 1477 | (structure) | E26 (HCl) | MS(ESI) m/z: 490([M + H]+) |
| 1478 | (structure) | E6 | MS(ESI) m/z: 518([M + H]+) |

TABLE 187-continued
| | | |
|---|---|---|
| 1182 | 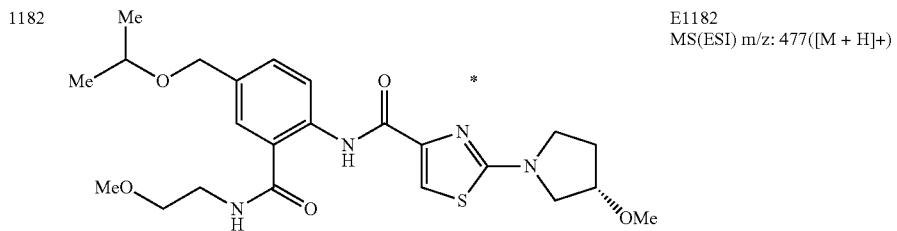 | E1182<br>MS(ESI) m/z: 477([M + H]+) |
TABLE 188
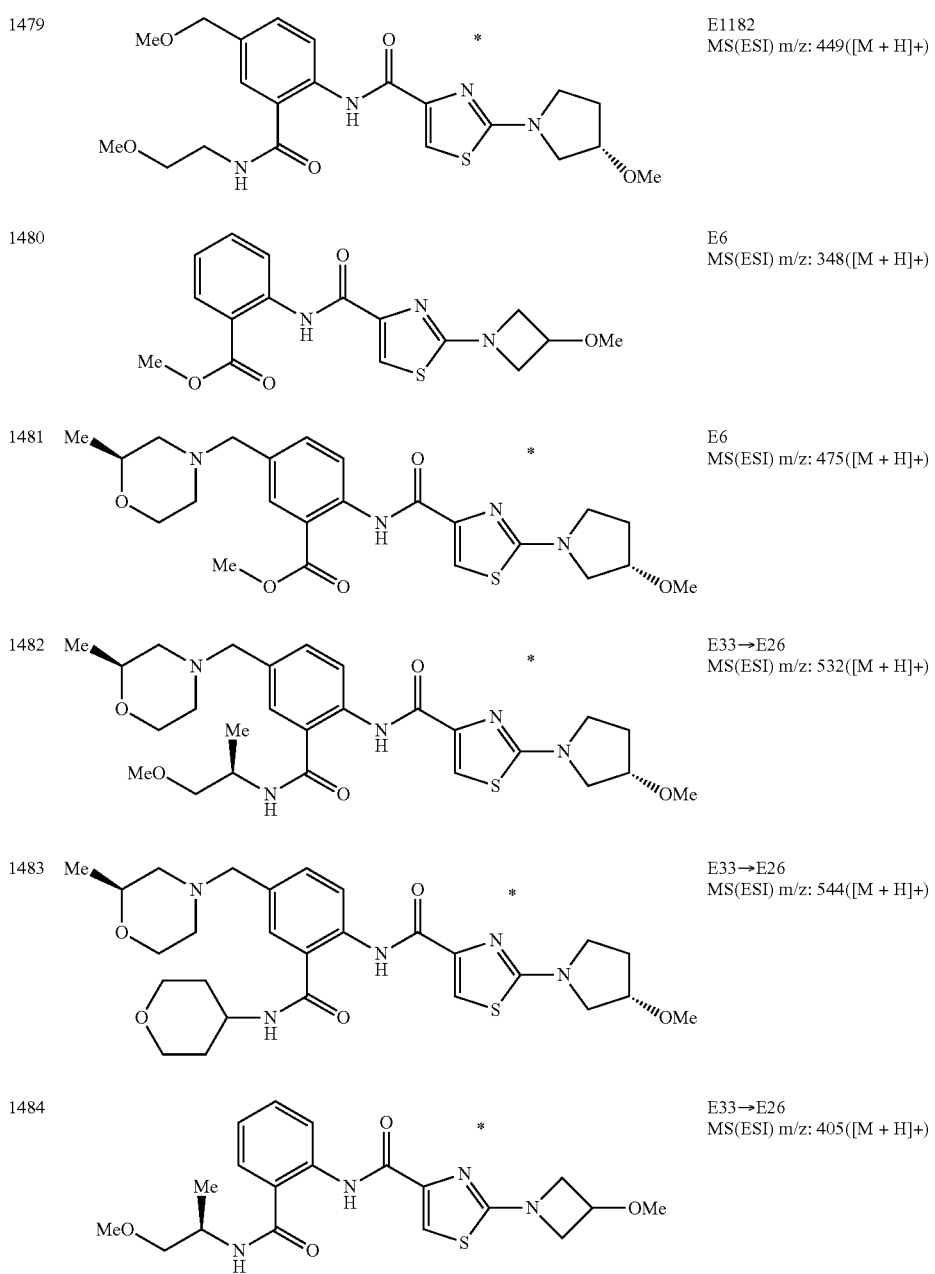
| 1479 | E1182 MS(ESI) m/z: 449([M + H]+) |
| 1480 | E6 MS(ESI) m/z: 348([M + H]+) |
| 1481 | E6 MS(ESI) m/z: 475([M + H]+) |
| 1482 | E33→E26 MS(ESI) m/z: 532([M + H]+) |
| 1483 | E33→E26 MS(ESI) m/z: 544([M + H]+) |
| 1484 | E33→E26 MS(ESI) m/z: 405([M + H]+) |

TABLE 188-continued
| | | |
|---|---|---|
| 1485 | 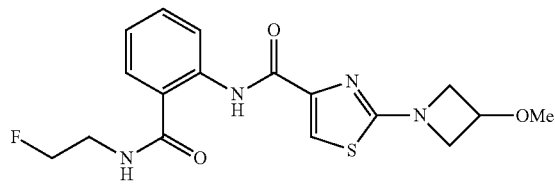 | E33→E26<br>MS(ESI) m/z: 379([M + H]+) |
| 1486 | 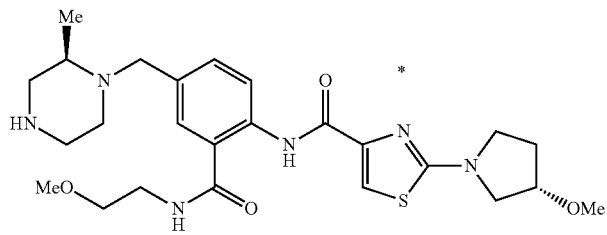 | E35 (3 HCl)<br>MS(ESI) m/z: 517([M + H]+) |
| 1487 | 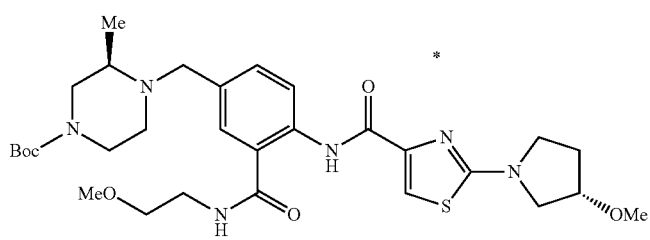 | E1181<br>MS(ESI) m/z: 617([M + H]+) |
TABLE 189
| | | |
|---|---|---|
| 1488 | 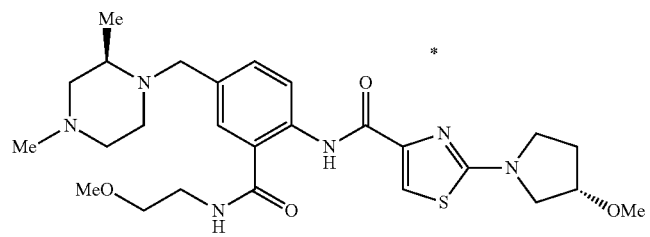 | E24 (2 Fum)<br>MS(ESI) m/z: 531([M + H]+) |
| 1489 | 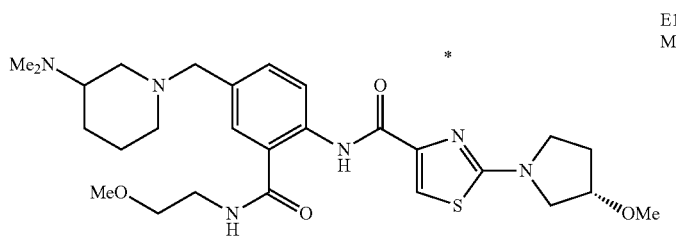 | E1181 (1.5 Fum)<br>MS(ESI) m/z: 545([M + H]+) |
| 1490 | 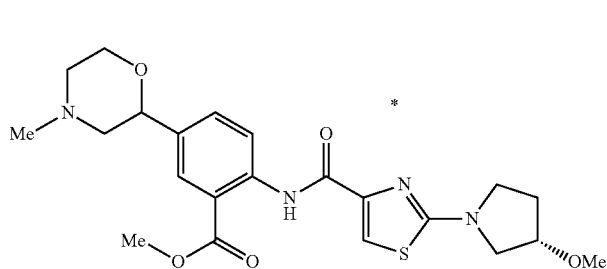 | E6<br>MS(ESI) m/z: 461([M + H]+) |

TABLE 189-continued
| | | |
|---|---|---|
| 1491 | 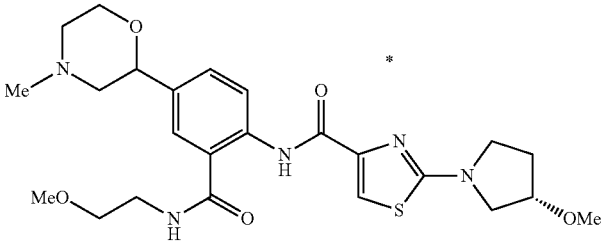 | E33→E26 (Fum)<br>MS(ESI) m/z: 504([M + H]+) |
| 1492 | 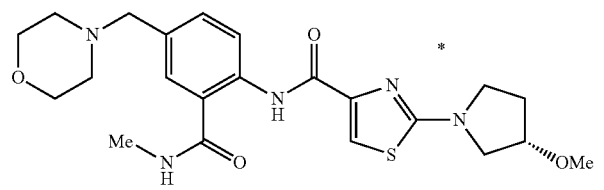 | E26 (Fum)<br>MS(ESI) m/z: 460([M + H]+) |
| 1493 | 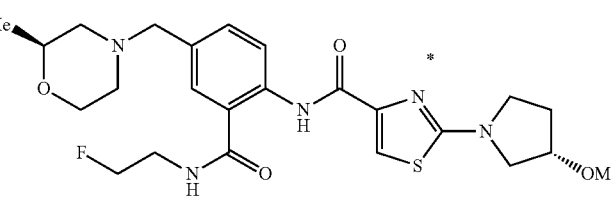 | E33→E26 (Fum)<br>MS(ESI) m/z: 506([M + H]+) |
| 1494 | 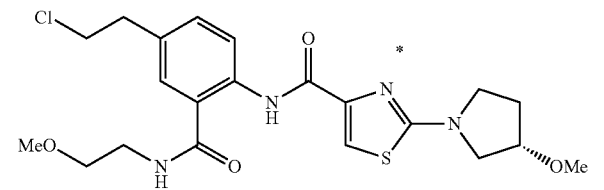 | E1188<br>MS(ESI) m/z: 467([M + H]+) |
| 1190 | 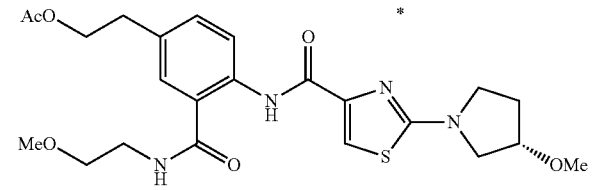 | E1190<br>MS(ESI) m/z: 491([M + H]+) |
TABLE 190
| | | |
|---|---|---|
| 1495 | 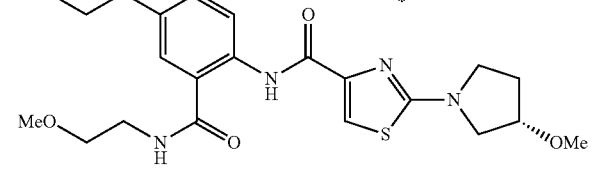 | E33<br>MS(ESI) m/z: 449([M + H]+) |
| 1496 | 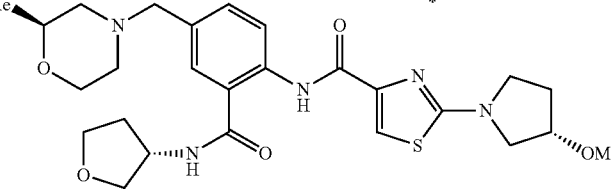 | E33→E26 (1.5 Fum)<br>MS(ESI) m/z: 530([M + H]+) |

TABLE 190-continued

| | | |
|---|---|---|
| 1497 | [structure] | E1182<br>MS(ESI) m/z: 477([M + H]+) |
| 1498 | [structure] | E1182<br>MS(ESI) m/z: 493([M + H]+) |
| 1499 | [structure] | E6<br>MS(ESI) m/z: 408([M + H]+) |
| 1500 | [structure] | E33→E26<br>MS(ESI) m/z: 451([M + H]+) |
| 1501 | [structure] | E6<br>MS(ESI) m/z: 463([M + H]+) |
| 1502 | [structure] | E33→E26<br>MS(ESI) m/z: 506([M + H]+) |
| 1503 | [structure] | E6<br>MS(ESI) m/z: 489([M + H]+) |

TABLE 191
| | | |
|---|---|---|
| 1504 | 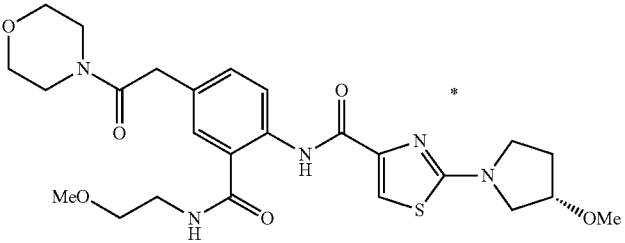 | E33→E26<br>MS(ESI) m/z: 532([M + H]+) |
| 1505 | 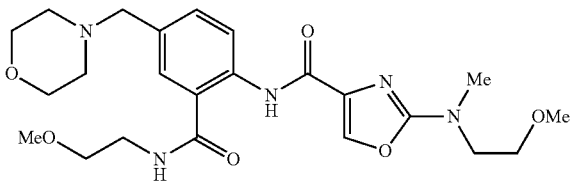 | E6<br>MS(ESI) m/z: 476([M + H]+) |
| 1506 | 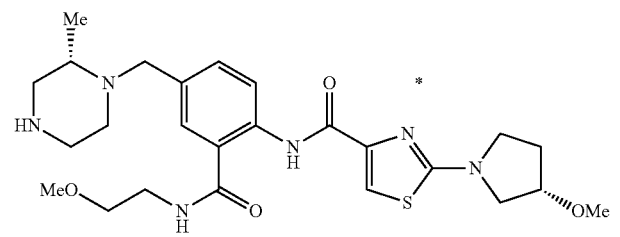 | E35 (3 HCl)<br>MS(ESI) m/z: 517([M + H]+) |
| 1507 | 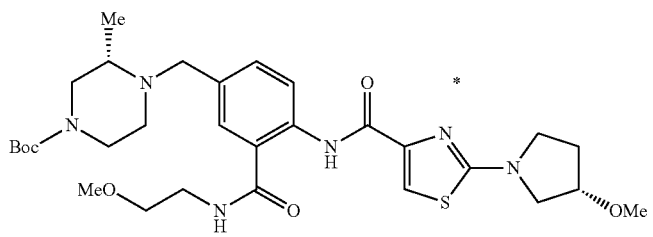 | E1181<br>MS(ESI) m/z: 617([M + H]+) |
| 1508 | 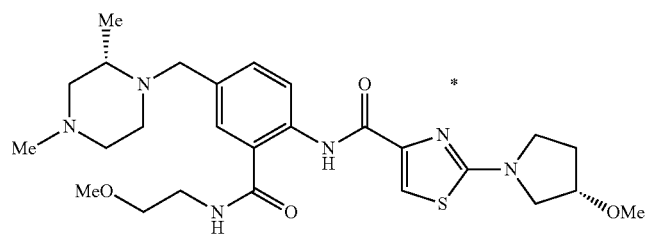 | E24 (2 Fum)<br>MS(ESI) m/z: 531([M + H]+) |
| 1191 | 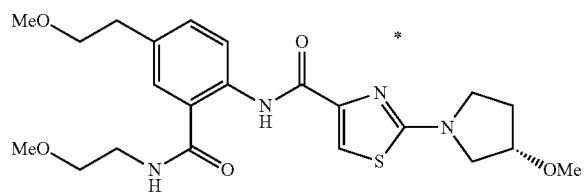 | E1191<br>MS(ESI) m/z: 463([M + H]+) |
| 1509 | 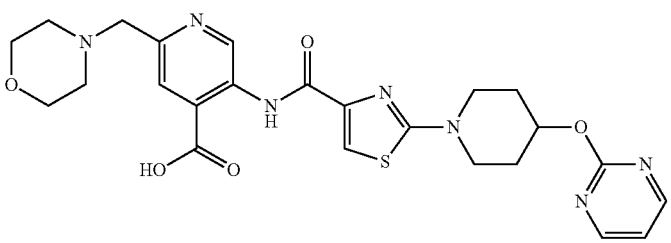 | E6→E33<br>MS(FAB) m/z: 526([M + H]+) |

TABLE 191-continued

| | | |
|---|---|---|
| 1510 | (structure) | E33<br>MS(ESI) m/z: 410([M + H]+) |

TABLE 192

| | | |
|---|---|---|
| 1511 | (structure) | E33<br>MS(ESI) m/z: 437([M + H]+) |
| 1512 | (structure) | E33<br>MS(ESI) m/z: 425([M + H]+) |
| 1513 | (structure) | E33<br>MS(ESI) m/z: 429([M + H]+) |
| 1514 | (structure) | E30<br>MS(ESI) m/z: 437([M − H]−) |
| 1515 | (structure) | P3→E23<br>MS(ESI) m/z: 424([M + H]+) |
| 1516 | (structure) | E23<br>MS(ESI) m/z: 451([M + H]+) |
| 1517 | (structure) | E1188<br>MS(FAB) m/z: 432, 434([M + H]+) |

TABLE 192-continued

| 1188 | (structure) | E1188 MS(ESI) m/z: 453, 455([M + H]+) |
| 1518 | (structure) | E1188 MS(ESI) m/z: 455([M + H]+) |

TABLE 193

| 1519 | (structure) | E1188 MS(ESI) m/z: 479([M + H]+) |
| 1520 | (structure) | E1188 MS(FAB) m/z: 531([M + H]+) |
| 1521 | (structure) | E1181 MS(ESI) m/z: 471([M + H]+) |
| 1522 | (structure) | E1181 MS(ESI) m/z: 513([M + H]+) |

TABLE 193-continued
| | | |
|---|---|---|
| 1523 | 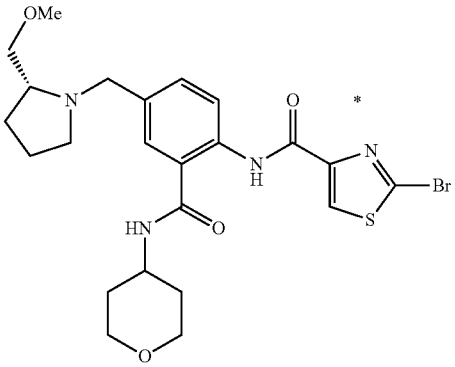 | E6<br>MS(ESI) m/z: 537([M + H]+) |
| 1524 | 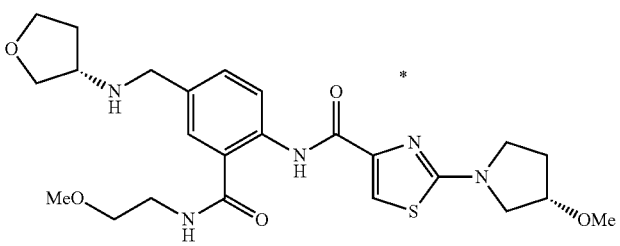 | E1181<br>MS(ESI) m/z: 504([M + H]+) |
| 1525 | 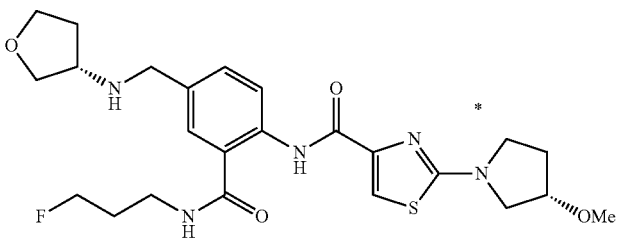 | E1181<br>MS(ESI) m/z: 506([M + H]+) |
TABLE 194
| | | |
|---|---|---|
| 1526 | 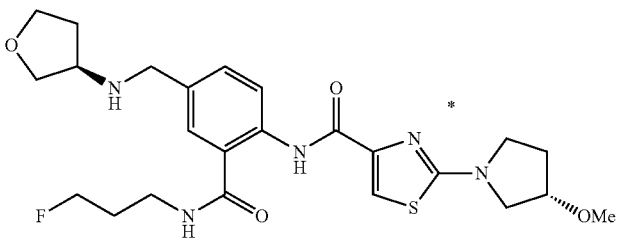 | E1181<br>MS(ESI) m/z: 506([M + H]+) |
| 1527 | 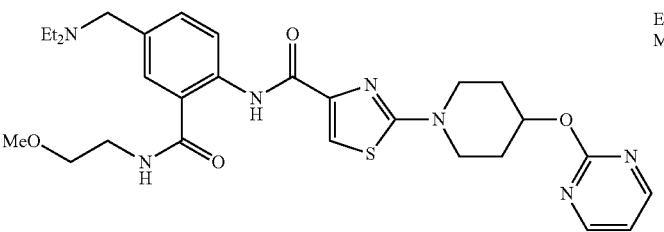 | E1181<br>MS(FAB) m/z: 568([M + H]+) |
| 1528 | 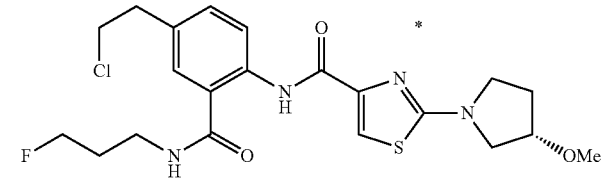 | E1188<br>MS(ESI) m/z: 469([M + H]+) |

TABLE 194-continued
| # | Structure | Ref / MS |
|---|---|---|
| 1529 | 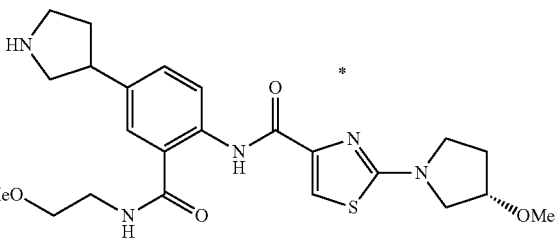 | E35<br>MS(ESI) m/z: 474([M + H]+) |
| 1189 | 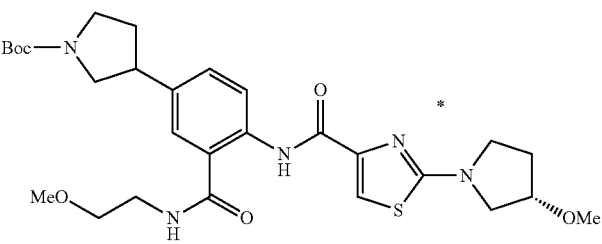 | E1189<br>MS(ESI) m/z: 574([M + H]+) |
| 1530 | 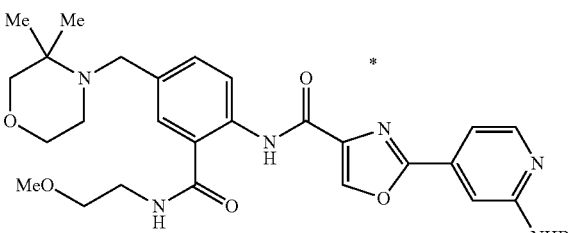 | E30<br>MS(ESI) m/z: 609([M + H]+) |
| 1531 | 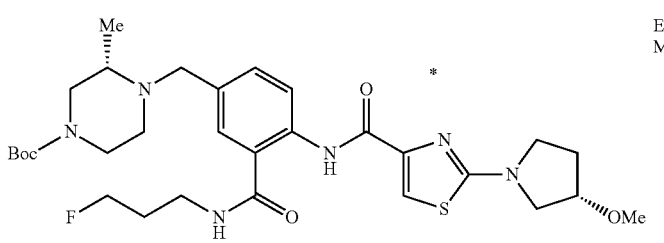 | E1181<br>MS(ESI) m/z: 619([M + H]+) |
| 1532 | 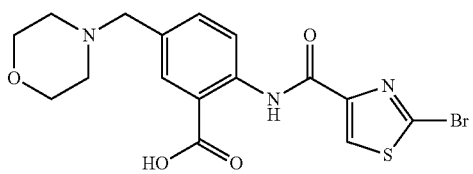 | E33<br>MS(ESI) m/z: 426, 428([M + H]+) |
| 1533 | 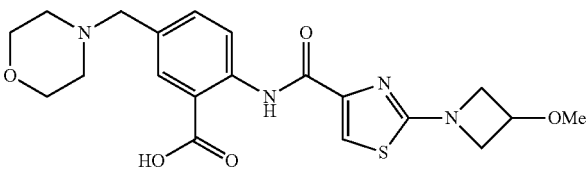 | E33<br>MS(ESI) m/z: 433([M + H]+) |
TABLE 195
| # | Structure | Ref / MS |
|---|---|---|
| 1534 | 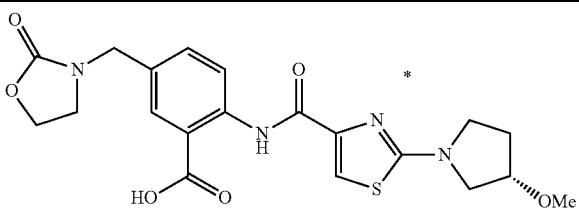 | E33<br>MS(ESI) m/z: 447([M + H]+) |

TABLE 195-continued

| | | | |
|---|---|---|---|
| 1535 | (structure) | | E33 MS(ESI) m/z: 447([M + H]+) |
| 1536 | (structure) | | E33 MS(ESI) m/z: 449([M + H]+) |
| 1537 | (structure) | | E33 MS(ESI) m/z: 459([M + H]+) |
| 1538 | (structure) | | E33 MS(ESI) m/z: 461([M + H]+) |
| 1539 | (structure) | | E33 MS(ESI) m/z: 461([M + H]+) |
| 1540 | (structure) | | E33 MS(ESI) m/z: 463([M + H]+) |
| 1541 | (structure) | | E33 MS(API) m/z: 463([M + H]+) |

TABLE 195-continued
| 1542 | 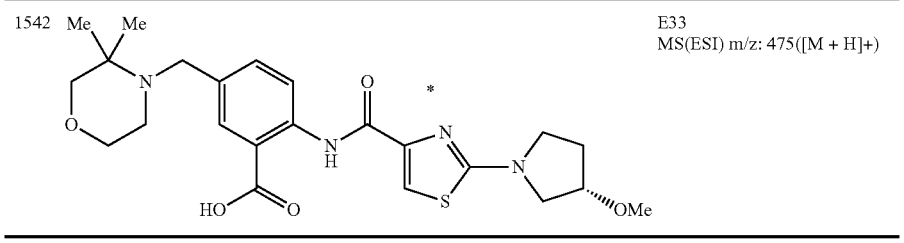 | E33 MS(ESI) m/z: 475([M + H]+) |
TABLE 196
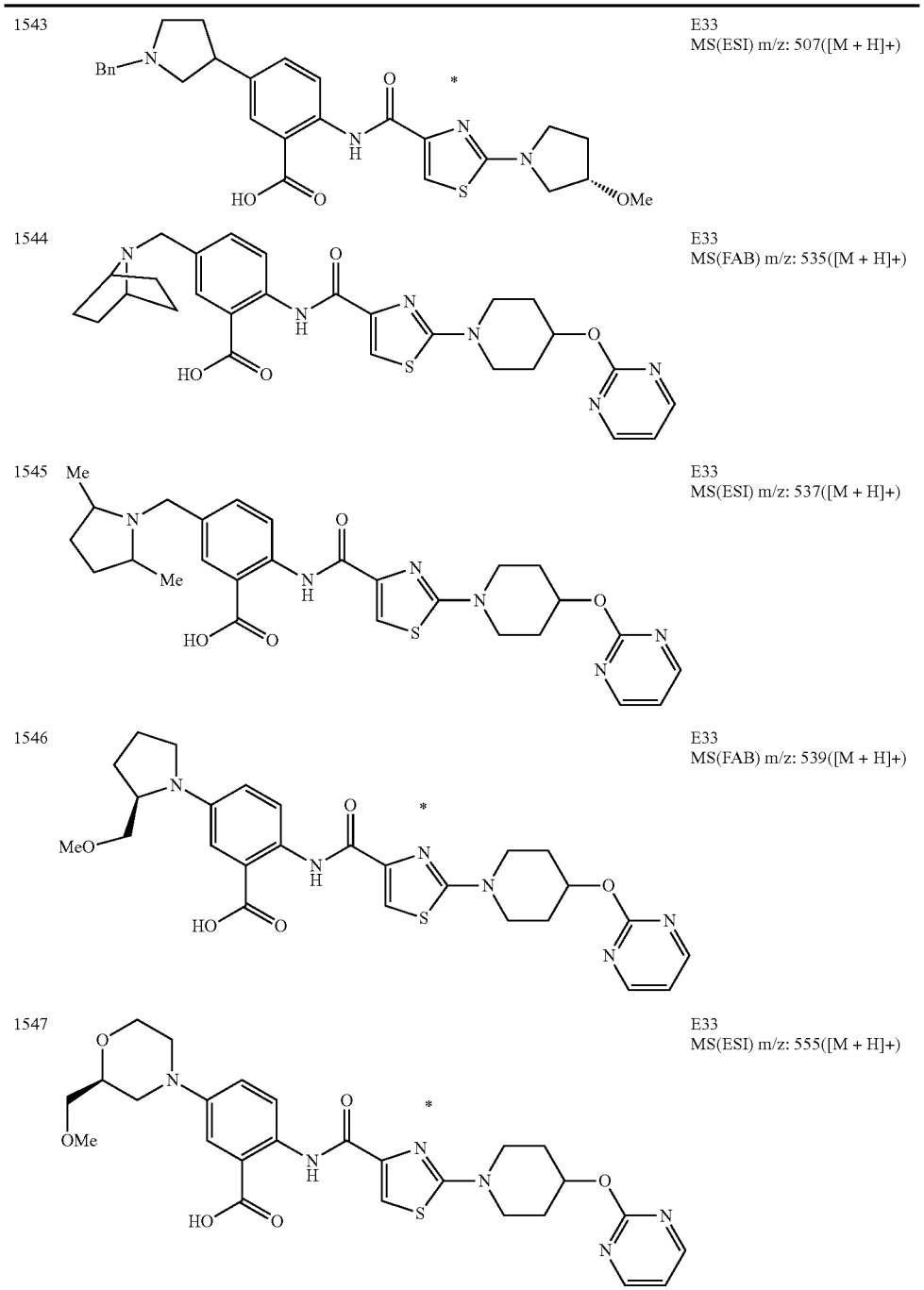
| 1543 | E33 MS(ESI) m/z: 507([M + H]+) |
| 1544 | E33 MS(FAB) m/z: 535([M + H]+) |
| 1545 | E33 MS(ESI) m/z: 537([M + H]+) |
| 1546 | E33 MS(FAB) m/z: 539([M + H]+) |
| 1547 | E33 MS(ESI) m/z: 555([M + H]+) |

TABLE 196-continued

| | | |
|---|---|---|
| 1548 | [structure] | E33 MS(API) m/z: 401([M − H]−) |
| 1549 | [structure] | E33 MS(ESI) m/z: 433([M + H]+) |
| 1550 | [structure] | E33 MS(ESI) m/z: 443([M − H]−) |

TABLE 197

| | | |
|---|---|---|
| 1551 | [structure] | E33 MS(ESI) m/z: 447([M + H]+) |
| 1552 | [structure] | E33 MS(ESI) m/z: 459([M − H]−) |
| 1553 | [structure] | E33 MS(ESI) m/z: 428([M + H]+) |
| 1554 | [structure] | E33 MS(ESI) m/z: 428([M + H]+) |

TABLE 197-continued
| 1555 | 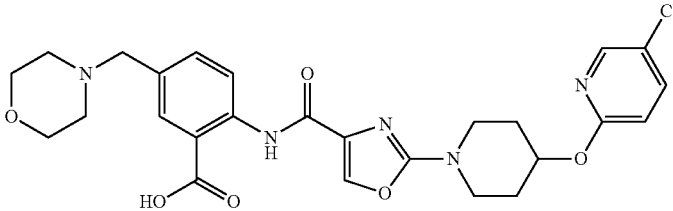 | E33 MS(ESI) m/z: 533([M + H]+) |
| 1556 | 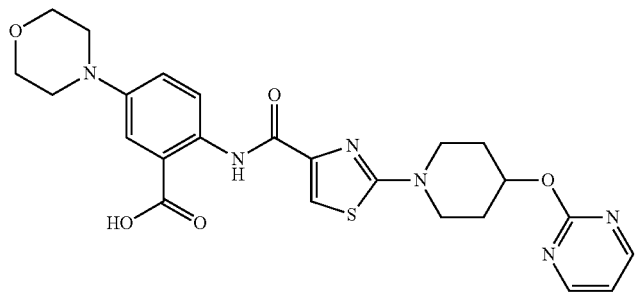 | E33 MS(FAB) m/z: 511([M + H]+) |
| 1557 | 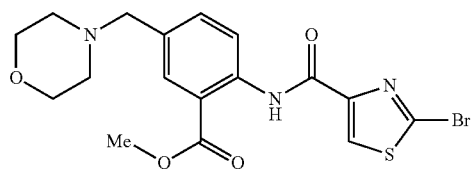 | E30 MS(FAB) m/z: 440, 442([M + H]+) |
| 1558 | 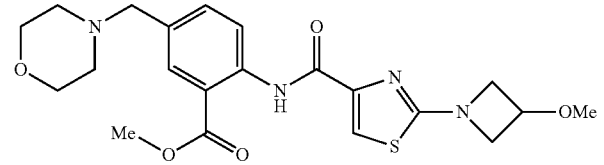 | E6 MS(ESI) m/z: 447([M + H]+) |
TABLE 198
| 1559 | 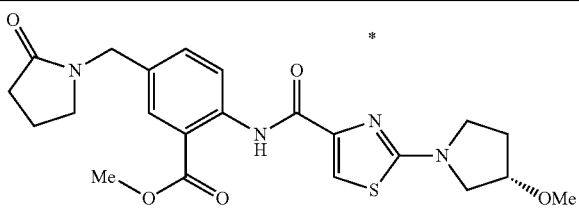 | E6 MS(ESI) m/z: 459([M + H]+) |
| 1560 | 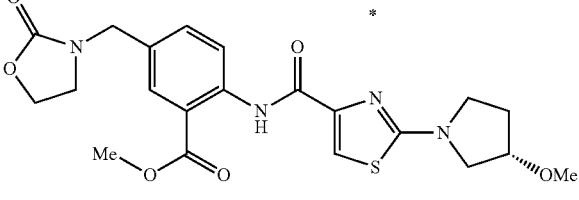 | E6 MS(ESI) m/z: 461([M + H]+) |
| 1561 | 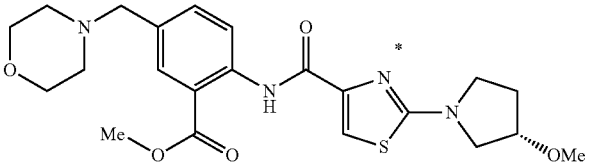 | E6 MS(ESI) m/z: 461([M + H]+) |

TABLE 198-continued

| 1562 | [structure] | E6 MS(ESI) m/z: 473([M + H]+) |
| 1563 | [structure] | E6 MS(ESI) m/z: 475([M + H]+) |
| 1564 | [structure] | E6 MS(ESI) m/z: 475([M + H]+) |
| 1565 | [structure] | E30 MS(ESI) m/z: 477([M + H]+) |
| 1566 | [structure] | E6 MS(ESI) m/z: 477([M + H]+) |
| 1567 | [structure] | E1188 MS(FAB) m/z: 488([M + H]+) |

TABLE 199

| | | |
|---|---|---|
| 1568 | [structure] | E6<br>MS(ESI) m/z: 489([M + H]+) |
| 1569 | [structure] | E6<br>MS(ESI) m/z: 521([M + H]+) |
| 1570 | [structure] | E6<br>MS(FAB) m/z: 549([M + H]+) |
| 1571 | [structure] | E6<br>MS(FAB) m/z: 551([M + H]+) |
| 1572 | [structure] | E1181<br>MS(ESI) m/z: 567([M + H]+) |
| 1573 | [structure] | E6<br>MS(ESI) m/z: 417([M + H]+) |
| 1574 | [structure] | E23<br>MS(ESI) m/z: 461([M + H]+) |

TABLE 199-continued

| | | | |
|---|---|---|---|
| 1575 | (structure) | | E23<br>MS(ESI) m/z: 459([M + H]+) |
| 1576 | (structure) | | E6<br>MS(API) m/z: 475([M + H]+) |

TABLE 200

| | | | |
|---|---|---|---|
| 1577 | (structure) | | E9<br>MS(ESI) m/z: 447([M + H]+) |

TABLE 201

| Ex | R | Syn (Sal) Dat |
|---|---|---|
| 1578 | (CH(Me)NHMe) | E1192<br>MS(ESI) m/z: 476([M + H]+) |
| 1579 | (CH2OMe-CH2NHMe) | E1192<br>MS(ESI) m/z: 492([M + H]+) |
| 1580 | (tetrahydropyran-4-yl-NH) | E1192<br>MS(ESI) m/z: 518([M + H]+) |
| 1581 | (CH(Me)NMe2) | E1192<br>MS(ESI) m/z: 490([M + H]+) |
| 1582 | (C(Me)2-ME-NMe2) | E1192<br>MS(ESI) m/z: 504([M + H]+) |
| 1583 | (CH(Me)CH2-NMe2) | E1192<br>MS(ESI) m/z: 504([M + H]+) |
| 1584 | (MeO-CH2CH2-NMe) | E1192<br>MS(ESI) m/z: 506([M + H]+) |
| 1585 | (MeO-CH2CH2-N-CH(Me)2) | E1192<br>MS(ESI) m/z: 534([M + H]+) |
| 1586 | (MeO-CH2CH2-NEt) | E1192<br>MS(ESI) m/z: 520([M + H]+) |

TABLE 201-continued

[Structure: R-CH2-C6H3(-C(=O)NH-CH2CH2-OMe)-NH-C(=O)-thiazole-N-pyrrolidine-OMe with * marker]

| Ex | R | Syn (Sal) Dat |
|---|---|---|
| 1587 | Me-C(Me)(Me)-O-CH2CH2-N(Me)-* , Me | E1192 MS(ESI) m/z: 548([M + H]+) |
| 1588 | cyclopentyl-N(Me)(Me)-* | E1192 MS(ESI) m/z: 516([M + H]+) |
| 1589 | cyclohexyl-N(Me)(Me)-* | E1192 MS(ESI) m/z: 530([M + H]+) |
| 1590 | tetrahydropyran-4-yl-N(Me)(Me)-* | E1192 MS(ESI) m/z: 532([M + H]+) |
| 1591 | tetrahydropyran-4-yl-CH2-N(Me)(Me)-* | E1192 MS(ESI) m/z: 546([M + H]+) |
| 1592 | 1-Me-piperidin-4-yl-N(Me)(Me)-* | E1192 MS(ESI) m/z: 545([M + H]+) |
| 1593 | 1-Me-piperidin-4-yl-CH2-N(Me)(Me)-* | E1192 MS(ESI) m/z: 559([M + H]+) |
| 1594 | (Me)(Me)CH-N(Et)(Me)-* | E1192 MS(ESI) m/z: 504([M + H]+) |
| 1595 | cyclohexyl-N(CH(Me)(Me))-* | E1192 MS(ESI) m/z: 558([M + H]+) |

TABLE 202

| Ex | R | Syn (Sal) Dat |
|---|---|---|
| 1596 | 3,3-difluoroazetidin-1-yl-* | E1192 MS(ESI) m/z: 510([M + H]+) |
| 1597 | 3-MeO-azetidin-1-yl-* | E1192 MS(ESI) m/z: 504([M + H]+) |
| 1598 | 3-PhO-azetidin-1-yl-* | E1192 MS(ESI) m/z: 566([M + H]+) |
| 1192 | pyrrolidin-1-yl-* | E1192 MS(ESI) m/z: 488([M + H]+) |
| 1599 | (HOCH2)-pyrrolidin-2-yl-* (1-Me) | E1192 MS(ESI) m/z: 518([M + H]+) |
| 1600 | (HOCH2)-pyrrolidin-2-yl-* (1-Me) | E1192 MS(ESI) m/z: 518([M + H]+) |
| 1601 | (H2N-C(=O))-pyrrolidin-2-yl-* (1-Me) | E1192 MS(ESI) m/z: 531([M + H]+) |
| 1602 | (H2N-C(=O))-pyrrolidin-2-yl-* (1-Me) | E1192 MS(ESI) m/z: 531([M + H]+) |
| 1603 | (Me)(Me)CH-pyrrolidin-2-yl-* (1-Me) | E1192 MS(ESI) m/z: 530([M + H]+) |
| 1604 | (Me)(Me)(Me)C-pyrrolidin-2-yl-* (1-Me) | E1192 MS(ESI) m/z: 544([M + H]+) |
| 1605 | cyclopentyl-pyrrolidin-2-yl-* (1-Me) | E1192 MS(ESI) m/z: 556([M + H]+) |

TABLE 202-continued

| | | |
|---|---|---|
| 1606 | MeS-CH2-(N-Me pyrrolidine) * | E1192 MS(ESI) m/z: 548([M + H]+) |
| 1607 | pyrrolidine-N-CH2-(N-Me pyrrolidine) * | E1192 MS(ESI) m/z: 571([M + H]+) |
| 1608 | pyrrolidine-N-CH2-(N-Me pyrrolidine) * | E1192 MS(ESI) m/z: 571([M + H]+) |
| 1609 | 2,5-diMe-N-Me pyrrolidine * | E1192 MS(ESI) m/z: 516([M + H]+) |
| 1610 | 2,5-bis(MeOCH2)-N-Me pyrrolidine * | E1192 MS(ESI) m/z: 576([M + H]+) |
| 1611 | 2,5-bis(MeOCH2)-N-Me pyrrolidine * | E1192 MS(ESI) m/z: 576([M + H]+) |
| 1612 | 2-Ph-N-Me pyrrolidine * | E1192 MS(ESI) m/z: 564([M + H]+) |
| 1613 | 2-(4-pyridyl)-N-Me pyrrolidine * | E1192 MS(ESI) m/z: 565([M + H]+) |

TABLE 203

| | | |
|---|---|---|
| 1614 | 2-(2-pyridyl)-N-Me pyrrolidine * | E1192 MS(ESI) m/z: 565([M + H]+) |
| 1615 | 2-(3-pyridyl)-N-Me pyrrolidine * | E1192 MS(ESI) m/z: 565([M + H]+) |
| 1616 | 2-Bn-N-Me pyrrolidine * | E1192 MS(ESI) m/z: 578([M + H]+) |
| 1617 | 2-(CH2CH2Ph)-N-Me pyrrolidine * | E1192 MS(ESI) m/z: 592([M + H]+) |
| 1618 | 3-Me-N-Me pyrrolidine * | E1192 MS(ESI) m/z: 502([M + H]+) |
| 1619 | 3-Me-N-Me pyrrolidine * | E1192 MS(ESI) m/z: 502([M + H]+) |
| 1620 | 3-F-N-Me pyrrolidine * | E1192 MS(ESI) m/z: 506([M + H]+) |
| 1621 | 3-F-N-Me pyrrolidine * | E1192 MS(ESI) m/z: 506([M + H]+) |
| 1622 | 3,3-diF-N-Me pyrrolidine * | E1192 MS(ESI) m/z: 524([M + H]+) |
| 1623 | 3,3,4,4-tetraF-N-Me pyrrolidine * | E1192 MS(ESI) m/z: 560([M + H]+) |
| 1624 | 3-HO-N-Me pyrrolidine * | E1192 MS(ESI) m/z: 504([M + H]+) |
| 1625 | 3-HO-N-Me pyrrolidine * | E1192 MS(ESI) m/z: 504([M + H]+) |

TABLE 203-continued

| | | |
|---|---|---|
| 1626 | Me₂N, pyrrolidine-N-Me * | E1192 MS(ESI) m/z: 531([M + H]+) |
| 1627 | Me₂N⋯ pyrrolidine-N-Me * | E1192 MS(ESI) m/z: 531([M + H]+) |
| 1628 | AcNH- pyrrolidine-N-Me * | E1192 MS(ESI) m/z: 545([M + H]+) |
| 1629 | AcNH⋯ pyrrolidine-N-Me * | E1192 MS(ESI) m/z: 545([M + H]+) |
| 1630 | Ph- pyrrolidine-N-Me * | E1192 MS(ESI) m/z: 564([M + H]+) |
| 1631 | Ph⋯ pyrrolidine-N-Me * | E1192 MS(ESI) m/z: 564([M + H]+) |
| 1632 | spiro[4.4] N-Me * | E1192 MS(ESI) m/z: 542([M + H]+) |
| 1633 | piperidine-N-Me * | E1192 MS(ESI) m/z: 502([M + H]+) |
| 1634 | tetrahydropyridine-N-Me * | E1192 MS(ESI) m/z: 500([M + H]+) |

TABLE 204

| | | |
|---|---|---|
| 1635 | 2-Me piperidine-N-Me * | E1192 MS(ESI) m/z: 516([M + H]+) |
| 1636 | 2-(CHMe₂) piperidine-N-Me * | E1192 MS(ESI) m/z: 544([M + H]+) |
| 1637 | 2-(CH₂OMe) piperidine-N-Me * | E1192 MS(ESI) m/z: 546([M + H]+) |

TABLE 204-continued

| | | |
|---|---|---|
| 1638 | 2,6-diMe piperidine-N-Me * | E1192 MS(ESI) m/z: 530([M + H]+) |
| 1639 | 3,3-diMe piperidine-N-Me * | E1192 MS(ESI) m/z: 530([M + H]+) |
| 1640 | 3,3-diF piperidine-N-Me * | E1192 MS(ESI) m/z: 538([M + H]+) |
| 1641 | 3-OH piperidine-N-Me * | E1192 MS(ESI) m/z: 518([M + H]+) |
| 1642 | 3-OH⋯ piperidine-N-Me * | E1192 MS(ESI) m/z: 518([M + H]+) |
| 1643 | spiro[5.5] N-Me * | E1192 MS(ESI) m/z: 570([M + H]+) |
| 1644 | 4-Me piperidine-N-Me * | E1192 MS(ESI) m/z: 516([M + H]+) |
| 1645 | 4,4-diMe piperidine-N-Me * | E1192 MS(ESI) m/z: 530([M + H]+) |
| 1646 | 4,4-diF piperidine-N-Me * | E1192 MS(ESI) m/z: 538([M + H]+) |
| 1647 | 4-CH₂OH piperidine-N-Me * | E1192 MS(ESI) m/z: 532([M + H]+) |
| 1648 | 4-OMe piperidine-N-Me * | E1192 MS(ESI) m/z: 532([M + H]+) |
| 1649 | 4-CH(Me)OMe piperidine-N-Me * | E1192 MS(ESI) m/z: 546([M + H]+) |
| 1650 | MeOCH₂CH₂-piperazine-N-Me * | E1192 MS(ESI) m/z: 561([M + H]+) |

TABLE 204-continued

| | | |
|---|---|---|
| 1651 | (1-methylpiperidin-4-yl)-NMe2 | E1192 MS(ESI) m/z: 545([M + H]+) |
| 1652 | 4-(1-methylpiperidin-4-yl)morpholine | E1192 MS(ESI) m/z: 587([M + H]+) |
| 1653 | (1-methylpiperidin-4-yl)methyl-NMe2 | E1192 MS(ESI) m/z: 559([M + H]+) |
| 1654 | 1-methylpiperidine-4-carboxamide | E1192 MS(ESI) m/z: 545([M + H]+) |
| 1655 | N-methyl-1-methylpiperidine-4-carboxamide | E1192 MS(ESI) m/z: 559([M + H]+) |

TABLE 205

| | | |
|---|---|---|
| 1656 | N,N-dimethyl-1-methylpiperidine-4-carboxamide | E1192 MS(ESI) m/z: 573([M + H]+) |
| 1657 | 4-phenoxy-1-methylpiperidine | E1192 MS(ESI) m/z: 594([M + H]+) |
| 1658 | 2-methyl-8-methyl-2,8-diazaspiro[4.5]decan-1-one | E1192 MS(ESI) m/z: 585([M + H]+) |
| 1659 | (4-methylmorpholin-3-yl)methanol | E1192 MS(ESI) m/z: 534([M + H]+) |
| 1660 | 3-phenyl-4-methylmorpholine | E1192 MS(ESI) m/z: 580([M + H]+) |
| 1661 | 3-benzyl-4-methylmorpholine | E1192 MS(ESI) m/z: 594([M + H]+) |
| 1662 | 1,4-dimethylpiperazine | E1192 MS(ESI) m/z: 517([M + H]+) |
| 1663 | 1-(1-methylethyl)-4-methylpiperazine | E1192 MS(ESI) m/z: 545([M + H]+) |
| 1664 | 1-(2,2,2-trifluoroethyl)-4-methylpiperazine | E1192 MS(ESI) m/z: 585([M + H]+) |
| 1665 | 7-methyl-octahydropyrrolo[1,2-a]pyrazine | E1192 MS(ESI) m/z: 543([M + H]+) |
| 1666 | 1,2-dimethyl-1,2,3,4-tetrahydropyrrolo[1,2-a]pyrazine | E1192 MS(ESI) m/z: 553([M + H]+) |
| 1667 | 4-methylpiperazin-2-one | E1192 MS(ESI) m/z: 517([M + H]+) |
| 1668 | 1,4-dimethylpiperazin-2-one | E1192 MS(ESI) m/z: 531([M + H]+) |
| 1669 | 3,4-dimethylpiperazin-2-one | E1192 MS(ESI) m/z: 531([M + H]+) |
| 1670 | 3,3,4-trimethylpiperazin-2-one | E1192 MS(ESI) m/z: 545([M + H]+) |
| 1671 | 1-acetyl-4-methylpiperazine | E1192 MS(ESI) m/z: 545([M + H]+) |
| 1672 | N,N-dimethyl-4-methylpiperazine-1-carboxamide | E1192 MS(ESI) m/z: 574([M + H]+) |

TABLE 205-continued
| | | |
|---|---|---|
| 1673 | 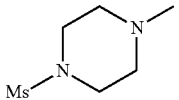 | E1192 MS(ESI) m/z: 581([M + H]+) |
| 1674 | 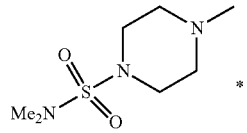 | E1192 MS(ESI) m/z: 610([M + H]+) |
| 1675 | 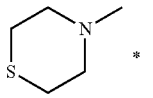 | E1192 MS(ESI) m/z: 520([M + H]+) |
| 1676 | 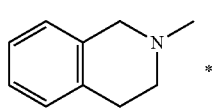 | E1192 MS(ESI) m/z: 550([M + H]+) |
| 1677 | 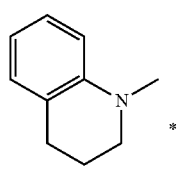 | E1192 MS(ESI) m/z: 550([M + H]+) |
TABLE 206
| | | |
|---|---|---|
| 1678 | 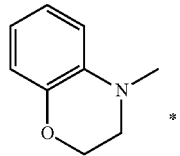 | E1192 MS(ESI) m/z: 552([M + H]+) |
| 1679 | 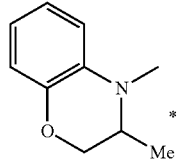 | E1192 MS(ESI) m/z: 566([M + H]+) |
| 1680 | 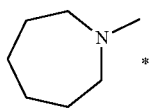 | E1192 MS(ESI) m/z: 516([M + H]+) |
| 1681 | 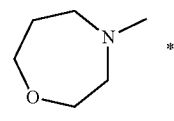 | E1192 MS(ESI) m/z: 518([M + H]+) |
| 1682 | 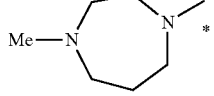 | E1192 MS(ESI) m/z: 531([M + H]+) |
| 1683 | 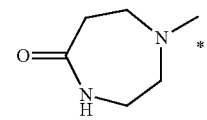 | E1192 MS(ESI) m/z: 531([M + H]+) |
TABLE 206-continued
| | | |
|---|---|---|
| 1193 | 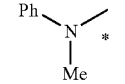 | E1193 MS(ESI) m/z: 524([M + H]+) |
| 1684 | 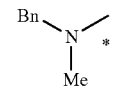 | E1193 MS(ESI) m/z: 538([M + H]+) |
| 1685 | 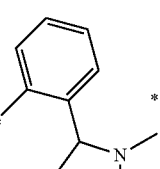 | E1193 MS(ESI) m/z: 578([M + H]+) |
| 1686 |  | E1193 MS(ESI) m/z: 578([M + H]+) |
| 1687 | 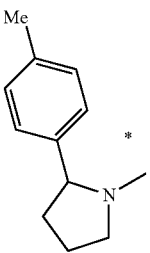 | E1193 MS(ESI) m/z: 578([M + H]+) |
| 1688 | 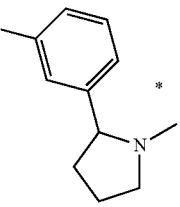 | E1193 MS(ESI) m/z: 582([M + H]+) |
| 1689 | 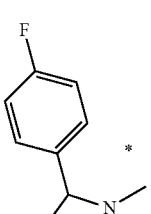 | E1193 MS(ESI) m/z: 582([M + H]+) |
| 1690 | 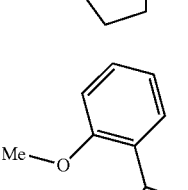 | E1193 MS(ESI) m/z: 594([M + H]+) |

TABLE 206-continued

| No. | Structure | Data |
|---|---|---|
| 1691 | 3-MeO-C6H4- pyrrolidine (N-Me) | E1193 MS(ESI) m/z: 594([M + H]+) |
| 1692 | 4-MeO-C6H4- pyrrolidine (N-Me) | E1193 MS(ESI) m/z: 594([M + H]+) |
| 1693 | 2-Cl-C6H4- pyrrolidine (N-Me) | E1193 MS(ESI) m/z: 598([M + H]+) |

TABLE 207

| No. | Structure | Data |
|---|---|---|
| 1694 | 3-Cl-C6H4- pyrrolidine (N-Me) | E1193 MS(ESI) m/z: 598([M + H]+) |
| 1695 | 4-Cl-C6H4- pyrrolidine (N-Me) | E1193 MS(ESI) m/z: 598([M + H]+) |
| 1696 | 4-CF3-C6H4- pyrrolidine (N-Me) | E1193 MS(ESI) m/z: 632([M + H]+) |

TABLE 207-continued

| No. | Structure | Data |
|---|---|---|
| 1697 | 4-NMe2-C6H4- pyrrolidine (N-Me) | E1193 MS(ESI) m/z: 607([M + H]+) |
| 1698 | 2,5-diMeO-C6H3- pyrrolidine (N-Me) | E1193 MS(ESI) m/z: 624([M + H]+) |
| 1699 | 2,4-diMeO-C6H3- pyrrolidine (N-Me) | E1193 MS(ESI) m/z: 624([M + H]+) |
| 1700 | furan-2-yl pyrrolidine (N-Me) | E1193 MS(ESI) m/z: 554([M + H]+) |
| 1701 | thiophen-3-yl pyrrolidine (N-Me) | E1193 MS(ESI) m/z: 570([M + H]+) |
| 1702 | 3-Me-1,2,4-oxadiazol-5-yl pyrrolidine (N-Me) | E1193 MS(ESI) m/z: 570([M + H]+) |
| 1703 | 3-(2-methoxyethyl)-1,2,4-oxadiazol-5-yl pyrrolidine (N-Me) | E1193 MS(ESI) m/z: 614([M + H]+) |

TABLE 207-continued
| | | |
|---|---|---|
| 1704 | 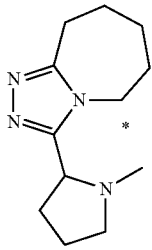 | E1193<br>MS(ESI) m/z:<br>623([M + H]+) |
| 1705 | 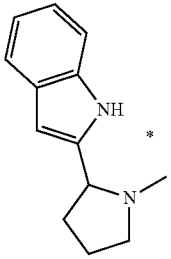 | E1193<br>MS(ESI) m/z:<br>603([M + H]+) |
| 1706 | 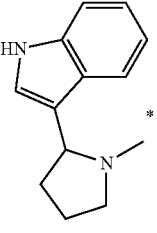 | E1193<br>MS(ESI) m/z:<br>603([M + H]+) |
| 1707 | 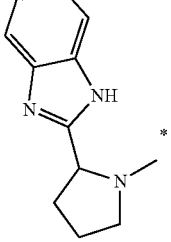 | E1193<br>MS(ESI) m/z:<br>604([M + H]+) |
TABLE 208
| | | |
|---|---|---|
| 1708 | 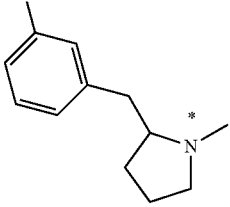 | E1193<br>MS(ESI) m/z:<br>615([M + H]+) |
| 1709 | 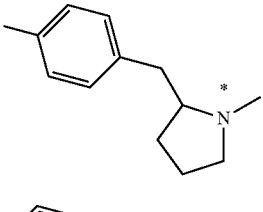 | E1193<br>MS(ESI) m/z:<br>592([M + H]+) |
| 1710 | 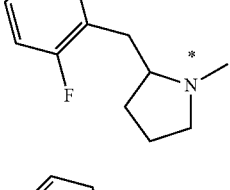 | E1193<br>MS(ESI) m/z:<br>592([M + H]+) |
| 1711 | 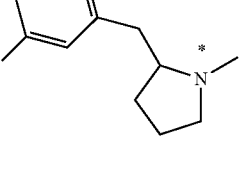 | E1193<br>MS(ESI) m/z:<br>592([M + H]+) |
| 1712 | 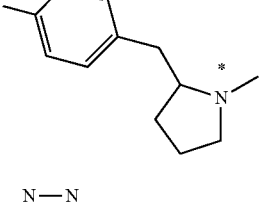 | E1193<br>MS(ESI) m/z:<br>596([M + H]+) |
| 1713 | 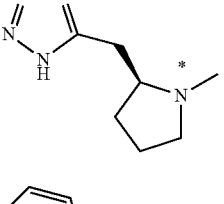 | E1193<br>MS(ESI) m/z:<br>612([M + H]+) |
| 1714 | 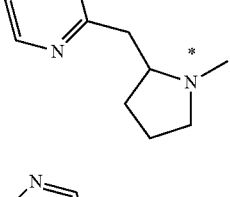 | E1193<br>MS(ESI) m/z:<br>608([M + H]+) |
| 1715 | 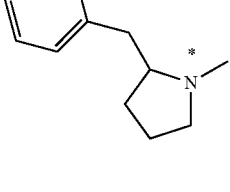 | E1193<br>MS(ESI) m/z:<br>570([M + H]+) |
| 1716 | 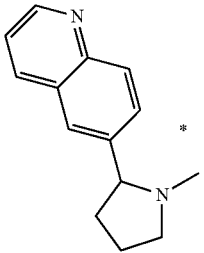 | E1193<br>MS(ESI) m/z:<br>579([M + H]+) |
| 1717 | 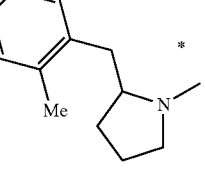 | E1193<br>MS(ESI) m/z:<br>579([M + H]+) |

TABLE 208-continued

| | | |
|---|---|---|
| 1718 | (2-Ph N-Me piperidine) | E1193 MS(ESI) m/z: 578([M + H]+) |
| 1719 | (2-(pyridin-2-yl) N-Me piperidine) | E1193 MS(ESI) m/z: 579([M + H]+) |
| 1720 | (2-(pyridin-4-yl) N-Me piperidine) | E1193 MS(ESI) m/z: 579([M + H]+) |
| 1721 | (2-(pyridin-3-yl) N-Me piperidine) | E1193 MS(ESI) m/z: 579([M + H]+) |
| 1722 | (2-(pyridin-3-yl) N-Me piperidine) | E1193 MS(ESI) m/z: 579([M + H]+) |
| 1723 | (2-(thiazol-2-yl) N-Me piperidine) | E1193 MS(ESI) m/z: 585([M + H]+) |

TABLE 209

| | | |
|---|---|---|
| 1724 | (3-(4-F-phenyl) N-Me morpholine) | E1193 MS(ESI) m/z: 598([M + H]+) |
| 1725 | (3-(2-Cl-phenyl) N-Me morpholine) | E1193 MS(ESI) m/z: 614([M + H]+) |
| 1726 | (3-(4-Cl-phenyl) N-Me morpholine) | E1193 MS(ESI) m/z: 614([M + H]+) |
| 1727 | (3-(2-OMe-phenyl) N-Me morpholine) | E1193 MS(ESI) m/z: 610([M + H]+) |
| 1728 | (3-(4-OMe-phenyl) N-Me morpholine) | E1193 MS(ESI) m/z: 610([M + H]+) |
| 1729 | (2-Ph N-Me morpholine) | E1193 MS(ESI) m/z: 580([M + H]+) |

TABLE 209-continued

| | | |
|---|---|---|
| 1730 | [pyridin-3-yl morpholine N-Me structure] | E1193 MS(ESI) m/z: 581([M + H]+) |
| 1731 | [Ph thiomorpholine N-Me structure] | E1193 MS(ESI) m/z: 596([M + H]+) |
| 1732 | [pyridin-3-yl thiomorpholine N-Me structure] | E1193 MS(ESI) m/z: 597([M + H]+) |
| 1733 | [Ph piperazine N,N-diMe structure] | E1193 MS(ESI) m/z: 593([M + H]+) |
| 1734 | [octahydropyrido pyrazine N-Me structure] | E1193 MS(ESI) m/z: 557([M + H]+) |
| 1735 | [Me tetrahydrothienopyridine N-Me structure] | E1193 MS(ESI) m/z: 570([M + H]+) |
| 1736 | [Ph pyrrolopyrazine N-Me structure] | E1193 MS(ESI) m/z: 615([M + H]+) |
| 1737 | [OEt phenyl pyrrolopyrazine N-Me structure] | E1193 MS(ESI) m/z: 659([M + H]+) |
| 1738 | [indoline N-Me structure] | E1193 MS(ESI) m/z: 536([M + H]+) |

TABLE 209-continued

| | | |
|---|---|---|
| 1739 | [indoline N-Me, 2-Me structure] | E1193 MS(ESI) m/z: 550([M + H]+) |

TABLE 210

| | | |
|---|---|---|
| 1740 | [decahydroquinoline N-Me structure] | E1193 MS(ESI) m/z: 556([M + H]+) |
| 1741 | [6-Me tetrahydroquinoline N-Me structure] | E1193 MS(ESI) m/z: 564([M + H]+) |
| 1742 | [8-Me tetrahydroquinoline N-Me structure] | E1193 MS(ESI) m/z: 564([M + H]+) |
| 1743 | [6-OMe tetrahydroquinoline N-Me structure] | E1193 MS(ESI) m/z: 580([M + H]+) |
| 1744 | [tetrahydroquinoline N-Me, 2-Me structure] | E1193 MS(ESI) m/z: 564([M + H]+) |
| 1745 | [6-F tetrahydroquinoline N-Me, 2-Me structure] | E1193 MS(ESI) m/z: 582([M + H]+) |
| 1746 | [benzoxazine N-Me, CH2OH structure] | E1193 MS(ESI) m/z: 582([M + H]+) |

TABLE 210-continued

| # | Structure | Data |
|---|---|---|
| 1747 | benzo-fused N-methyl dihydroquinoxalinone with Me substituent, attachment * | E1193 MS(ESI) m/z: 579([M + H]+) |
| 1748 | Me$_2$N-CH$_2$-(N-methylpyrrolidin-2-yl)-* | E1193 MS(ESI) m/z: 545([M + H]+) |
| 1749 | azepan-1-yl-CH$_2$-(N-methylpyrrolidin-2-yl)-* | E1193 MS(ESI) m/z: 599([M + H]+) |
| 1750 | PhNH-CH$_2$-(N-methylpyrrolidin-2-yl)-* | E1193 MS(ESI) m/z: 593([M + H]+) |
| 1751 | PhNH-CH$_2$-(N-methylpyrrolidin-2-yl)-* (other enantiomer) | E1193 MS(ESI) m/z: 593([M + H]+) |
| 1752 | EtO-CH$_2$-(N-methylpyrrolidin-2-yl)-* | E1193 MS(ESI) m/z: 546([M + H]+) |
| 1753 | Me-propyl-(N-methylpyrrolidin-2-yl)-* | E1193 MS(ESI) m/z: 544([M + H]+) |
| 1754 | cyclohexyl-(N-methylpyrrolidin-2-yl)-* | E1193 MS(ESI) m/z: 570([M + H]+) |
| 1755 | cyclohexyl-(N-methylpyrrolidin-3-yl)-* | E1193 MS(ESI) m/z: 570([M + H]+) |
| 1756 | Et$_2$N-(N-methylpyrrolidin-3-yl)-* | E1193 MS(ESI) m/z: 559([M + H]+) |
| 1757 | morpholin-4-yl-(N-methylpyrrolidin-3-yl)-* | E1193 MS(ESI) m/z: 573([M + H]+) |

TABLE 211

| # | Structure | Data |
|---|---|---|
| 1758 | pyrrolidin-1-yl-CH$_2$-(N-methylpiperidin-2-yl)-* | E1193 MS(ESI) m/z: 585([M + H]+) |
| 1759 | morpholin-4-yl-CH$_2$-(N-methylpiperidin-2-yl)-* | E1193 MS(ESI) m/z: 601([M + H]+) |
| 1760 | piperidin-1-yl-CH$_2$CH$_2$-(N-methylpiperidin-2-yl)-* | E1193 MS(ESI) m/z: 613([M + H]+) |
| 1761 | morpholin-4-yl-CH$_2$CH$_2$-(N-methylpiperidin-2-yl)-* | E1193 MS(ESI) m/z: 615([M + H]+) |
| 1762 | Me$_2$N-(N-methylpiperidin-3-yl)-* | E1193 MS(ESI) m/z: 545([M + H]+) |
| 1763 | Et-substituted piperazinone-* | E1193 MS(ESI) m/z: 545([M + H]+) |

TABLE 211-continued

| | | |
|---|---|---|
| 1764 | [structure: methylpiperazine with N-Ph, Me substituent] | E1193 MS(ESI) m/z: 593([M + H]+) |
| 1765 | [structure: piperazinone with N-Ph, Me, =O] | E1193 MS(ESI) m/z: 593([M + H]+) |
| 1194 | [structure: 1-methyl-2-methylimidazole] | E1194 MS(ESI) m/z: 499([M + H]+) |
| 1766 | [structure: 1-methyl-2-phenylimidazole] | E1194 MS(ESI) m/z: 561([M + H]+) |
| 1195 | [structure: 1-methyl-2-phenylpiperazine with HN] | E1195 MS(ESI) m/z: 579([M + H]+) |
| 1767 | [structure: 1-methyl-1,2,3,4-tetrahydroquinoline with NH2] | E1195 MS(ESI) m/z: 565([M + H]+) |

Hereinafter, the NMR data of several Example compounds are shown in Tables 212 to 215. The data represents δ (ppm) of peaks in $^1$H-NMR where tetramethylsilane is used as internal standard, unless particularly described, DMSO-d6 is used as a solvent for measuring.

Further, (CDCl$_3$) represents δ (ppm) of peaks in $^1$H-NMR in CDCl$_3$.

TABLE 212

| Ex | Dat (NMR) |
|---|---|
| 2 | 1.75-2.25 (4H, m), 2.73-2.87 (3H, m), 2.98-4.17 (12H, m), 4.31 (2H, s), 5.17-5.32 (1H, m), 7.10-7.23 (1H, m), 7.53-7.78 (2H, m), 7.90-8.06 (1H, m), 8.54-8.83 (3H, m), 10.61-10.97 (1H, m), 12.10-12.35 (1H, m) |
| 8 | 3.18 (3H, s), 3.29 (3H, s), 3.20-3.56 (4H, m), 3.68 (2H, t, J = 5.2 Hz), 3.80 (2H, t, J = 5.2 Hz), 3.76-4.12 (4H, m), 5.18 (2H, brs), 7.32 (1H, t, J = 7.9 Hz), 7.59 (1H, s), 7.77 (1H, t, J = 7.9 Hz), 7.99 (1H, d, J = 7.9 Hz), 8.78 (1H, d, J = 7.9 Hz), 10.67 (1H, brs), 12.49 (1H, brs) |
| 9 | 1.57-1.67 (1H, m), 1.76-1.98 (3H, m), 3.32-3.36 (1H, m), 3.61-3.79 (2H, m), 3.83-3.95 (1H, m), 4.79-4.96 (1H, m), 7.24-7.30 (1H, m), 7.41 (1H, dd, J = 8.0, 4.6 Hz), 7.56-7.65 (2H, m), 7.90 (1H, d, J = 7.7 Hz), 8.25 (1H, d, J = 8.0 Hz), 8.34 (1H, d, J = 3.6 Hz), 8.63 (1H, d, J = 8.0 Hz), 8.97 (1H, s), 10.74 (1H, s), 11.99 (1H, s) |
| 10 | (CDCl$_3$) 3.15 (3H, s), 3.29 (3H, s), 3.57 (2H, t, J = 5.1 Hz), 3.73 (2H, t, J = 5.1 Hz), 4.37 (2H, s), 7.12-7.20 (1H, m), 7.24-7.31 (1H, m), 7.38 (1H, s), 7.56-7.64 (2H, m), 8.02 (1H, dd, J = 8.0, 1.4 Hz), 8.54 (2H, brs), 8.96 (1H, dd, J = 8.6, 1.0 Hz), 12.90 (1H, brs) |
| 11 | 3.44-3.47 (4H, m), 3.71-3.74 (4H, m), 7.31 (1H, dd, J = 7.9, 7.8 Hz), 7.65 (1H, dd, J = 8.7, 7.9 Hz), 7.95-8.02 (2H, m), 8.3 (1H, s), 8.54 (1H, d, J = 7.8 Hz), 8.64-8.68 (2H, m), 9.34 (1H, d, J = 2.0 Hz), 11.39 (1H, brs), 11.40 (1H, brs) |
| 24 | 2.05-2.61 (2H, m), 2.71-3.19 (6H, m), 3.19-4.00 (4H, m), 4.18-5.34 (1H, m), 7.31 (1H, t, J = 7.6 Hz), 7.56-8.09 (4H, m), 8.30-8.73 (3H, m), 9.08-9.43 (1H, m), 10.67-12.14 (2H, m) |
| 26 | 1.13 (3H, t, J = 7.3 Hz), 1.77-1.91 (2H, m), 2.09-2.20 (2H, m), 2.29-2.41 (4H, m), 3.22-3.62 (10H, m), 3.83-3.94 (2H, m), 5.21-5.30 (1H, m), 7.15 (1H, t, J = 4.8 Hz), 7.44 (1H, dd, J = 8.5, 1.7 Hz), 7.58 (1H, s), 7.58 (1H, d, J = 1.7 Hz), 8.55 (1H, d, J = 8.5 Hz), 8.63 (2H, d, J = 4.8 Hz), 8.67 (1H, t, J = 5.4 Hz), 12.25 (1H, s) |
| 28 | 1.17 (3H, t, J = 6.8 Hz), 1.49-1.64 (4H, m), 1.76-1.84 (2H, m), 1.89-1.98 (2H, m), 3.28-3.60 (7H, m), 3.76-3.83 (2H, m), 3.85-3.92 (2H, m), 3.95-4.05 (1H, m), 7.13-7.19 (1H, m), 7.48-7.54 (1H, m), 7.55-7.57 (1H, m), 7.67 (1H, d, J = 7.6 Hz), 8.56-8.63 (2H, m), 12.09 (1H, s) |
| 30 | 1.18-1.34 (2H, m), 1.45-1.58 (2H, m), 1.95-2.1 (1H, m), 3.06 (3H, s), 3.15-3.24 (2H, m), 3.48 (2H, d, J = 7.3 Hz), 3.74-3.82 (2H, m), 7.23-7.32 (1H, m), 7.41 (1H, dd, J = 8.3, 4.6 Hz), 7.50 (1H, s), 7.58-7.65 (1H, m), 7.91 (1H, d, J = 7.8 Hz), 8.15-8.22 (1H, m), 8.33-8.37 (1H, m), 8.68 |

TABLE 213

| Ex | Dat (NMR) |
|---|---|
| 44 | 1.43-1.55 (2H, m), 1.83-1.92 (2H, m), 3.27-3.36 (2H, m), 3.73-3.87 (3H, m), 7.25-7.31 (1H, m), 7.58 (1H, s), 7.62-7.68 (1H, m), 8.00 (1H, dd, J = 8.6, 5.4 Hz), 8.08 (1H, dd, J = 7.8, 5.4 Hz), 8.62-8.69 (2H, m), 8.80 (1H, d, J = 9 Hz), 9.36 (1H, d, J = 2.4 Hz), 11.58 (1H, s), 11.99 (1H, s) |
| 103 | 3.12 (3H, s), 3.23 (3H, s), 3.63 (2H, t, J = 5.2 Hz), 3.72 (2H, t, J = 5.2 Hz), 7.26-7.33 (1H, m), 7.53 (1H, s), 7.62-7.69 (1H, m), 7.93-8.01 (2H, m), 8.62-8.69 (3H, m), 9.30 (1H, d, J = 2.2 Hz), 11.34 (1H, s), 11.90 (1H, s) |
| 112 | 2.75 (3H, s), 2.92 (3H, s), 3.05 (3H, s), 4.51 (2H, s), 7.22-7.31 (1H, m), 7.43 (1H, dd, J = 11.0, 6.3 Hz), 7.54 (1H, s), 7.57-7.66 (1H, m), 7.87-7.93 (1H, m), 8.03-8.10 (1H, m), 8.36 (1H, dd, J = 6.3, 1.9 Hz), 8.65 (1H, d, J = 11.0 Hz), 8.95 (1H, d, J = 3.2 Hz), 10.71 (1H, s), 11.82 (1H, s) |
| 206 | 1.96-2.13 (2H, m), 3.25 (3H, s), 3.32-3.59 (4H, m), 4.02-4.10 (1H, m), 7.28 (1H, t, J = 7.9 Hz), 7.42 (1H, dd, J = 8.3, 4.7 Hz), 7.61 (1H, t, J = 7.9 Hz), 7.87 (1H, d, J = 7.9 Hz), 8.12-8.20 (1H, m), 8.22 (1H, s), 8.34 (1H, d, J = 4.7 Hz), 8.52 (1H, d, J = 7.9 Hz), 8.94 (1H, d, J = 2.5 Hz), 10.72 (1H, s), 11.26 (1H, s) |
| 210 | 2.07-2.35 (2H, m), 3.45-3.57 (1H, m), 3.58-3.77 (3H, m), 5.34-5.53 (1H, m), 7.26-7.03 (1H, m), 7.43 (1H, dd, J = 8.3, 4.9 Hz), 7.58-7.63 (1H, m), 7.88 (1H, dd, J = 7.9, 1.5 Hz), 8.56 (1H, ddd, J = 8.3, 2.4, 1.5 Hz), 8.25 (1H, s), 8.35 (1H, dd, J = 4.6, 1.5 Hz), 8.50-8.54 (1H, m), 8.64 (1H, d, J = 2.4 Hz), 10.71 (1H, s), 11.27 (1H, brs) |
| 343 | 1.50-1.64 (2H, m), 1.73-1.85 (2H, m), 2.06-2.19 (2H, m), 3.28-3.49 (4H, m), 3.78-3.83 (4H, m), 3.95-4.07 (1H, m), 5.17-5.29 (1H, m), 7.15 (1H, d, J = 4.7 Hz), 7.18 (1H, td, J = 7.7, 1.0 Hz), 7.48-7.54 (1H, m), 7.71 (1H, dd, J = 7.9, 1.5 Hz), 8.23 (1H, s), 8.51 (1H, dd, J = 8.3, 1.0 Hz), 8.57 (1H, d, J = 7.7 Hz), 8.62 (2H, d, J = 4.7 Hz), 11.62 (1H, brs) |
| 361 | (CDCl$_3$) 1.46-1.67 (2H, m), 1.86-2.11 (2H, m), 3.21 (3H, s), 3.38 (3H, s), 3.45-3.59 (2H, m), 3.66 (4H, s), 3.94-4.05 (2H, m), 4.12-4.30 (1H, m), 5.99-6.09 (1H, m), 7.06-7.16 (1H, m), 7.42-7.53 (2H, m), 7.79 (1H, s), 8.54-8.63 (1H, m), 11.59 (1H, s) |
| 387 | 0.84 (6H, s), 3.13-3.20 (4H, m), 3.48-3.54 (4H, m), 3.71-3.78 (4H, m), 4.56 (1H, t, J = 5.8 Hz), 7.18 (1H, ddd, J = 7.8, 7.4, 1.2 Hz), 7.52 (1H, ddd, J = 8.3, 7.4, 1.4 Hz), 7.62 (1H, s), 7.72 (1H, dd, J = 7.8, 1.4 Hz), 8.47-8.63 (2H, m), 12.16 (1H, s) |

TABLE 213-continued

| | |
|---|---|
| 512 | 1.13 (3H, t, J = 7.1 Hz), 1.45-1.70 (4H, m), 1.76-2.00 (4H, m), 3.10-4.11 (12H, m), 7.78 (1H, s), 8.70-8.78 (1H, m), 8.79-8.85 (1H, m), 9.00-9.10 (2H, m), 12.85 (1H, brs) |

TABLE 214

| | |
|---|---|
| 564 | 1.78-1.91 (2H, m), 1.78-1.91 (2H, m), 2.09-2.22 (2H, m), 2.30-2.42 (4H, m), 3.24 (3H, s), 3.38-3.63 (10H, m), 3.83-3.95 (2H, m), 5.21-5.30 (1H, m), 7.15 (1H, t, J = 4.8 Hz), 7.45 (1H, dd, J = 8.6, 1.8 Hz), 7.58 (1H, s), 7.61 (1H, d, J = 1.8 Hz), 8.57 (1H, d, J = 8.6 Hz), 8.63 (2H, d, J = 4.8 Hz), 8.74 (1H, t, J = 5.4 Hz), 12.28 (1H, s) |
| 573 | 1.79-1.88 (2H, m), 2.11-2.19 (2H, m), 2.33-2.40 (4H, m), 3.43-3.62 (10H, m), 3.84-3.92 (2H, m), 4.56 (2H, dt, J = 47.4, 5.0 Hz), 5.21-5.29 (1H, m), 7.15 (1H, t, J = 4.8 Hz), 7.47 (1H, d, J = 8.5, 1.7 Hz), 7.59 (1H, s), 7.63 (1H, d, J = 1.6 Hz), 8.57 (1H, d, J = 8.5 Hz), 8.63 (2H, d, J = 4.8 Hz), 8.90 (1H, t, J = 5.5 Hz), 12.23 (1H, s) |
| 602 | 1.52-1.64 (2H, m), 1.78-1.88 (4H, m), 2.12-2.18 (2H, m), 3.29-3.36 (2H, m), 3.49-3.55 (4H, m), 3.82-4.04 (5H, m), 5.22-5.30 (1H, m), 7.14-7.17 (1H, m), 7.05 (1H, s), 8.51-8.52 (1H, m), 8.58-8.59 (1H, m), 8.62-8.64 (2H, m), 8.78-8.83 (2H, m), 12.43 (1H, brs) |
| 603 | 1.50-1.64 (2H, m), 1.77-1.88 (4H, m), 2.12-2.20 (2H, m), 3.29-3.36 (2H, m), 3.48-3.54 (2H, m), 3.81-4.00 (5H, m), 5.20-5.30 (1H, m), 7.14-7.17 (1H, m), 7.62-7.66 (2H, m), 8.43-8.44 (1H, m), 8.62-8.63 (2H, m), 8.85-8.88 (1H, m), 9.74 (1H, s), 11.80 (1H, brs) |
| 819 | 1.58-1.70 (2H, m), 1.79-1.83 (2H, m), 3.11-4.01 (21H, m), 4.35-4.36 (2H, m), 7.51 (1H, s), 7.63-7.66 (1H, m), 8.08 (1H, brs), 8.62-8.65 (1H, m), 8.68-8.71 (1H, m), 10.97 (1H, brs), 12.16 (1H, brs) |
| 821 | 1.51-1.66 (4H, m), 1.72-1.77 (2H, m), 1.78-1.86 (2H, m), 3.11 (3H, m), 3.29 (3H, m), 3.34-3.43 (2H, m), 3.65 (2H, t, J = 5.3 Hz), 3.73 (2H, t, J = 5.3 Hz), 3.85-3.94 (2H, m), 3.95-4.06 (1H, m), 7.49 (1H, s), 7.51-7.55 (2H, m), 8.59 (1H, d, J = 9.3 Hz), 8.66 (1H, d, J = 7.5 Hz), 12.1 (1H, s) |
| 842 | 3.12 (3H, s), 3.23 (3H, s), 3.62-3.65 (2H, m), 3.71-3.74 (2H, m), 3.89 (3H, s), 7.26 (1H, dd, J = 9.2, 3.0 Hz), 7.48 (1H, s), 7.61 (1H, d, J = 3.0 Hz), 8.10 (1H, dd, J = 8.6, 5.4 Hz), 8.53 (1H, d, J = 9.2 Hz), 8.72 (1H, d, J = 5.4 Hz), 8.88 (1H, d, J = 8.6 Hz), 9.42 (1H, d, J = 2 Hz), 11.65 (1H, s), 11.71 (1H, s) |
| 930 | 1.29-1.45 (2H, m), 1.50-1.68 (4H, m), 1.73-1.87 (2H, m), 2.03-2.18 (1H, m), 2.28-2.42 (4H, m), 3.06 (3H, s), 3.25-3.41 (4H, m), 3.46 (2H, s), 3.51-3.64 (6H, m), 3.81-3.94 (4H, m), 3.99-4.11 (1H, m), 7.45 (1H, s), 7.45 (1H, dd, J = 8.5, 1.7 Hz), 7.62 (1H, d, J = 1.7 Hz), 8.54 (1H, d, J = 7.6 Hz), 8.59 (1H, d, J = 8.5 Hz), 12.3 (1H, s) |
| 1114 | 1.57-1.64 (2H, m), 1.78-1.83 (4H, m), 2.10-2.16 (2H, m), 3.33-3.48 (4H, m), 3.81-3.87 (4H, m), 4.00-4.06 (1H, m), 5.18-5.24 (1H, m), 7.13-7.16 (1H, m), 8.33 (1H, s), 8.49-8.51 (1H, m), 8.58-8.63 (3H, m), 8.76-8.79 (1H, m), 8.86 (1H, brs), 11.97 (1H, brs) |

TABLE 215

| | |
|---|---|
| 1169 | 1.53-1.65 (2H, m), 1.76-1.84 (2H, m), 2.36 (3H, s), 3.06 (2H, s), 3.24-3.65 (17H, m), 3.85-3.92 (2H, m), 3.95-4.05 (1H, m), 7.42-7.47 (1H, m), 7.56-7.59 (1H, m), 8.14 (1H, s), 8.44-8.49 (1H, m), 8.53-8.58 (1H, m), 11.58 (1H, s) |
| 1170 | 2.39 (3H, s), 3.05 (3H, s), 3.23 (3H, s), 3.55-3.59 (4H, m), 7.08-7.11 (1H, m), 7.40-7.44 (1H, m), 7.80-7.83 (1H, m), 8.15-8.20 (2H, m), 8.33-8.35 (1H, m), 8.43 (1H, brs), 8.93-8.94 (1H, m), 10.62 (1H, brs), 11.56 (1H, brs) |
| 1181 | 1.03 (3H, d, J = 6.2 Hz), 1.70-1.78 (1H, m), 2.00-2.08 (1H, m), 2.11-2.17 (2H, m), 2.66 (2H, dd, J = 11.0, 25.2 Hz), 3.27 (3H, s), 3.28 (3H, s), 3.40-3.55 (10H, m), 3.57-3.60 (2H, m), 3.73 (1H, d, J = 9.7 Hz), 4.11-4.15 (1H, m), 6.62 (2H, s), 7.44 (1H, dd, J = 1.9, 8.4 Hz), 7.47 (1H, s), 7.59 (1H, d, J = 1.9 Hz), 8.54 (1H, d, J = 8.5 Hz), 8.68-8.74 (1H, m) 12.10 (1H, s) |

TABLE 215-continued

| | |
|---|---|
| 1343 | 1.08 (6H, s), 2.08-2.22 (2H, m), 2.26-2.38 (2H, m), 3.27 (3H, s), 3.28-3.30 (5H, m), 3.38-3.63 (12H, m), 4.10-4.16 (1H, m), 7.44 (1H, d, J = 1.8 Hz), 7.47 (1H, s), 7.58 (1H, d, J = 1.8 Hz), 8.52 (1H, d, J = 8.5 Hz), 8.70 (1H,m), 12.06 (1H, s) |
| 1435 | 2.34-2.40 (4H, m), 3.26 (3H, s), 3.28 (3H, s), 3.42-3.47 (4H, m), 3.49-3.53 (2H, m), 3.56-3.61 (4H, m), 3.90-3.95 (2H, m), 4.29 (2H, dd, J = 6.4, 9.0 Hz), 4.38-4.55 (1H, m), 6.62 (2H, s), 7.45 (1H, d, J = 1.9 Hz), 7.59-7.61 (2H, m), 8.52 (1H, d, J = 8.5 Hz), 8.70-8.75 (1H, m), 12.01 (1H, s) |
| 1439 | 1.17 (3H, d, J = 6.8 Hz), 2.33-2.40 (4H, m), 3.26 (3H, s), 3.28 (3H, s), 3.29-3.34 (1H, m), 3.43-3.46 (3H, m), 3.56-3.60 (4H, m), 3.92 (2H, dd, J = 3.9, 9.7 Hz), 4.20-4.31 (3H, m), 4.39-4.44 (1H, m), 7.43-7.47 (1H, m), 7.58 (1H, d, J = 1.8 Hz), 7.60 (1H, s), 8.46 (1H, d, J = 8.0 Hz), 8.51 (1H, d, J = 8.5 Hz), 11.90 (1H, s) |
| 1449 | (CDCl3) 1.26 (3H, t, J = 7.0 Hz), 2.11-2.25 (2H, m), 3.385 (3H, s), 3.390 (3H, s), 3.53-3.59 (4H, m), 3.61-3.70 (6H, m), 4.11-4.16 (1H, m), 4.48 (2H, s), 6.52-6.60 (1H, m), 7.38 (1H, s), 7.44 (1H, dd, J = 1.8, 8.6 Hz), 7.50 (1H, d, J = 1.8 Hz), 8.71 (1H, d, J = 8.5 Hz), 12.10 (1H, s) |
| 1469 | 2.35-2.39 (4H, m), 3.12 (3H, s), 3..27 (3H, s), 3.29 (3H, s), 3.40-3.54 (6H, m), 3.56-3.61 (4H, m), 3.62-3.66 (2H, m), 3.70-3.75 (2H, m), 7.43-7.46 (1H, m), 7.47 (1H, s), 7.61 (1H, d, J = 1.8 Hz), 8.57 (1H, d, J = 8.5 Hz), 8.71-8.75 (1H, m), 12.28 (1H, s) |
| 1470 | 2.33-2.40 (4H, m), 3.27 (3H, s), 3.40-3.85 (16H, m), 5.50 (1H, d, J = 53 Hz), 7.42-7.48 (1H, m), 7.52 (1H, s), 7.60 (1H, d, J = 1.7 Hz), 8.55 (1H, d, J = 8.5 Hz), 8.69-8.76 (1H, m), 12.12 (1H, s) |

INDUSTRIAL AVAILABILITY

The compound of the present invention has potent trkA receptor inhibitory action, and therefore, it is useful as a pharmaceutical, particularly as a therapeutic agent for urinary frequency, urinary urgency, urinary incontinence, and lower urinary tract pain associated with various lower urinary tract diseases including overactive bladder, and various diseases accompanied by pain.

The invention claimed is:

1. An azolecarboxamide compound represented by formula (I) or a salt thereof:

$$\text{(I)}$$

wherein:

X is S or O, $R^1$ is a group represented by formula (II), or a group represented by formula (III):

$$\text{(II)}$$

$$\text{(III)}$$

each Alk is the same as or different from each other, each representing lower alkylene, $R^{1a}$ is lower alkyl substituted with one or two —OH, -Alk-O-lower alkyl, -Alk-SO$_2$-lower alkyl, -Alk-O—SO$_2$-lower alkyl, -Alk-aryl, -Alk-O-aryl, -Alk-heteroaryl, -Alk-O-heteroaryl, -Alk-CO-saturated hetero ring group, -Alk-NR$^A$R$^B$, -Alk-CO—NR$^A$R$^B$, saturated hetero ring group, wherein the saturated hetero ring group may be substituted with lower alkyl, lower alkenyl, -Alk-O-lower alkyl or -Alk-aryl, or -Alk-saturated hetero ring group, wherein the saturated hetero ring group in the -Alk-saturated hetero ring group may be substituted with lower alkyl or —OH, $R^A$ and $R^B$ are the same as or different from each other, each representing —H or lower alkyl, $R^{1b}$ is lower alkyl or -Alk-aryl, Q is cyclic amino which may be substituted with group(s) selected from Group $G_1$ below:

Group $G_1$ is halogen, —OH, —CN, lower alkyl, halogeno-lower alkyl, -Alk-OH, —O— lower alkyl, —O-halogeno-lower alkyl, -Alk-O-lower alkyl, —O-Alk-O-lower alkyl, —O-cycloalkyl, —O-Alk-cycloalkyl, —CO$_2$H, —CO—O-lower alkyl, —CO-lower alkyl, —CO—NR$^A$R$^B$, —CO—NH-Alk-OH, -Alk-CO—NR$^A$R$^B$, —SO$_2$-lower alkyl, —SO$_2$—NR$^A$R$^B$, aryl, —O-aryl, heteroaryl which may be substituted with (—O-lower alkyl), -Alk-heteroaryl, —O-(heteroaryl which may be substituted with group(s) selected from the group consisting of halogen, lower alkyl, -G-lower alkyl, —CN and —OH), -Alk-O-heteroaryl, —SO$_2$-heteroaryl, —S-(heteroaryl which may be substituted with lower alkyl), oxo, —NR$^C$R$^D$, and -Alk-aryl, wherein, in -Alk-aryl of Group $G_1$, the Alk may be substituted with —OH, and the aryl may be substituted with —CO$_2$H or —CO—O-lower alkyl, and two substituents on the ring group Q may be combined to form -Alk-, saturated hetero ring which may be substituted with group(s) selected from the group consisting of lower alkyl and oxo, or cycloalkane, may be spiro bonded on the ring group Q, heteroarene which may be substituted with lower alkyl, arene, or cycloalkane, may be condensed with the ring group Q, $R^C$ is —H or lower alkyl, $R^D$ is lower alkyl, —CO-lower alkyl, —CO—O-lower alkyl, -Alk-CO—NR$^A$R$^B$, or heteroaryl, $R^2$ is a group represented by formula (IV) or (V),

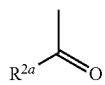

(IV)

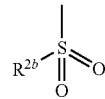

(V)

$R^{2a}$ is —O—R$^E$, —CH$_2$—R$^F$, —NR$^G$R$^H$, or heteroaryl, $R^E$ is —H or lower alkyl, $R^F$ is —H, heteroaryl, or saturated hetero ring group, $R^G$ is —H or lower alkyl, $R^H$ is (1) —H, (2) —O-lower alkyl, (3) cycloalkyl which may be substituted with group(s) selected from the group consisting of —OH, —NR$^A$R$^B$, —NH—CO—O-lower alkyl, —CN, —CO$_2$H, —CO—O-lower alkyl and —CONH$_2$, (4) cycloalkenyl which may be substituted with -Alk-OH or —CONH$_2$, (5) saturated hetero ring group which may be substituted with group(s) selected from the group consisting of —OH, lower alkyl, -Alk-cycloalkyl, —CO-lower alkyl and oxo, (6) aryl which may be substituted with group(s) selected from the group consisting of —OH, —CN and halogen, (7) heteroaryl, or (8) lower alkyl which may be substituted with group(s) selected from Group $G_2$ below:

Group $G_2$ is halogen, halogeno-lower alkyl, —OH, cycloalkyl, —O-lower alkyl, —O-cycloalkyl, —O-Alk-OH, —CN, —S-lower alkyl, —SO$_2$-lower alkyl, —CONH$_2$, —CONH-lower alkyl, —NHCO-lower alkyl, —CO$_2$H, —CO—O-lower alkyl, —NR$^A$R$^B$, saturated hetero ring group, —CO-saturated hetero ring group, aryl, and heteroaryl, wherein, in Group $G_2$, the cycloalkyl may be substituted with —OH, —CO—O-lower alkyl, -Alk-OH or -Alk-NR$^A$R$^B$, the saturated hetero ring group may be substituted with —OH, lower alkyl, -Alk-OH, -Alk-O-lower alkyl, -Alk-aryl, —NR$^A$R$^B$, —CO—O-lower alkyl or oxo, and the heteroaryl may be substituted with —OH, lower alkyl, —CO$_2$H or —CO—O-lower alkyl, and $R^G$ and $R^H$ may be combined with the N atom to which they are bonded to form nitrogen-containing saturated hetero ring which may be substituted with group(s) selected from the group consisting of —OH, lower alkyl, —CO—O-lower alkyl, -Alk-aryl and —CO-saturated hetero ring group, $R^{2b}$ is lower alkyl, halogeno-lower alkyl, -Alk-R$^K$, —NR-$^L$R$^M$, aryl or saturated hetero ring group, wherein the saturated hetero ring group may be substituted with —CO—O-Alk-aryl, $R^K$ is —CN, —OH, —N$_3$, —CONH$_2$, —O—CO-lower alkyl, —NR$^A$R$^B$, —NH—CO-lower alkyl, —O—SO$_2$-lower alkyl, heteroaryl or saturated hetero ring group, $R^L$ is —H or lower alkyl, $R^M$ is heteroaryl or saturated hetero ring group, A is

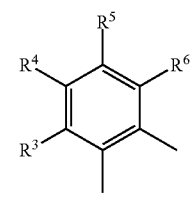

$R^3$ is —H, halogen, lower alkyl, —O-lower alkyl or —CN, $R^4$ is —H, halogen, —OH, —O-Alk-R$^{4a}$, cycloalkyl which may be substituted with —CN, —CN, —CO$_2$H, —CO—O-lower alkyl, —CO—NH-heteroaryl, —CO—NH—SO$_2$-lower alkyl, —CO—NH—SO$_2$—NR$^A$R$^B$, saturated hetero ring group, —O-saturated hetero ring group, —CO-saturated hetero ring group, —SO$_2$-saturated hetero ring group, —CO—NR$^{4b}$R$^{4c}$, or lower alkyl which may be substituted with group(s) selected from Group $G_3$ below, $R^{4a}$ is —H, —OH, —O-lower alkyl, —O-Alk-aryl, —S-lower alkyl, —SO$_2$-lower alkyl or —NH—R$^o$, $R^O$ is —H, —CO—O-lower alkyl, —CO-lower alkyl or —SO$_2$-lower alkyl, $R^{4b}$ is the same as or different from each other, each representing —H or lower alkyl, $R^{4c}$ is the same as or different from each other, each representing —H, lower alkyl, -Alk-O-lower alkyl, -Alk- $NR^AR^B$, -Alk-aryl, -Alk-saturated hetero ring group, cycloalkyl, aryl or saturated hetero ring group, Group $G_3$ is halogen, —OH, —O-lower alkyl, —O—CO-lower alkyl, —O-Alk-O-lower alkyl, —CN, —$CO_2H$, —CO—O-lower alkyl, —$NR^{4b}R^{4c}$, cyclic amino and —CO-saturated hetero ring group, wherein each saturated hetero ring group in $R^4$, the saturated hetero ring group in the —CO-saturated hetero ring group of Group $G_3$, and the cyclic amino in Group $G_3$ may be substituted with group(s) selected from Group $G_4$ below, and two substituents on the cyclic amino in Group $G_3$ may be combined to form -Alk-, saturated hetero ring which may be substituted with group(s) selected from the group consisting of lower alkyl and oxo, or cycloalkane, may be spiro bonded on the cyclic amino, and arene which may be substituted with group(s) selected from the group consisting of halogen, lower alkyl, and —O-lower alkyl, heteroarene, cycloalkane or saturated hetero ring, may be condensed with the cyclic amino, Group $G_4$ is halogen, lower alkyl, halogeno-lower alkyl, —OH, —O-lower alkyl, —O-aryl, —O—CO-lower alkyl, —O-lower alkyl, —$NR^AR^B$, —NH—CO-lower alkyl, -Alk-OH, -Alk-O-lower alkyl, —CO-lower alkyl, —CO—$NR^AR^B$, -Alk-aryl, -Alk-heteroaryl, -Alk-$NR^AR^B$, -Alk-CO—$NR^AR^B$, -Alk-cyclic amino, -Alk-NH-aryl, -Alk-S-lower alkyl, -Alk-halogeno-lower alkyl, cycloalkyl, aryl, heteroaryl, cyclic amino, —$SO_2$-lower alkyl, —$SO_2$—$NR^AR^B$, oxo and —CN, wherein each aryl and each heteroaryl in Group $G_4$ may be substituted with group(s) selected from Group $G_5$ below, Group $G_5$ is halogen, lower alkyl, halogeno-lower alkyl, —O-lower alkyl, —$NR^AR^B$ and -Alk-O-lower alkyl, $R^5$ is —H, halogen, lower alkyl, —OH, —O-lower alkyl, —CN, halogeno-lower alkyl, -Alk-OH, -Alk-O-lower alkyl, -Alk-CN, —O-Alk-$NH_2$, —O-Alk-NH—CO—O-lower alkyl, —O-Alk-aryl or —$CONH_2$, wherein $R^4$ and $R^5$ may be combined with the carbon atom on the benzene ring to which they are bonded to form (1) pyrazole ring, (2) 2,3-dihydro-1,4-dioxine ring, or (3) cyclopentene ring which may be substituted with —OH or oxo, $R^6$ is —H, halogen, lower alkyl, or —O-lower alkyl.

2. The compound or a salt thereof according to claim 1, wherein $R^2$ is a group represented by formula (IV).

3. The compound or a salt thereof according to claim 2, wherein $R^3$ and $R^5$ are the same as or different from each other, and each represents —H, halogen, lower alkyl or —O-lower alkyl, $R^4$ is (1) —H, (2) halogen, (3) —O-lower alkyl, (4) cycloalkyl which may be substituted with —CN, (5) saturated hetero ring group which may be substituted with group(s) selected from the group consisting of lower alkyl and -Alk-O-lower alkyl, (6) —O-saturated hetero ring group, or (7) lower alkyl which may be substituted with group(s) selected from Group $G_{3A}$, and $R^6$ is —H or —O-lower alkyl; wherein Group $G_{3A}$ is —O-lower alkyl, —O-Alk-O-lower alkyl, -Nee and cyclic amino, $R^{4d}$ is lower alkyl, $R^{4e}$ is lower alkyl, -Alk-O-lower alkyl, or -Alk-saturated hetero ring group, and the cyclic amino in Group $G_3A$ may be substituted with group(s) selected from the group consisting of F, lower alkyl, —O-lower alkyl and -Alk-O-lower alkyl, two substituents on the cyclic amino in Group $G_{3A}$ may be combined to form -Alk-, saturated hetero ring which may be substituted with group(s) selected from the group consisting of lower alkyl and oxo, or cycloalkane, may be spiro bonded on the cyclic amino, and arene which may be substituted with group(s) selected from the group consisting of halogen, lower alkyl and —O-lower alkyl, heteroarene, cycloalkane or saturated hetero ring, may be condensed with the cyclic amino.

4. The compound or a salt thereof according to claim 3, wherein in $R^1$, $R^{1a}$ of the group represented by the formula (II) is (1)-Alk-O-lower alkyl, (2) saturated hetero ring group which may be substituted with group(s) selected from the group consisting of lower alkyl, lower alkenyl, -Alk-O-lower alkyl and -Alk-aryl, or (3)-Alk-(saturated hetero ring group which may be substituted with lower alkyl or —OH), $R^{1b}$ is lower alkyl, and the cyclic amino represented by the formula (III) is cyclic amino which may be substituted with group(s) selected from Group $G_{1A}$ below;

Group $G_{1A}$ is F, —OH, lower alkyl, —O-lower alkyl, -Alk-O-lower alkyl and —O-(heteroaryl which may be substituted with group(s) selected from the group consisting of halogen, lower alkyl, —O-lower alkyl, —CN and —OH).

5. The compound or a salt thereof according to in claim 4, wherein in $R^2$, $R^{2a}$ of the group represented by the formula (IV) is —O—$R^E$, —$CH_2$—$R^F$ or —$NR^GR^H$, wherein $R^E$ is lower alkyl, $R^F$ is —H, heteroaryl or saturated hetero ring group, $R^G$ is —H, and $R^H$ is (1) —H, (2) cycloalkyl, (3) saturated hetero ring group which may be substituted with lower alkyl, (4) heteroaryl, or (5) lower alkyl which may be substituted with group(s) selected from the group consisting of F, —OH, cycloalkyl, —O-lower alkyl, saturated hetero ring group, and heteroaryl.

6. The compound or a salt thereof according to claim 5, wherein $R^3$, and $R^6$ are —H.

7. An azolecarboxamide compound represented by formula (I-A) or a salt thereof:

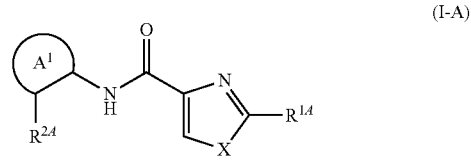

(I-A)

wherein

X is S or O, $R^{1A}$ is a group represented by formula (II-A) or a group represented by formula (III-A)

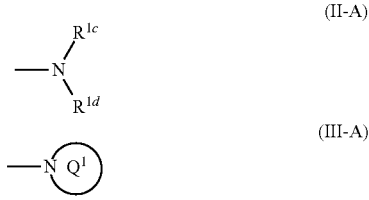

(II-A)

(III-A)

each Alk is the same as or different from each other, each representing lower alkylene, $R^{1c}$ is -Alk-O-lower alkyl, saturated hetero ring group which may be substituted with lower alkyl, or -Alk-saturated hetero ring group, $R^{1d}$ is lower alkyl, $Q^1$ is cyclic amino which may be substituted with group(s) selected from Group $G_{1B}$ below, Group $G_{1B}$ is F, —OH, —O-lower alkyl, or —O-(heteroaryl which may be substituted with group(s) selected from the group consisting of halogen, lower alkyl, —O-lower alkyl, —CN, and —OH), $R^{2A}$ is

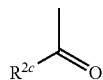

(IV-A)

$R^{2c}$ is —O-lower alkyl, —CH$_2$—$R^W$ or —NH—$R^X$, $R^W$ is —H, heteroaryl or saturated hetero ring group, $R^X$ is (1) —H, (2) cycloalkyl, (3) saturated hetero ring group, (4) heteroaryl, or (5) lower alkyl which may be substituted with group(s) selected from the group consisting of F, cycloalkyl, —O-lower alkyl and saturated hetero ring group, $A^1$ is

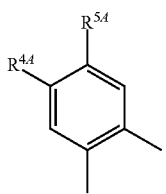

$R^{4A}$ is (1) —H, (2) cycloalkyl substituted with one —CN, (3) saturated hetero ring group which may be substituted with group(s) selected from the group consisting of lower alkyl and -Alk-O-lower alkyl, (4) —O-lower alkyl, (5) —O-saturated hetero ring group, or (6) lower alkyl which may be substituted with one group selected from Group $G_{3B}$ below, Group $G_{3B}$ is —O-lower alkyl, —NR$^{4f}$R$^{4g}$ and cyclic amino, $R^{4f}$ is lower alkyl, $R^{4g}$ is lower alkyl which is the same as or different from $R^{4f}$, which may be substituted with one group selected from the group consisting of —O-lower alkyl and saturated hetero ring group, wherein the cyclic amino in Group $G_{3B}$ may be substituted with group(s) selected from the group consisting of F, lower alkyl, —O-lower alkyl and -Alk-O-lower alkyl, and cycloalkane may be Spiro bonded on the cyclic amino in Group $G_{3B}$, and arene or cycloalkane may be condensed with the cyclic amino in Group $G_{3B}$, and $R^{5A}$ is —H, lower alkyl or —O-lower alkyl.

8. The compound or a salt thereof according to claim 7, wherein $R^{2c}$ is —NH—$R^X$.

9. The compound according to claim 1, which is selected from the group consisting of:

2-morpholin-4-yl-N-[2-(pyridin-3-ylcarbamoyl)phenyl]-1,3-oxazole-4-carboxamide, 2-(4-ethoxypiperidin-1-yl)-N-[2-(tetrahydro-2H-pyran-4-ylcarbamoyl)phenyl]-1,3-thiazole-4-carboxamide, 2-[(2-methoxyethyl)(methyl)amino]-N-[2-(pyridin-3-ylcarbamoyl)phenyl]-1,3-thiazole-4-carboxamide, 2-[(3S)-3-methoxypyrrolidin-1-yl]-N-[2-(pyridin-3-ylcarbamoyl)phenyl]-1,3-oxazole-4-carboxamide, 2-[(2-methoxyethyl)(methyl)amino]-N-[2-(tetrahydro-2H-pyran-4-ylcarbamoyl)phenyl]-1,3-oxazole-4-carboxamide, N-{2-[(2-methoxyethyl)carbamoyl]-4-(morpholin-4-ylmethyl)phenyl}-2-[4-(pyrimidin-2-yloxy)piperidin-1-yl]-1,3-thiazole-4-carboxamide, 2-[(2-methoxyethyl)(methyl)amino]-N-[4-methoxy-2-(pyridin-3-ylcarbamoyl)phenyl]-1,3-thiazole-4-carboxamide, 2-[methyl(tetrahydro-2H-pyran-4-ylmethyl)amino]-N-[4-(morpholin-4-ylmethyl)-2-(tetrahydro-2H-pyran-4-ylcarbamoyl)phenyl]-1,3-thiazole-4-carboxamide, N-(2-[(2-methoxyethyl)carbamoyl]-4-{[(2S)-2-methylmorpholin-4-yl]methyl}phenyl)-2-[(3S)-3-methoxypyrrolidin-1-yl]-1,3-thiazole-4-carboxamide, N-{4-[(3,3-dimethylmorpholin-4-yl)methyl]-2-[(2-methoxyethyl)carbamoyl]phenyl}-2-[(3S)-3-methoxypyrrolidin-1-yl]-1,3-thiazole-4-carboxamide, 2-(3-methoxyazetidin-1-yl)-N-{2-[(2-methoxyethyl)carbamoyl]-4-(morpholin-4-ylmethyl)phenyl}-1,3-thiazole-4-carboxamide, 2-(3-methoxyazetidin-1-yl)-N-[2-{[(1R)-2-methoxy-1-methylethyl]carbamoyl}-4-(morpholin-4-ylmethyl)phenyl]-1,3-thiazole-4-carboxamide, N-{4-(ethoxymethyl)-2-[(2-methoxyethyl)carbamoyl]phenyl}-2-[(3S)-3-methoxypyrrolidin-1-yl]-1,3-thiazole-4-carboxamide, N-{2-[(2-methoxyethyl)carbamoyl]-4-(morpholin-4-ylmethyl)phenyl}-2-[(2-methoxyethyl)(methyl)amino]-1,3-thiazole-4-carboxamide, and 2-[(3S)-3-fluoropyrrolidin-1-yl]-N-{2-[(2-methoxyethyl)carbamoyl]-4-(morpholin-4-ylmethyl)phenyl}-1,3-thiazole-4-carboxamide, or a salt thereof.

10. A pharmaceutical composition comprising the compound or a salt thereof according to claim 1 and a pharmaceutically acceptable excipient.

11. A method for treating urinary frequency, urinary urgency, urinary incontinence and lower urinary tract pain associated with overactive bladder, interstitial cystitis, or chronic prostatitis, which comprises administering to a patient an effective amount of the compound or a salt thereof according to in claim 1.

12. A method for treating pain, which comprises administering to a patient an effective amount of the compound or a salt thereof according to claim 1.

13. The method according to claim 12, wherein said pain is caused by osteoarthritis.

14. The compound according to claim 9, which is 2-morpholin-4-yl-N-[2-(pyridin-3-ylcarbamoyl)phenyl]-1,3-oxazole-4-carboxamide or a salt thereof.

15. The compound according to claim 9, which is 2-(4-ethoxypiperidin-1-yl)-N-[2-(tetrahydro-2H-pyran-4-ylcarbamoyl)phenyl]-1,3-thiazole-4-carboxamide or a salt thereof.

16. The compound according to claim 9, which is 2-[(2-methoxyethyl)(methyl)amino]-N-[2-(pyridin-3-ylcarbamoyl)phenyl]-1,3-thiazole-4-carboxamide or a salt thereof.

17. The compound according to claim 9, which is 2-[(3S)-3-methoxypyrrolidin-1-yl]-N-[2-(pyridin-3-ylcarbamoyl)phenyl]-1,3-oxazole-4-carboxamide or a salt thereof.

18. The compound according to claim 9, which is 2-[(2-methoxyethyl)(methyl)amino]-N-[2-(tetrahydro-2H-pyran-4-ylcarbamoyl)phenyl]-1,3-oxazole-4-carboxamide or a salt thereof.

19. The compound according to claim 9, which is N-{2-[(2-methoxyethyl)carbamoyl]-4-(morpholin-4-ylmethyl)

phenyl}-2-[4-(pyrimidin-2-yloxy)piperidin-1-yl]-1,3-thiazole-4-carboxamide or a salt thereof.

20. The compound according to claim 9, which is 2-[(2-methoxyethyl)(methyl)amino]-N-[4-methoxy-2-(pyridin-3-ylcarbamoyl)phenyl]-1,3-thiazole-4-carboxamide or a salt thereof.

21. The compound according to claim 9, which is 2-[methyl(tetrahydro-2H-pyran-4-ylmethyl)amino]-N-[4-(morpholin-4-ylmethyl)-2-(tetrahydro-2H-pyran-4-ylcarbamoyl)phenyl]-1,3-thiazole-4-carboxamide or a salt thereof.

22. The compound according to claim 9, which is N-(2-[(2-methoxyethyl)carbamoyl]-4-{[(2S)-2-methylmorpholin-4-yl]methyl}phenyl)-2-[(3S)-3-methoxypyrrolidin-1-yl]-1,3-thiazole-4-carboxamide or a salt thereof.

23. The compound according to claim 9, which is N-{4-[(3,3-dimethylmorpholin-4-yl)methyl]-2-[(2-methoxyethyl)carbamoyl]phenyl}-2-[(3S)-3-methoxypyrrolidin-1-yl]-1,3-thiazole-4-carboxamide or a salt thereof.

24. The compound according to claim 9, which is 2-(3-methoxyazetidin-1-yl)-N-{2-[(2-methoxyethyl)carbamoyl]-4-(morpholin-4-ylmethyl)phenyl}-1,3-thiazole-4-carboxamide or a salt thereof.

25. The compound according to claim 9, which is 2-(3-methoxyazetidin-1-yl)-N-[2-{[(1R)-2-methoxy-1-methylethyl]carbamoyl}-4-(morpholin-4-ylmethyl)phenyl]-1,3-thiazole-4-carboxamide or a salt thereof.

26. The compound according to claim 9, which is N-{4-(ethoxymethyl)-2-[(2-methoxyethyl)carbamoyl]phenyl}-2-[(3S)-3-methoxypyrrolidin-1-yl]-1,3-thiazole-4-carboxamide or a salt thereof.

27. The compound according to claim 9, which is N-{2-[(2-methoxyethyl)carbamoyl]-4-(morpholin-4-ylmethyl)phenyl}-2-[(2-methoxyethyl)(methyl)amino]-1,3-thiazole-4-carboxamide or a salt thereof.

28. The compound according to claim 9, which is 2-[(3S)-3-fluoropyrrolidin-1-yl]-N-{2-[(2-methoxyethyl)carbamoyl]-4-(morpholin-4-ylmethyl)phenyl}-1,3-thiazole-4-carboxamide or a salt thereof.

* * * * *

UNITED STATES PATENT AND TRADEMARK OFFICE
CERTIFICATE OF CORRECTION

PATENT NO. : 8,304,547 B2
APPLICATION NO. : 12/739433
DATED : November 6, 2012
INVENTOR(S) : Keizo Sugasawa et al.

It is certified that error appears in the above-identified patent and that said Letters Patent is hereby corrected as shown below:

IN THE CLAIMS:

Column 444, line 24, Claim 5, "according to in claim 4" should read "according to claim 4"

Column 446, line 43, Claim 11, "according to in claim 1." should read "according to claim 1."

Signed and Sealed this
Eleventh Day of December, 2012

David J. Kappos
*Director of the United States Patent and Trademark Office*